(12) United States Patent
Park et al.

(10) Patent No.: US 11,065,343 B2
(45) Date of Patent: Jul. 20, 2021

(54) COMPOUND BEARING BETA-GALACTOSIDE-INTRODUCED SELF-IMMOLATIVE LINKER

(71) Applicant: IntoCell Inc., Daejeon (KR)

(72) Inventors: Tae Kyo Park, Daejeon (KR); Sung Ho Woo, Daejeon (KR); Sun Young Kim, Daejeon (KR); Doo Hwan Jung, Daejeon (KR); Sang Kwang Lee, Daejeon (KR); Jong Un Cho, Daejeon (KR); Jae Ho Lee, Sejong (KR); Su Ho Park, Daejeon (KR); Dong Hoon Seo, Daejeon (KR); Hyang Sook Lee, Daejeon (KR); Beom Seok Seo, Daejeon (KR); Ji Yeon Lim, Daejeon (KR)

(73) Assignee: IntoCell Inc., Daejeon (KR)

( * ) Notice: Subject to any disclaimer, the term of this patent is extended or adjusted under 35 U.S.C. 154(b) by 109 days.

(21) Appl. No.: 16/472,983

(22) PCT Filed: Dec. 28, 2017

(86) PCT No.: PCT/KR2017/015613
§ 371 (c)(1),
(2) Date: Jun. 24, 2019

(87) PCT Pub. No.: WO2018/124758
PCT Pub. Date: Jul. 5, 2018

(65) Prior Publication Data
US 2019/0328902 A1    Oct. 31, 2019

(30) Foreign Application Priority Data

Dec. 28, 2016 (KR) .................. 10-2016-0180628
Dec. 27, 2017 (KR) .................. 10-2017-0181411

(51) Int. Cl.
| | | |
|---|---|---|
| A61K 47/68 | (2017.01) | |
| A61K 47/54 | (2017.01) | |
| A61K 45/06 | (2006.01) | |
| A61K 31/40 | (2006.01) | |
| C07K 16/32 | (2006.01) | |
| A61K 47/64 | (2017.01) | |

(52) U.S. Cl.
CPC .......... *A61K 47/6889* (2017.08); *A61K 31/40* (2013.01); *A61K 45/06* (2013.01); *A61K 47/549* (2017.08); *A61K 47/6415* (2017.08); *A61K 47/6801* (2017.08); *A61K 47/6855* (2017.08); *C07K 16/32* (2013.01); *C07K 2317/24* (2013.01)

(58) Field of Classification Search
None
See application file for complete search history.

(56) References Cited

U.S. PATENT DOCUMENTS

| | | |
|---|---|---|
| 4,816,567 A | 3/1989 | Cabilly et al. |
| 5,225,539 A | 7/1993 | Winter |
| 5,514,548 A | 5/1996 | Krebber et al. |
| 5,545,806 A | 8/1996 | Lonberg et al. |
| 5,545,807 A | 8/1996 | Surani et al. |
| 5,569,825 A | 10/1996 | Lonberg et al. |
| 5,591,669 A | 1/1997 | Krimpenfort et al. |
| 5,635,483 A | 6/1997 | Pettit et al. |
| 7,091,186 B2 | 8/2006 | Senter et al. |
| 7,423,116 B2 | 9/2008 | Doronina et al. |
| 7,498,298 B2 | 3/2009 | Doronina et al. |
| 8,568,728 B2 | 10/2013 | Jeffrey |
| 9,000,135 B2 | 4/2015 | Papot et al. |
| 9,669,107 B2 | 6/2017 | Kim et al. |
| 9,919,057 B2 | 3/2018 | Kim et al. |
| 2007/0276018 A1 | 11/2007 | Vite et al. |
| 2009/0105461 A1 | 4/2009 | Kunz et al. |
| 2016/0303254 A1 | 10/2016 | Kolakowski et al. |

FOREIGN PATENT DOCUMENTS

| | | |
|---|---|---|
| EP | 1391213 A1 | 2/2004 |
| KR | 1020150137015 A | 12/2015 |
| WO | 197017852 A1 | 5/1997 |
| WO | 02088172 A2 | 11/2002 |
| WO | 2009026177 A1 | 2/2009 |
| WO | 2015095755 A1 | 6/2015 |
| WO | 2016040684 A1 | 3/2016 |

OTHER PUBLICATIONS

Renoux, B., Raes, F., Legigan, T., Péraudeau, E., Eddhif, B., Poinot, P., . . . Papot, S. (2017). Targeting the tumour microenvironment with an enzyme-responsive drug delivery system for the efficient therapy of breast and pancreatic cancers. Chemical science, 8(5), 3427-3433. (Year: 2017).*

Alley et al., "Contribution of Linker Stability to the Activities of Anticancer Immunoconjugates," Bioconjugate Chem, 2008, pp. 759-765, vol. 19.

Alsarraf et al., "A dendritic Beta-galactosidase-responsive folate-monomethylauristatin E conjugate," Chem. Commun., 2015, pp. 15792-15795, vol. 51.

Badescu et al., "A New Reagent for Stable Thiol-Specific Conjugation," Bioconjugate Chemistry, 2014, pp. 460-469, vol. 25.

Barbas III, et al., "In vitro evolution of a neutralizing human antibody to human immunodeficiency virus type 1 to enhance affinity and broaden strain cross-reactivity", Proc. Natl. Acad. Sci. USA, 1994, pp. 3809-3813, vol. 91.

(Continued)

*Primary Examiner* — Dale R Miller
(74) *Attorney, Agent, or Firm* — The Webb Law Firm

(57) ABSTRACT

The present invention relates to a compound bearing a self-immolative linker having β-galactoside-introduced thereto. In a compound bearing a β-galactoside-introduced self-immolative linker according to the present invention, particularly, the self-immolative linker may form a glycosidic bond with a protein (e.g., an oligopeptide, polypeptide, an antibody, etc.) or ligand which has specific affinity for a desired target or with an active agent (e.g., a drug, a toxin, a ligand, a detection probe, etc.), which has a specific function or activity so as to allow the selective release of the active agent within a target cell.

14 Claims, 7 Drawing Sheets

(56) References Cited

OTHER PUBLICATIONS

Brennan et al., "Preparation of Bispecific Antibodies by Chemical Recombination of Monoclonal Immunoglobulin G1 Fragments", Science, 1985, pp. 81-83, vol. 229, No. 4708.

Burke et al., "Design, Synthesis, and Biological Evaluation of Antibody—Drug Conjugates Comprised of Potent Camptothecin Analogues", Bioconjugate Chem., 2009, pp. 1242-1250, vol. 20.

Carter et al., "High Level *Escherichia coli* Expression and Production of a Bivalent Humanized Antibody Fragment", Bio/Technology, 1992, pp. 163-167, vol. 10.

Casi et al., Antibody—"Drug Conjugates and Small Molecule—Drug Conjugates: Opportunities and Challenges for the Development of Selective Anticancer Cytotoxic Agents", J. Med. Chem., 2015, pp. 8751-8761, vol. 58.

Chari, "Targeted Cancer Therapy: Conferring Specificity to Cytotoxic Drugs", Accounts of Chemical Research, 2008, pp. 98-107, vol. 41, No. 1.

Clarkson et al., "Making antibody fragments using phage display libraries", Nature, 1991, pp. 624-628, vol. 352.

Dal Corso, et al., "AvBeta3 Integrin—Targeted Peptide/Peptodomimetic-Drug Conjugates: In-Depth Analysis of the Linker Technology", Current Topics in Medicinal Chemistry, 2016, pp. 314-329, vol. 16.

Devalapally et al., "Beta-Galactoside Prodrugs of Doxorubicin for Application in Antibody Directed Enzyme Prodrug Therapy/Prodrug Mono Therapy", Arch Pharm Res, 2007, pp. 723-732, vol. 30., No. 6.

Devalapally et al., "Safety, Pharmacokinetics and Biodistribution Studies of a Beta-galactoside Prodrug of Doxorubicin for Improvement of Tumor Selective Chemotherapy", Drug Development and Industrial Pharmacy, 2008, pp. 789-795, vol. 34, No. 8.

Dosio et al., "Advances in Anticancer Antibody-Drug Conjugates and Immunotoxins", Recent Patents on Anti-Cancer Drug Discovery, 2014, pp. 35-65, vol. 9.

Ducry et al., "Antibody—Drug Conjugates: Linking Cytotoxic Payloads to Monoclonal Antibodies", Bioconjugate Chem., 2010, pp. 5-13, vol. 21.

Florianczyk et al., "Activity of beta-glucuronidase in blood serum of patients with breast cancer", Journal of Chinese Clinical Medicine, 2010, pp. 480-482, vol. 5, No. 8.

Florio et al., "Rapid access to uronic acid-based mimetics of Kdn2en from D-glucurono-6,3-lactone", Carbohydrate Research, 2000, pp. 445-448, vol. 328.

Gilad et al., "Synthesis, biological studies and molecular dynamics of new anticancer RGD-based peptide conjugates for targeted drug delivery", Bioorganic & Medicinal Chemistry, 2016, pp. 294-303, vol. 24.

Ginj et al., "Radiolabeled somatostatin receptor antagonists are preferable to agonists for in vivo peptide receptor targeting of tumors", PNAS, 2006, pp. 16436-16441, vol. 103, No. 44.

Hartley et al., "SG2285, a Novel C2-Aryl-Substituted Pyrrolobenzodiazepine Dimer Prodrug That Cross-links DNA and Exerts Highly Potent Antitumor Activity", Cancer Research, 2010, p. 6849-6858, vol. 70, No. 17.

Hawkins et al., "Selection of Phage Antibodies by Binding Affinity Mimicking Affinity Maturation", J. Mol. Biol., 1992, pp. 889-896, vol. 226.

Hinman et al., "Preparation and Characterization of Monoclonal Antibody Conjugates of the Calicheamicins: A Novel and Potent Family of Antitumor Antibiotics", Cancer Research, 1993, pp. 3336-3342, vol. 53.

Jackson et al., "In Vitro Antibody Maturation—Improvement of a High Affinity, Neutralizing Antibody Against IL-1Beta", The Journal of Immunology, 1995, pp. 3310-3319, vol. 154.

Jakobovits et al., "Analysis of homozygous mutant chimeric mice: Deletion of the immunoglobulin heavy-chain joining region blocks B-cell development and antibody production", Proc. Natl. Acad. Sci., 1993, pp. 2551-2555, vol. 90.

Jakobovits et al., "Germ-line transmission and expression of a human-derived yeast artificial chromosome", Nature, 1993, pp. 255-258, vol. 362.

Kerr et al., "Listeriolysin O Potentiates Immunotoxin and Bleomycin Cytotoxicity", Bioconjugate Chemistry, 1997, pp. 781-784, vol. 8, No. 6.

Jeffrey et al., "A Potent Anti-CD70 Antibody—Drug Conjugate Combining a Dimeric Pyrrolobenzodiazepine Drug with Site-Specific Conjugation Technology", Bioconjugate Chemistry, 2013, pp. 1256-1263, vol. 24.

Jeffrey et al., "Expanded Utility of the Beta-Glucuronide Linker: ADCs That Deliver Phenolic Cytotoxic Agents", ACS Medicinal Chemistry Letters, 2010, pp. 277-280, vol. 1.

Jones et al., "Replacing the complementarity-determining regions in a human antibody with those from a mouse", Nature, 1986, pp. 522-525, vol. 321.

Junutula et al., "Site-specific conjugation of a cytotoxic drug to an antibody improves the therapeutic index", Nature Biotechnology, 2008, pp. 925-932, vol. 26, No. 8.

Kilpatrick et al., "Rapid Development of Affinity Matured Monoclonal Antibodies Using RIMMS", Hybridoma, 1997, pp. 381-391, vol. 16, No. 4.

Kohler et al., "Continuous cultures of fused cells secreting antibody of predefined specificity", Nature, 1975, pp. 495-497, vol. 256.

Kornilova et al., "Development of a fluorescence polarization binding assay for folate receptor", Analytical Biochemistry, 2013, pp. 59-62, vol. 432.

Krall et al., "A bivalent small molecule-drug conjugate directed against carbonic anhydrase IX can elicit complete tumour regression in mice", Chemical Science, 2014, pp. 3640-3644, vol. 5.

Lambert, "Twists and Turns on the Development Path of a Novel Immunoconjugate—Lorvotuzumab Mertansine", World ADC Summit, 2010, pp. 1-28.

Legigan et al., "The First Generation of Beta-Galactosidase-Responsive Prodrugs Designed for the Selective Treatment of Solid Tumors in Prodrug Monotherapy", Angew. Chem. Int. Ed., 2012, pp. 11606-11610, vol. 51.

Leu et al., "Design and Synthesis of Water-Soluble Glucuronide Derivatives of Camptothecin for Cancer Prodrug Monotherapy and Antibody-Directed Enzyme Prodrug Therapy (ADEPT)", J. Med. Chem., 1999, pp. 3623-3628, vol. 42.

Low et al., "Discovery and Development of Folic-Acid-Based Receptor Targeting for Imaging and Therapy of Cancer and Inflammatory Diseases", Accounts of Chemical Research, 2008, pp. 120-129, vol. 41, No. 1.

Marks et al., "By-Passing Immunization: Building High Affinity Human Antibodies by Chain Shuffling", Bio/Technology, 1992, pp. 779-783, vol. 10.

Marks et al., "By-passing Immunization Human Antibodies from V-gene Libraries Displayed on Phage", J. Mol. Biol., 1991, pp. 581-597, vol. 222.

McCafferty et al., "Phage antibodies: filamentous phage displaying antibody variable domains", Nature, 1990, pp. 552-554, vol. 348.

Miyazaki et al., "Synthesis and Antitumor Activity of Novel Dolastatin 10 Analogs", Chem. Pharm. Bull., 1995, pp. 1706-1718, vol. 43, No. 10.

Morimoto et al., "Single-step purification of F(ab')2 fragments of mouse monoclonal antibodies (immunoglobulins G1) by hydrophobic interaction high performance liquid chromatography using TSKgel Phenyl-5PW", Journal of Biochemical and Biophysical Methods, 1992, pp. 107-117, vol. 24.

Norden et al., "Gm1 Ganglioside Beta-Galactosidase A Purification and Studies of the Enzyme from Human Liver", The Journal of Biological Chemistry, 1974, pp. 7969-7976, vol. 249, No. 24.

Oflazoglu et al., "Potent Anticarcinoma Activity of the Humanized Anti-CD70 Antibody h1F6 Conjugated to the Tubulin Inhibitor Auristatin via an Uncleavable Linker", Clin Cancer Res, 2008, pp. 6171-6180, vol. 14, No. 19.

Ohto et al., "Crystal Structure of Human Beta-Galactosidase Structural Basis of GM1 Gangliosidosis and Morquio B Diseases", Journal of Biological Chemistry, 2012, pp. 1801-1812, vol. 287, No. 3.

(56) References Cited

OTHER PUBLICATIONS

Phillips et al., "Targeting HER2-Positive Breast Cancer with Trastuzumab-DM1, an Antibody-Cytotoxic Drug Conjugate", Cancer Res, 2008, pp. 9280-9290, vol. 68, No. 22.
Poli et al., "Radretumab Radioimmunotherapy in Patients with Brain Metastasis: A 124I-L19SIP Dosimetric PET Study", Cancer Immunol Res, 2013, pp. 134-144, vol. 1, No. 2.
Rao et al., "Development and validation of a UPLC-MS/MS method for the novel folate-targeted small molecule drug conjugate EC1456 and its metabolites in tumor homogenates from mice", Journal of Pharmaceutical and Biomedical Analysis, 2016, pp. 148-156, vol. 122.
Riechmann et al., "Reshaping human antibodies for therapy", Nature, 1988, pp. 323-327, vol. 332, No. 24.
Roy et al., "DUPA Conjugation of a Cytotoxic Indenoisoquinoline Topoisomerase I Inhibitor for Selective Prostate Cancer Cell Targeting", J. Med. Chem., 2015, pp. 3094-3103, vol. 58.
Schier et al., "Identification of functional and structural amino-acid residues by parsimonious mutagenesis", Gene, 1996, pp. 147-155, vol. 169.
Seitz et al., "Design, synthesis and biological evaluation of a highly-potent and cancer cell selective folate-taxoid conjugate", Bioorganic & Medicinal Chemistry, 2015, pp. 2187-2194, vol. 23.
Shinmi et al., "One-Step Conjugation Method for Site-Specific Antibody-Drug Conjugates through Reactive Cysteine-Engineered Antibodies", Bioconjugate Chem, 2016, pp. 1324-1331, vol. 27.
Srinivasarao et al., "Principles in the design of ligand-targeted cancer therapeutics and imaging agents", Nature Reviews, 2015, pp. 203-219, vol. 14.
Tietze et al., "Synthesis and Biological Studies of Different Duocarmycin Based Glycosidic Prodrugs for Their Use in the Antibody-Directed Enzyme Prodrug Therapy", J. Med. Chem., 2009, pp. 537-543, vol. 52.
Tranoy-Opalinski et al., "Beta-Glucuronidase-responsive prodrugs for selective cancer chemotherapy: An update", European Journal of Medicinal Chemistry, 2014, pp. 302-313, vol. 74.
Vallabhajosula et al., "99mTc-Labeled Small-Molecule Inhibitors of Prostate-Specific Membrane Antigen: Pharmacokinetics and Biodistribution Studies in Healthy Subjects and Patients with Metastatic Prostate Cancer", J Nucl Med, 2014, pp. 1791-1798, vol. 55.
Verhoeyen et al., "Reshaping Human Antibodies: Grafting an Antilysozyme Activity", Science, 1988, pp. 1534-1536, vol. 239, No. 4847.
Waszkiewicz et al., "The activity of serum beta-galactosidase in colon cancer patients with a history of alcohol and nicotine dependence: preliminary data", Postepy Hig Med Dosw (online), 2013, pp. 896-900, vol. 67.
Waterhouse et al., "Combinatorial infection and in vivo recombination: a strategy for making large phage antibody repertoires", Nucleic Acids Research, 1993, pp. 2265-2266, vol. 21, No. 9.
Wichert et al., "Dual-display of small molecules enables the discovery of ligand pairs and facilities affinity maturation", Nature Chemistry, 2015, pp. 241-249, vol. 7.
Wong et al., "Mechanisms of Drug Release in Nanotherapeutic Delivery Systems", Chem. Rev., 2015, pp. 3388-3432, vol. 115.
Wring et al., "Shorter development of immunoassay for drugs: application of the novel RIMMS technique enables rapid production of monoclonal antibodies to ranitidine", Journal of Pharmaceutical and Biomedical Analysis, 1999, pp. 695-707, vol. 19.
Yan et al., "A Novel Monoclonal Antibody Against Mouse B7-H3 Developed in Rats", Hybridoma, 2012, 267-271, vol. 31, No. 4.
Yelton et al., "Affinity Maturation of the BR96 Anti-Carcinoma Antibody by Codon-Based Mutagenesis", The Journal of Immunology, 1995, pp. 1994-2004, vol. 155.
Zhang et al., "A Remote Arene-Binding Site on Prostate Specific Membrane Antigen Revealed by Antibody-Recruiting Small Molecules", J. Am. Chem. Soc., 2010, pp. 12711-12716, vol. 132.

* cited by examiner

COMPOUND BEARING BETA-GALACTOSIDE-INTRODUCED SELF-IMMOLATIVE LINKER

CROSS-REFERENCE TO RELATED APPLICATIONS

This application is the United States national phase of International Application No. PCT/KR2017/015613 filed Dec. 28, 2017, and claims priority to Korean Patent Application Nos. 10-2016-0180628 and 10-2017-0181411, filed Dec. 28, 2016 and Dec. 27, 2017, respectively, the disclosures of which are hereby incorporated by reference in their entirety.

TECHNICAL FIELD

The present invention relates to a compound comprising a self-immolative linker having β-galactoside-introduced thereto. More particularly, a compound comprising a β-galactoside-introduced self-immolative linker according to the present invention comprises a protein (for example, an oligopeptide, a polypeptide, an antibody, etc) or a ligand having a binding specificity for the desired target, an active agent (for example, drug, toxin, ligand, probe for a detection) having a specific function or activity and a self-immolative linker comprised of a glycosidic bond which may render the active agent to be selectively released in the target cell.

BACKGROUND ART

Many small molecule drugs used as chemotherapy cause various side effects since the drugs act not only on cancer cells but also on normal cells. In order to resolve such non-selectivity problems, the research regarding the development for a targeted conjugate, such as, an antibody-drug, a peptide-drug, a small molecule ligand-drug, etc., is actively being conducted (Recent Patents on Anti-Cancer Drug Discovery 2014, 9, 35-65; Bioorganic & Medicinal Chemistry 2015, 23, 2187-2194; Nature Reviews Drug Discovery 2015, 14, 203-219).

The antibody drug conjugate (ADC) belongs to the most representative category of therapeutic substances among targeted anti-cancer agents, which are designed to effectively release drugs bound to an antibody in a target cancer cell via selective binding ability between an antigen and an antibody. Brentuximab vedotin (commercial product name, Adcetris) as an agent for treating Hodgkin lymphoma and ado-trastuzumab emtansine (commercial product name, Kadcyla) as an agent for treating HER2 positive breast cancer have been approved by the FDA in 2011 and 2013, respectively. These substances are present in a mixture of the form wherein a drug is linked to thiol of cysteine or amino group of lysine. By 2016, at least fifteen (15) ADCs were being clinically tested.

According to the recent reports, in the case of an ADC, only less than 1% of the administered ADC reaches to the cancer tissue. This suggests that the drug also acts on normal cells (for example, liver or endothelial tissue) and may induce side effects (Cancer Immunol Res 2013, 134-143; World ADC Summit, Oct. 27-28, 2010, ImmunoGen). In addition, in the process of delivering the drug into the cell via an internalization process by an antigen-antibody conjugate, an antibody having high molecular weight (~150 kDa) has been reported to reise a problem in which the antibody cannot penetrate into the cancer tissue (J. Med. Chem. 2015, 58, 8751-8761). An antibody used in an ADC requires substantial cost and efforts to develop an antibody itself. In order to derive a new therapeutic strategy to overcome such a problem, a method for a small molecule ligand-drug conjugates (SMDC) has been attempted (J. Med. Chem. 2015, 58, 8751-8761; Journal of Pharmaceutical and biomedical analysis 2016, 122, 148-156).

Small molecule ligands in small molecule drug-conjugates present advantages over high molecular antibodies, such as easier preparation and better pentration into the cancer tissue. Research using folic acid (Acc. Chem. Res. 2008, 41, 120-129) and Prostate-specific membrane antigen, PSMA (J. Nucl. Med. 2014, 55, 1791-1798), somatostatin analogues (Proc. Natl. Acad. Sci. U.S.A. 2006, 103, 16436-16441), carbonic anhydrase IX, CAIX (Nat. Chem. 2015, 7, 241-249; Chem. Sci. 2014, 5, 3640-3644), Integrin targeted peptide (Bioorg. Med. Chem. 2016, 24, 294-303; Current Topics in Medicinal Chemistry, 2016, 16, 314-329) are underway and in particular, research using folic acid and PSMA among those are most actively being pursued (Nat. Rev. Drug Discovery 2015, 14, 203-219).

A targeted anti-cancer agent comprises a drug and a targeting group which can selectively bind the cancer cell, and a linker connecting the targeting group and the drug. An antibody, a protein or ligand, etc., which is present in the targeting group plays a role in effectively delivering the drug to the cancer cell by specifically binding to antigens or receptors which are over-expressed in the cancer cell. Therefore, targeted anti-cancer agents may highly reduce the risk of side-effects, compared to traditional anti-cancer agents. However, to achieve sufficient cancer cell killing effect, drugs with substantially higher, should be linked to the conjugate, since the number of most antigens or receptors expressed on the surface of the cancer cell is low ($\sim 1 \times 10^5$ receptors/cell).

It is very important to carefully design highly toxic drugs in the conjugates (for example, pyrrolobenzodiazepine derivatives, maytansinoids, auristatinoid(s), etc.) so that they are delivered into the cancer cell without being separated during blood circulation in the body. Most conjugates are linked through the thiol-maleimide linkage wherein cysteine and maleimide are connected. However, thiol-maleimide linkage, due to its intrinsic instability and being subjected to retro-Michael reaction in the body, can be cleaved off back into thiol and maleimide, and thus raises severe toxicity problems (Bioconjugate Chemistry 2008, 19, 759-765; Bioconjugate Chemistry 2010, 21, 5-13). In results, the use of an unstable linker in conjugates may affect a pharmaceutical effect toxicity, and PK etc. Therefore, stability of the linker should be considered as one of the core characteristics of drug conjugates.

Up to now, Linkers in the conjugates may be divided into a non-cleavable linker and a cleavable linker.

Non-cleavable linker mainly comprises thioether bonds and is made by reacting thiol group with maleimide or haloacetamide group. Linkers used in the conjugates of T-DM1 (Cancer Res 2008, 68, 9280-9290) and anti-CD70-mc-MMAF (SGN-75, Clin Cancer Res 2008, 14, 6171-6180) are the representative examples of non-cleavable linkers. However, when drug is linked through non-cleavable linker to an antibody or a ligand, the cytotoxic activity of the drug may be attenuated compared to the drug itself. In that case, employing a proper cleavable linker to cleave/hydrolyze and release a drug itself in the target cell might be a better option.

The cleavable linker may be categorized into a chemically liable linker and an enzyme cleavable linker (Bioconjugate Chem. 2010, 21, 5-13).

The chemically liable linker mainly utilizes a mechanism which releases the drug by hydrolyzing a disulfide bond, hydrazone or oxime, etc. or by disulfide exchange reaction. The linker with a disulfide bond uses a principle wherein the drug is released in the cell, where higher glutathione concentration is present compared to outside the cell, but has an unavoidable limitation wherein the drug can be released during systemic circulation with the presence, albeit low, of free thiols in glutathione, cysteine, etc (Bioconjugate Chemistry 2008(19) 759-765). Hydrazone and oxime linker are relatively stable in the blood but can be rapidly hydrolyzed since they may be unstable under the high acidic environment, and thus may induce a side-effect by acting on normal cells as well as target cancer cells (Bioconjugate Chemistry 2010, 21, 5-13)

The enzyme cleavable linker mainly employs a structure to specifically separate the drug by lysosomal enzymes, such as cathepsin B or β-glucuronidase, etc., which is over-expressed in the cancer cell.

Val-Cit (valine-citrulline) and Phe-Lys (phenylalanine-lysine), which are mainly used as the peptide linker, are known as being selectively hydrolyzed by cathepsin B. Stability of these linkers, compared to the chemically liable linker, is excellent but water-solubility is not good and thus raises a aggregation problem (U.S. Pat. No. 8,568,728/U.S. Pat. No. 7,091,186). Therefore, a study was conducted with a linker containing β-glucuronide and β-galactoside which are more hydrophilic than the peptide linker. They are designed to release a drug by enzyme (for example, β-glucuronidase and β-galactosidase), which are over-expressed in cancer cell lysosomes but rarely in normal human blood (Chem. Rev. 2015, 115, 3388-3432; European Journal of Med. Chem., 2014, 74, 302-313; Chem Commun., 2015, 51, 15792-15795).

Human β-glucuronidase (EC 3.2.1.31) hydrolyzes glycocidic bond of glucuronide having R-configuration and is rarely present in blood but is more expressed in the cancer cell and peripheral tissue thereof. Drug-conjugates comprising β-glucuronide hardly released a drug in the blood but selectively released in the cancer cell to be targeted. β-Glucuronide linker, due to improved physicochemical property compared to peptide linker, has been used to manufacture antibody drug conjugates (J. Med. Chem. 1999, 42, 3623-3628).

Human β-galactosidase (EC 3.2.1.23, R-Gal) is an enzyme hydrolyzing β-galactosidic bond and present in a lysosome of the cell. The enzyme is present as an inactive monomer form at physiological pH 7.4 but forms an active dimer only in low pH is active form only in low pH and is present as a monomer which is inactive form in physiological pH, 7.4, so introduction of new β-galactoside linker can remarkably reduce a risk that the drug is released in blood circulation (J Biol Chem 2012, 287, 1801-1812, J Biol Chem 1974, 249, 7969-7976).

In addition, it has been reported that activities of β-glucuronidase and β-galactosidase increase in the blood of patient with. β-Glucuronidase shows higher activity, two (2)-times higher than in normal human serum of a patient with breast cancer, but β-galactosidase showed only a 24% activity increase in the serum of a patient with infiltrative colon cancer (Journal of Chinese Clinical Medicine, 2010. Vol 5, 480-482; PostepyHig Med Dosw (online), 2013; 67: 896-900). Based on these results, the linker containing β-galactoside, a substrate of an enzyme having relatively weak activity in the blood of patient with cancer, might present advantage in terms of stability and safety in the blood of patient with cancer, than the linker containing β-glucuronide.

Jeffrey (Bioconjugate Chem. 2009, 20, 1242-1250; ACS Med. Chem. Lett. 2010, 1, 277-280) etc., reported examples of the conjugates containing β-glucuronide with a variety of drugs (for example, doxorubicin, Camptothecin analog, CBI, and Auristatins). The antibody-drug conjugate containing β-glucuronide has been reported stable in rat plasma but the stability in mouse plasma has not been reported.

KR 10-2015-0137015 reported a β-glucuronide introduced self-immolative linker, which is more stable in mouse plasma than a conjugate with β-glucuronide, which was reported by Jeffrey, etc. However, developing the conjugates with β-glucuronide might have a disadvantage in linking drugs with complex structure, such as maytansinoids, Cryptophycin, etc., due to difficult handling of there drugs.

The prodrug prepared by linking doxorubicin to β-galactoside showed more than 1,000 times stability, compared to the stability of the drug itself (Arch Pharm Res, 2007, 30, 723-732). The administration of the prodrug to a mouse shows a maximum tolerance dose (MTD) which is higher than the dose when the drug itself is administered (Drug Development and Industrial Pharmacy 2008, 34, 789-795). β-Glucuronide appears to be better than β-glucuronide in terms of the stability, compared with β-glucuronide and MMAE (monomethylauristatin E) conjugate of Papot, etc., as previously described, showing that the activity of the conjugate is 100 times lower than when the drug itself is administered.

In addition, Papot (Angew. Chem. Int. Ed. 2012, 51, 11606-11610; U.S. Pat. No. 9,000,135) etc. developed a galactoside prodrug linked to a small molecule substance (for example, a ligand such as folic acid) instead of an antibody with which it is difficult to permeate the cancer cell due to a high molecular weight. However, according to the report, the conjugate using β-galactoside has a limitation that produces not a single substance.

Accordingly, the present invention provides a compound comprising a β-galactoside introduced self-immolative linker which is very stable in the blood and releases the drug only to the target cancer cell. This self-immolative group improves physicochemical properties of the conjugates, provided easier preparation, and overcomes limitations of existing β-glucuronide and β-galactoside as described up to now, and in particular, provides a compound comprising a self-immolative linker having an excellent universal use which can be applied to the drug which was difficult with β-glucuronide.

DISCLOSURE

Technical Problem

An object of present invention is to provide a compound comprising a self-immolative linker containing β-galactoside, that is designed to show an efficacy of an active agent which is selectively cleavable by β-galactosidase, an enzyme over-expressed in the cancer cell, with having a high affinity for water.

Technical Solution

In one general aspect, there is provided a compound comprising a β-galactoside-introduced self-immolative linker represented by Chemical Formula 1 below:

[Chemical Formula 1]

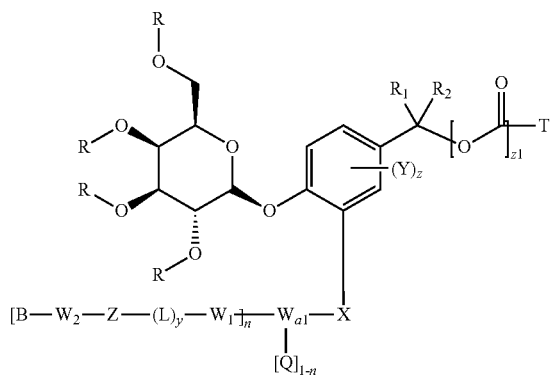

in Chemical Formula 1,
R is hydrogen or a hydroxy protecting group;
X is —C(=O)—, —NH—, —O—, or —S—;
T is an active agent;
Q is B'—U1-$(CH_2CH_2X_3)_{p4}$—$(CH_2)_{p3}$—$W_{a4}$-$Q_2$-$W_{a3}$—$W_1$–;
n is an integer of 0 or 1;
Y is hydrogen, halo$C_1$-$C_8$alkyl, halogen, cyano or nitro;
z is an integer of 1 to 3, and Y may be the same or different from each other, if z is an integer of not less than 2;
z1 is an integer of 0 or 1;
$W_1$ is ⊢$W_{a2}$—$(CH_2)_{a1}$—$W_{b1}$-$Q_1$–;
$W_2$ is ⊢$W_{a4}$-$Q_2$-$W_{a3}$–;
$W_{a1}$ and $W_{a2}$ are each independently —NH—, —C(=O)—, or —$CH_2$—;
$W_{a3}$ and $W_{a4}$ are each independently —NH—, —C(=O)—, —$CH_2$—, —C(=O)NH—, —NHC(=O)—, or triazolylene;
$W_{b1}$ is an amide bond or triazolylene;
L is an amino acid, peptide, or amide bond as a linker connecting $W_{a2}$ and Z;
Z is a single bond, —$W_{a5}$—$(CH_2)_{a2}$—$W_{b2}$—$(CH_2)_{a3}$—$W_{a6}$—, or —$W_{a7}$—$(CH_2)_{a4}$—CR'R"—X"—;
R' is $C_1$-$C_8$alkyl or B—$W_{a8}$-$Q_3$-$W_{c1}$—$(CH_2)_{a5}$—;
R" is B—$W_{a8}$-$Q_3$-$W_{c1}$—$(CH_2)_{a5}$—;
$Q_1$, and $Q_3$ are each independently —$(CH_2)_{a6}$—$(X_1CH_2CH_2)_{b1}$—$(CH_2)_{a7}$—;
$X_1$ and $X_3$ are each independently —O—, —S—, —NH—, or —$CH_2$—;
X" is —NHC(=O)—$(CH_2)_{a8}$—$W_{a9}$— or —C(=O)NH—$(CH_2)_{a8}$—$W_{a9}$—;
$W_{a5}$, $W_{a6}$, $W_{a7}$, $W_{a8}$, and $W_{a9}$ are each independently —NH—, —C(=O)—, or —$CH_2$—;
$W_{b2}$ is an amide bond or triazolylene;
$W_{c1}$ is —NHC(=O)— or —C(=O)NH—;
$Q_2$ is a saturated or unsaturated alkylene, which is linear or branched with a carbon number of 1 to 50, satisfying any one of (i) to (iii) below;
(i) at least one —$CH_2$— in the alkylene is substituted with one or more heteroatoms selected from —NH—, —C(=O)—, —O—, and —S—,
(ii) at least one arylene or heteroarylene is included in the alkylene,
(iii) the alkylene is further substituted with one or more selected from the group consisting of $C_1$-$C_{20}$alkyl, $C_6$-$C_{20}$aryl$C_1$-$C_8$alkyl, —$(CH_2)_{s1}$$COOR_3$, —$(CH_2)_{s1}$$COR_3$, —$(CH_2)_{s2}$$CONR_4R_5$, and —$(CH_2)_{s2}$$NR_4R_5$;
arylene or heteroarylene of (ii) above may be further substituted with nitro;
$R_3$, $R_4$, and $R_5$ are each independently hydrogen or $C_1$-$C_{15}$ alkyl;
$X_2$ is —O—, —S—, —NH—, or —$CH_2$—;
U1 is bound to B' in the position of asterisk (*) with a linking group selected from the following structures:

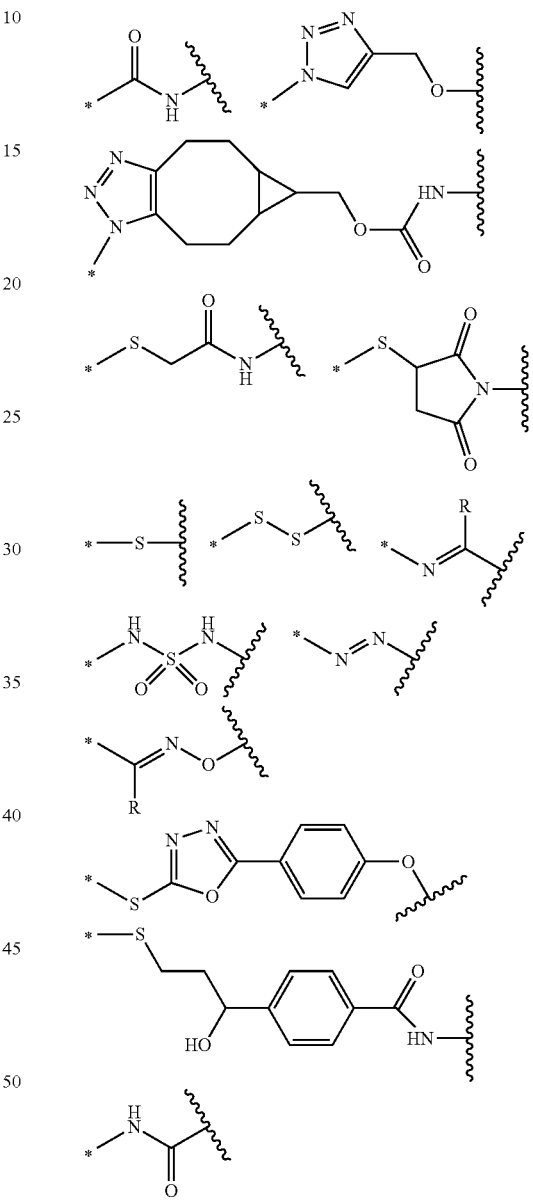

R is C1-C10 alkyl, C6-20 aryl or C2-C20 heteroaryl;
B and B' are each independently a ligand or a protein having properties selectively targeting a particular organ with a drug, a tissue or a cell, that is, properties binding to a receptor;
a1, a2, a3, a4, a5, a6, a8, b1, p1, p2, p3, and p4 are each independently an integer of 1 to 10;
a7, y, s1, s2, and s4 are each independently an integer of 0 to 10; and
$R_1$ and $R_2$ are each independently hydrogen, $C_1$-$C_8$alkyl or $C_3$-$C_8$cycloalkyl.

In another general aspect, there is provided a compound represented by Chemical Formula 2 below, as an intermediate for preparing a compound of Chemical Formula 1.

[Chemical Formula 2]

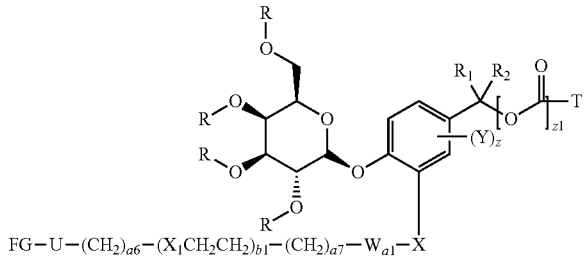

in Chemical Formula 2,

R is hydrogen or a hydroxy protecting group;
X is —C(=O)—, —NH—, —O—, —CH$_2$— or —S—;
W$_{a1}$ is —NH—, —CH$_2$— or —C(=O)—;
T is an active agent;
Y is hydrogen, haloC$_1$-C$_8$alkyl, halogen, cyano or nitro;
U is a single bond or

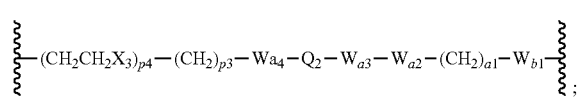

W$_{a2}$ is —NH—, —C(=O)—, or —CH$_2$—;
W$_{a3}$ and W$_{a4}$ are each independently —NH—, —C(=O)—, —CH$_2$—, —C(=O)NH—, —NHC(=O)—, or triazolylene;
Q$_2$ is

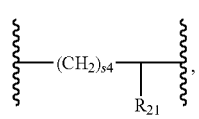

R$_{21}$ is C$_1$-C$_{20}$alkyl, C$_6$-C$_{20}$arylC$_1$-C$_8$alkyl, —(CH$_2$)$_{s1}$COOR$_3$, —(CH$_2$)$_{s1}$COR$_3$, —(CH$_2$)$_{s2}$CONR$_4$R$_5$ or —(CH$_2$)$_{s2}$NR$_4$R$_5$;

R$_3$, R$_4$, and R$_5$ are each independently hydrogen or C$_1$-C$_{15}$ alkyl;

s1 and s2 are each independently an integer of 0 to 10;
W$_{b1}$ is —C(=O)NH—, —NHC(=O)—,

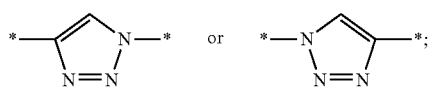

a1 is each independently an integer of 1 to 10;
s4 is an integer of 0 to 10;
p3 and p4 are each independently an integer of 1 to 10;
FG is —NH$_2$, —C≡CH, C$_4$-C$_{10}$cycloalkynyl, —N$_3$, —COOH, —SO$_3$H, —OH, —NHOH, —NHNH$_2$, —SH, haloacetamide (—NHC(O)CH$_2$-hal, wherein hal is halogen), maleimide

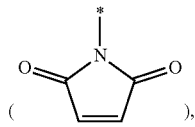 [SMILES: *N1C(=O)C=CC1=O]

halogen, tosylate (TsO$^-$), aldehyde (~COH), ketone (~COR, wherein R is C1-C10alkyl, C6-C20aryl, C2-C20 heteroaryl), diene,

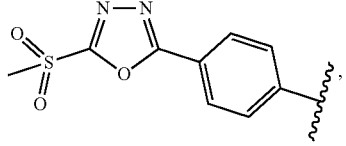

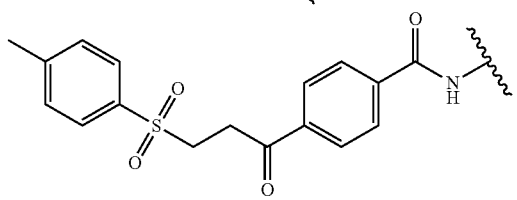

or —OP(=O)(OH)$_2$;
X$_1$ and X$_3$ are each independently —O—, —S—, —NH—, or —CH$_2$—;
a6 and b1 are each independently an integer of 1 to 10;
a7 is an integer of 0 to 10;
z is an integer of 1 to 3, and Y may be the same or different from each other, if z is an integer of not less than 2;
z1 is an integer of 0 or 1;
R$_1$ and R$_2$ are each independently hydrogen, C$_1$-C$_8$alkyl or C$_3$-C$_8$cycloalkyl.

Advantageous Effects

A β-galactoside-introduced self-immolative linker according to the present invention is more simple than an existing known linker in terms of a method for preparation thereof, and since it does not induce a side-reaction, it is expediently purified and separated. In addition, the linker has a better affinity for water and thus improves physical properties of a conjugate prepared by the same.

In addition, a compound comprising the β-galactoside-introduced self-immolative linker according to the present invention comprises a protein (for example, an oligopeptide, a polypeptide, an antibody, etc) or a ligand having a binding specificity for the desired target, an active agent having a specific function or activity (for example, drug, toxin, ligand, probe for a detection) and a self-immolative linker comprised of a glycosidic bond which may render the active agent to be selectively released in the target cell and thus has an advantage designed to selectively release the active agent by using β-galactosidase which is an enzyme over-expressed in the target cell. In particular, it may be used in drugs to which β-glucuronide is difficult to be applied, and thus may be well utilized in a development of an anti-cancer agent for the target treatment.

BEST MODE

Figure 1:
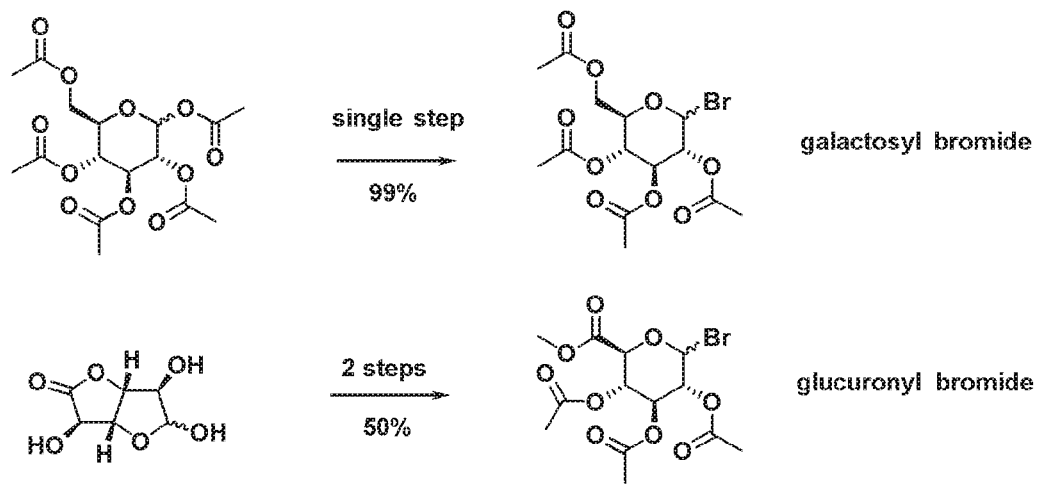
FIG. 1-comparison of process steps and yields for preparing Galactosyl bromide [Example 1] and glucuronyl bromide (Example 1 of Korean Laid-Open Publication No. 10-2015-0137015]
Figure 2:
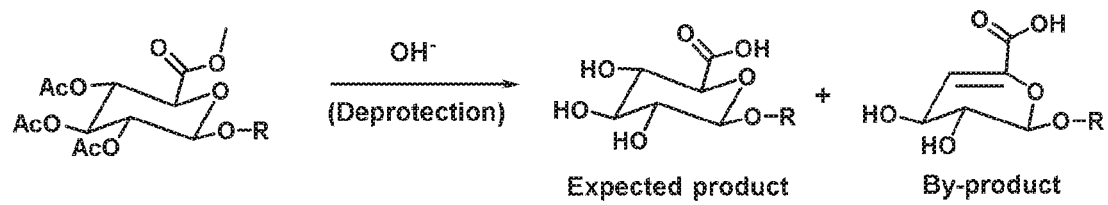
FIG. 2-comparison of steps for de-protecting β-glucuronide (BG; upper) and β-galactoside (BGal; lower)
Figure 2:
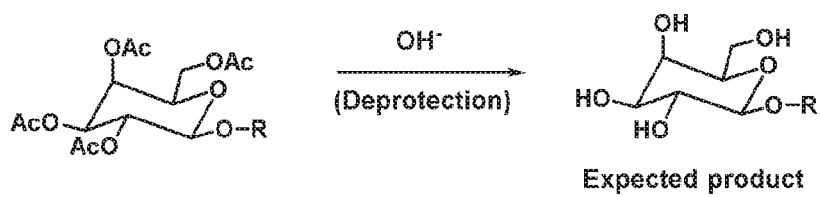

The present invention relates to a compound comprising a β-galactoside-introduced self-immolative linker, wherein the self-immolative linker has a basic skeleton based on substituted benzoic acid derivatives, β-galactoside, capable of hydrolysis by an enzyme reaction, is bound in ortho-position of benzoic acid, and active agent (for example, a drug, a toxin, a ligand, a probe for the detection, etc.) having a specific function or activity is bound in a meta-position of benzoic acid, and a carboxyl group of benzoic acid comprises an amide bond into which the linker capable of binding with a protein (for example, oligopeptide, polypeptide, antibody, etc.) or a ligand, etc. having a binding specificity for the desired target is introduced.

More specifically, a compound comprising the β-galactoside-introduced self-immolative linker is represented by Chemical Formula 1 below.

[Chemical Formula 1]

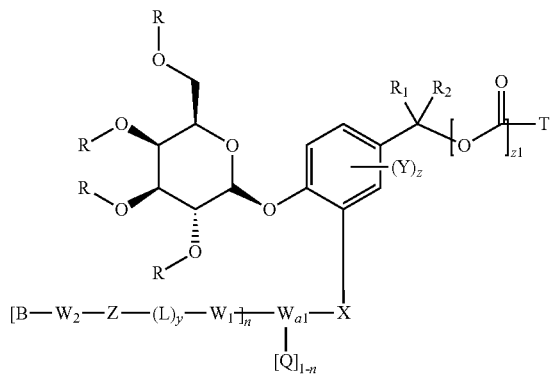

in Chemical Formula 1,
R is hydrogen or a hydroxy protecting group;
X is —C(=O)—, —NH—, —O—, or —S—;
T is an active agent;
Q is B'—U1-$(CH_2CH_2X)_{p4}$—$(CH_2)_{p3}$—$W_{a4}$-$Q_2$-$W_{a3}$—$W_1$-;
n is an integer of 0 or 1;
Y is hydrogen, halo$C_1$-$C_8$alkyl, halogen, cyano or nitro;
z is an integer of 1 to 3, and Y may be the same or different from each other, if z is an integer of not less than 2;
z1 is an integer of 0 or 1;
$W_1$ is ⊢$W_{a2}$—$(CH_2)_{a1}$—$W_{b1}$-$Q_1$-⊣;
$W_2$ is ⊢$W_{a4}$-$Q_2$-$W_{a3}$-⊣;

$W_{a1}$ and $W_{a2}$ are each independently —NH—, —C(=O)—, or —CH$_2$—;
$W_{a3}$ and $W_{a4}$ are each independently —NH—, —C(=O)—, —CH$_2$—, —C(=O)NH—, —NHC(=O)—, or triazolylene;
$W_{b1}$ is an amide bond or triazolylene;
L is an amino acid, peptide, or amide bond as a linker connecting $W_{a2}$ and Z;
Z is a single bond, —$W_{a5}$—$(CH_2)_{a2}$—$W_{b2}$—$(CH_2)_{a3}$—$W_{a6}$—, or —$W_{a7}$—$(CH_2)_{a4}$—CR'R''—X''—;
R' is $C_1$-$C_8$alkyl or B—$W_{a8}$-$Q_3$-$W_{c1}$—$(CH_2)_{a5}$—;
R'' is B—$W_{a8}$-$Q_3$-$W_{c1}$—$(CH_2)_{a5}$—;
$Q_1$, and $Q_3$ are each independently —$(CH_2)_{a6}$—$(X_1CH_2CH_2)_{b1}$—$(CH_2)_{a7}$—;
$X_1$ and $X_3$ are each independently —O—, —S—, —NH—, or —CH$_2$—;
X'' is —NHC(=O)—$(CH_2)_{a8}$—$W_{a9}$— or —C(=O)NH—$(CH_2)_{a8}$—$W_{a9}$—;
$W_{a5}$, $W_{a6}$, $W_{a7}$, $W_{a8}$ and $W_{a9}$ are each independently —NH—, —C(=O)—, or —CH$_2$—;
$W_{b2}$ is an amide bond or triazolylene;
$W_{c1}$ is —NHC(=O)— or —C(=O)NH—;
$Q_2$ is a saturated or unsaturated alkylene, which is linear or branched with a carbon number of 1 to 50, satisfying any one of (i) to (iii) below;
(i) at least one —CH$_2$— in the alkylene is substituted with one or more heteroatoms selected from —NH—, —C(=O), —O—, and —S—,
(ii) at least one arylene or heteroarylene is included in the alkylene,
(iii) the alkylene is further substituted with one or more selected from the group consisting of $C_1$-$C_{20}$alkyl, $C_6$-$C_{20}$aryl$C_1$-$C_8$alkyl, —$(CH_2)_{s1}$COOR$_3$, —$(CH_2)_{s1}$COR$_3$, —$(CH_2)_{s2}$CONR$_4$R$_5$, and —$(CH_2)_{s2}$NR$_4$R$_5$;
arylene or heteroarylene of (ii) above may be further substituted with nitro;
$R_3$, $R_4$, and $R_5$ are each independently hydrogen or $C_1$-$C_{15}$ alkyl;
$X_2$ is —O—, —S—, —NH—, or —CH$_2$—;
U1 is bound to B' in the position of asterisk (*) with a linking group selected from the following structures:

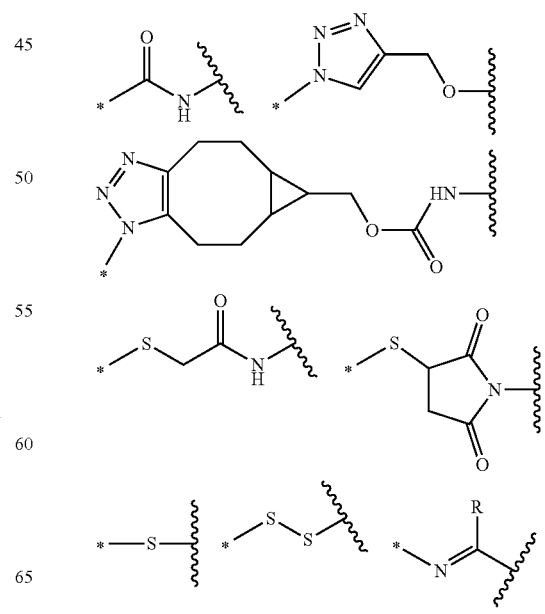

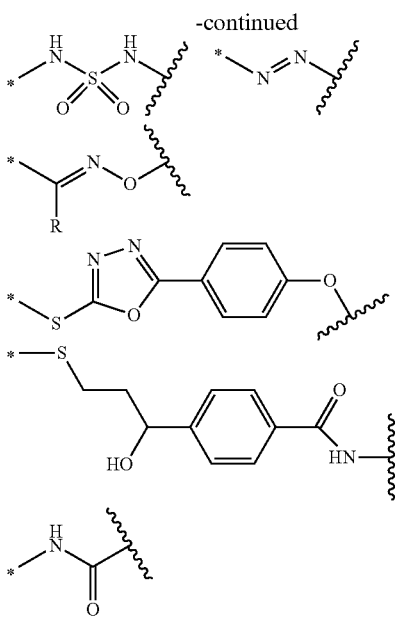

R is C1-C10 alkyl, C6-20 aryl or C2-C20 heteroaryl;

B and B' are each independently a ligand or protein having properties selectively targeting particular organ with a drug, a tissue or a cell, that is, properties binding to a receptor;

a1, a2, a3, a4, a5, a6, a8, b1, p1, p2, p3 and p4 are each independently an integer of 1 to 10;

a7, y, s1, s2 and s4 are each independently an integer of 0 to 10; and $R_1$ and $R_2$ are each independently hydrogen, $C_1$-$C_8$ alkyl or $C_3$-$C_8$ cycloalkyl.

In the compound comprising the self-immolative linker according to the present invention, the hydroxy protecting group is a conventional protecting group which can be used in an organic synthesis, but is not limited thereto, more preferably, methyl ether, methoxymethyl ether (MOM), methylthiomethyl ether (MTM), 2-methoxyethoxymethyl ether (MEM), bis(2-chloroethoxy)methyl ether, tetrahydrophyranyl ether (THP), tetrahydrothiopyranyl ether, 4-methyoxytetrahydropyranyl ether, 4-methoxytetrahydrothiopyranyl ether, tetrahydrofuranyl ether, 1-ethyoxyethyl ether, 1-methyl-1-methoxyethyl ether, 2-(phenylselenyl) ethyl ether, t-butyl ether, allyl ether, benzyl ether, o-nitrobenzyl ether, triphenylmethyl ether, α-naphtyldiphenylmethyl ether, p-methoxyphenyldiphenylmethyl ether, 9-(9-phenyl-10-oxo)anthryl ether, trimethylsilyl ether (TMS), isopropyldimethylsilyl ether, t-butyldimethylsilyl ether (TBDMS), t-butyldiphenyl silyl ether, tribenzylsilyl ether, triisopropylsilyl ether, formate ester, acetate, ester, trichloroacetate ester, phenoxyacetate ester, isobutyrate ester, pivaloate ester, adamantoate ester, benzoate ester, 2,4,6-trimethylbenzoate (Mesitoate) ester, methyl carbonate, 2,2,2-trichloroethyl carbonate, allyl carbonate, p-nitrophenyl carbonate, benzyl carbonate, p-nitrobenzyl carbonate, S-benzyl thiocarbonate, N-phenylcarbamate, nitrate ester, 2,4-dinitrophenylsulfenate ester, etc., but is not limited thereto.

In the compound comprising the self-immolative linker according to the present invention, the L may be an amino acid, a peptide unit, or an amide bond as a linker connecting $W_{a2}$ and Z, wherein the amino acid or the peptide unit can be one or more repeated, and comprises one or two or more functionalities in an amine group, a carboxylic acid group, a thiol group, etc. which is an amino acid residue.

A click chemical reaction is conducted under a mild condition, and allows the protein to be easily handled. The click chemical reaction represents very high reaction specificity. Accordingly, although the protein has another functional group (for example, in a branched residue or in a C-terminal or an N-terminal), the functional group is not affected by the click chemical reaction. For example, the click chemical reaction between an azide group and an acetylene group of the protein may occur during when the other functional group of the protein is not affected by the click chemical reaction. Also, the click chemical reaction is not affected by a kind of accompanied ligands and may specifically occur. In some cases, the ligand may be selected to improve an efficacy of the whole reaction. For example, azide-acetylene click chemistry may produce triazol with high yield.

Azide and acetylene groups are functional groups which are not present in the amino acid sequence of the natural protein. If a conjugation reaction arises by the functional group, any one of the branched residue and N-terminal and C-terminal functional groups is not affected by the click chemical reaction.

In the compound comprising the self-immolative linker according to the present invention, L may comprise one or more units represented by Chemical Formula A or B.

[Chemical Formula A]
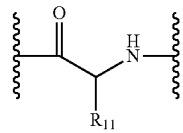

[Chemical Formula B]
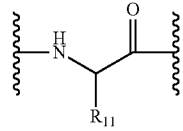

In Chemical Formulas A and B, $R_{11}$ is hydrogen, $C_1$-$C_8$ alkyl, —$(CH_2)_{s3}COOR_{13}$, —$(CH_2)_{s3}COR_{13}$, —$(CH_2)_{s3}CONR_{14}R_{15}$ or —$(CH_2)_{s4}NR_{14}R_{15}$;

$R_{13}$, $R_{14}$ and $R_{15}$ are each independently hydrogen or $C_1$-$C_{15}$ alkyl;

s3 and s4 are each independently an integer of 1 to 10;

$X_3$ is —O—, —S—, —NH—, or —$CH_2$—; and p3 and p4 are each independently an integer of 1 to 10.

In the compound comprising the self-immolative linker according to the present invention, $R_{11}$ may be —$(CH_2)_{s3}$ COOH or —$(CH_2)_{s4}NH_2$, and s3 and s4 are each independently an integer of 0 to 10.

In the compound comprising the self-immolative linker according to the present invention, it is preferable that X is —C(=O)—, and $W_{a1}$ is —NH—.

In the compound comprising the self-immolative linker according to the present invention, Z is a single bond or selected from the following structures.

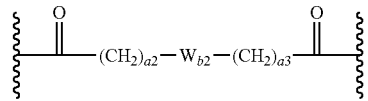

-continued

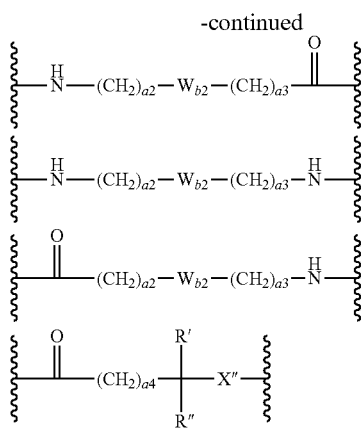

In the structure above, $W_{b2}$ is —C(=O)NH—, —NHC(=O)—,

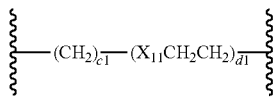

R' is $C_1$-$C_8$alkyl or B—NH—$(CH_2)_{a6}$—$(X_1CH_2CH_2)_{b1}$—NH—C(=O)—$(CH_2)_{a5}$—;

R" is B—NH—$(CH_2)_{a6}$—$(X_1CH_2CH_2)_{b1}$—NH—C(=O)—$(CH_2)_{a5}$—;

X" is —NHC(=O)—$(CH_2)_{a8}$—NH— or —C(=O)NH—$(CH_2)_{a8}$—NH—;

a2, a3, a4, a5, a6, a8 and b1 are each independently an integer of 1 to 10;

$X_1$ is —O—, —S—, —NH—, or —CH$_2$—; and

B is the same as defined in Chemical Formula 1 above.

In the compound comprising the self-immolative linker according to the present invention, Z is a single bond or may be selected from the following structures.

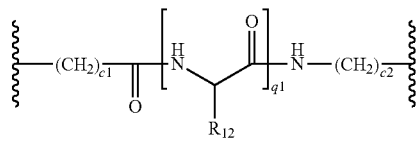

R' is $C_1$-$C_8$alkyl or B—NH—$(CH_2)_{a6}$—$(X_1CH_2CH_2)_{b1}$—NH—C(=O)—$(CH_2)_{a5}$—;

R" is B—NH—$(CH_2)_{a6}$—$(X_1CH_2CH_2)_{b1}$—NH—C(=O)—$(CH_2)_{a5}$—;

a4, a5, a6, a8 and b1 are each independently an integer of 1 to 10;

$X_1$ is —O—, —S—, —NH—, or —CH$_2$—; and

B is the same as defined in Chemical Formula 1 above.

In the compound comprising the self-immolative linker according to the present invention, $Q_2$ may preferably be selected from following formula C to formula

[Chemical Formula C]

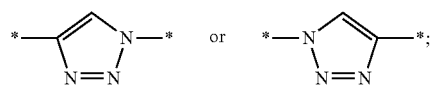

[Chemical Formula D]

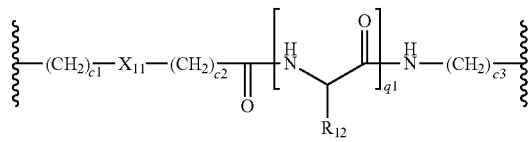

[Chemical Formula E]

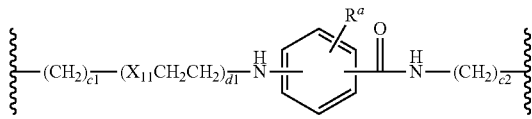

[Chemical Formula F]

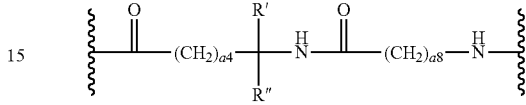

[Chemical Formula G]

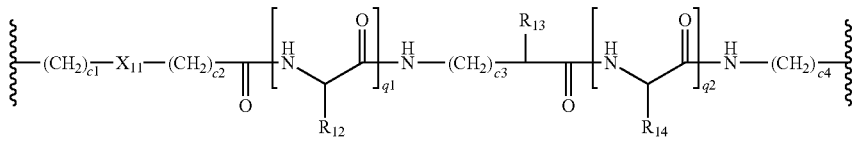

[Chemical Formula H]

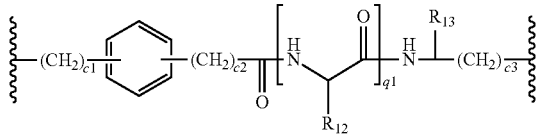

[Chemical Formula I]

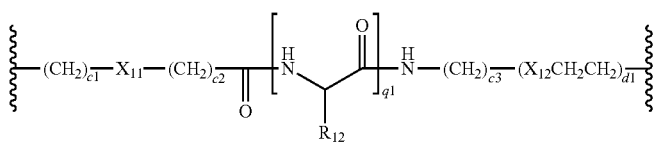

In Chemical Formulas C to I, $X_{11}$ and $X_{12}$ are each independently —O—, —S—, —NH—, or —$CH_2$—;

$R_{12}$ to $R_{14}$ are each independently hydrogen, $C_1$-$C_{20}$alkyl, $C_6$-$C_{20}$aryl$C_1$-$C_8$alkyl, —$(CH_2)_{s1}COOR_3$, —$(CH_2)_{s1}COR_3$, —$(CH_2)_{s2}CONR_4R_5$ or —$(CH_2)_{s2}NR_4R_5$;

$R_3$, $R_4$, and $R_5$ are each independently hydrogen or $C_1$-$C_{15}$ alkyl;

$X_2$ is —O—, —S—, —NH—, or —$CH_2$—;

$R^a$ is hydrogen or nitro;

c1, c2, c3, c4 and d1 are each independently an integer of 1 to 10;

q1 and q2 are each independently an integer of 0 to 5;

s1 and s2 are each independently an integer of 0 to 5;

p1 and p2 are each independently an integer of 1 to 10.

In the compound comprising the self-immolative linker according to the present invention, β-galactoside bound to the self-immolative linker is primarily hydrolyzed by a β-galactosidase enzyme and has a mechanism wherein the active agent is released via a 1,6-elimination reaction (reaction scheme 1).

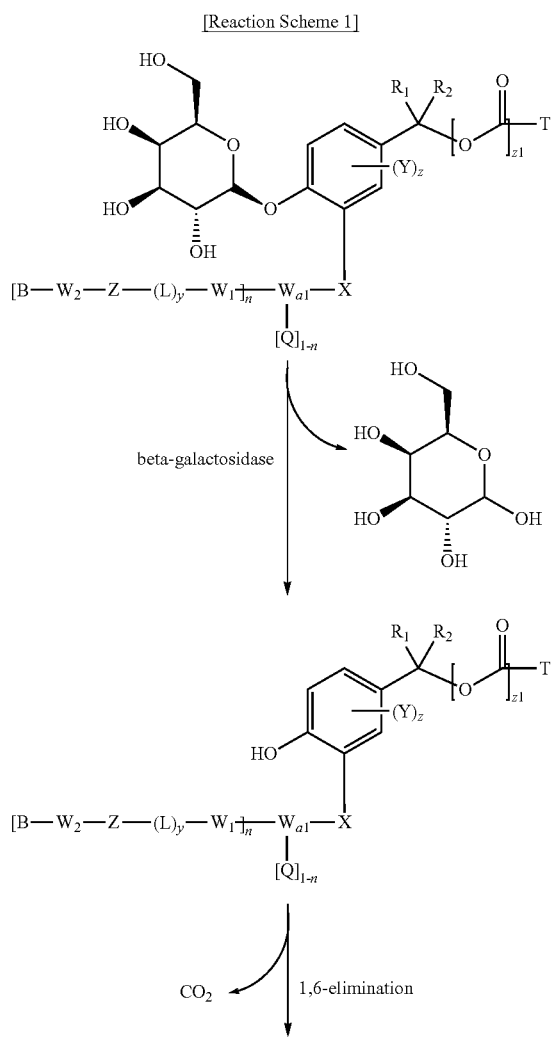

[Reaction Scheme 1]

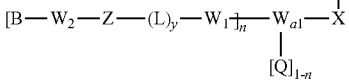

The compound comprising the self-immolative linker to which β-galactoside according to the present invention is bound, is more expediently synthesized than a similar type of self-immolative linker derivative as previously known, and results regarding in vitro effects for the cell-penetration and stability in the plasma, and the cancer cell may be confirmed to be good.

U.S. Pat. No. 8,568,728 and KR 10-2015-037015 elucidate an example for preparing an antibody-drug conjugate to which the self-immolative linker comprising β-glucuronide is introduced. The self-immolative linker comprising β-glucuronide as disclosed in KR 10-2015-037015 was improved in a stability in the plasma of a mouse, compared with the self-immolative linker derivative having a similar structure as disclosed in U.S. Pat. No. 8,568,728, but several problems are involved in the preparation thereof.

As shown in FIG. 1, a process for preparing β-glucuronide is longer than a process for preparing the self-immolative linker comprising β-galactoside intended to be developed by the present invention, and a yield for preparing glucuronyl bromide (methyl 2,3,4-tri-O-acetyl-alpha-D-glucopyranosyluronate bromide, catalog number A8292, 334, 000 won/1 g, www.sigmaaldrich.com) used as an intermediate is also low (50%) (The contents disclosed in Carbohydrate Research 2000, 328, 445-448 show the preparation with lower yield of 38%.).

For β-glucuronide in the preparation process, an acetyl group and a methyl group used to protect an alcohol group and a carboxylic acid group are eliminated under a basic condition. However, under such a condition, the elimination reaction proceeds due to the difference of a reaction speed for two protection groups different from each other, and since side products produced thereby are difficult to be purified and separated, it has a disadvantage that renders yield and purity of the final products to be lower.

Papot group reported study results regarding a β-galactoside derivative which can be hydrolyzed by R-galactosidase. A structure of the self-immolative linker has a structural characteristics to which benzyl alcohol group is introduced to release drugs via a 1,6-elimination reaction (U.S. Pat. No. 9,000,135; Arch Pharm Res Vol 30, No 6, 723-732, 2007; Journal of Medicinal Chemistry, 2009, 52, 537-543; Drug Development and Industrial Pharmacy, 34:789-795, 2008). However, in the case of this substance, it has a disadvantage to have low yield since the reaction speed in the process binding secondary alcohol to the drug is slower than a primary alcohol and involves problems that a secondary alcohol group is synthesized in the form of a stereoisomer containing a chiral carbon and it is difficult to prepare the conjugate with a single substance. In addition, in the preparation process, since a $NO_2$ group is unstable under the condition of the reduction reaction, there are many limitations in the process for preparing the substance and it can produce a toxicity due to a high possibility for the dissociation of the drug when it is metabolized to amine etc., in the body.

Regarding the self-immolative linker comprising β-galactoside intended to be developed by the present invention, the synthesis of galactosyl bromide derivative (2,3,4,6-tetra-O-acetyl-alpha-D-glucopyranosyl bromide catalog number A1750, 872,000 won/100 g, www.sigmaaldrich.com) is quantitatively conducted, and since the same protecting group (for example, acetyl group) for four alcohol groups of β-galactoside is used and a side-reaction which occurs during the preparation of a β-glucuronide derivative using the protecting groups different from each other is completely absent, it has an advantage to have high yield. In particular, it can be applied to a drug (maytansinoids, Cryptophycin series, etc.) which has difficulty in introducing β-glucuronide by using one protecting group, and thus it is advantageous that it can be developed as a linker superior in terms of versatility than β-glucuronide.

In the compound comprising the self-immolative linker according to the present invention, the active agent may be a drug, a toxin, an affinity ligand, a probe for the detection or a combination thereof.

The drugs are selected from the group consisting of erlotinib (TARCEVA; Genentech/OSI Pharm.); bortezomib (VELCADE; MilleniumPharm.); fulvestrant (FASLODEX; AstraZeneca); sutent (SU11248; Pfizer); letrozole (FEMARA; Novartis); imatinib mesylate (GLEEVEC; Novartis); PTK787/ZK 222584 (Novartis); oxaliplatin (Eloxatin; Sanofi); 5-fluorouracil (5-FU); leucovorin; rapamycin (Sirolimus, RAPAMUNE; Wyeth); lapatinib (TYKERB, GSK572016; GlaxoSmithKline); lonafarnib (SCH 66336); sorafenib (BAY43-9006; Bayer Labs.); gefitinib (IRESSA; Astrazeneca); AG1478, AG1571 (SU 5271; Sugen); alkylating agent (for example, thiotepa or CYTOXAN® cyclophosphamide); alkyl sulfonate (for example, busulfan, improsulfan or piposulfan); aziridine (for example, benzodopa, carboquone, meturedopa or uredopa); ethylenimine, methylmelamine, altretamine, triethylenemelamine, triethylenephosphoramide, triethylenethiophosphoramide, trimethylolmelamine; acetogenins (for example, bullatacin or bullatacinone); camptothecin comprising synthetic analogue topotecan; bryostatin; callystatin; CC-1065 (comprising adozelesin, carzelesin or bizelesin synthetic analogues thereof); cryptophycins (for example, cryptophycin 1 or cryptophycin 8); dolastatin; duocarmycin (comprising synthetic analogues, KW-2189 and CB1-TM1); eleutherobin; pancratistatin; sarcodictyin; spongistatin; nitrogen mustard (for example, chlorambucil, chlornaphazine, cholophosphamide, estramustine, ifosfamide, mechlorethamine, mechlorethamine oxide hydrochloride, melphalan, novembichin, phenesterine, prednimustine, trofosfamide or uracil mustard); nitrousurea (for example, carmustine, chlorozotocin, fotemustine, lomustine, nimustine or ranimnustine); antibiotics (for example, as enediyne antibiotics, calicheamycin selected from calicheamycin gammal and calicheamycin omega11 or dynemicin comprising dynemicin A); bisphosphonate (for example, clodronate); esperamicin, neocarzinostatin chromophore or related chromoprotein enediyne antibiotic chromophores, aclacinomysins, actinomycin, antrmycin, azaserine, bleomycins, cactinomycin, carabicin, carninomycin, carzinophilin, chromomycins, dactinomycin, daunorubicin, detorubicin, 6-diazo-5-oxo-L-norleucine, ADRLIMYCIN® doxorubicin (for example, morpholino-doxorubicin, cyanomorpholino-doxorubicin, 2-pyrrolino-doxorubucin, liposomal doxorubicin or deoxydoxorubicin), epirubicin, esorubicin, marcellomycin, mitomycins (for example, mitomycin C, mycophenolic acid, nogalamycin, olivomycins, peplomycin, potfiromycin, puromycin, quelamycin, rodorubicin, streptomigrin, streptozocin, tuberci din, ubenimex, zinostatin or zorubicin); anti-metabolites (for example, 5-fluorouracil, 5-FU); folic acid analogues (for example, denopterin, methotrexate, pteropterin or trimetrexate); purine analogs (for example, fludarabine, 6-mercaptopurine, thiamiprine or thiguanine); pyrimidine analogs (for example, ancitabine, azacitidine, 6-azauridine, carmofur, cytarabine, dideoxyuridine, doxifluridine, enocitabine or floxuridine); androgens (for example, calusterone, dromostanolone propionate, epitiostanol, mepitiostane or testolactone); anti-adrenals (for example, aminoglutethimide, mitotane or trilostane); folic acid replenisher (for example, folinic acid); aceglatone; aldophosphamide glycoside; aminolevulinic acid; eniluracil; amsacrine; bestrabucil; bisantrene; edatraxate; defofamine; demecolcine; diaziquone; elfornithine; elliptinium acetate; epothilone; etoglucid; gallium nitrate; hydroxyurea; lentinan; lonidainine; maytansinoids (for example, maytansine or ansamitocins; trichothecene T-2 toxin, verracurin A, roridin A or anguidine); mitoguazone; mitoxantrone; mopidanmol; nitraerine; pentostatin; phenamet; pirarubicin; losoxantrone; 2-ethylhydrazide; procarbazine; PSK® polysaccharide; razoxane; rhizoxin; sizofiran; spirogermanium; tenuazonic acid; triaziquone; 2,2',2"-trichlorotriethylamine; trichothecenes (in particular, T-2 toxin, verracurin A, rodidin A and anguidine); urethane; vindesine; dacarbazine; mannomustine; mitobronitol; mitolactol; pipobroman; gacytosine; arabinoside, 'Ara-C'); cyclophosphamide; thiotepa; taxoids (for example, TAXOL® paclitaxel (Bristol-Myers Squibb Oncology, Princeton, N.J.), ABRAXANE™ cremophor-free), albumin-engineered nanoparticle formulation of paclitaxel, American Pharmaceutical Partners, Schaumber, Ill.) or TAXOTERE® doxetaxel ((Rhone-Poulenc Rorer, Antony, France))); chloranbucil; gemcitabine; 6-thioguanine; mercaptopurine; platinum analog (for example, cisplatin or carboplatin); vinblastine; platinum; etoposide, ifosfamide; mitoxantrone; vincristine; NAVELBINE® vinorelbine; novantrone; teniposide; edatrexate; daunomycin; aminopterin; xeloda; ibandronate; CPT-11; topoisomerase inhibitor RFS 2000; difluorometlhylornithine, DFMO; retinoid (for example, retinoic acid); capecitabine; and pharmaceutically acceptable salts, solvates, acids or derivatives thereof, but absolutely are not limited to thereto.

Additional drugs comprise the following, but are not limited thereto: (i) for example, anti-hormone agent serving to control or inhibit the hormone function for a tumor, such as anti-estrogen and selective estrogen receptor regulator (SERM), comprising tamoxifen (comprising NOLVADEX® tamoxifen), raloxifene, droroxifene, 4-hydroxytamoxifene, trioxifene, keoxifene, LY117018, onapriston and FAREATON® toremifene; (ii) aromatase inhibitor inhibiting aromatase enzyme, controlling a production of intra-adreno estrogen, for example, 4(5)-imidazole, aminoglutethimide, MEGASE® megestrol acetate, AROMASIN® exemestane, FEMARA® retrozole and ARIMIDEX® anastrozole; (iii) anti-androgen, for example, flutamide, nilutamide, bicalutamide, leuprolide and goserelin; and troxacitabin (1,3-dioxolane nucleoside cytosine analogue); (iv) aromatase inhibitor; (v) protein kinase inhibitor; (vi) lipid kinase inhibitor; (vii) antisense oligonucleotide, in particular, those inhibiting the gene expression in a signaling route associated with an adhesion cell, for example, PKC-alpha, Raf, H-Ras; (viii) ribozyme, for example, a VEGF inhibitor, for example, an ANGIOZYME ribozyme and a HER2 expression inhibitor; (ix) a vaccine, for example, a gene treatment vaccine; ALLOVECTIN® vaccine, LEUVECTIN vaccine and VAXID vaccine; PROLEUKIN® rlL-2; LURTOTECAN® topoisomerase 1 inhibitor; ABARELIX® rmRH; (x) anti-angiogenesis, for example, vebaxizumab (AVASTIN, Genentech); and (xi) pharmaceutically acceptable salts thereof, solvates, acids or derivatives.

Also, the drugs may be cytokine, an immuno-regulatory compound, an anti-cancer agent, an anti-virus agent, an anti-bacteria agent, an anti-fungi agent, a helminthic or a combination thereof.

The cytokine is a small cell-signaling protein molecule secreted by a number of cells, and is a category of a signaling molecule broadly used in the information exchange in cells. This comprises monokine, lympokine, traditional polypeptide hormone, etc. Examples of cytokine comprises the following, but are not limited thereto: a growth hormone (for example, human growth hormone, N-methionyl human growth hormone or bovine growth hormone); parathyroid hormone; thyroxine; insulin; a pro-insulin; relaxin; prorelaxin; a glycoprotein hormone (for example, follicle stimulating hormone (FSH), thyroid stimulating hormone (TSH) or luteinizing hormone (LH)); a hepatic growth factor; a fibroblast growth factor; prolactin; placental lactogen; tumornecrosis factor-α, tumornecrosis factor-β; a mullerian-inhibiting substance; a mouse gonadotropin-associated peptide; inhibin; activin; a vascular endothelial growth factor; integrin, thrombopoietin (TPO); a nerve growth factor (for example, NGF-β); a platelet-growth factor; a transforming growth factor (TGF) (for example, TGF-α or TGF-β); an insulin-like growth factor-I, insulin-like growth factor-II; erythropoietin (EPO); an osteoinductive factor; an interferon (for example, interferon-α, interferon-β or interferon-γ); a colony stimulating factor (CSF) (for example, macrophage-CSF (M-CSF), granulocyte-macrophage-CSF (GM-CSF) or granulocyte-CSF, G-CSF); interleukin (IL) (for example, IL-1, IL-α, IL-2, IL-3, IL-4, IL-5, IL-6, IL-7, IL-8, IL-9, IL-10, IL-11 or IL-12); a tumor necrosis factor (for example, TNF-α or TNF-β); and a polypeptide factor (for example, LIF or kit ligand (KL)). In addition, the term cytokine is derived from the natural source or comprises a recombinant cell culture of basic sequence cytokine and biologically active equivalents of a cytokine.

The immune regulatory compound may be selected from the group consisting of aminocaproic acid, azathioprine, bromocriptine, chloroquine, chlorambucil, cyclosporine, cyclosporine A, danazol, DHEA (dehydroepiandrosterone), dexamethasone, etanercept, hydroxychloroquine, hydrocortisone, infliximab, meloxicam, methotrexate, cyclophosphamide, mycophenylate mofetil, prednisone, sirolimus and tacrolimus. The anti-cancer agent may be selected from the group consisting of methotrexate, taxol, L-asparaginase, mercaptopurine, thioguanine, hydroxyurea, cytarabine, cyclophosphamide, ifosfamide, nitrosourea, cisplatin, carboplatin, mitomycin, dacarbazine, procarbazine, topotecan, nitrogen mustard, cytoxan, etoposide, 5-fluorouracil, BCNU (bis-chloroethylnitrosourea), irinotecan, camptothecin, bleomycin, doxorubicin, idarubicin, daunorubicin, dactinomycin, plicamycin, mitoxantrone, asparaginase, vinblastine, vincristine, vinorelbine, paclitaxel, docetaxel, chlorambucil, melphalan, carmustine, lomustine, busulfan, treosulfan, decarbazine, etoposide, teniposide, topotecan, 9-aminocamptothecin, crisnatol, mitomycin C, trimetrexate, mycophenolic acid, tiazofurin, ribavirin, EICAR (5-ethynyl-1-beta-D-ribofuranosylimidazole-4-carboxamide), hydroxyurea, deferoxamine, floxuridine, doxifluridine, raltitrexed, cytarabine (ara C)), cytosine arabinoside, fludarabine, tamoxifen, raloxifene, megestrol, goserelin, leuprolide acetate, flutamide, bicalutamide, EB1089, CB1093, KH1060, verteporfin, phthalocyanine, photosensitizer Pe4, demethoxy-hypocrellin A, Interferon-α, Interferon-γ, tumor necrosis factor, Gemcitabine, velcade, revamid, thalamid, lovastatin, 1-methyl-4-phenylpyridinium ion, staurosporine, actinomycin D, dactinomycin, bleomycin A, bleomycin B2, peplomycin, epirubicin, pirarubicin, zorubicin, mitoxantrone, verapamil and thapsigargin. The anti-virus agent may be selected from the group consisting of pencicyclovir, valacyclovir, gancicyclovir, foscarnet, rivavirin, idoxuridine, vidarabine, trifluridine, acyclovir, famcicyclovir, amantadine, rimantadine, cidofovir, antisense oligonucleotide, immunoglobulin andinterferon. The anti-bacterial agent may be selected from the group consisting of chloramphenicol, vancomycin, metronidazole, trimethoprin, sulfamethazole, quinupristin, dalfopristin, rifampin, spectinomycin and nitrofurantoin. The anti-fungal agent may be selected from the group consisting of amphotericin B, Candicidin, filipin, hamycin, natamycin, nystatin, rimocidin, Bifonazole, Butoconazole, Clotrimazole, Econazole, Fenticonazole, Isoconazole, Ketoconazole, Luliconazole, Miconazole, Omoconazole, Oxiconazole, Sertaconazole, Sulconazole, Tioconazole, Albaconazole, Fluconazole, Isavuconazole, Itraconazole, Posaconazole, Ravuconazole, Terconazole, Voriconazole, Abafungin, Amorolfin, Butenafine, Naftifine, Terbinafine, Anidulafungin, Caspofungin, Micafungin, benzoic acid, ciclopirox, flucytosine, griseofulvin, haloprogin, tolnaftate, undecylenic acid, crystal violet, balsam of peru, Ciclopirox olamine, Piroctone olamine, Zinc pyrithione and Selenium sulfide. The anthelmintics may be selected from the group consisting of mebendazole, pyrantel pamoate, thiabendazole, diethylcarbamazine, ivermectin, niclosamide, praziquantel, albendazole, rifampin, amphotericin B, melarsoprol, eflornithine, metronidazole, tinidazole and miltefosine.

The toxin may be a small molecule, a peptide or a protein which may induce a disease upon contact with a body tissue or absorption thereby, interacting with toxic substance produced in a living cell or an organism, for example, biological macromolecules such as an enzyme or cell receptors. In addition, a toxin comprises a plant toxin and an animal toxin. Examples of an animal toxin comprise, but are not limited to thereto, diphtheria toxin, botulium toxin, tetanus toxin, dysentery toxin, cholera toxin, tetrodotoxin, brevetoxin, and ciguatoxin. Examples of a plant toxin comprise, but are not limited to thereto, ricin and AM-toxin.

Examples of small molecule toxin comprise, but are not limited to thereto, auristatin, tubulysin, geldanamycin (Kerr et al., 1997, Bioconjugate Chem. 8(6):781-784), maytansinoid (EP 1391213, ACR 2008, 41, 98-107), calicheamycin (US 2009105461, Cancer Res. 1993, 53, 3336-3342), daunomycin, doxorubicin, methotrexate, vindesine, SG2285 (Cancer Res. 2010, 70(17), 6849-6858), dolastatin, dolastatin analog's auristatin (U.S. Pat. No. 563/548,603), cryptophycin, camptothecin, rhizoxin derivative, CC-1065 analogue or derivative, duocarmycin, enediyne antibiotic, esperamicin, epothilone, PBD (pyrrolobenzodiazepine) derivative, α-amanitin and toxoid. The toxin may represent cell toxicity and activity for inhibiting cell growth by tubulin bond, DNA bond, an inhibition of topoisomerase, etc.

The affinity ligand is a molecule which delivers a signal by binding a given site of a target protein, as a molecule capable of forming a complex with a target bio-molecule. This may be a substrate, an inhibitor, a stimulator, a nerve-delivering substance or radio-isotope.

"Detection moiety" or "label" refers to a composition detectable with spectrometry, optical chemistry, biochemistry, immuno-chemistry, radio or chemical means. For example, available label comprises $^{32}$P, 35S, fluorescent dyes, electron-dense reagents, enzymes (for example, those used conventionally in ELISA), biotin-streptavidin, dioxigenin, haptens, and proteins for which antisera or monoclonal antibodies are available, or nucleic acid molecules with a sequence complementary to a target. Detection moiety often produces a measurable signal, for example, a radio, chromogenic or fluorescent signal, which can be used in quantifying an amount of detection moiety bound to a sample. A quantity of the signal is achieved by a direct analysis, for example, with scintillation counting, densitometer, fluid cell analysis, ELISA or wild type or a mass spectrometry of the peptide digested subsequently (one or more peptides can be analyzed). One skilled in this art is familiar with the technology and detection means for a label compound of interest. The technology and method are conventional and are well known in this art.

The probe for the detection means substances (i) providing the detection moiety, (ii) modifying the detectable signal provided by the first probe or the second probe, such as the fluorescent-resonance energy transfer (FRET) resulting from interacting with the first probe and the second probe, (iii) stabilizing the interaction with antigen or ligand or increasing a binding affinity, (iv) affecting electrophoretogram or a cell-penetration action by a physical parameter such as an electric charge and hydrophobicity, or (v) capable of regulating ligand-affinity, antigen-antibody binding or ion-complex formation.

In the compound comprising the self-immolative linker according to the present invention, a ligand of B refers to a molecule of an antibody, hormone, pharmaceutical agent, etc. binding to a receptor. A ligand is a substance selectively targeting drugs to a particular organ, tissue or cell. The ligand specifically binds to a receptor which is over-expressed in the cancer cell, compared with the normal cell, and may be differentiated into ligands of monoclonal antibodies (mAbs) or an antibody fragment, and a low molecular non-antibody. It is preferable that it is selected from the group consisting of peptides, tumor cell-specific peptides, tumor cell-specific aptamers, tumor cell-specific carbohydrates, tumor cell-specific monoclonal or polyclonal antibodies, and antibody fragments, confirmed by the library screen.

Examples of the ligand comprise, but are not limited to thereto, carnitine, inositol, lipoic acid, pyridoxal, ascorbic acid, niacin, pantothenic acid, folic acid, riboflavin, thiamine, biotin, vitamin $B_{12}$, the other water soluble vitamin type of vitamin B, lipid soluble vitamin type (vitamin A,D,E,K), RGD (Arg-Gly-Asp), NGR (Asn-Gly-Arg), transferein, VIP (vasoactive intestinal peptide) receptor, APRPG (Ala-Pro-Arg-Pro-Gly) peptide, TRX-20 (thioredoxin-20), integrin, nucleolin, Aminopeptidase N(CD13), endoglin, vascular epithelial growth factor receptor, low density lipoprotein receptor, transferrin receptor, somatostatin receptor, bombesin, Neuropeptide Y, lutenizing hormone releasing hormone receptor, folic acid receptor, epidermal growth factor receptor, transforming growth factor, fibroblast growth factor receptor, asialoglycoprotein receptor, galectin-3 receptor, E-selectin receptor, hyaluronic acid receptor, Prostate-specific membrane antigen (PSMA), Cholecystokinin A receptor, Cholecystokinin B receptor, Discoidin domain receptor, mucin receptor, Opioid receptor, Plasminogen receptor, Bradykinin receptor, insulin receptor, insulin-like growth factor receptor, angiotensin AT1 receptor, angiotensin AT2 receptor, GM-CSF receptor, Galactosamine receptor, Sigma-2 receptor, Delta-like 3 (DLL-3), Aminopeptidase P, melanotransferrin, leptin, tetanus toxin Tet1, tetanus toxin G23, RVG (Rabies Virus Glycoprotein) peptide, HER2 (human epidermal growth factor receptor 2), GPNMB (glycoprotein non-metastatic b), Ley, CA6, CanAng, SLC44A4 (Solute carrier family 44 member 4), CEACAM5 (Carcinoembryonic antigen-related cell adhesion molecule 5), Nectin-4, Carbonic Anhydrase 9, TNNB2, 5T4, CD30, CD37, CD74, CD70, PMEL17, EphA2 (EphrinA2 receptor), Trop-2, SC-16, Tissue factor, ENPP-3 (AGS-16), SLITRK6 (SLIT and NTRK like family member 6), CD27, Lewis Y antigen, LIV1, GPR161 (G Protein-Coupled Receptor 161), PBR (peripheral-type benzodiazeoine receptor), MERTK (Mer receptor tyrosine kinase) receptor, CD71, LLT1 (Lectin-like transcript 1 or CLED2D), interleukin-22 receptor, sigma 1 receptor, peroxisome proliferator-activated receptor, DLL3, C4.4a, cKIT, EphrinA, CTLA4 (Cytotoxic T-Lymphocyte Associated Protein 4), FGFR2b (fibroblast growth factor receptor 2b), N-acetylcholine receptor, gonadotropin releasing hormone receptor, gastrin-releasing peptide receptor, Bone morphogenetic protein receptor-type 1B (BMPR1B), E16 (LAT1, SLC7A5), STEAP1 (six transmembrane epithelial antigen of prostate), 0772P (CA125, MUC16), MPF (MSLN, mesothelin), Napi3b (SLC34A2), Sema5b (semaphorin 5b), ETBR (Endothelin type B receptor), MSG783 (RNF124), STEAP2 (six transmembrane epithelial antigen of prostate 2), TrpM4 (transient receptor potential cation 5 channel, subfamily M, member 4), CRIPTO (teratocarcinoma-derived growth factor), CD21, CD79b, FcRH2 (IFGP4), HER2 (ErbB2), NCA (CEACM6), MDP (DPEP1), IL20R-alpha (IN20Ra), Brevican (BCAN), EphB2R, ASLG659 (B7h), PSCA (prostate stem cell antigen precursor), GEDA, BAFF-R (BR3), CD22 (BL-CAM), CD79a, CXCR5, HLA-DOB, P2X5, CD72, LY64, FcRH1, IRTA2, TENB2, SSTR2, SSTR5, SSTR1, SSTR3, SSTR4, ITGAV (Integrin, alpha 5), ITGB6 (Integrin, beta 6), MET, MUC1, EGFRvIII, CD33, CD19, IL2RA (interleukin 2 receptor, alpha), AXL, BCMA, CTA (cancer tetis antigens), CD174, CLEC14A, GPR78, CD25, CD32, LGR5 (GPR49), CD133 (Prominin), ASG5, ENPP3 ((Ectonucleotide Pyrophosphatase/Phosphodiesterase 3), PRR4 (Proline-rich protein 4), GCC (guanylate cyclase 2C), Liv-1 (SLC39A6), CD56, CanAg, TIM-1, RG-1, B7-H4, PTK7, CD138, Claudins, Her3 (ErbB3), RON (MST1R), CD20, TNC (Tenascin C), FAP, DKK-1, CD52, CS1 (SLAMF7), Annexin A1, V-CAM, gp100, MART-1, MAGE-1 (Melanoma antigen-encoding gene-1), MAGE-3 (Melanoma-associated antigen 3), BAGE, GAGE-1, MUM-1 (multiple myeloma oncogene i), CDK4, TRP-1 (gp75), TAG-72 (Tumor-Associated Glycoprotein-72), ganglioside GD2, GD3, GM2, GM3, VEP8, VEP9, My1, VIM-D5, D156-22, OX40, RNAK, PD-L1, TNFR1, TNFR2, etc.

In the compound comprising the self-immolative linker according to the present invention, the protein of B above comprises oligopeptide, polypeptide, antibody, fragment of an antigenic polypeptide and artificial antibody (Repebody).

The protein comprises two or more of independently selected natural or non-natural amino acids connected by a covalent bond (for example, peptide bond), and the peptide can comprise 2, 3, 4, 5, 6, 7, 8, 9, 10, 11, 12, 13, 14, 15, 16, 17, 18, 19, 20 or more of natural or non-natural amino acids connected by a peptide bond. The polypeptide comprises the sequence of shorter amino acids (for example, fragment of natural protein or fragment of synthetic polypeptide) as well as an entire length of a protein (for example, pre-processed protein).

The antibody refers to immunoglobulin molecule which recognizes targets, for example, a protein, a polypeptide, a peptide, a carbohydrate, a polynucleotide, a lipid or a combination thereof, and specifically binds to them, via a recognition site of one or more antigens within variable parts of the immunoglobulin molecule. The antibody comprises an intact polyclonal antibody, an intact monoclonal antibody, an antibody fragment (for example, Fab, Fab', F(ab')$_2$, Fd and Fv fragment), a single chain Fv (scFv) mutant, a multispecific antibody, for example, a bispecific antibody produced from two or more of an intact antibody, a chimeric antibody, a humanized antibody, a human antibody, a fusion protein comprising an antigenic determinant portion of an antibody, and a modified immunoglobulin molecule comprising an antigen recognition site, as long as the antibody represents a desired biological activity. The antibody may have any of five classes of the immunoglobulins: IgA, IgD, IgE, IgG, and IgM, or subclasses thereof (isotype) (for example, IgG1, IgG2, IgG3, IgG4, IgA1 and IgA2), based on the identity of constant domains of heavy chains, represented by alpha, delta, epsilon, gamma and mu. Different classes of the immunoglobulin have a subunit structure and a tertiary dimension form which are different and well-known.

The term "antibody fragment" represents a portion of the intact antibody and represents an antigen-determinant variable portion. Examples of the antibody fragment comprise, but are not limited thereto, Fab, Fab', F(ab')$_2$, Fd and Fv fragment, linear antibody, single chain antibody and a multiple-specific antibody formed from antibody fragments.

The term "monoclonal antibody" refers to the same type of individual antibody with very specific recognition and a bond for a single antigenic determinant or epitope. This is in contrast with polyclonal antibodies which comprise different types of antibodies directed conventionally toward different antigenic determinants. The term "monoclonal antibody" also comprises an antibody fragment (for example, Fab, Fab', F(ab')$_2$, Fd, Fv), single chain (scFv) mutant, a fusion protein comprising antibody portions and any other modified immunoglobulin molecule comprising an antibody recognition site, as well as both of intact and entire length of monoclonal antibody. Further, the term "monoclonal antibody" refers to antibodies prepared by hybridoma, phage selection, re-combinant expression and transforming animals with any number of mode, but are not limited thereto.

The term "humanized antibody" refers to a form of a non-human (for example, murine) antibody comprising a specific immunoglobulin chain, a chimeric immunoglobulin or a minimum of non-human (for example, murine) sequence, or a fragment thereof. Conventionally, the humanized antibody is a human immunoglobulin wherein the residues from complementary determinant region (CDR) are replaced with the residues from CDR of non-human species (for example, mouse, rat, rabbit, hamster) with the desired specificity, affinity and function (see Jones et al., 1986, Nature, 321:522-525; Riechmann et al., 1988, Nature, 332: 323-327; Verhoeyen et al., 1988, Science, 239:1534-1536). In some cases, the residues of Fvframework region (FR) of human immunoglobulin are replaced with the corresponding residues within the antibody from non-human species, having the desired specificity, affinity and function. The humanized antibody may be optimized with the improved antibody specificity, affinity and/or function by being further modified with the replacement of further residues in Fv framework portion and/or the replaced non-human residues. Generally, the humanized antibody comprises two or three conventional entire variable domains comprising an entire CDR portion substantially corresponding to non-human immunoglobulin or a substantial entire non-human immunoglobulin, whereas an entire FR portion or a substantial entire FR has the sequence corresponding to the human immunoglobulin. The humanized antibody may comprise the constant portion or domain (Fc) of the immunoglobulin, at least a part of conventional human immunoglobulin. Examples of a method used in producing the humanized antibody are disclosed in U.S. Pat. No. 5,225,539.

The term "human antibody" means an antibody having an amino acid sequence corresponding to the antibody produced by the human or the antibody produced by the human made with any known techniques in this art. Such definition for the human antibody comprises an antibody comprising one or more of the human heavy chain and/or light chain polypeptides, such as the intact or entire length of antibody, fragment thereof, and/or for example, an antibody comprising murine light chain and human heavy chain polypeptide.

The term "chimeric antibody" refers to an antibody wherein the amino acid sequence of the immunoglobulin molecule is derived from two or more species. Conventionally, a variable portion of both a light chain and a heavy chain corresponds to a variable portion of an antibody derived from one species of mammal (for example, mouse, rat, rabbit etc) with the desired specificity, affinity and function, and a constant portion is homologous to the sequence derived from the particular species (conventional human), thereby avoiding inducing the immune response of said species.

The term "epitope" or "antigenic determinant" is interchangeably used herein and refers to an antigen part which can be recognized and specifically bound by the particular antibody. If the antigen is a polypeptide, the epitope can be formed from both of non-contiguous and contiguous amino acids in parallel by tertiary folding of the protein. The epitope formed from the contiguous amino acid is conventionally retained upon a denaturation of the protein, whereas the epitope formed by the tertiary folding is conventionally lost upon the denaturation of the protein. The epitope conventionally comprises three or more, five or more or 8 to 10 or more amino acids in a unique space form.

"Specifically binding" to the epitope or antigen molecule of the antibody means that the antibody responds or binds to the epitope or antigen molecule, more frequently, rapidly, for a longer period, with higher affinity or any combination thereof than an alternative substance comprising the non-relevant protein. In a particular embodiment, "specifically binding" means that the antibody binds to the protein with $K_D$ of not more than about 1.0 mM, more conventionally less than about 1 µM. In a particular embodiment, "specifically binding" means that the antibody binds to the protein with $K_D$ of not more than at least about 0.1M, alternatively not more than at least about 0.01 µM. Due to the sequence identity between the same type of proteins in different chemistry species, specific binding may comprise that the antibody recognizes particular proteins with more than one species. It would be understood that an antibody or a binding residue which specifically binds to the first target may or may not specifically bind to the second target. As such, "specific binding" does not need absolutely exclusive binding, that is, the binding to a single target (although it may be comprised). Generally, not necessarily, referring to the binding means specific binding.

Antibody comprising a monoclonal antibody and a fragment/derivative thereof may be obtained by using a method known in this art (see McCafferty et al., Nature 348:552-554 (1990); Clackson et al., Nature 352:624-628; Marks et al., J. Mol. Biol. 222:581-597 (1991); Marks et al., Bio/Technology 10:779-783 (1992); Waterhouse et al., Nucleic. Acids Res. 21:2265-2266 (1993); Morimoto et al., Journal of Biochemical and Biophysical Methods 24:107-117 (1992);

Brennan et al., Science 229:81(1985); Carter et al., Bio/Technology 10:163-167 (1992); Kohler et al., Nature 256: 495 (1975); U.S. Pat. No. 4,816,567); Kilpatrick et al., Hybridoma 16(4):381-389 (1997); Wring et al., J. Pharm. Biomed. Anal. 19(5):695-707 (1999); Bynum et al., Hybridoma 18(5):407-411 (1999), Jakobovits et al., Proc. Natl. Acad. Sci. USA, 90:2551 (1993); Jakobovits et al., Nature, 362:255-258 (1993); Bruggemann et al., Year in Immuno. 7:33 (1993); Barbas et al., Proc. Nat. Acad. Sci. USA 91:3809-3813 (1994); Schier et al., Gene 169:147-155 (1995); Yelton et al., J. Immunol. 155:1994-2004 (1995); Jackson et. al., J. Immunol. 154(7):3310-9 (1995); Hawkins et al., J. Mol. Biol. 226:889-896 (1992), U.S. Pat. Nos. 5,514,548, 5,545,806, 5,569,825, 5,591,669, 5,545,807; WO 97/17852, all of which are incorporated herein in its entirety).

It is preferable that the antibody is selected from the group consisting of the following, but is not limited thereto: Muromonab-CD3 Abciximab, Rituximab, Daclizumab, Palivizumab, Infliximab, Trastuzumab (also referred to as herceptin), Etanercept, Basiliximab, Gemtuzumab ozogamicin, Alemtuzumab, Ibritumomab tiuxetan, Adalimumab, Alefacept, Omalizumab, Efalizumab, Tositumomob-1[131], Cetuximab, Bevacizumab, Natalizumab, Ranibizumab, Panitumumab, Eculizumab, Rilonacept, Certolizumab pegol, Romiplostim, AMG-531, CNTO-148, CNTO-1275, ABT-874, LEA-29Y, Belimumab, TACI-Ig, Second generation anti-CD20, ACZ-885, Tocilizumab, Atlizumab, Mepolizumab, Pertuzumab, CD20 (Humax CD20), Tremelimumab (CP-675 206), Ticilimumab, MDX-010, IDEC-114, Inotuzumab ozogamycin, HuMax EGFR, Aflibercept, VEGF Trap-Eye, HuMax-CD4, Ala-Ala, ChAglyCD3, TRX4, Catumaxomab, IGN101, MT-201, Pregovomab, CH-14.18, WX-G250, AMG-162, AAB-001, Motavizumab, MEDI-524, efumgumab, Aurograb®, Raxibacumab, Third generation anti-CD20, LY2469298, and Veltuzumab.

The artificial antibody (Repebody) is polypeptide which is optimized with the concensus design to fuse N-terminal of an internal line having LRR protein structure based on a similarity of the VLR structure and may comprise all fused LPR family of proteins with water soluble expression and biological properties improved by the method for all proteins belonging to LPR family with a repetitive module.

If the protein is a monoclonal antibody, one or more light chain of a monoclonal antibody, one or more heavy chains of a monoclonal antibody or both of them may comprise amino acid sites having an amino acid motif which can be recognized by isoprenoid transferase.

One skilled in this art may immediately select the protein (for example, a target cell of a subject), which is selectively bound to the target of interest. The present invention is not limited to the proteins exemplified above, but comprises an antibody or a fragment of the antigen specifically binding to the target of interest.

In the compound comprising the self-immolative linker according to the present invention, it is more preferable that the protein is an antibody or an artificial antibody (Repebody).

The compound comprising the self-immolative linker according to the present invention may be more preferably selected from the following structures.

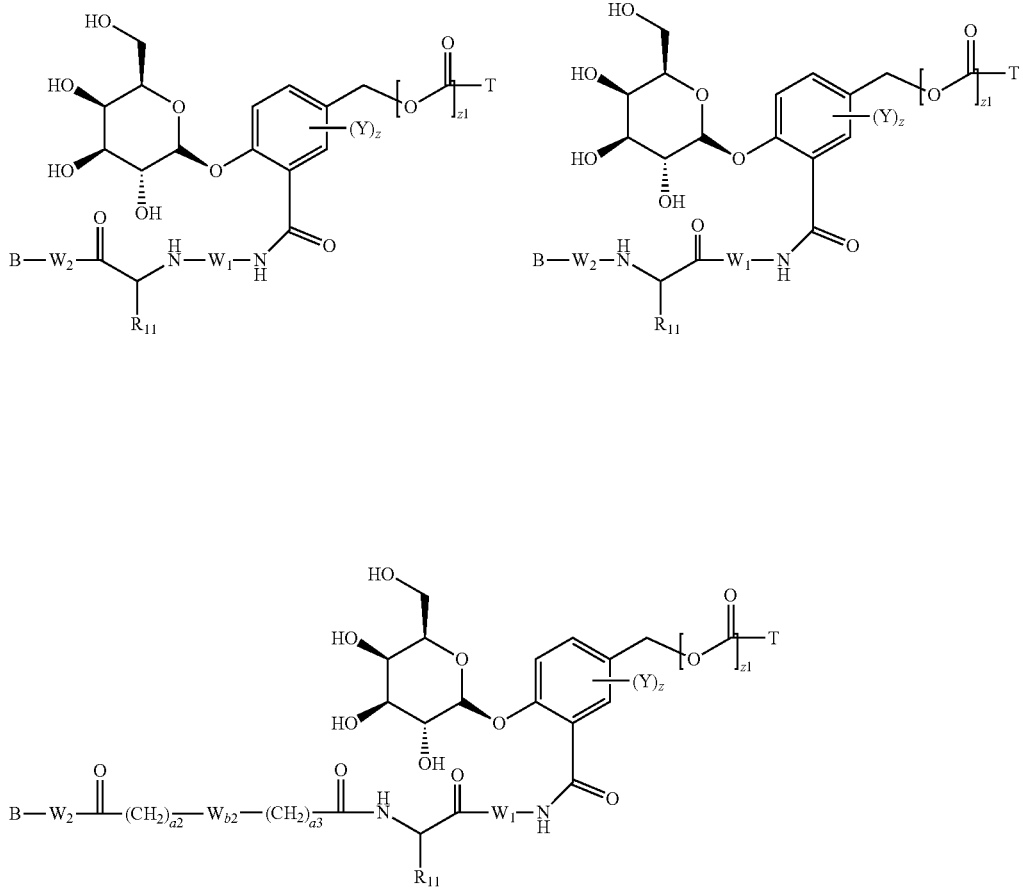

-continued
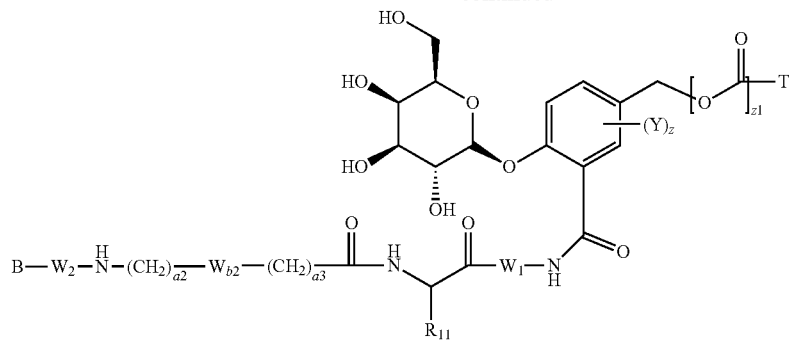
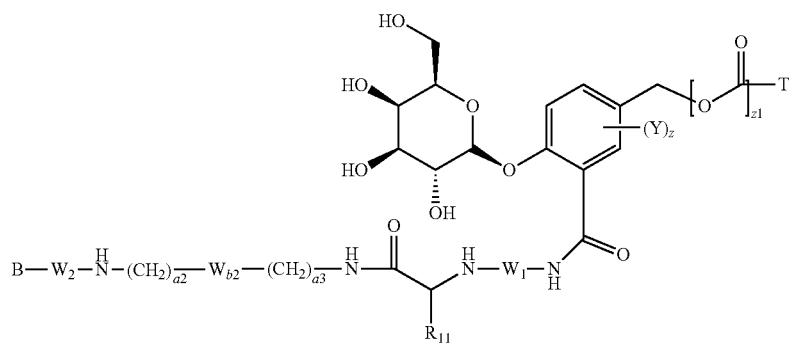
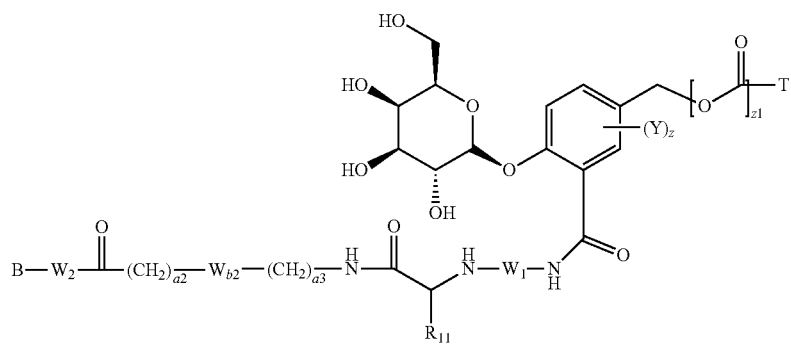
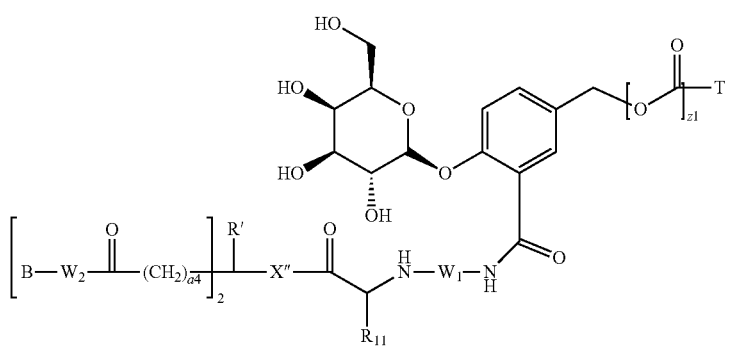

-continued
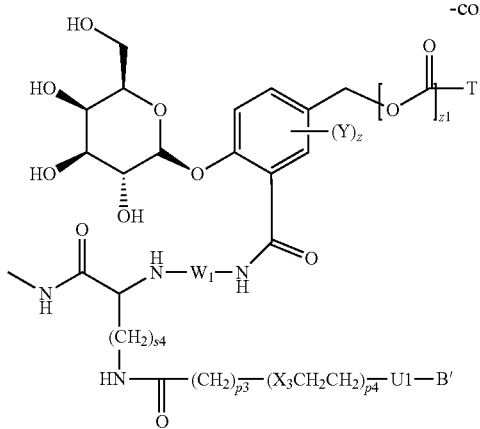
in the structures,
Y is hydrogen, haloC$_1$-C$_8$alkyl, halogen, cyano or nitro;
z is an integer of 1 to 3, and Y may be the same or different from each other, if z is an integer of not less than 2;
z1 is an integer of 0 or 1;
W$_1$ is selected from the following structures:
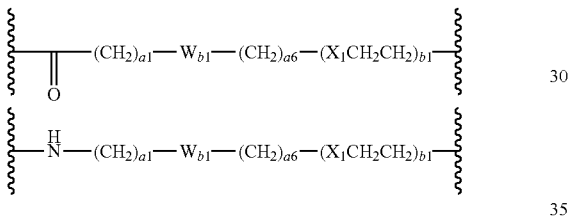
W$_2$ is selected from the following structures:
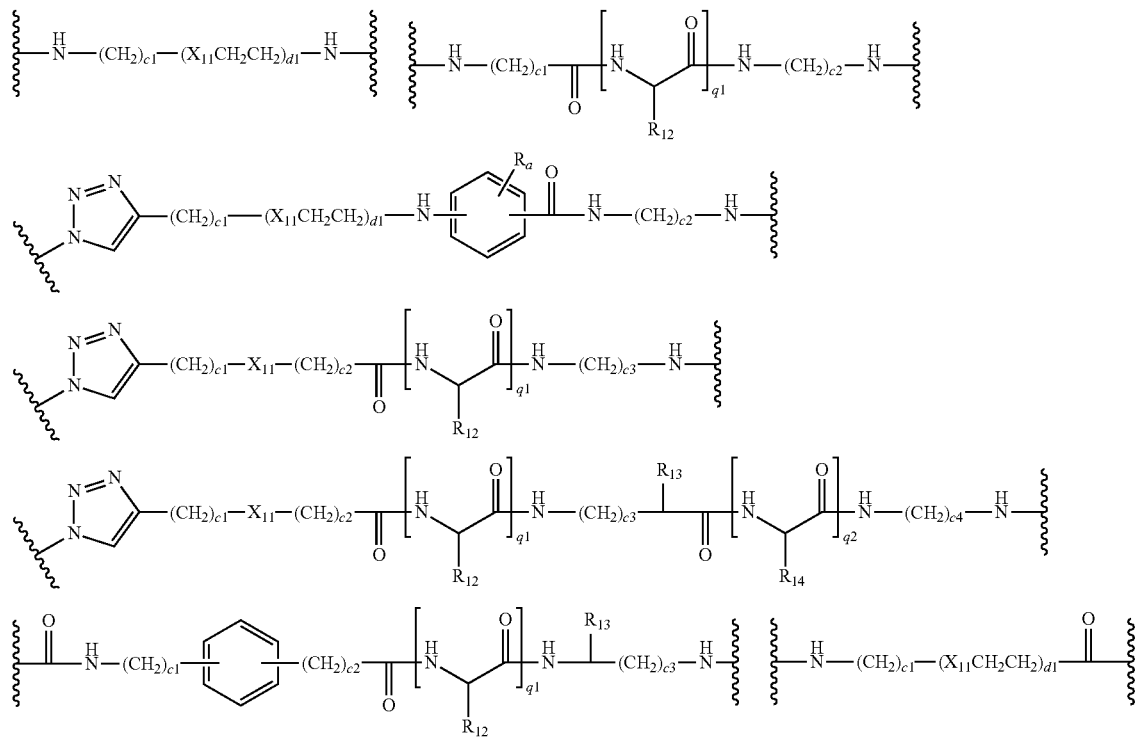

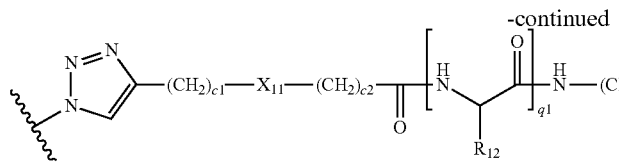

$X_1$, $X_{11}$ and $X_{12}$ are each independently —O—, —S—, —NH—, or —CH$_2$—;

$W_{b1}$ and $W_{b2}$ are each independently —C(=O)NH—, —NHC(=O)—,

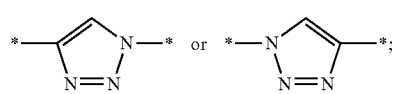

$R_{11}$ is hydrogen, $C_1$-$C_8$alkyl, —(CH$_2$)$_{s3}$COOR$_{13}$, (CH$_2$)$_{s3}$COR$_{13}$, —(CH$_2$)$_{s3}$CONR$_{14}$R$_{15}$ or —(CH$_2$)$_{s4}$NR$_{14}$R$_{15}$, R$_{13}$, R$_{14}$ and R$_{15}$ are each independently hydrogen or $C_1$-$C_{15}$ alkyl;

$X_3$ is —O—, —S—, —NH—, or —CH$_2$—;

$R_{12}$ to $R_{14}$ are each independently hydrogen, $C_1$-$C_{20}$alkyl, $C_6$-$C_{20}$arylC$_1$-$C_8$alkyl, —(CH$_2$)$_{s1}$COOR$_3$, —(CH$_2$)$_{s1}$COR$_3$, —(CH$_2$)$_{s2}$CONR$_4$R$_5$ or —(CH$_2$)$_{s2}$NR$_4$R$_5$;

$R_3$, $R_4$, and $R_5$ are each independently hydrogen or $C_1$-$C_{15}$ alkyl;

$X_2$ is —O—, —S—, —NH—, or —CH$_2$—;

$R^a$ is hydrogen or nitro;

R' is $C_1$-$C_8$alkyl or B—NH—(CH$_2$)$_{a6}$—(X$_1$CH$_2$CH$_2$)$_{b1}$—NH—C(=O)—(CH$_2$)$_{a5}$—;

X" is —NHC(=O)—(CH$_2$)$_{a8}$—NH— or —C(=O)NH—(CH$_2$)$_{a8}$—NH—;

a1, a2, a3, a4, a5, a6, a8, b1, c1, c2, c3, c4, d1, p1, p2, p3 and p4 are each independently an integer of 1 to 10;

q1 and q2 are each independently an integer of 0 to 5;

s1, s2, s3 and s4 are each independently an integer of 0 to 5;

B'—U1— is

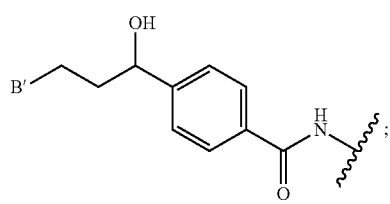

B' is an antibody;

B is a ligand selected from the following structures:

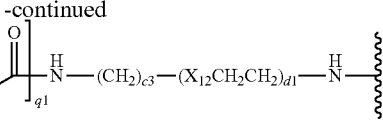

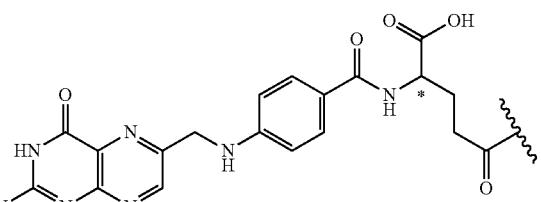

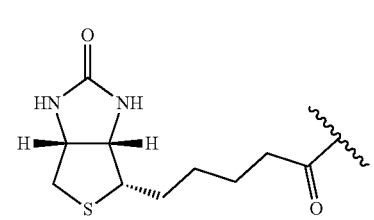

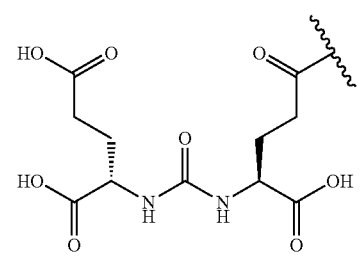

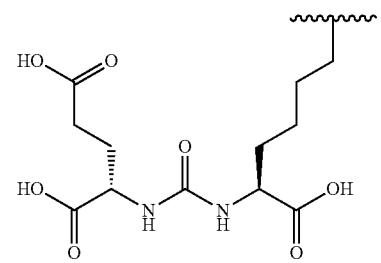

T is a drug selected from the following structures:

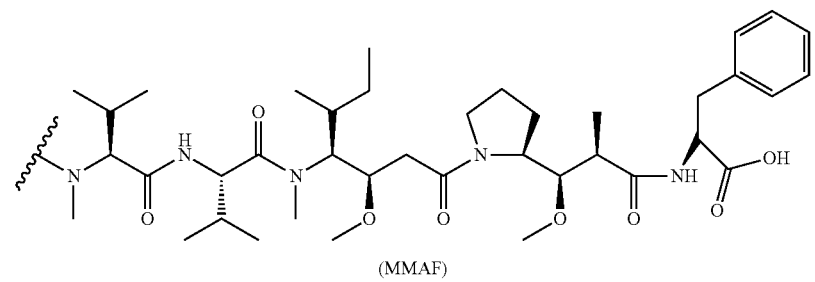

(MMAF)

-continued
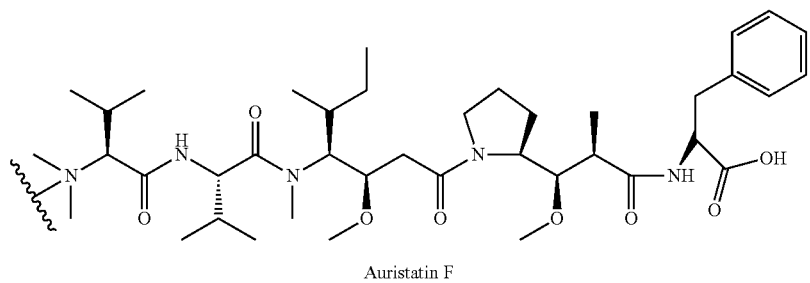
Auristatin F
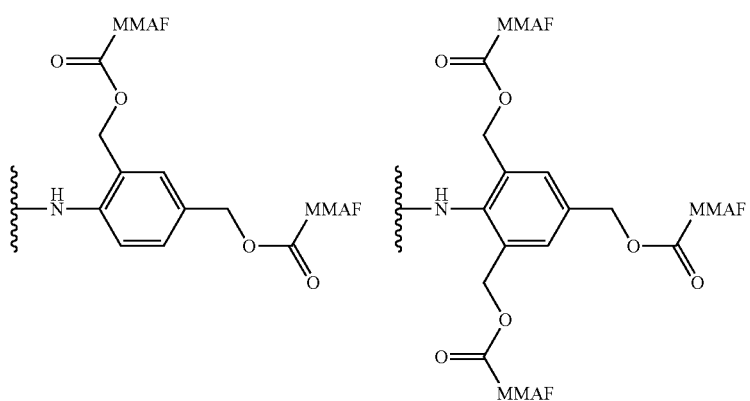
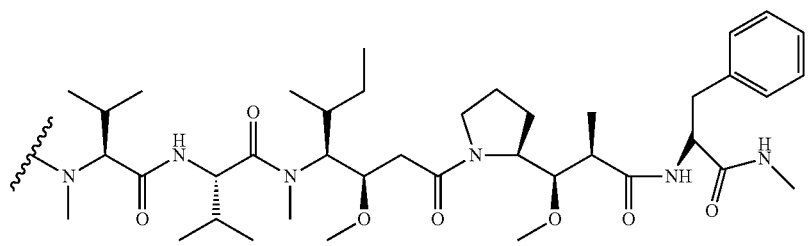
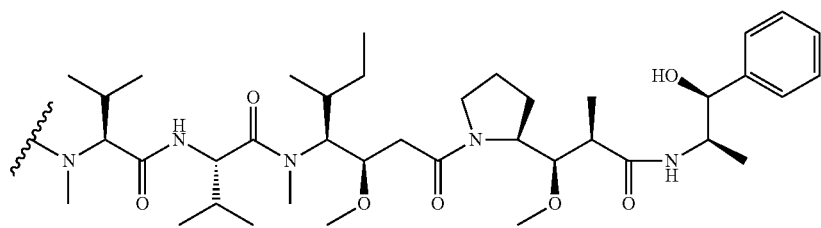
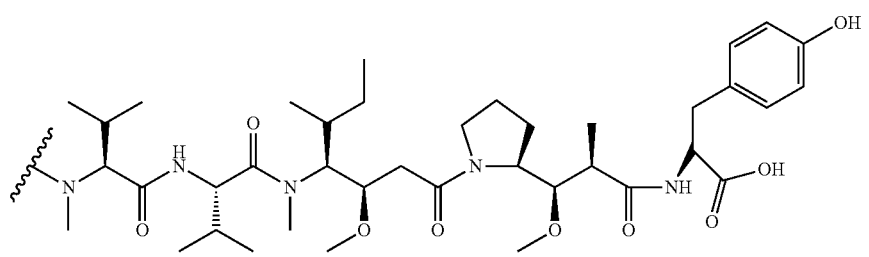

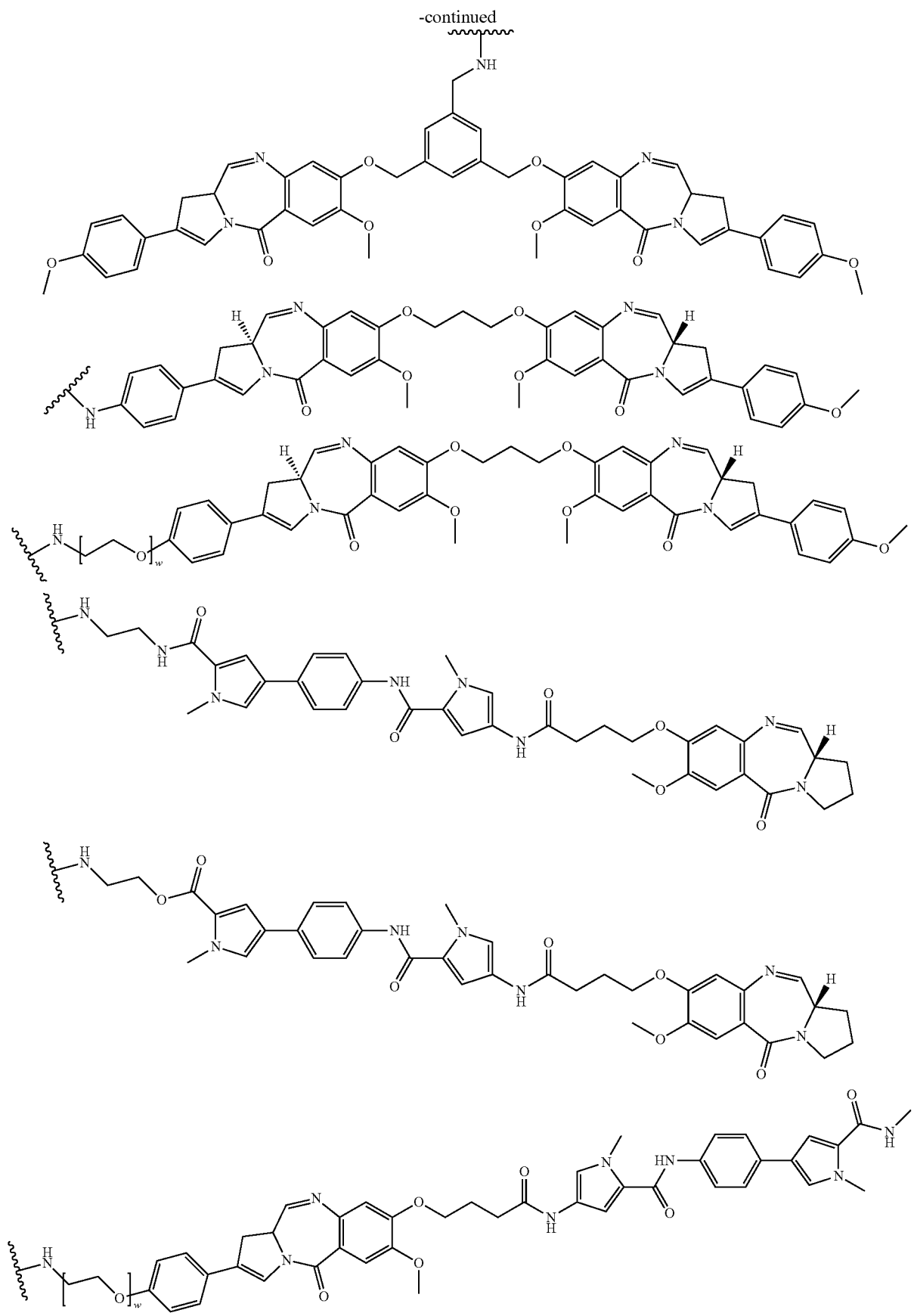

w is an integer of 1 to 10.

In the compound comprising the self-immolative linker according to the present invention, $W_1$ may be selected from the following structures.

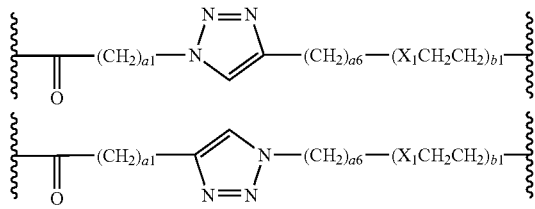

In the structures, $X_1$ is —O—, —S—, —NH—, or —CH$_2$—, more preferably —O—; a1, a6 and b1 are each independently an integer of 1 to 10.

In the compound comprising the self-immolative linker according to the present invention, $W_2$ may be selected from the following structure.

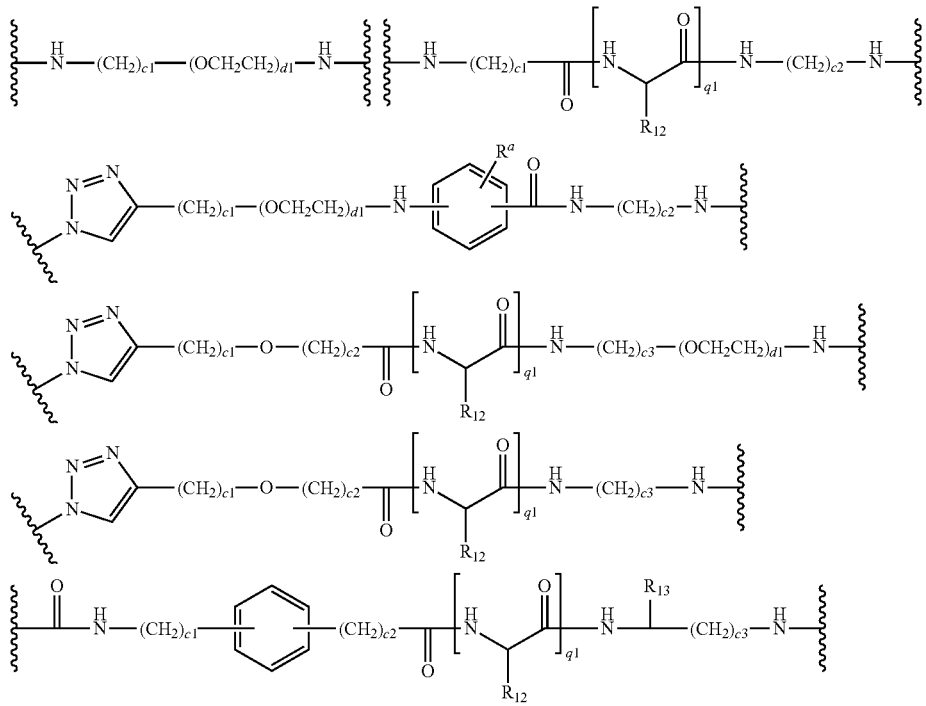

In the structures, $R_{12}$ to $R_{14}$ are each independently $C_6$-$C_{20}$aryl$C_1$-$C_8$alkyl, —(CH$_2$)$_{s1}$COOH, —(CH$_2$)$_{s2}$NH$_2$ or —(CH$_2$)$_{s1}$COR$_3$; $R_3$ is $C_1$-$C_8$alkoxy; $R^a$ is hydrogen or nitro; c1, c2, c3, c4 and d1 are each independently an integer of 1 to 10; s1 and s2 are each independently an integer of 0 to 5; q1 and q2 are each independently an integer of 1 to 5.

In the compound comprising the self-immolative linker of Chemical Formula 1 according to the present invention, if B is a protein and T is an active agent, the compound may be used to treat a subject by delivering the active agent to a target cell of the subject (for example, the subject requiring the active agent) with a method for preparing a composition known to one skilled in this art.

The composition is prepared in an injectable form as a liquid solution or a suspension. A solid form suitable for an injection may be also prepared with a polypeptide as an emulsion or as being capsulated in liposome. The compound comprising the self-immolative linker may be combined with a pharmaceutically acceptable carrier, comprising any carrier which does not induce the production of the antibody harmful to the subject receiving the carrier. A suitable carrier comprises a large macromolecule which is slowly metabolized, for example, a protein, a polysaccharide, a polylactic acid, a polyglycolic acid, a polymeric an amino acid, amino acid copolymer, a lipid aggregate etc. Such a carrier is well known to one skilled in this art.

The composition may also contain a diluent, for example, water, brine, glycerol, or ethanol. An auxiliary substance, for example, a wetting agent or an emulsifying agent, a pH buffering substance etc. may be also present. The protein may be formulated into a vaccine as a neutral or basic form. The composition may be parenterally administered by an injection; and the injection may be a subcutaneous or intra-muscular administration. An additional formulation is suitable for the other administration form, such as, for example, by a suppository or oral form. The oral composition may be administered as a solution, a suspension, a tablet, a pill, a capsule or a slow-released formulation.

The composition is administered in the mode compatible with a dose form. The composition comprises a compound comprising a therapeutically effective amount of the self-immolative linker. The therapeutically effective amount means the amount effective in the treatment or prevention of a disease or disorder, with the composition which is administered in a single dose or multiple dose schedule. The administration dose is varied depending on the subject, the health of the subject to be treated and the body state, the desired degree of protection and the other related factors. A precise amount of active ingredients required depends on a judgment of a physician.

For example, a compound comprising a therapeutical amount of the self-immolative linker or the composition comprising the same may treat cancer or a tumor by administering the compound to a patient suffering with cancer or a tumor.

The compound comprising a therapeutic effective amount of the self-immolative linker or the composition comprising the same may treat or prevent the infection caused by a pathogen (for example, a virus, bacteria, fungi, or a parasite) by administering it to the patient. Such a method comprises a step of administering a therapeutic or preventive amount of the compound comprising the self-immolative linker to the mammal in an amount sufficient to treat the disease or disorder, under the condition that the disease or disorder is treated or prevented.

The compound comprising the self-immolative linker according to the present invention or the composition comprising the same may be administered in the form of a pharmaceutically acceptable salt or solvate thereof. In some embodiments, the compound may be administered with a pharmaceutically acceptable carrier, pharmaceutically acceptable excipient and/or a pharmaceutically acceptable additive. A pharmaceutically effective amount and pharmaceutically acceptable salt or solvate, excipients and a type of additive may be measured by a standard method (see Remington's Pharmaceutical Sciences, Mack Publishing Co., Easton, Pa., 18th edition, 1990).

The term "therapeutic effective amount" used herein regarding the cancer or tumor means an amount which can reduce the number of cancer cells; reduce the size of the cancer cells; inhibit or reduce the penetration of the cancer cells into the peripheral system; inhibit or reduce the expansion of the cancer cells into the other system; inhibit the growth of the cancer cell; or ameliorate one or more symptoms related with the cancer. In the treatment of the cancer, the efficacy of drug may be assayed by a tumor to tumor proceeding (TTP) and/or a response (reaction) speed (RR).

The term "therapeutic effective amount" regarding the infection by the pathogen means an amount to prevent, treat or reduce a symptom related with the infection.

The term "pharmaceutically acceptable salt" comprises an organic salt and inorganic salt. Such examples comprise, but not limited to thereto, hydrochloride, hydrobromide, hydroiodide, sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantonate, bitartrate, ascorbate, succinate, maleate, gentisinate, fumarate, gluconate, glucoronate, saccharate, formate, benzoate, glutamate, methane sulfonate, ethane sulfonate, benzen sulfonate, p-toluene sulfonate and pamoate (that is, 1,1'-methylenebis-(2-hydroxy-3-naphthoate)). A pharmaceutically acceptable salt may comprise another molecule (for example, acetate ion, succinate ion and the other counter ion). This may comprise one or more charged atom. This also may comprise one or more counter ion.

An exemplified solvate which can be used in a pharmaceutically acceptable solvate of the compound comprising the self-immolative linker according to the present invention comprises, but not limited to thereto, water, isopropanol, ethanol, methanol, DMSO, ethylacetate, acetic acid and ethanol amine.

In addition, the present invention provides a compound represented by Chemical Formula 2 below, as an intermediate for preparing a compound of Chemical Formula 1:

[Chemical Formula 2]

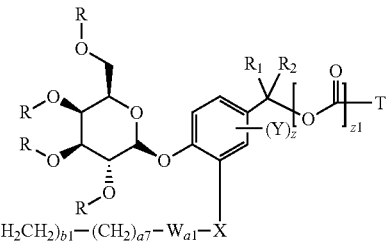

$FG-U-(CH_2)_{a6}-(X_1CH_2CH_2)_{b1}-(CH_2)_{a7}-W_{a1}-X$ in Chemical Formula 2, R is hydrogen or a hydroxy protecting group;

X is —C(=O)—, —NH—, —O—, —CH$_2$— or —S—;

$W_{a1}$ is —NH—, —CH$_2$— or —C(=O)—;

T is an active agent;

Y is hydrogen, haloC$_1$-C$_8$alkyl, halogen, cyano or nitro;

U is a single bond or

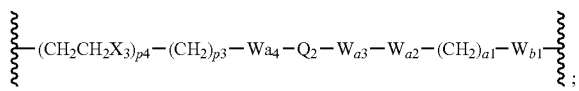

$W_{a2}$ is —NH—, —C(=O)—, or —CH$_2$—;

$W_{a3}$ and $W_{a4}$ are each independently —NH—, —C(=O)—, —CH$_2$—, —C(=O)NH—, —NHC(=O)—, or triazolylene;

Q$_2$ is

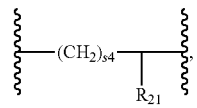

$R_{21}$ is C$_1$-C$_{20}$alkyl, C$_6$-C$_{20}$arylC$_1$-C$_8$alkyl, —(CH$_2$)$_{s1}$COOR$_3$, —(CH$_2$)$_{s1}$COR$_3$, —(CH$_2$)$_{s2}$CONR$_4$R$_5$ or —(CH$_2$)$_{s2}$NR$_4$R$_5$;

R$_3$, R$_4$, and R$_5$ are each independently hydrogen or C$_1$-C$_{15}$ alkyl;

s1 and s2 are each independently an integer of 0 to 10;

$W_{b1}$ is —C(=O)NH—, —NHC(=O)—,

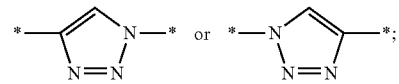

a1 is each independently an integer of 1 to 10;

s4 is an integer of 0 to 10;

p3 and p4 are each independently an integer of 1 to 10;

FG is —NH$_2$, —C≡CH, C$_4$-C$_{10}$cycloalkynyl, —N$_3$, —COOH, —SO$_3$H, —OH, —NHOH, —NHNH$_2$, —SH, haloacetamide (—NHC(O)CH$_2$-hal, wherein hal is halogen), maleimide

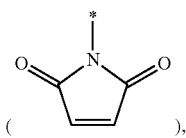

halogen, tosylate (TsO⁻), aldehyde (—COH), ketone (—COR, wherein R is C1-C10alkyl, C6-C20aryl, C2-C20 heteroaryl), diene,

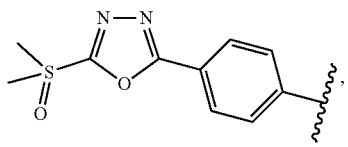

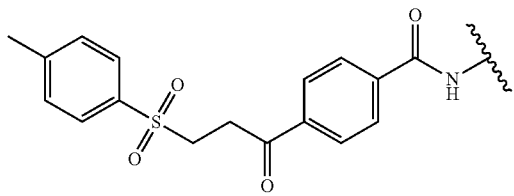

or —OP(=O) (OH)$_2$;

$X_1$ and $X_3$ are each independently —O—, —S—, —NH—, or —CH$_2$—;

a6 and b1 are each independently an integer of 1 to 10;

a7 is an integer of 0 to 10;

z is an integer of 1 to 3, and Y may be the same or different from each other, if z is an integer of not less than 2;

z1 is an integer of 0 or 1;

$R_1$ and $R_2$ are each independently hydrogen, $C_1$-$C_8$alkyl or $C_3$-$C_8$cycloalkyl.

In one example of the present invention, the compound of Chemical Formula 2 above can be represented by the following Chemical Formula 3.

[Chemical Formula 3]

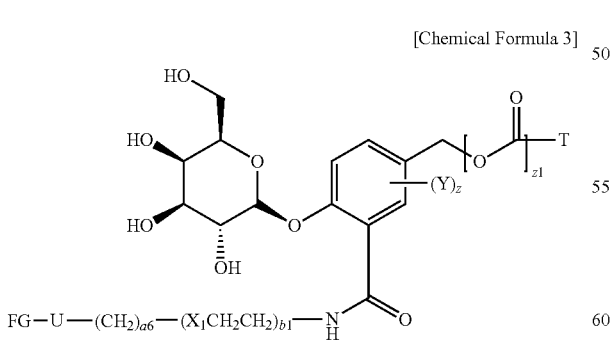

in Chemical Formula 3,

Y is hydrogen, haloC$_1$-C$_8$alkyl, halogen, cyano or nitro;

z is an integer of 1 to 3, and Y may be the same or different from each other, if z is an integer of not less than 2;

z1 is an integer of 0 or 1;

U is a single bond or

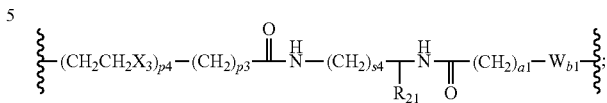

$R_{21}$ is $C_1$-$C_{20}$alkyl, $C_6$-$C_{20}$aryl$C_1$-$C_8$alkyl, —(CH$_2$)$_{s1}$COOR$_3$, —(CH$_2$)$_{s1}$COR$_3$, —(CH$_2$)$_{s2}$CONR$_4$R$_5$ or —(CH$_2$)$_{s2}$NR$_4$R$_5$;

$R_3$, $R_4$, and $R_5$ are each independently hydrogen or $C_1$-$C_{15}$ alkyl;

s1 and s2 are each independently an integer of 0 to 10;

$W_{b1}$ is —C(=O)NH—, —NHC(=O)—,

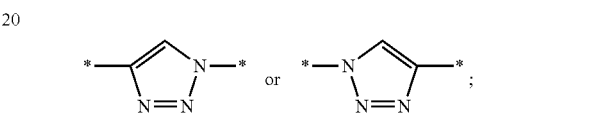

a1 is each independently an integer of 1 to 10;

s4 is an integer of 0 to 10;

p3 and p4 are each independently an integer of 1 to 10;

FG is —NH$_2$, —C≡CH, C$_4$-C$_{10}$cycloalkynyl, —N$_3$, —COOH, —SO$_3$H, —OH, —NHOH, —NHNH$_2$, —SH, haloacetamide (—NHC(O)CH$_2$-hal, wherein hal is halogen), maleimide

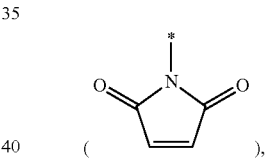

halogen, tosylate (TsO⁻), aldehyde (—COH), ketone (—COR, wherein R is C$_1$-C$_{10}$alkyl, C$_6$-C$_{20}$aryl, C$_2$-C$_{20}$ heteroaryl), diene,

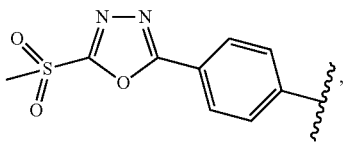

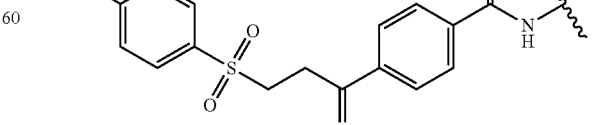

or —OP(=O)(OH)$_2$;

$X_1$ and $X_3$ are each independently —O—, —S—, —NH—, or —CH$_2$—;
a6 and b1 are each independently an integer of 1 to 10;
T is a drug selected from the following structures: and
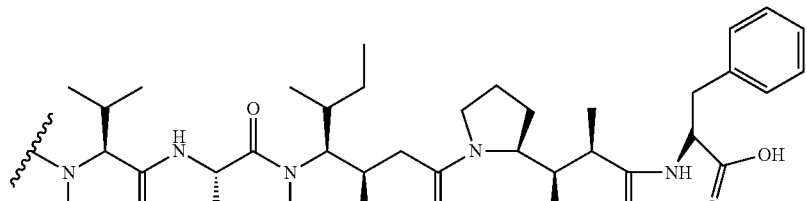
(MMAF)
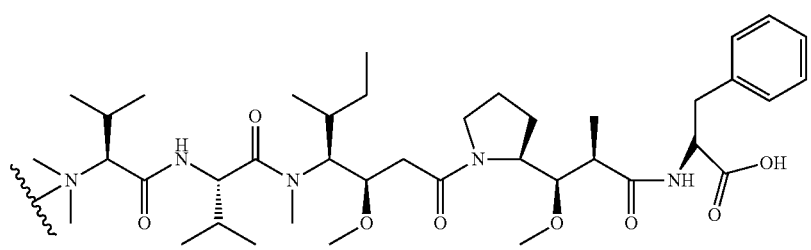
Auristatin F
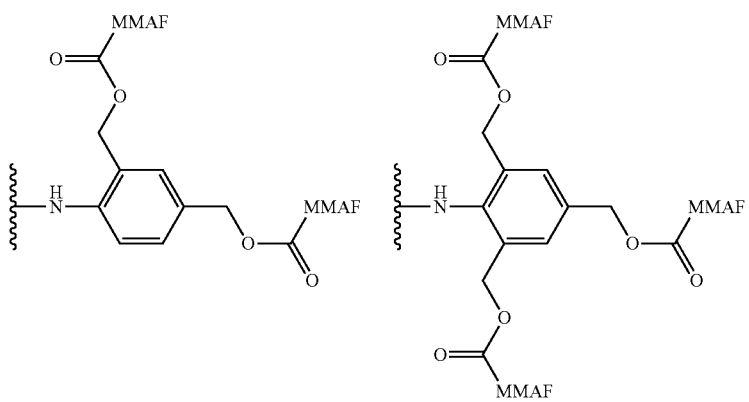
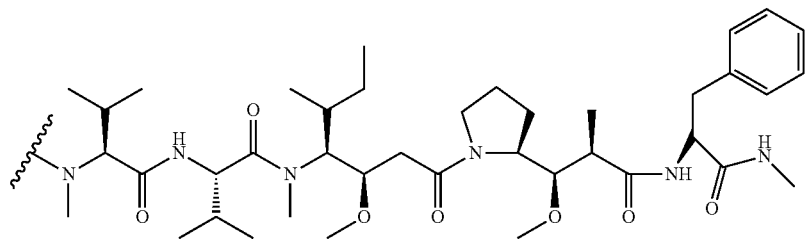
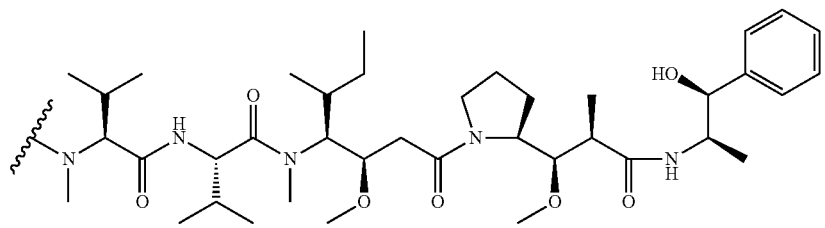

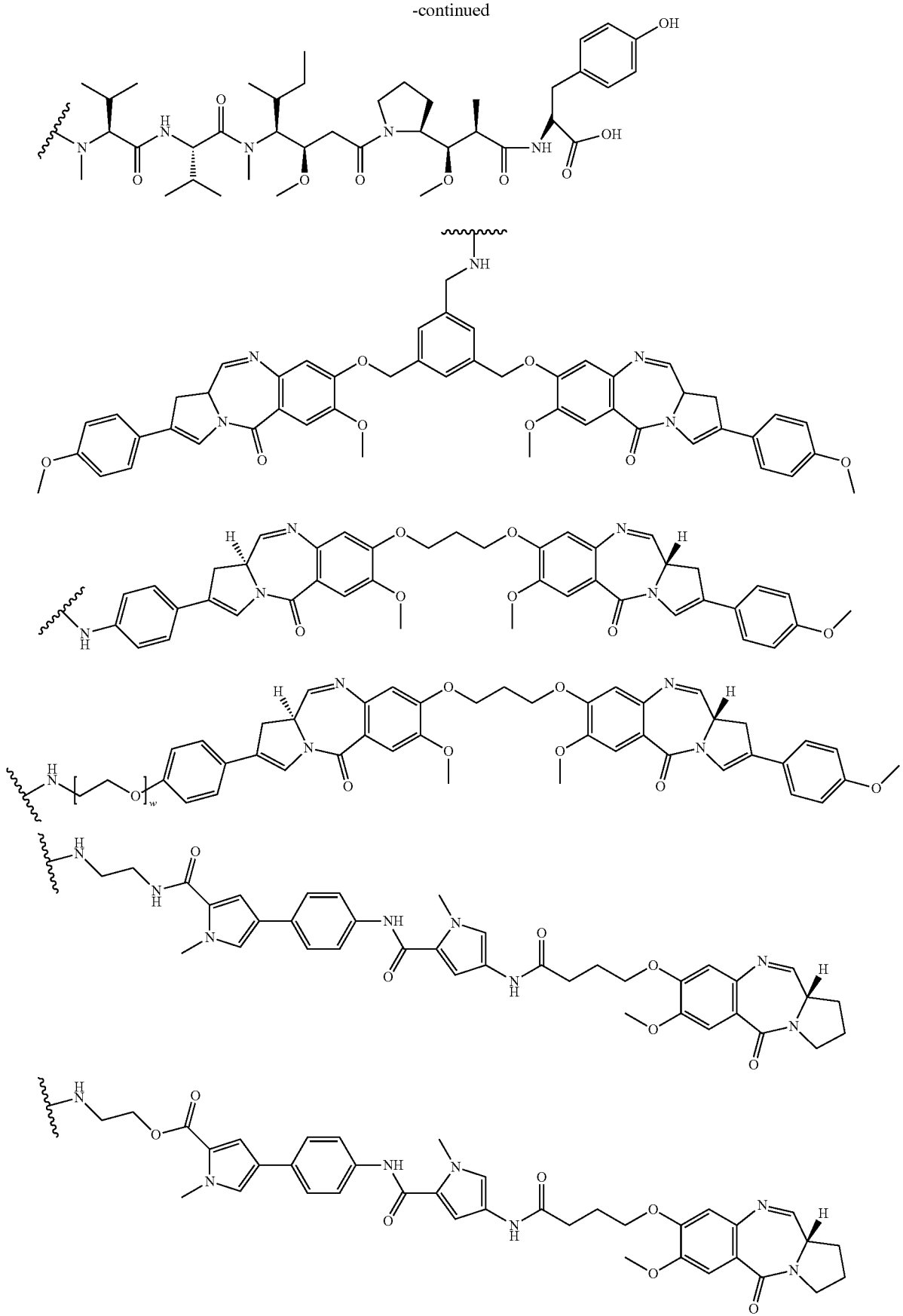

-continued

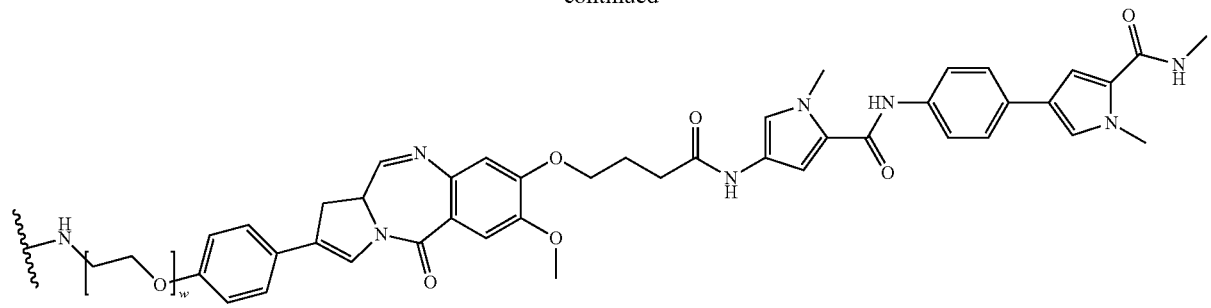

w is an integer of 1 to 10.

In the compound comprising the self-immolative linker according to the present invention, the FG may further comprise a functional group capable of conducting a hetero-diels reaction, a nucleophilic substitution reaction, a 1,3-bipolar ring addition reaction, a non-aldol type of carbonyl reaction, an addition reaction for a carbon-carbon multiple bond, an oxidation reaction or a click reaction. Also, FG of Chemical Formula 2 above may comprise functional groups (thiol, haloacetamide, maleimide, halide, tosylate, aldehyde, sulfonate, phosphonic acid, ketone, carboxylic acid, acetylene, azide, amine, hydroxy, hydroxy amine, hydrazine, etc) connectable directly to B.

In the compound of Chemical Formula 3 according to one example of the present invention, more preferably the FG may be —C≡CH or —N$_3$.

The compound of Chemical Formula 1 may be prepared by conducting a click reaction of a compound of Chemical Formula 2 with a ligand or a protein having a terminal functional group capable of conducting a click reaction with FG of Chemical Formula 2.

If FG of Chemical Formula 2 above is

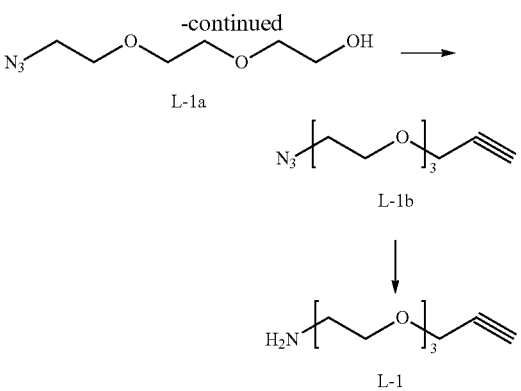

or maleimide, the compound of Chemical Formula 1 above may be prepared via a direct bond with B.

In the following, the present invention is specifically described with the examples, but the following examples are not intended to limit the scope of the present invention, since they serve to aid the understanding of the present invention.

[Preparation Example 1] Preparation of Linker L-1

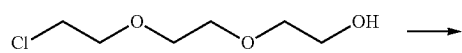

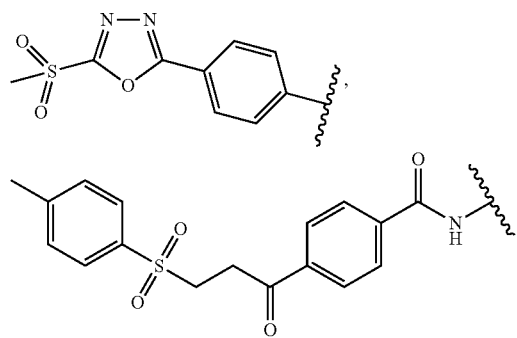

Preparation of Compound L-1a 2-(2-(2-chloroethoxy)ethoxy)ethanol (5 g, 29.65 mmol) was dissolved in DMF (N,N-Dimethylformamide) (10 mL) at room temperature under a nitrogen atmosphere. NaN$_3$ (2.89 g, 44.47 mmol) was added and stirred for 16 hours at 100° C. After the reaction was completed, the mixture was extracted with DCM (dichloromethane) (25 mL×3) and brine (25 mL). The organic layer was dried over anhydrous Na$_2$SO$_4$, filtered and concentrated under reduced pressure to obtain compound L-1a (4.96 g, 95.5%).

$^1$H NMR (400 MHz, CDCl$_3$) δ 3.75-3.73 (m, 2H), 3.70-3.67 (m, 6H), 3.63-3.61 (t, J=4.8 Hz, 2H), 3.41-3.39 (t, J=4.8 Hz, 2H).

Preparation of Compound L-1b

A solution of compound L-1a (3 g, 17.12 mmol) in DMF (28 mL) at room temperature under a nitrogen atmosphere was treated with 60% NaH (822 mg, 20.55 mmol) at 0° C. Propagyl bromide (2.6 mL, 34.25 mmol) was added dropwise to the mixture for 20 minutes and the mixture was allowed to warm up to room temperature and stirred for 2 hours. After the reaction was completed, the mixture was cooled to 0° C. and quenched with distilled water. The mixture was extracted with distilled water (20 mL) and EA (Ethyl acetate) (30 mL×3). The organic layer was washed with brine (20 mL) three times and dried over anhydrous Na$_2$SO$_4$, filtered and concentrated under the reduced pressure. The residue was purified by column chromatography to obtain compound L-1b (3.41 g, 93%).

$^1$H NMR (400 MHz, CDCl$_3$) δ 4.21 (d, J=2.4 Hz, 2H), 3.72-3.67 (m, 10H), 3.41-3.38 (t, J=5.2 Hz, 2H), 2.44-2.43 (t, J=2.4 Hz, 1H).

Preparation of Compound L-1

To a solution of compound L-1b (3.41 g, 15.99 mmol) in THF (Tetrahydrofuran) (30 mL) and distilled water (3 mL) at room temperature under a nitrogen atmosphere was added triphenylphosphine (4.40 g, 16.79 mmol), and the mixture was stirred for 16 hours at room temperature. After the reaction was completed, the mixture was concentrated under reduced pressure and diluted with distilled water (30 mL) and EA (30 mL), the resulting reaction mixture was adjusted to pH 2 by addition of 1N HCl solution and extracted. The water layer was washed with EA (30 mL) two more times and then pH was adjusted to 10 with 2N NaOH solution and the resulting mixture was extracted with DCM (30 mL) ten times. The organic layer was dried over anhydrous $Na_2SO_4$, filtered and concentrated under reduced pressure. The residue was purified by column chromatography to obtain the desired compound L-1 (2.75 g, 92%).

$^1$H NMR (400 MHz, $CDCl_3$) δ 4.21 (d, J=2.4 Hz, 2H), 3.72-3.53 (m, 8H), 3.53-3.51 (t, J=4.8 Hz, 2H), 2.88-2.86 (t, J=5.2 Hz, 2H), 2.44-2.43 (t, J=2.4 Hz, 1H); EI-MS m/z: 188 ($M^+$).

[Preparation Example 2] Synthesis of Linker L-2

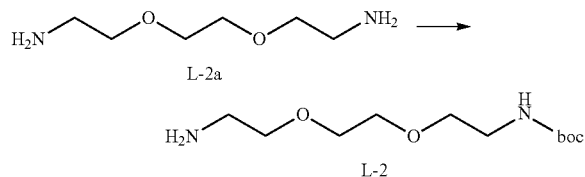

To a solution of compound L-2a (50 g, 337.4 mmol) in DCM (300 mL) at room temperature under a nitrogen atmosphere was added dropwise $(Boc)_2O$ (14.7 g, 67.47 mmol) dissolved in DCM (200 mL), and the mixture was stirred for 13 hours at room temperature. After the reaction was completed, the mixture was extracted with distilled water (500 mL). The organic layer was washed with brine (150 mL×3). The organic layer was dried over anhydrous sodium sulfate, filtered and then concentrated under reduced pressure to obtain compound L-2 (14.4 g, 86%).

$^1$H NMR (400 MHz, $CDCl_3$) δ 5.14 (s, 1H), 3.64-3.50 (m, 8H), 3.35-3.31 (m, 2H), 2.89-2.87 (t, J=5.6 Hz, 2H), 1.44 (s, 9H); EI-MS m/z: 249 ($M^+$).

[Preparation Example 3] Synthesis of Linker L-3

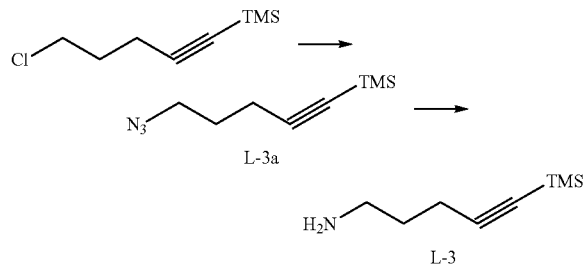

Preparation of Compound L-3a (5-chloro-1-pentynyl)trimethylsilane (5.0 g, 28.61 mmol) was dissolved in DMF (30 mL) at room temperature under a nitrogen atmosphere and $NaN_3$ (2.05 g, 31.47 mmol) was added thereto. After stirring at 50° C. for κ hours, the mixture was extracted with EA (500 mL) and distilled water (200 mL). The organic layer was dried over anhydrous $Na_2SO_4$, filtered and concentrated in vacuo to obtain compound L-3a (5.18 g, 99%).

$^1$H NMR (400 MHz, $CDCl_3$) δ 3.41 (t, J=6.4 Hz, 2H), 2.35 (t, J=6.4 Hz, 2H), 1.82-1.74 (m, 2H) 1.15 (s, 9H).

Preparation of Compound L-3

Compound L-3a (5.18 g, 28.61 mmol) was dissolved in THF (200 mL) and distilled water (200 mL) at room temperature under a nitrogen atmosphere and then triphenylphosphine (9.38 g, 35.77 mmol) was added and the mixture was stirred for 13 hours at 50° C. After the reaction was completed, diethylether (500 mL) and distilled water (100 mL) were added thereto. The organic layer was dried over anhydrous $Na_2SO_4$, filtered and concentrated in vacuo to obtain compound L-3 (3.12 g, 71%).

$^1$H NMR (400 MHz, $CDCl_3$) δ 2.80 (t, J=6.8 Hz, 2H), 2.30 (t, J=6.8 Hz, 2H), 1.69-1.61 (m, 2H) 1.35 (br, 2H), 1.15 (s, 9H)

[Preparation Example 4] Synthesis of Linker L-4

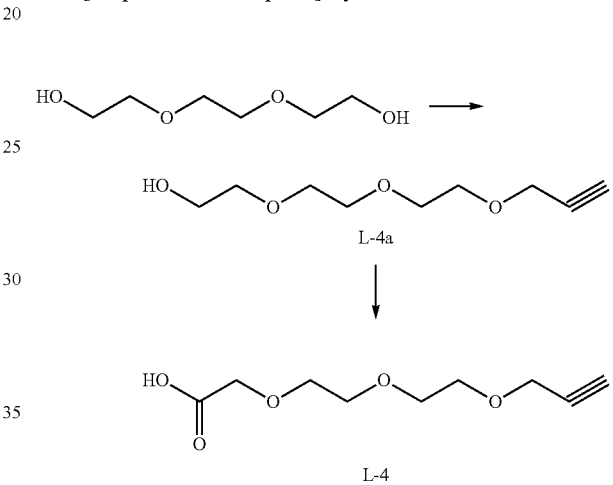

Preparation of Compound L-4a

To a solution of triethyleneglycol (15.14 g, 100.87 mmol) in THF (500 mL) at 0° C. under a nitrogen atmosphere was added NaH (60 wt %, 672 mg, 16.81 mmol), and the mixture was stirred for 5 minutes. And then propagylbromide (80% w/w in toluene, 2.5 g, 16.81 mmol) was added to the mixture, the mixture was stirred for 5 hours. After the reaction was completed, the mixture was extracted with EA (150 mL), distilled water (300 mL), and brine (100 mL). The organic layer was dried over anhydrous $Na_2SO_4$, filtered and concentrated in vacuo. The residue was purified by column chromatography to obtain compound L-4a (1.63 g, 52%).

$^1$H NMR (400 MHz, $CDCl_3$) δ 4.2-4.20 (m, 2H), 3.77-3.65 (m, 10H), 3.62 (t, J=4.8 Hz, 2H), 2.50 (s, 1H), 2.44 (s, 1H).

Preparation of Compound L-4

Compound L-4a (1.0 g, 5.31 mmol) was dissolved in acetone (20 mL) at 0° C. under a nitrogen atmosphere, and then Jones reagent (8 mL) was added and stirred for 3 hours. After the reaction was completed, the mixture was extracted with EA (150 mL) and distilled water (50 mL). The organic layer was dried over anhydrous $Na_2SO_4$, filtered and concentrated in vacuo to obtain compound L-4(903 mg, 84%).

$^1$H NMR (400 MHz, $CDCl_3$) δ 4.25-4.17 (m, 4H), 3.82-3.68 (m, 8H), 2.45 (s, 1H).

[Preparation Example 5] Synthesis of Linker L-5

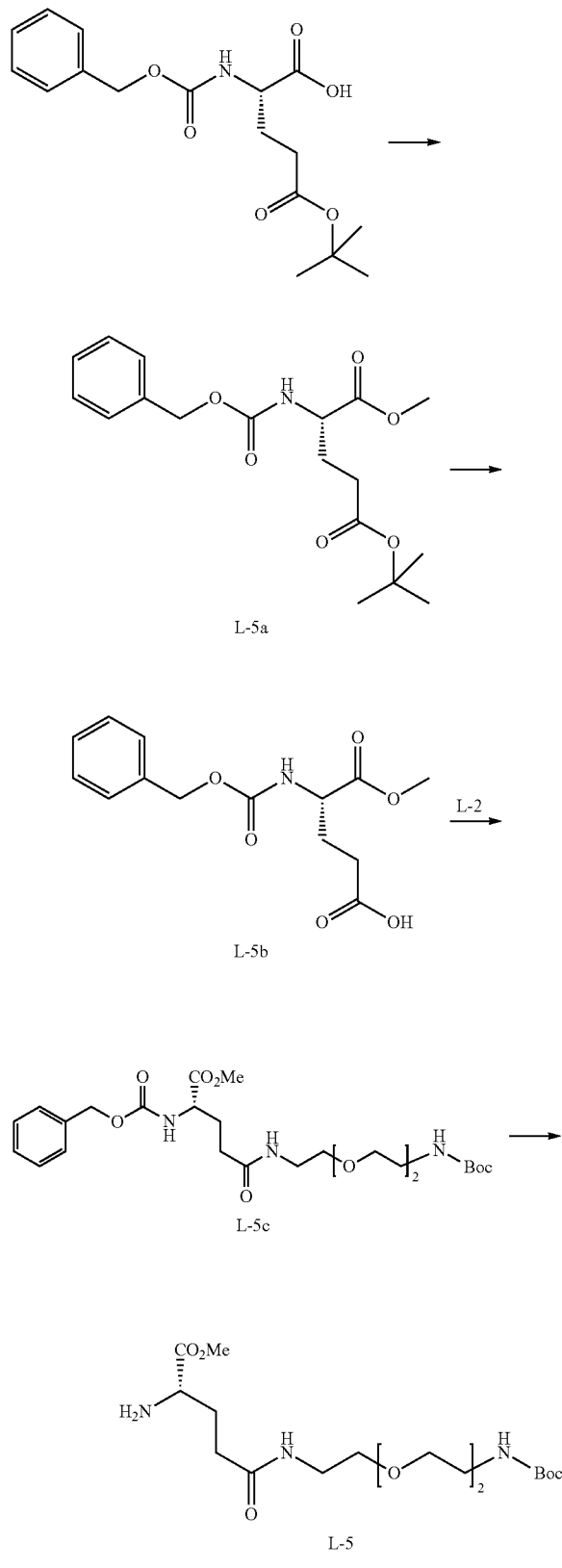

Preparation of Compound L-5a z-Glu (OtBu)—OH (Z-L-glutamic acid 5-tert-butyl ester) (5 g, 14.82 mmol) and 4-dimethylaminopyridine (362 mg, 1.48 mmol) were dissolved in DCM (50 mL), and methanol (2 mL, 44.13 mmol). The mixture was stirred for 30 minutes at room temperature, DCC (N,N'-dicyclohexylcarbodiimide) (3.05 g, 14.82 mmol) was added at 0° C., the mixture was stirred for 15 hours at room temperature. After the reaction was completed, The solid was removed by celite and the filtrate was concentrated under reduced pressure and the residue was purified by column chromatography to obtain compound L-5a (4.66 g, 90%).

$^1$H NMR (400 MHz, CDCl$_3$) δ 7.40-7.28 (m, 5H), 5.46-5.36 (d, J=7.2 Hz 2H), 5.10 (s, 2H), 4.40 (q, J=8.0, 5.2 Hz, 1H), 3.75 (s, 3H), 2.42-2.24 (m, 2H), 2.20-2.08 (m, 1H), 2.02-1.88 (m, 1H); EI-MS m/z: 352 (M$^+$).

Preparation of Compound L-5b

To a solution of compound L-5a (4.6 g, 13.10 mmol) in DCM (50 mL) at 0° C. under a nitrogen atmosphere was added TFA (Trifluoroacetic acid (5 mL) and the mixture was stirred for 2.5 hours at room temperature. After the reaction was completed, the reaction mixture was concentrated under reduced pressure. The residue was concentrated under reduced pressure four times by using toluene (20 mL) as a co-solvent, thereby removing TFA. Compound L-5b was used directly in the next step without further purification (4.0 g, 99%).

$^1$H NMR (400 MHz, CDCl$_3$) δ 7.40-7.30 (m, 5H), 5.47 (d, J=7.2 Hz, 2H), 5.10 (s, 2H), 4.42 (q, J=7.6 Hz, J=5.6 Hz, 1H), 3.76 (s, 3H), 2.54-2.38 (m, 2H), 2.30-2.14 (m, 1H), 2.04-1.92 (m, 1H); EI-MS m/z: 296 (M$^+$).

Preparation of Compound L-5c

To a solution of compound L-5b (3.87 g, 13.1 mmol) in THF (40 mL) at room temperature under a nitrogen atmosphere were added compound L-2 (3.6 g, 14.41 mmol), HBTU (2-(1H-Benzotriazole-1-yl)-1,1,3,3-tetramethyluronium hexafluorophosphate) (6 g, 15.72 mmol), and DIPEA (N,N-Diisopropylethylamine) (3.4 mL, 19.65 mmol). The mixture was stirred overnight at room temperature. After the reaction was completed, the mixture was concentrated under reduced pressure and extracted with EA (100 mL) and distilled water (100 mL). The organic layer was dried over anhydrous Na$_2$SO$_4$, filtered and concentrated under reduced pressure. The residue was purified by column chromatography to obtain compound L-5c (3.8 g, 56%).

$^1$H NMR (400 MHz, CDCl$_3$) δ 7.40-7.30 (m, 5H), 6.30 (br, 1H), 5.85 (br, 1H), 5.10 (s, 2H), 4.38 (q, J=8.0, 3.2 Hz, 1H), 3.74 (s, 3H), 3.55 (s, 3H), 3.54 (t, J=8.0 Hz, 4H), 3.58-3.36 (m, 2H), 3.34-3.22 (m, 2H), 3.0 (br, 1H), 2.36-2.26 (m, 2H), 2.26-2.16 (m, 1H), 2.06-1.96 (m, 1H); EI-MS m/z: 526 (M$^+$).

Preparation of Compound L-5

To a solution of compound L-5c (3.8 g, 7.23 mmol) in methanol (20 mL) was added 5% Pd/C (2.3 g, 1.09 mmol). Hydrogen gas was introduced to replace the air then stirred for 3 hours at room temperature. The reaction mixture was filtered through celite and the filtrate was concentrated under reduced pressure to obtain compound L-5 (2.8 g, quant.). EI-MS m/z: 392 (M$^+$).

[Preparation Example 6] Synthesis of Linker L-6 and L-7

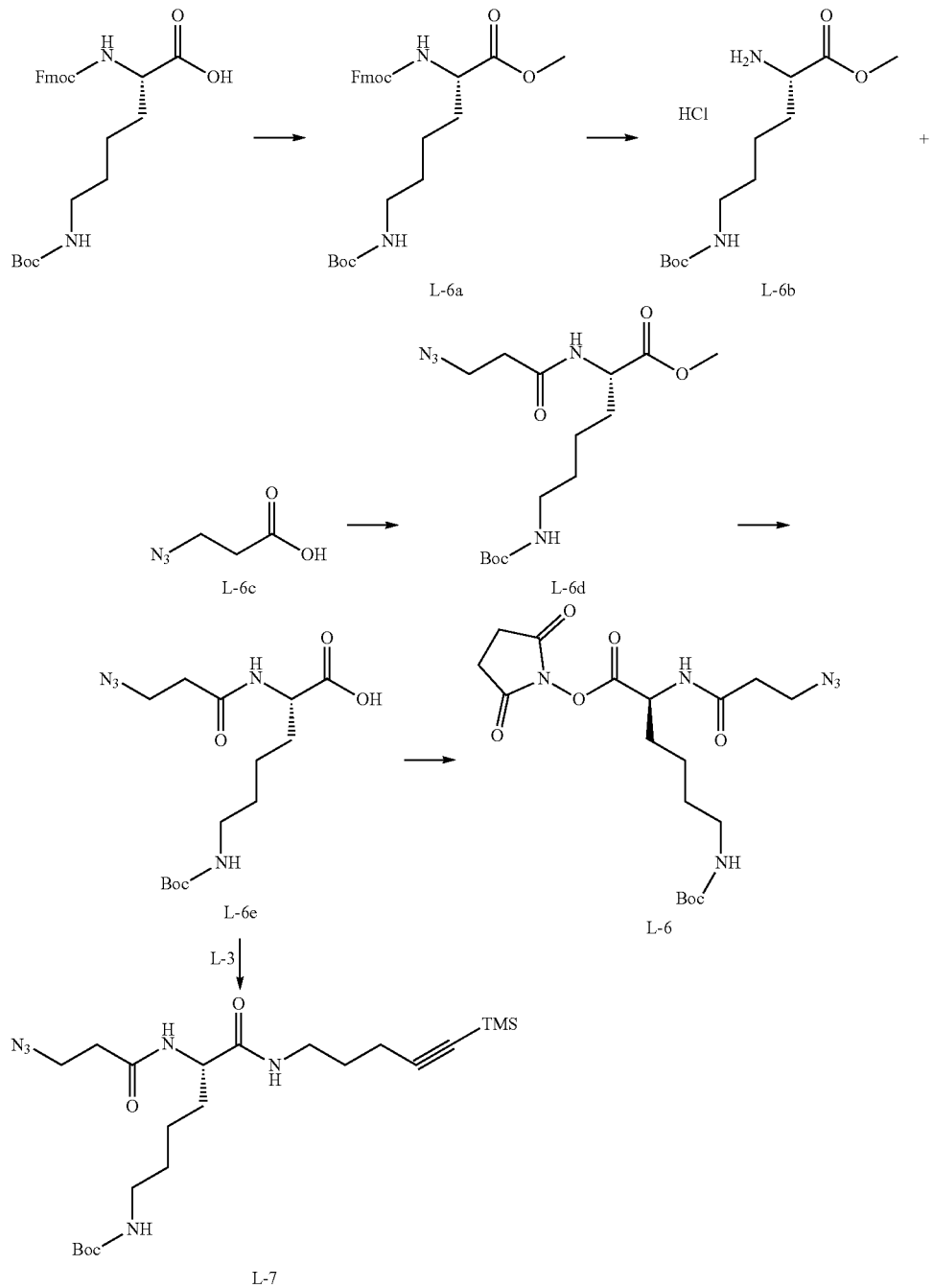

Preparation of Compound L-6a

To a solution of Fmoc-Lys(Boc)-OH (Fmoc=9-Fluorenylmethoxycarbonyl, 4 g, 8.54 mmol) in DCM (40 mL) at 0° C. under a nitrogen atmosphere was added HOBT (1-Hydroxybenzotriazole) (1.27 g, 9.39 mmol) and DIC (N,N'-diisopropylcarbodiimide) (1.45 mL, 9.39 mmol). The mixture was stirred for 30 minutes, Methanol (0.35 mL, 8.54 mmol) was added. After being stirred another 15 minutes, the mixture was extracted with DCM and distilled water. The organic layer was dried over anhydrous $Na_2SO_4$, filtered and concentrated under reduced pressure. The residue was purified by column chromatography to obtain compound L-6a (3.55 g, 86%).

$^1$H NMR (400 MHz, $CDCl_3$) δ 7.88-7.64 (m, 4H), 7.42-7.26 (m, 4H), 6.80-6.76 (m, 1H), 4.30-4.15 (m, 3H), 4.00-3.84 (m, 1H), 3.58 (s, 3H), 2.95-2.82 (m, 2H), 1.67-1.47 (m, 2H), 1.38-1.15 (m, 13H); EI-MS m/z: 483 ($M^+$).

Preparation of Compound L-6b

A solution of compound L-6a (3.45 g, 7.15 mmol) and diethylamine (20 mL) in DCM (25 mL) at room temperature under a nitrogen atmosphere was treated with diethylamine (20 mL) and stirred at room temperature. After the reaction mixture was concentrated under reduced pressure, 4 M HCl in Dioxane (17.8 mL) was added at 0° C. and then the solid was collected by filtration, washed with EA to obtain compound L-6b (2 g, 95%).

$^1$H NMR (400 MHz, DMSO-d$_6$) δ 8.49 (br, 3H), 6.80-6.76 (m, 1H), 3.95 (t, J=6.4 Hz, 1H), 3.71 (s, 3H), 2.88-2.83 (m, 2H), 1.77-1.71 (m, 2H), 1.40-1.19 (m, 13H); EI-MS m/z: 261 (M$^+$).

Preparation of Compound L-6c 3-bromopropionic acid (10 g, 65.37 mmol) was dissolved in acetonitrile (100 mL) at room temperature under a nitrogen atmosphere and then NaN$_3$ (4.7 g, 71.91 mmol) was added and stirred for 12 hours at 50° C. After the reaction was completed, the reaction mixture was extracted with ethylacetate (500 mL), distilled water (300 mL), and 2N HCl aqueous solution (50 mL). The organic layer was dried over anhydrous Na$_2$SO$_4$, filtered and concentrated under reduced pressure to obtain compound L-6c (5.1 g, 68%).

$^1$H NMR (400 MHz, CDCl$_3$) δ 3.60 (t, J=6.4 Hz, 2H), 2.65 (t, J=6.4 Hz, 2H).

Preparation of Compound L-6d

A solution of compound L-6d (1.8 g, 6.13 mmol) and compound L-6c (1.06 g, 9.19 mmol) in DMF (10 mL) at room temperature under a nitrogen atmosphere were added PyBOP (benzotriazol-1-yl-oxytripyrrolidinophosphonium hexafluorophosphate) (4.78 g, 9.19 mmol) and DIPEA (1.6 mL, 9.19 mmol) at 0° C. and stirred for 3 hours at room temperature. After the reaction was completed, the mixture was extracted with EA and distilled water. The organic layer was dried over anhydrous Na$_2$SO$_4$, filtered and concentrated under reduced pressure. The residue was purified by column chromatography to obtain compound L-6d (1.57 g, 72%).

$^1$H NMR (400 MHz, CDCl$_3$) δ 6.36-6.33 (m, 1H), 4.68-4.56 (m, 2H), 3.76 (s, 3H), 3.70-3.56 (m, 2H), 3.14-3.04 (m, 2H), 2.45 (t, J=6.4 Hz, 2H), 1.92-1.82 (m, 1H), 1.76-1.66 (m, 1H), 1.58-1.26 (m, 13H); EI-MS m/z: 358 (M$^+$).

Preparation of Compound L-6e

Compound L-6d (2.9 g, 8.11 mmol) was dissolved in 1,4-dioxane (30 mL) and distilled water (30 mL) at room temperature under a nitrogen atmosphere and then LiOH (340.5 mg, 8.11 mmol) was added at 0° C. and the mixture was stirred for 90 minutes at room temperature. The pH of the reaction mixture was adjusted to 2-3 with 2N HCl aqueous solution. The mixture was extracted with DCM and distilled water. The organic layer was dried over anhydrous Na$_2$SO$_4$, filtered and concentrated under reduced pressure to obtain compound L-6e (2.7 g, 99%).

$^1$H NMR (400 MHz, CDCl$_3$) δ 6.82-6.78 (m, 1H), 4.78-4.58 (m, 2H), 3.71-3.56 (m, 2H), 3.14-3.08 (m, 2H), 2.58-2.44 (m, 2H), 1.96-1.74 (m, 2H), 1.58-1.36 (m, 13H); EI-MS m/z: 344 (M$^+$).

Preparation of Compound L-6

To a solution of compound L-6e (56 mg, 0.16 mmol) in DMF (2 mL) at room temperature under a nitrogen atmosphere were added EDCI (1-Ethyl-3-(3-dimethylaminopropyl)carbodiimide) (37.5 mg, 0.20 mmol) and NHS (N-hydroxysuccinimide) (22.5 mg, 0.20 mmol) stirred for 2.5 hours. After the reaction was completed, compound L-6 was used in the next reaction without further purification. EI-MS m/z: 441 (M$^+$).

Preparation of Compound L-7

A solution of compound L-6e (1.44 g, 4.20 mmol) and L-3 (782 mg, 5.04 mmol) prepared in Preparation Example 3 in DMF (20 mL) at 0° C. under a nitrogen atmosphere were treated with DIPEA (1.10 mL, 6.29 mmol) and PyBOP (3.27 g, 6.29 mmol) and stirred for 3 hours at room temperature. After the reaction was completed, the mixture was extracted with EA (200 mL) and distilled water (100 mL). The organic layer was dried over anhydrous Na$_2$SO$_4$, filtered and concentrated under reduced pressure. The residue was purified by column chromatography to obtain compound L-7 (1.60 g, 80%). EI-MS m/z: 481 (M$^+$).

[Preparation Example 7] Synthesis of MMAF

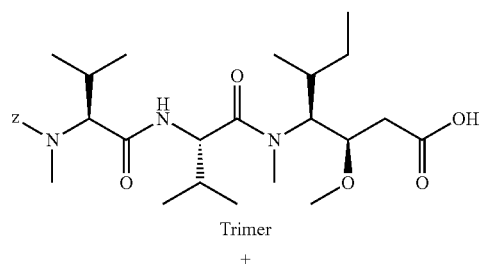

Trimer

+

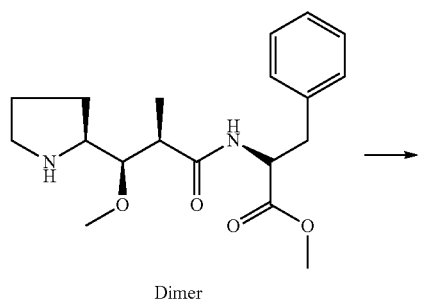

Dimer

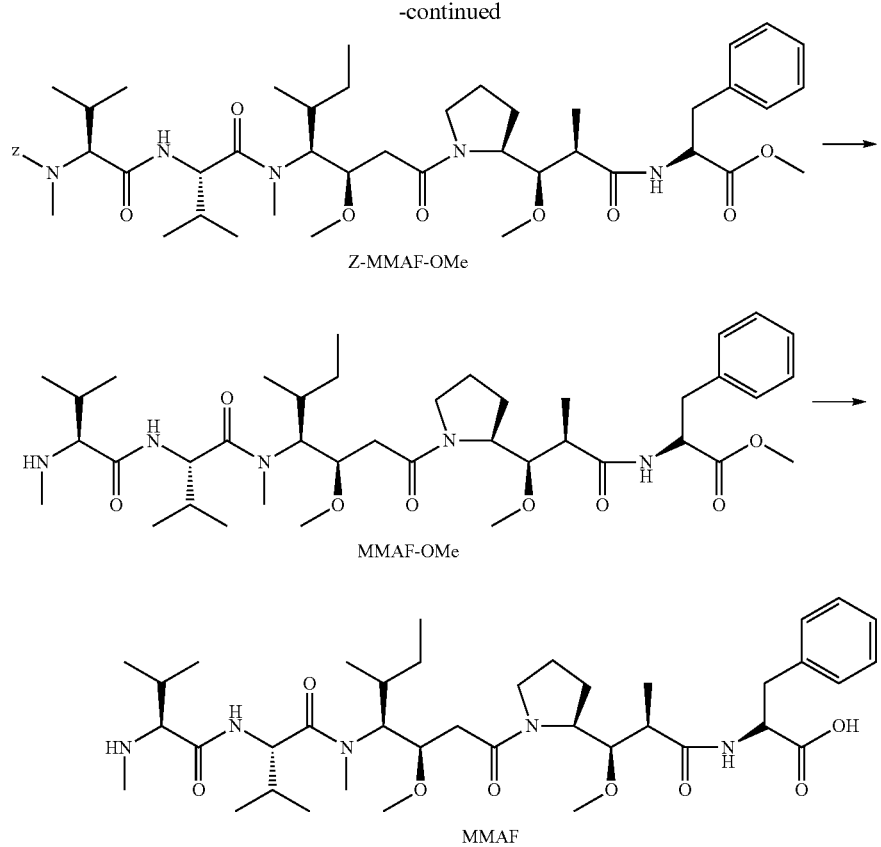
MMAF was synthesized by a similar method as described in U.S. 61/483,698, Chem Pharm Bull, 1995. 43(10). 1706-1718, U.S. Pat. Nos. 7,423,116, 7,498,298, and WO2002/088172.
[Preparation Example 8] Preparation of Ligand-Linkers (L-8) and (L-9)
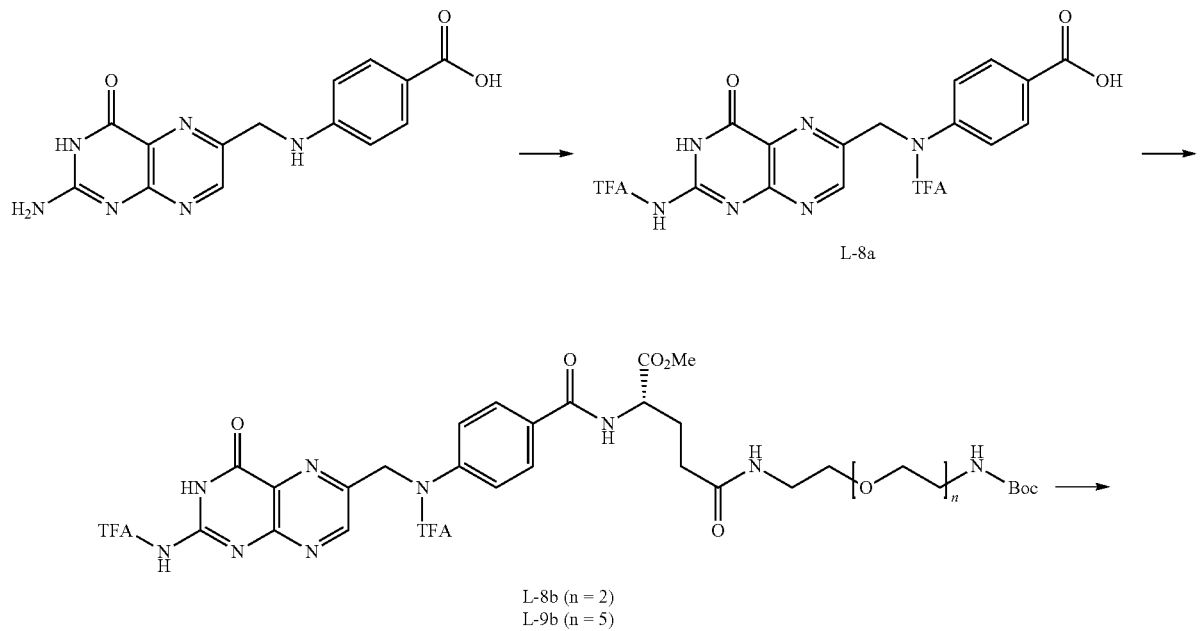

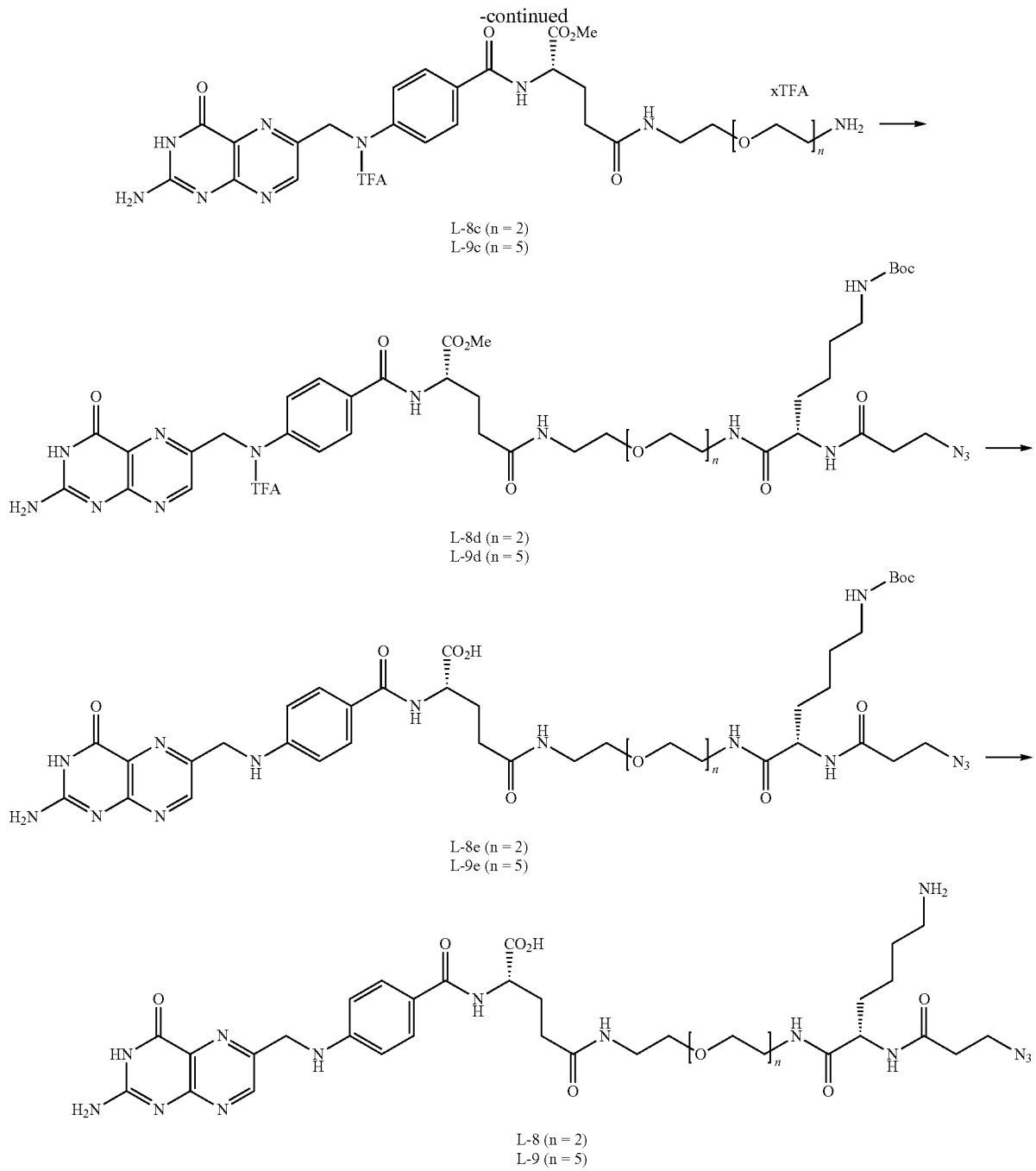

L-8c (n = 2)
L-9c (n = 5)

L-8d (n = 2)
L-9d (n = 5)

L-8e (n = 2)
L-9e (n = 5)

L-8 (n = 2)
L-9 (n = 5)

Preparation of Compound L-8a

Compound L-8a (7.1 g, 88%) was obtained by a similar method as described in US 20070276018. EI-MS m/z: 505 (M+).

Preparation of Compound L-8b

A solution of compound L-8a (3.6 g, 7.1 mmol) and L-5 (2.8 g, 7.15 mmol) prepared in Preparation Example 5 in DMF (10 mL) at room temperature under a nitrogen atmosphere were treated HBTU (3.3 g, 8.58 mmol) and DIPEA (1.87 mL, 10.73 mmol) and the mixture was stirred for 15 hours at room temperature. After the reaction was completed, the reaction mixture was extracted with EA and water. The organic layer was dried over anhydrous $Na_2SO_4$, filtered and concentrated under reduced pressure. The residue was purified by column chromatography to obtain compound L-8b (4.7 g, 75%). EI-MS m/z: 878 (M+).

Preparation of Compound L-8c

Compound L-8b (1.76 g, 1.94 mmol) was dissolved in DCM (50 mL) at 0° C. under a nitrogen atmosphere and then TFA (5 mL) was added dropwise thereto. After the mixture was stirred for 30 minutes at room temperature. The residue was suspended in toluene (20 mL) and evaporated to remove any remaining TFA. The solid was recrystallized from methanol and diethylether to obtain compound L-8c (1.5 g, 85%). EI-MS m/z: 682 (M+).

Preparation of Compound L-8d

TEA (22 μL, 0.16 mmol) and compound L-8c (92.6 mg, 0.14 mmol) were added to compound L-6 (71.8 mg, 0.16 mmol) prepared by Preparation Example 6 at room temperature under a nitrogen atmosphere and the mixture was stirred for 2.5 hours. After the reaction was completed, the reaction mixture was extracted with EA and water. Then the organic layer was dried over anhydrous Na$_2$SO$_4$, filtered and concentrated under reduced pressure. The residue was purified by column chromatography to obtain compound L-8d (44.8 mg, 33%). EI-MS m/z: 1008 (M$^+$).

Preparation of Compound L-8e

To a solution of compound L-8d (200 mg, 0.20 mmol) in 1,4-dioxane (4 mL) and distilled water (4 mL) at 0° C. was added LiOH (21 mg, 0.50 mmol), and the mixture was stirred for 2.5 hours at room temperature. After the reaction was completed, the reaction mixture was cooled to 0° C. and adjusted to have pH of 2 to 3 with 2N HCl. The mixture was concentrated under reduced pressure to remove water, and then the compound L-8e was used directly in the next reaction without further purification. EI-MS m/z: 897 (M$^+$).

Preparation of Compound L-8

To a solution of compound L-8e in DCM (5 mL) at 0° C. was added dropwise TFA (1 mL) and stirred for 2 hours at room temperature. After the reaction was completed, the reaction mixture was concentrated under reduced pressure, and the residue was subjected to prep-HPLC to obtain compound L-8 (155.9 mg, 2 steps 69%/L-8e to L-8). EI-MS m/z: 797 (M$^+$).

Preparation of Compound L-9b

Compound L-9b was prepared by a similar method to the preparation method of the compound L-8b of Preparation Example 8, thereby obtaining a compound L-9b (Yield 62.4%). EI-MS m/z: 1010 (M$^+$)).

Preparation of Compound L-9c

Compound L-9c was prepared by a similar method to the preparation method of the compound L-8c of Preparation Example 8, thereby obtaining a compound L-9c (Quantitative yield). EI-MS m/z: 814 (M$^+$).

Preparation of Compound L-9d

Compound L-9d was prepared by a similar method to the preparation method of the compound L-8d of Preparation Example 8, thereby obtaining a compound L-9d (Yield 33%). EI-MS m/z: 1130 (M$^+$)).

Preparation of Compound L-9e

Compound L-9e was prepared by a similar method to the preparation method of the compound L-8e of Preparation Example 8, thereby obtaining a compound L-9e. EI-MS m/z: 1030 (M$^+$).

Preparation of Compound L-9

Compound L-9 was prepared by a similar method to to the preparation method of the compound L-8 of Preparation Example 8, thereby obtaining a compound L-9 (Yield 40%). EI-MS m/z: 930 (M$^+$).

[Preparation Example 9] Preparation of Ligand-Linker (L-10)

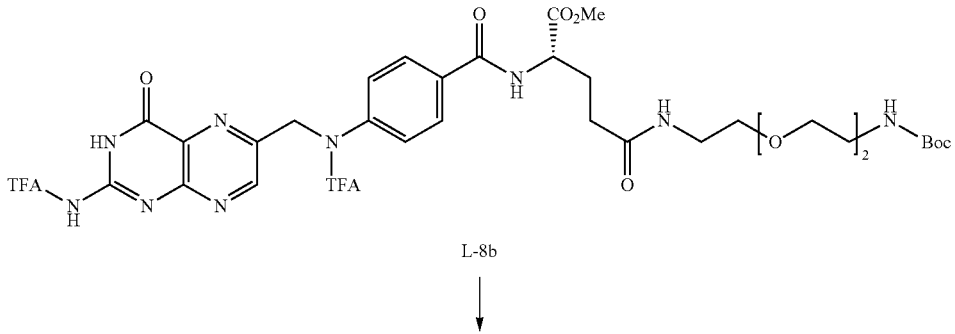

L-8b

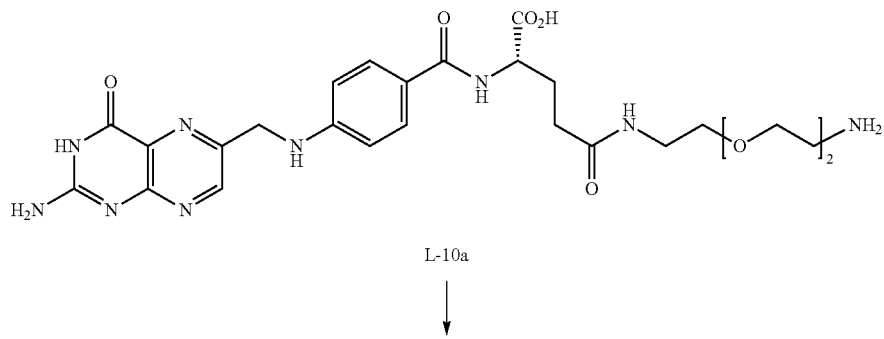

L-10a

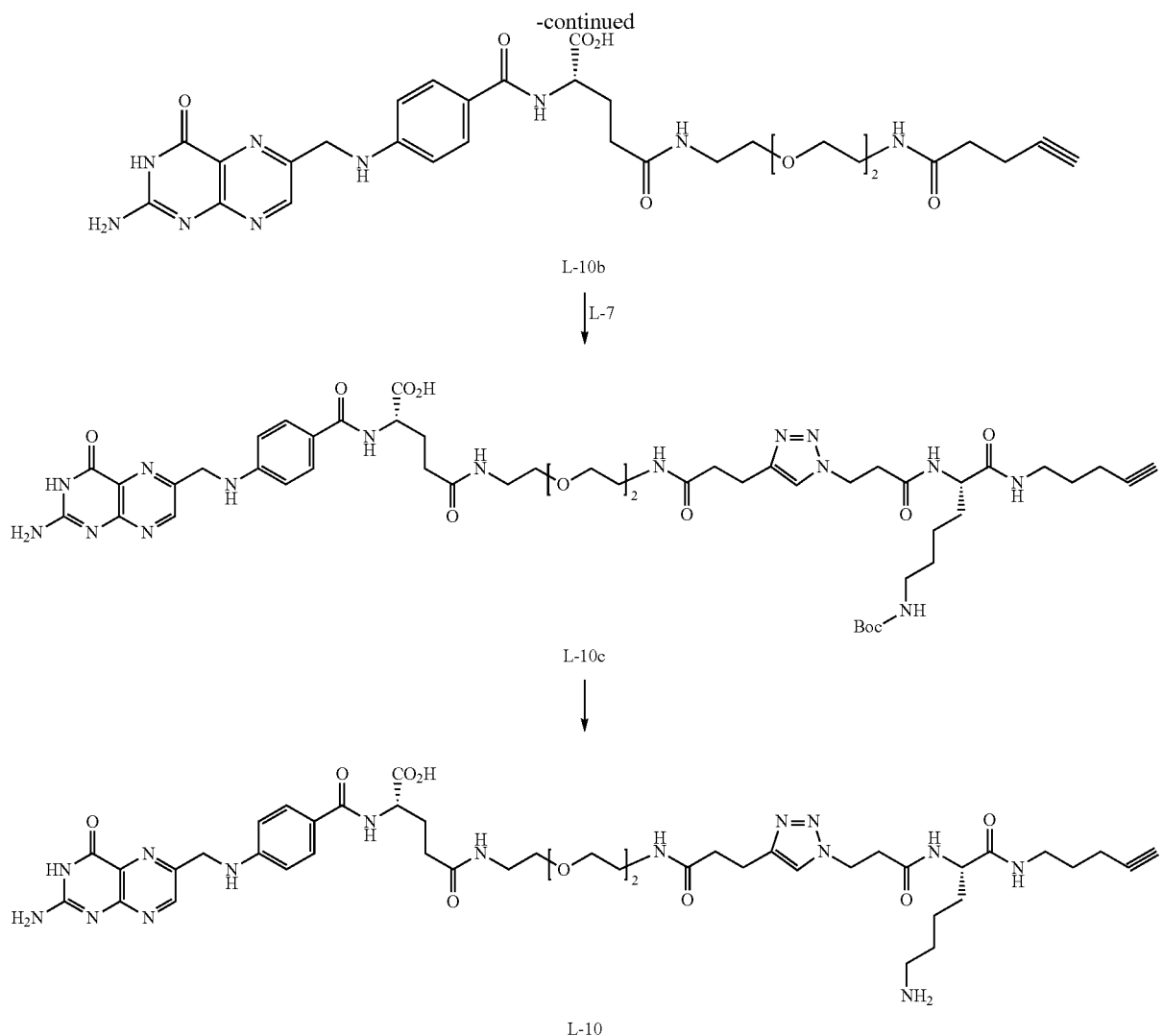

Preparation of Compound L-10a

To a solution of compound L-8b (260 mg, 0.29 mmol) prepared by Preparation Example 8 in 6N HCl (7 mL) at room temperature under a nitrogen atmosphere was added compound L-8b (260 mg, 0.29 mmol) and heated for 30 minutes at 50° C. After concentration, the mixture was adjusted to have pH of 10 with 6N NaOH and stirred for 20 minutes, followed by separation and purification using prep-HPLC to obtain compound L-10a (84 mg, 50%). EI-MS m/z: 572 (M+).

Preparation of Compound L-10b 4-pentynoic acid (0.5 g, 5.09 mmol) was dissolved in THF (10 mL) at room temperature under a nitrogen atmosphere and then N-hydroxysuccimide (0.59 g, 5.09 mmol) was added thereto. After the mixture was cooled to 0° C., DCC (1.26 g, 6.11 mmol) was added and stirred for one hour at room temperature. After the reaction was completed, the precipitate was filtered and then the filtrate was concentrated under reduced pressure. The synthesized compound (57 mg, 0.29 mmol) and compound L-10a (84 mg, 0.15 mmol) was dissolved in DMSO (3 mL), TEA (62 μL, 0.44 mmol) was added. After the mixture was stirred for 2 hours at room temperature. the mixture was separated and purified with a prep HPLC to obtain compound L-10b (25 mg, 26%). EI-MS m/z: 652 (M+).

Preparation of Compound L-10c

A solution of compound L-10b (25 mg, 0.03 mmol) and compound L-7 (17.2 mg, 0.04 mmol) prepared by Preparation Example 6 in EtOH (3 mL) and distilled water (0.5 mL) at room temperature under a nitrogen atmosphere were added 1M Sodium ascorbate (64 μL, 0.06 mmol) and 0.1M CuSO$_4$ (128 μL, 0.01 mmol) and stirred for 17 hours. After the reaction was completed, tetrabutylammoniumfluoride (1M in THF) (60 μL, 0.06 mmol) was added to the reaction mixture at 0° C. under a nitrogen atmosphere, and the mixture was stirred for 30 minutes. After the reaction was completed, the resulting mixture was separated and purified with a prep HPLC to obtain compound L-10c (8.0 mg). EI-MS m/z: 1061 (M+).

Preparation of Compound L-10

To a solution of compound L-10c (8 mg) in DCM (1.0 mL) at 0° C. under a nitrogen atmosphere was added TFA (0.2 mL) and stirred for 1.5 hours at room temperature. The compound L-10 was used directly in the next reaction without purification (12 mg). EI-MS m/z: 961 (M+).

[Preparation Example 11] Preparation of Linkers L-11-1 and L-11-2

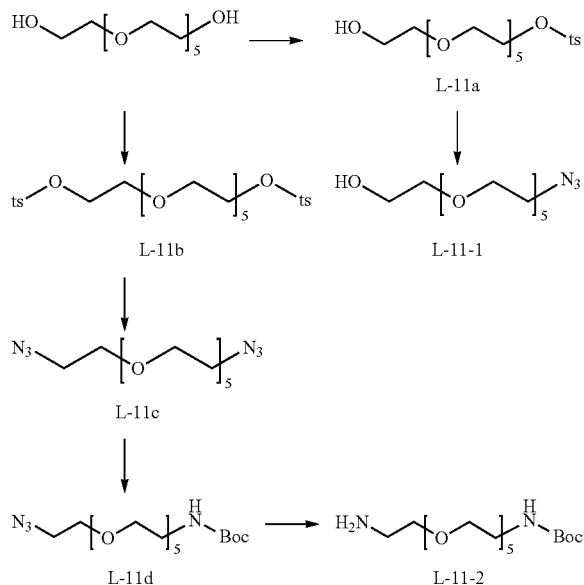

Preparation of Compound L-11a

Hexaethylene glycol (5.0 g, 17.71 mmol) was dissolved in anhydrous DCM (dichloromethane) (178 mL) at room temperature under a nitrogen atmosphere and then KI (249 mg, 1.17 mmol), $Ag_2O$ (4.92 g, 21.25 mmol), and p-TsCl (p-Toluenesulfonyl chloride) (3.71 g, 19.48 mmol) were dropwise added and the mixture was stirred overnight at room temperature. After the reaction was completed, the reaction mixture was filtered by celite filtration to remove $Ag_2O$ and the filtrate was concentrated under reduced pressure. The residue was purified by column chromatography to obtain compound L-11a (5.98 g, 73%).

$^1$H NMR (400 MHz, $CDCl_3$) δ 7.80 (d, J=8.4 Hz, 2H), 7.35 (d, J=8.0 Hz, 2H), 4.16 (t, J=4.8 Hz, 2H), 3.71-3.58 (m, 22H), 2.88 (brs, 1H), 2.45 (s, 3H).

Preparation of Compound L-11-1

To a solution of compound L-11a (5.98 g, 13.70 mmol) in DMF (30 mL) at room temperature under a nitrogen atmosphere was added $NaN_3$ (1.34 g, 20.55 mmol) dropwise, and stirred for 1 hour at 110° C. After the reaction was completed, the solid was filtered and the filtrate was concentrated under reduced pressure. The residue was purified by column chromatography to obtain compound L-11 (4.1 g, 91%).

$^1$H NMR (400 MHz, $CDCl_3$) δ 3.72-3.60 (m, 22H), 3.39 (t, J=4.8 Hz, 2H) 2.78 (brs, 1H).

Preparation of Compound L-11b

To a solution of Hexaethyleneglycol (15.0 g, 77.23 mmol) in DCM (400 mL) at 0° C. under a nitrogen atmosphere were added KOH (35.g, 617.8 mmol) and p-TsCl (29.5 g, 154.5 mmol), and stirred overnight at room temperature. After the reaction was completed, the reaction mixture was extracted with DCM (500 mL), distilled water (200 mL), and brine (100 mL). Then the organic layer was dried over anhydrous $Na_2SO_4$, filtered and concentrated under reduced pressure and immediately used in the subsequent reaction without purification.

$^1$H NMR (400 MHz, $CDCl_3$) δ 7.30 (d, J=8.1 Hz, 4H), 7.30 (d, J=8.1 Hz, 4H), 4.18 (t, J=4.8 Hz, 4H) 3.70 (t, J=4.8 Hz, 4H), 3.64 (s, 8H), 3.55 (s, 8H), 2.42 (s, 6H).

Preparation of Compound L-11c

To a solution of compound L-11b (1.4 g) in DMF (10 mL) at room temperature under a nitrogen atmosphere was added $NaN_3$ (0.2 g), and stirred for 15 hours at 100° C. After the reaction was completed, the reaction mixture was concentrated under reduced pressure. The residue was purified by column chromatography to obtain compound L-11c (510 mg).

$^1$H NMR (400 MHz, $CDCl_3$) δ 3.69-3.67 (m, 20H), 3.39 (t, J=5.2 Hz, 2H).

Preparation of Compound L-11d

To a solution of compound L-11c (510 mg, 1.53 mmol) in THF (4 mL), distilled water (2 mL), and diethylether (2 mL) at room temperature under a nitrogen atmosphere was added triphenylphosphine (423 mg, 1.61 mmol), and stirred for 14 hours. After the reaction was completed, $(Boc)_2O$ (670 mg, 3.07 mmol) dissolved in 1,4-dioxane (2 mL) and distilled water (3 mL) was added dropwise, $NaHCO_3$ (387 mg, 4.60 mmol) was added thereto, followed by stirring for 3 hours. Then, the reaction solution was concentrated under reduced pressure, the residue was subjected to the column chromatography to obtain compound L-11d (360 mg, 58%).

$^1$H NMR (400 MHz, $CDCl_3$) δ 5.11 (brs, 1H), 3.69-3.63 (m, 18H), 3.54 (t, J=4.8 Hz, 2H), 3.39 (t, J=4.8 Hz, 2H), 3.32-3.31 (m, 2H), 1.45 (s, 9H).

Preparation of Compound L-11-2

Compound L-11d (360 mg, 0.89 mmol) was dissolved in ethanol (10 mL) at room temperature, 10% Pd/C (94 mg, 0.89 mmol) was added thereto, and the mixture was stirred for 5 hours while injection hydrogen at room temperature. After the reaction was completed, the mixture was filtered by celite, and then concentrated under reduced pressure to obtain compound L-11-2 (315 mg, 94%).

$^1$H NMR (400 MHz, $CDCl_3$) δ 5.19 (brs, 1H), 3.67-3.50 (m, 20H), 3.32-3.31 (m, 2H), 2.88-2.79 (m, 2H), 1.45 (s, 9H).

[Preparation Example 12] Preparation of Linker L-12

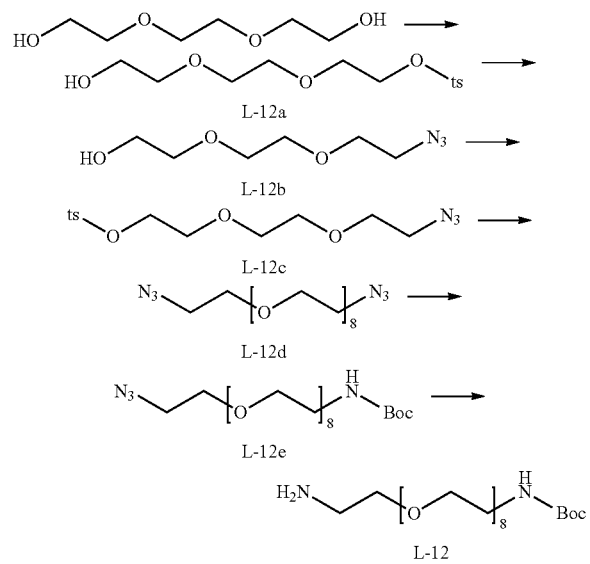

Preparation of Compound L-12a

Compound L-12a was prepared by a similar method to the preparation method of the compound L-11a of Preparation Example 11, thereby obtaining a compound L-12a.

$^1$H NMR (400 MHz, CDCl$_3$) δ 7.79 (d, J=8.8 Hz, 2H), 7.34 (d, J=8.0 Hz, 2H), 4.16 (t, J=4.8 Hz, 2H), 3.70 (t, J=4.8 Hz, 4H), 3.58 (s, 4H), 3.56 (t, J=5.0 Hz, 2H), 2.44 (s, 3H), 2.32 (brs, 1H).

Preparation of Compound L-12b

Compound L-12b was prepared by a similar method to the preparation method of the compound L-11-1 of Preparation Example 11, thereby obtaining a compound-12b.

$^1$H NMR (400 MHz, CDCl$_3$) δ 3.75-3.69 (m, 8H), 3.62 (t, J=4.8 Hz, 2H), 3.41 (t, J=4.8 Hz, 2H), 2.41 (brs, 1H).

Preparation of Compound L-12c

Compound L-12c was prepared by a similar method similar to the preparation method of the compound L-11a of Preparation Example 11, thereby obtaining a compound L-12c.

$^1$H NMR (400 MHz, CDCl$_3$) δ 7.80 (d, J=8.8 Hz, 2H), 7.35 (d, J=8.0 Hz, 2H), 4.17 (t, J=4.8 Hz, 2H), 3.70 (t, J=4.8 Hz, 2H), 3.64 (t, J=4.8 Hz, 2H), 3.34 (t, J=4.8 Hz, 2H), 2.45 (s, 3H).

Preparation of Compound L-12d

Compound L-12d was prepared by a similar method to the preparation method of the compound L-11-1 of Preparation Example 11, thereby obtaining a compound L-12d.

$^1$H NMR (400 MHz, CDCl$_3$) δ 3.68-3.64 (m, 32H), 3.38 (t, J=4.8 Hz, 4H). EI-MS m/z: 487 (M+Na)

Preparation of Compound L-12e

To a solution of compound L-12d (1.22 g, 2.63 mmol) in Ether (5 ml), THF (10 mL) and distilled water (5 mL) at room temperature under a nitrogen atmosphere was added triphenylphosphine (758 mg, 2.89 mmol) and stirred overnight at room temperature. After the reaction was completed, the reaction mixture was concentrated under reduced pressure, and the the mixture was dissolved in 1,4-dioxane (6 mL), NaHCO$_3$ (441.2 mg, 5.25 mmol) and Boc$_2$O (678 mg, 3.15 mmol) were dropwise added, and stirred for 6 hours at room temperature. After the reaction was completed, the reaction mixture was extracted with EA (50 mL) and distilled water (20 mL). The organic layer was dried over anhydrous Na$_2$SO$_4$, filtered and concentrated under reduced pressure. The residue was purified by column chromatography to obtain compound L-12e (1.0 g, 79%). EI-MS m/z: 538 (M$^+$).

Preparation of Compound L-12

Compound L-12e (1.0 g, 1.86 mmol) was dissolved in ethanol (5 mL), 5% Pd/C (435 mg, 0.204 mmol) was added thereto, and the mixture was stirred at the room temperature for 1 hour while injecting hydrogen gas. After the reaction was completed, the mixture was filtered by celite, and then concentrated under reduced pressure to obtain compound L-12 (909.3 mg, 96%).

[Preparation Example 13] Preparation of Linkers L-13-1 and L-13-2

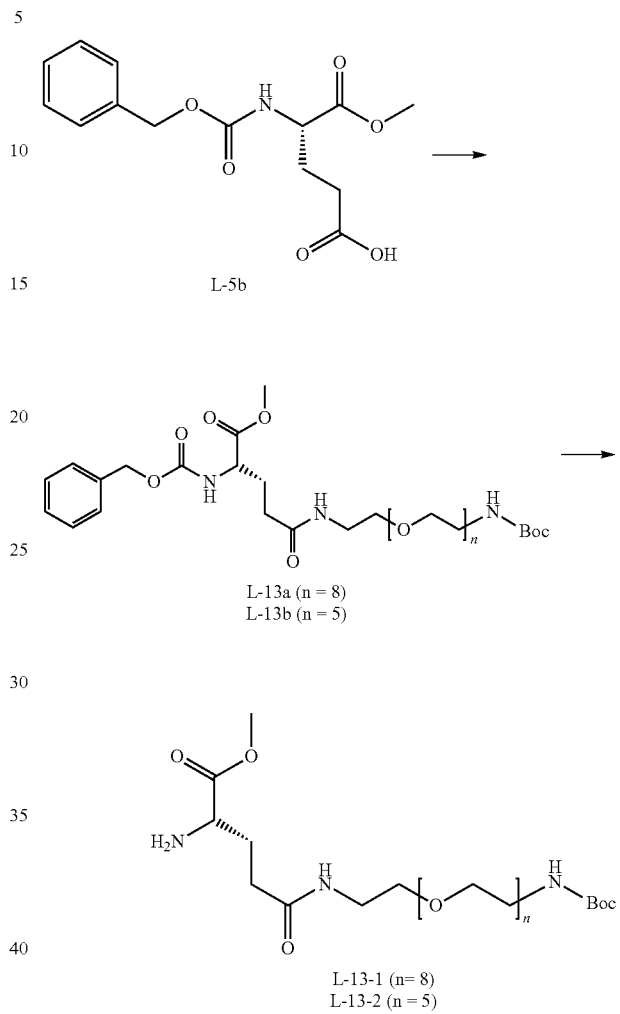

Preparation of Compound L-13a

Compound L-13a was prepared by a similar method to the preparation method of the compound L-5c of Preparation Example 5, thereby obtaining the compound L-13a (Yield 80%). EI-MS m/z: 790 (M$^+$).

Preparation of Compound L-13-1

Compound L-13-1 was prepared by a similar method to the preparation method of the compound L-5 of Preparation Example 5, thereby obtaining the compound L-13-1 (Yield 98%). EI-MS m/z: 656 (M$^+$).

Preparation of Compound L-13b

Compound L-13b was prepared by a similar method to the preparation method of the compound L-5c of Preparation Example 5, thereby obtaining the compound L-13b (Yield 98%). EI-MS m/z: 658 (M$^+$)).

Preparation of Compound L-13-2

Compound L-13-2 was prepared by a similar method to the preparation method of the compound L-5 of Preparation Example 5, thereby obtaining the compound L-13-2 (Yield 99%). EI-MS m/z: 524 (M$^+$).

[Preparation Example 14] Preparation of Ligand-Linker L-14

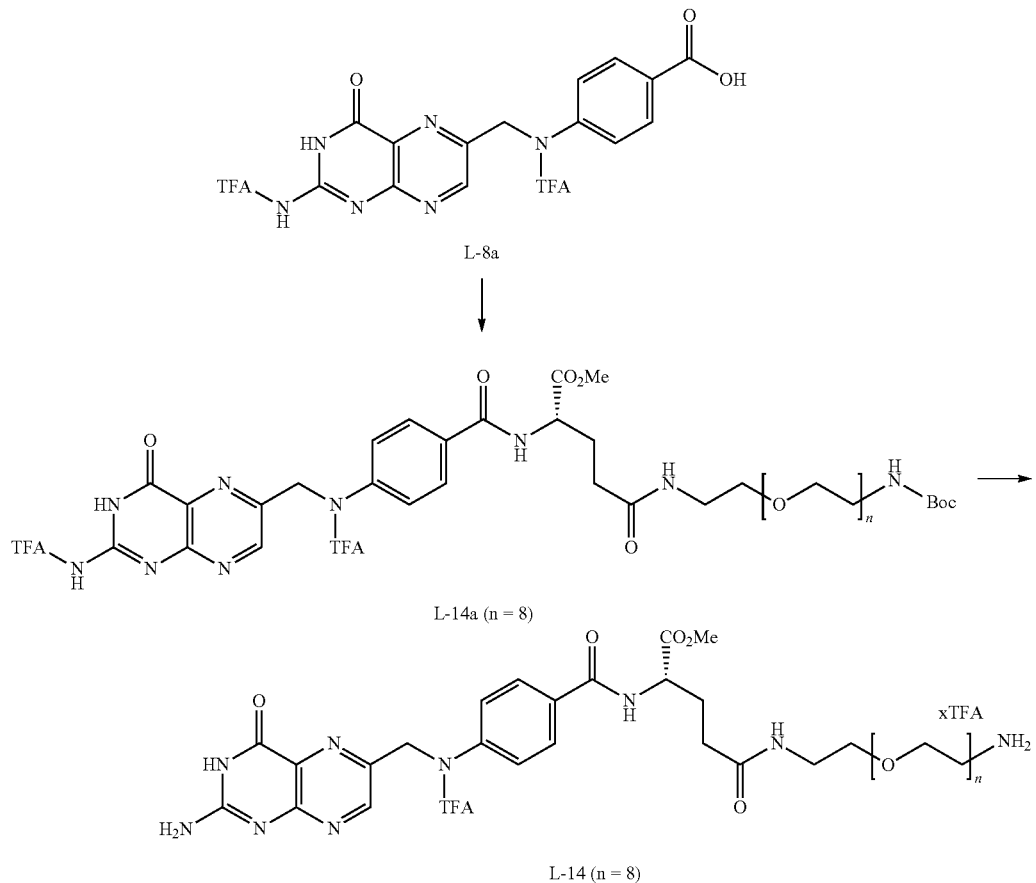

Preparation of Compound L-14a

Compound L-9b was prepared by a similar method to the preparation method of the compound L-8b of Preparation Example 8m thereby obtaining the compound L-14a (Yield 53%). EI-MS m/z: 1046 (M+).

Preparation of Compound L-14

Compound L-14 was prepared by a similar method to the preparation method of the compound L-8c of Preparation Example 8, thereby obtaining the compound L-14 (Yield 99%). EI-MS m/z: 946 (M+).

[Preparation Example 15] Preparation of Linker L-16

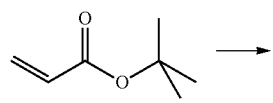

-continued

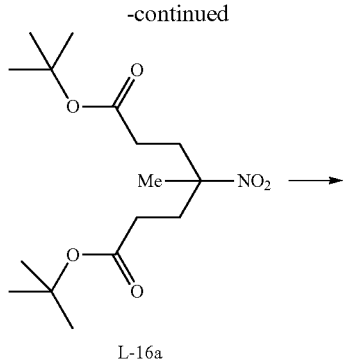

L-16a

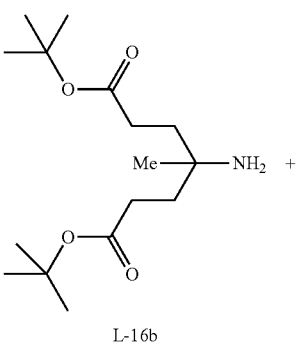

L-16b

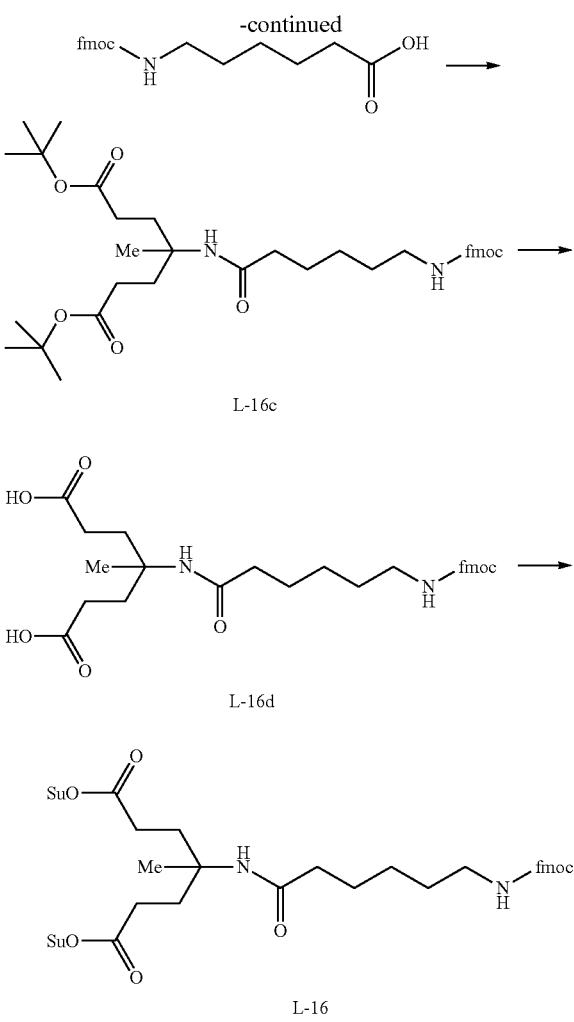

To a solution of Nitroethane (7.5 g, 100 mmol) in DME (1,2-dimethoxyethane) (20 mL) was added tetramethylammonium hydroxide pentahydrate (540 mg), and then t-butyl acrylate (30.7 mL, 210 mmol) was added dropwise for 10 minutes at 75° C. Tetramethylammonium hydroxide pentahydrate (540 mg) was further added, then the mixture was stirred for 30 minutes. Then tetramethylammonium hydroxide pentahydrate (540 mg) was added at room temperature, the reaction mixture was concentrated under reduced pressure and extracted with EA (200 mL) and 0.1 N HCl solution (50 mL). The organic layer was dried over anhydrous $Na_2SO_4$, filtered and concentrated under reduced pressure to obtain compound L-16a (30.9 g, 93.3%).

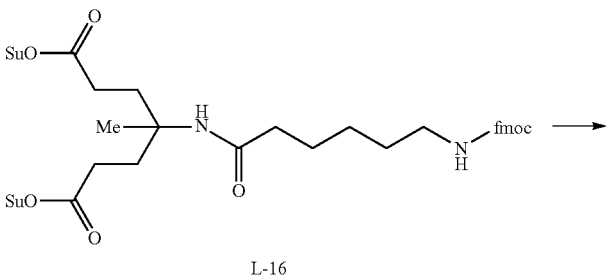

Preparation of Compound L-16b

Compound L-16a (3.0 g, 9.05 mmol) was dissolved in ethanol (20 mL). Raney Ni was added thereto, and the mixture was stirred at room temperature for 3 hours while injecting hydrogen gas at room temperature. After the reaction was completed, the mixture was filtered by celite to remove Raney Ni and concentrated under reduced pressure to obtain compound L-16b (2.72 g, quant.). EI-MS m/z: 302 ($M^+$).

Preparation of Compound L-16c

Compound L-16b (1.5 g, 4.98 mmol) and 6-(Fmoc-amino)hexanoic acid (1.76 g, 4.98 mmol, CAS No. 88574-06-5) were dissolved in DMF (10 mL) at room temperature under a nitrogen atmosphere, and then, PyBOP (3.11 g, 5.97 mmol), DIPEA (1.3 mL, 7.46 mmol) were added, the mixture was stirred for 5 hours at room temperature. After the reaction was completed, the reaction mixture was extracted with EA (20 mL) and distilled water (20 mL). Then the organic layer was dried over anhydrous $Na_2SO_4$, filtered and concentrated under reduced pressure. The residue was purified by column chromatography to obtain compound L-16c (2.66 g, 84%).

$^1$H NMR (400 MHz, $CDCl_3$) δ 7.76 (d, J=8.0 Hz, 2H), 7.60 (d, J=7.2 Hz, 2H), 7.40 (t, J=7.6 Hz, 2H), 7.31 (t, J=7.6 Hz, 2H), 5.79 (s, 1H), 5.30 (s. 1H), 4.39 (d, J=7.2 Hz, 2H), 4.21 (t, J=7.2 Hz, 1H), 3.20 (q, J=6.0, 5.2 Hz, 1H), 5.10 (s, 2H), 4.38 (q, J=8.0, 3.2 Hz, 1H), 2.24 (t, J=7.6 Hz, 4H), 2.12-2.04 (m, 4H), 1.92-1.85 (m, 2H), 1.66-1.59 (m, 2H), 1.55-1.51 (m, 2H), 1.43 (s, 18H), 1.36-1.32 (m, 2H), 1.29 (s, 3H); EI-MS m/z: 637 ($M^+$).

Preparation of Compound L-16d

To a solution of compound L-16c (2.66 g, 4.18 mmol) in DCM (20 mL) at 0° C. under a nitrogen atmosphere was added TFA (5 mL) and stirred for 4.5 hours at room temperature. After the reaction was completed, the mixture was concentrated under reduced pressure four times by using toluene (20 mL) as a co-solvent, thereby removing TFA. The compound L-16d was used directly in the next step without further purification (1.77 g, 81%).

$^1$H NMR (400 MHz, DMSO-$d_6$) δ 12.02 (s, 1H), 7.89 (d, J=8.0 Hz, 2H), 7.53 (d, J=7.6 Hz, 2H), 7.41 (t, J=7.2 Hz, 2H), 7.33 (t, J=7.2 Hz, 2H), 7.26 (t, J=7.6 Hz, 1H) 7.20 (s, 1H), 4.28 (d, J=6.8 Hz, 2H), 4.20 (t, J=7.2 Hz, 1H), 2.95 (q, J=8.0, 6.4 Hz, 2H), 2.16-2.10 (m, 4H), 2.04-2.01 (m, 4H), 1.73-1.66 (m, 2H), 1.46-1.37 (m, 4H), 1.26-1.16 (m, 2H), 1.08 (s, 3H); EI-MS m/z: 525 ($M^+$).

Preparation of Compound L-16

Compound L-16d (500 mg, 0.95 mmol) was dissolved in THF (5 mL) at room temperature under a nitrogen atmosphere and then DCC (432.6 mg, 2.10 mmol) and NHS (N-hydroxysuccinimide) (241.3 mg, 2.10 mmol) were added, the mixture was stirred overnight at room temperature. After the reaction was completed, EA (1 mL) and Ether (10 mL) were added thereto. The mixture was filtered, and concentrated under reduced pressure to obtain L-16 (526 mg, 77%). EI-MS m/z: 719 ($M^+$).

[Preparation Example 16] Preparation of Ligand-Linker L-18 and L-19

73 74
-continued
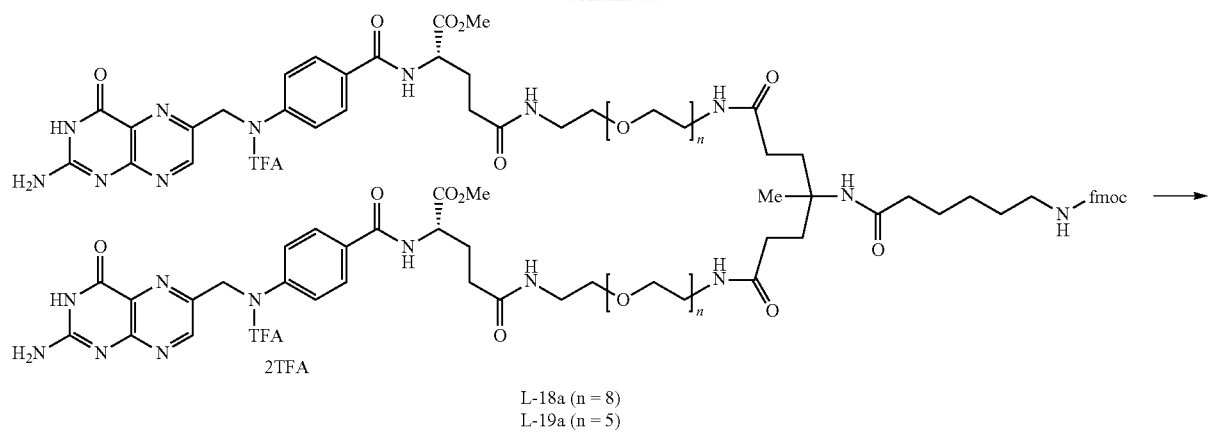
L-18a (n = 8)
L-19a (n = 5)
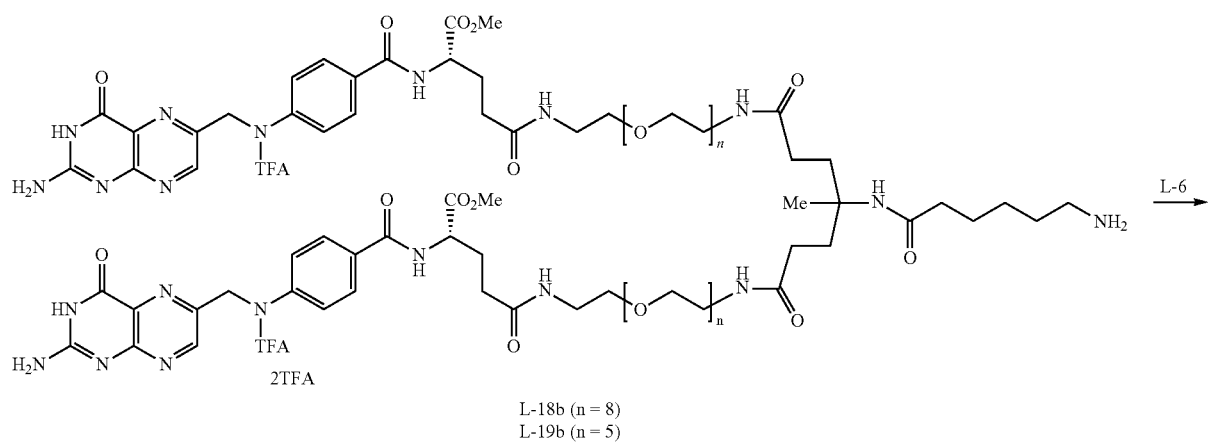
L-18b (n = 8)
L-19b (n = 5)
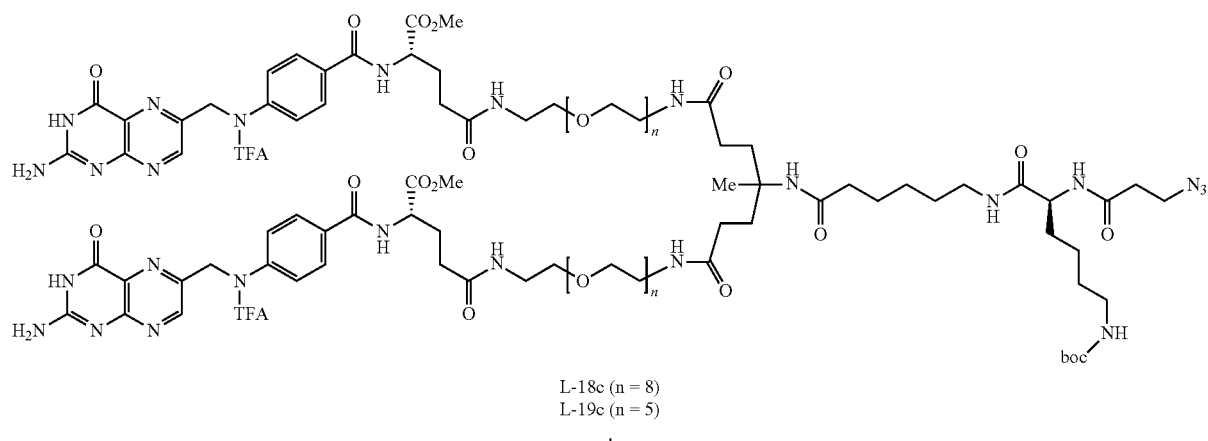
L-18c (n = 8)
L-19c (n = 5)

-continued

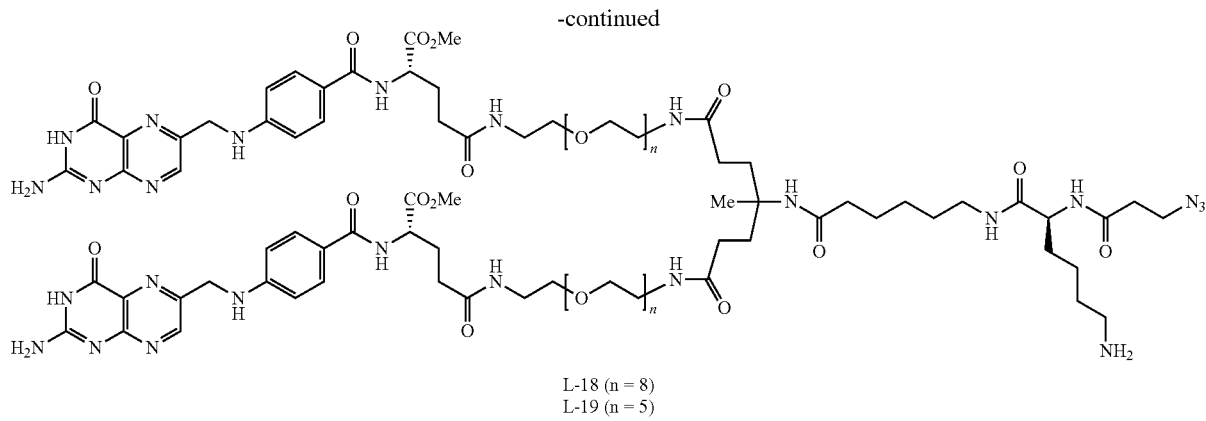

L-18 (n = 8)
L-19 (n = 5)

Preparation of Compound L-18a

Compound L-18a was prepared by a similar method to the preparation method of the compound L-8d of Preparation Example 8, using compound L-16 and compound L-14. Yield 52%; EI-MS m/z: 2381 ($M^+$).

Preparation of Compound L-18b

To a solution of compound L-18a (261.3 mg, 0.1 mmol) in DMF (4 mL) under a nitrogen atmosphere was added dropwise piperidine (0.06 mL, 0.6 mmol). The mixture was stirred for 4 hours at room temperature. After the reaction was completed, methanol (5 mL) and EA (15 mL) were added, and a brown solid was collected by filtration, washed with EA and ether to obtain compound L-18b (172.5 mg, Yield 80%). EI-MS m/z: 2484 ($M^+$).

Preparation of Compound L-18c

Compound L-18c was prepared by a similar method to the preparation method of the compound L-8d of Preparation Example 8, using compound L-18b and compound L-6. EI-MS m/z: 2484 ($M^+$).

Preparation of Compound L-18

Compound L-18 was prepared by a similar method to the preparation method of the compound L-8 of Preparation Example 8, using compound L-18c. Yield 30%; EI-MS m/z: 2164 ($M^+$).

Preparation of Compound L-19a

Compound L-19a was prepared by a similar method to the preparation method of the compound L-18a using compound L-16 and compound L-9c. Yield 40%; EI-MS m/z: 2117 ($M^+$).

Preparation of Compound L-19b

Compound L-19b was prepared by a similar method to the preparation method of the compound L-18b using compound L-19a. Yield 57%; EI-MS m/z: 1894 ($M^+$).

Preparation of Compound L-19c

Compound L-19c was prepared by a similar method to the preparation method of the compound L-18c using compound L-19c and compound L-6. Yield 63%; EI-MS m/z: 2219 ($M^+$).

Preparation of Compound L-19

Compound L-19 was prepared by a similar method to the preparation method of the compound L-18d using compound L-19c. Yield 20%; EI-MS m/z: 1899 ($M^+$).

[Preparation Example 17] Preparation of Linker L-20

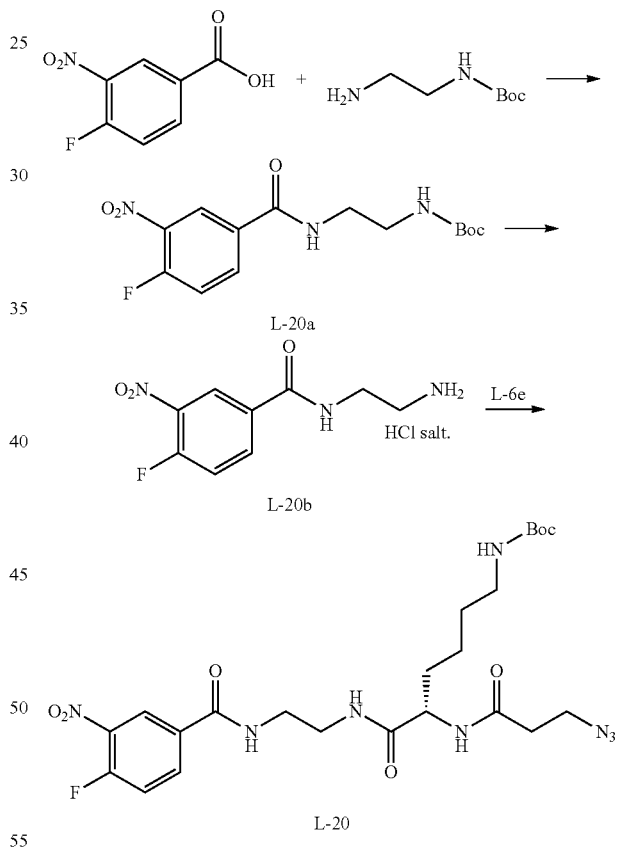

Preparation of Compound L-20a

A solution of 4-fluoro-3-nitrobenzoic acid (500 mg, 2.70 mM) and N-Boc-ethylenediamine (433 mg, 2.70 mM) in DCM (10 mL) at 0° C. under a nitrogen atmosphere was added EDC HCl (1-(3-Dimethylaminopropyl)-3-ethylcarbodiimide hydrochloride) (621 mg, 3.24 mM), and then the mixture was stirred for 2 hours at the same temperature. After the reaction was completed, the mixture was extracted with DCM (100 mL), distilled water (100 mL), and brine (100 mL). Then, the organic layer was dried over anhydrous $Na_2SO_4$, filtered and concentrated under reduced pressure.

The residue was purified by column chromatography to obtain compound L-20a (814 mg, 97%).

¹H NMR (400 MHz, CD3OD) δ 8.58 (m, 1H), 8.20 (m, 1H), 7.53 (m, 1H), 3.45 (t, J=6.0 Hz, 2H), 3.27 (t, J=6.0 Hz, 2H), 1.41 (s, 9H).

Preparation of Compound L-20b

To a solution of compound L-20a (375 mg, 1.14 mM) in ACN (6 mL) at 0° C. was added dropwise 4M-HCl/dioxane (2 mL), and then the mixture was stirred for 1 hour. After the reaction was completed, the mixture was concentrated under reduced pressure and dried under high vacuum to obtain compound L-20b (302 mg, 99%).

¹H NMR (400 MHz, CD₃OD) δ 8.64 (dd, J=6.8, 2.0 Hz, 1H), 8.24 (m, 1H), 7.56 (dd, J=10.8, 8.8 Hz, 1H), 3.68 (t, J=6.0 Hz, 2H), 3.18 (t, J=6.0 Hz, 2H).

Preparation of Compound L-20

A solution of compound L-20b (302 mg, 1.14 mM) and L-6e (377 mg, 1.14 mM) in DMF (6 mL) at 0° C. under a nitrogen atmosphere were added TEA (Triethylamine) (320 μL, 2.29 mM) and EDC.HCl (220 mg, 1.37 mM) and the mixture was stirred for 2 hours at the same temperature. After the reaction was completed, the mixture was extracted with EA (100 mL), distilled water (100 mL), and brine (100 mL). Then, the organic layer was dried over anhydrous Na₂SO₄, filtered and concentrated under reduced pressure. The residue was purified by column chromatography to obtain compound L-20 (417 mg, 69%). EI-MS m/z: 553 (M⁺).

[Preparation Example 18] Preparation of Ligand-Linker L-21

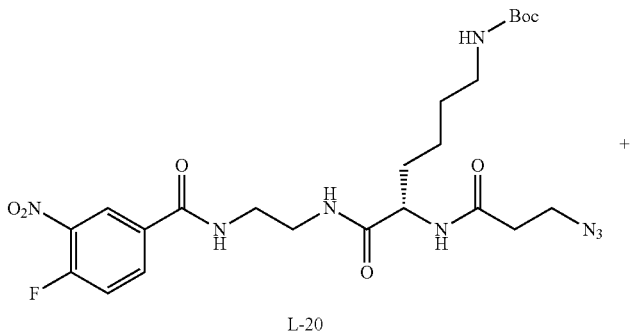

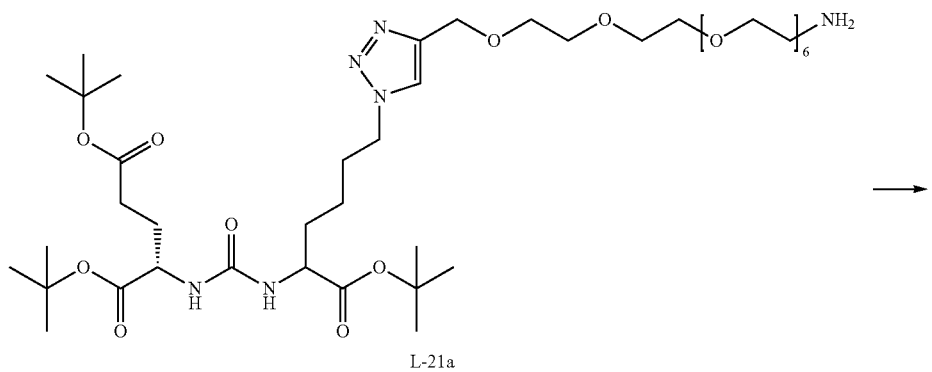

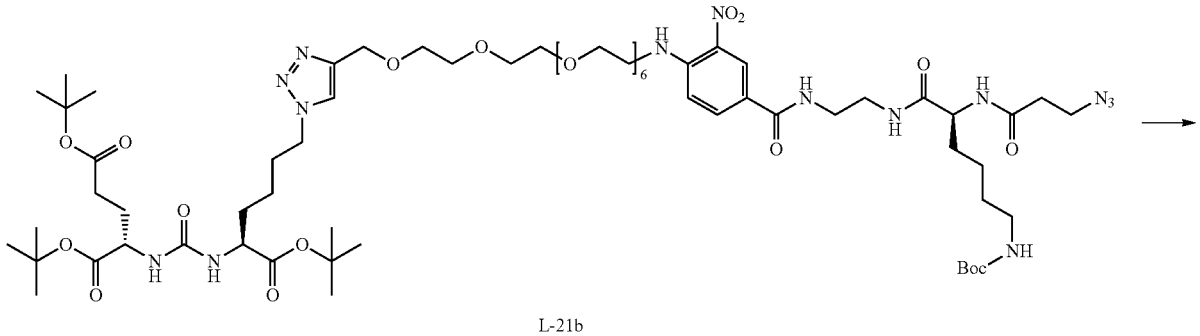

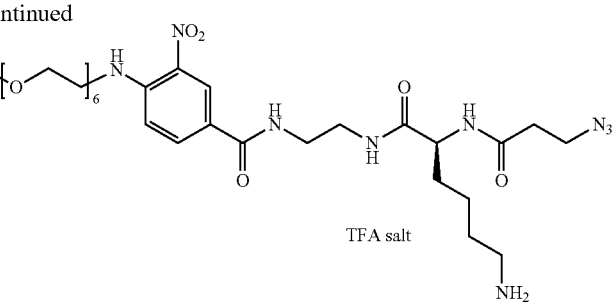
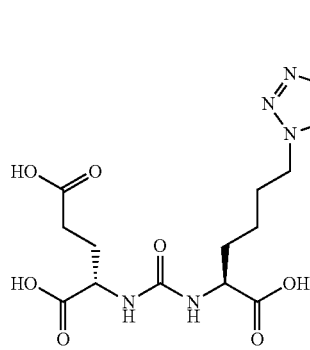

L-21

Preparation of Compound L-21b

A solution of compound L-21a (166 mg, 0.172 mM) obtained by performing a reaction in a similar method described in 'J. AM. CHEM. SOC. 2010, 132, 12711-12716' and compound L-20 (57 mg, 0.103 mM) in DCM (2 mL) at 0° C. under a nitrogen atmosphere was added DIPEA (Diisopropylamine) (60 µL, 0.34 mM), and then the mixture was stirred for 3 hours at room temperature. After the reaction was completed, the mixture was extracted with EA (100 mL), distilled water (100 mL), and brine (100 mL). Then, the organic layer was dried over anhydrous $Na_2SO_4$, filtered and concentrated under reduced pressure. The residue was purified by column chromatography to obtain compound L-21b (87 mg, 56%). EI-MS m/z: 1498 (M+).

Preparation of Compound L-21

To a solution of compound L-21b (32 mg, 0.021 mM) in DCM (1.5 mL) at 0° C. was added dropwise TFA (0.5 mL), and stirred for 3 hours at room temperature. After the reaction was completed, the mixture was concentrated under reduced pressure and dried in vacuum to obtain compound L-21(26.2 mg, 99%). EI-MS m/z: 1498 (M+), 615 (M+/2).

[Preparation Example 19] Preparation of Linker L-22

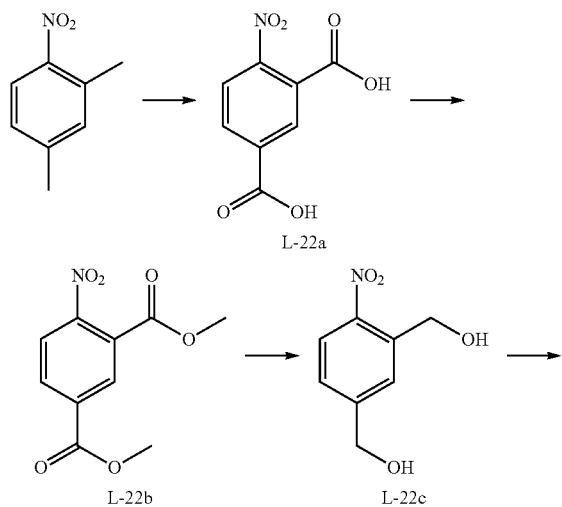

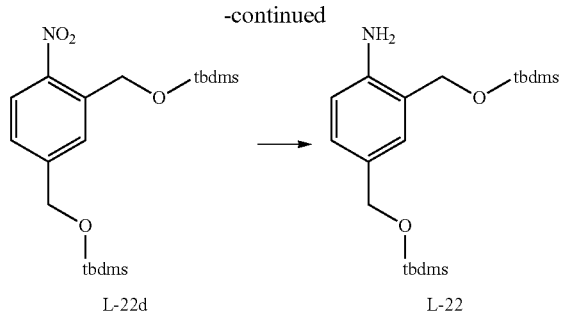

Preparation of Compound L-22a

To a solution of 2,4-dimethyl-1-nitrobenzene (4.0 g, 26.46 mmol) in distilled water (100 mL) at room temperature under a nitrogen atmosphere was added $KMnO_4$ (21 g, 132.30 mmol). After stirring for 28 hours at 110° C., the mixture was extracted with 2N HCl aqueous solution (300 mL). Then, the organic layer was dried over anhydrous $Na_2SO_4$, filtered and concentrated under reduced pressure. The residue was purified by column chromatography to obtain compound L-22a (4.42 g, 81%).

$^1$H NMR (400 MHz, DMDO-$d_6$) δ 8.32 (s, 1H), 8.25 (d, J=8.4 Hz, 1H), 8.07 (d J=8.4 Hz, 1H).

Preparation of Compound L-22b

To a solution of compound L-22a (4.4 g, 20.84 mmol) in methanol (50 mL) at room temperature under a nitrogen atmosphere was added $H_2SO_4$ (2 mL), and stirred for 3 hours at 75° C. After the reaction was completed, the reaction mixture was extracted with EA (500 mL) and $NaHCO_3$ (300 mL), and then organic layer was dried over anhydrous $Na_2SO_4$, filtered and concentrated under reduced pressure. The residue was purified by column chromatography to obtain compound L-22b (2.0 g, 40%).

$^1$H NMR (400 MHz, CDCl$_3$) δ 8.45 (s, 1H), 8.29 (d, J=7.2 Hz, 1H), 7.93 (d, J=8.0 Hz, 1H), 3.99 (s, 3H), 3.96 (s, 3H).

Preparation of Compound L-22c

To a solution of compound L-22b (2.0 g, 8.36 mmol) in THF (50 mL) at room temperature under a nitrogen atmosphere was added LiBH$_4$ (17 mL, 33.45 mmol) dissolved in THF, and stirred for 24 hours. After the reaction was completed, methanol (0.5 mL) was added thereto. The mixture was extracted with EA (500 mL) and 2N HCl (200 mL), and organic layer was dried over anhydrous $Na_2SO_4$, filtered and concentrated under reduced pressure. The residue was purified by column chromatography to obtain compound L-22c (751 mg, 51%).

¹H NMR (400 MHz, CDCl₃) δ 8.13 (d, J=8.4 Hz, 1H), 7.74 (s, 1H), 7.48 (d, J=8.4 Hz, 1H), 5.00 (d, J=6.0 Hz, 2H), 4.84 (d, J=4.8 Hz, 2H), 2.53 (t, J=6.4 Hz, 1H), 1.91 (t, J=5.6 Hz, 1H).

Preparation of Compound L-22d

To a solution of compound L-22c (750 mg, 4.09 mmol) in THF (20 mL) at 0° C. under a nitrogen atmosphere were added TBDMS-Cl (tert-butyldimethylsilyl chloride) (1.54 g, 10.24 mmol) and imidazole (697 mg, 10.24 mmol) and stirred for 3 hours at room temperature. After the reaction was completed, the reaction mixture was extracted with EA (500 mL) and distilled water (200 mL), and then organic layer was dried over anhydrous Na₂SO₄, filtered and concentrated under reduced pressure. The residue was purified by column chromatography to obtain compound L-22d (1.2 g, 75%).

¹H NMR (400 MHz, CDCl₃) δ 8.09 (d, J=8.4 Hz, 1H), 7.88 (s, 1H), 7.36 (d, J=8.4 Hz, 1H), 5.11 (s, 2H), 4.82 (s, 2H), 0.97 (s, 9H), 0.95 (s, 9H), 0.15 (s, 6H), 0.13 (s, 6H).

Preparation of Compound L-22

To a solution of compound L-22d (1 g, 2.43 mmol) in methanol (25 mL) at room temperature was added 10% Pd/C (78 mg, 0.73 mmol), and the mixture was stirred for one hour while injecting hydrogen gas at the same temperature. After the reaction was completed, the mixture was filtered by celite, and concentrated under reduced pressure to obtain compound L-22 (578 mg, 62%).

¹H NMR (400 MHz, CDCl₃) δ 7.05 (d, J=7.6 Hz, 1H), 6.99 (s, 1H), 6.63 (d, J=8.0 Hz, 1H), 4.67 (s, 2H), 4.61 (s, 2H), 4.15 (br, 2S), 0.92 (s, 9H), 0.89 (s, 9H), 0.07 (s, 12H).

[Preparation Example 20] Preparation of Ligand-Linker L-23

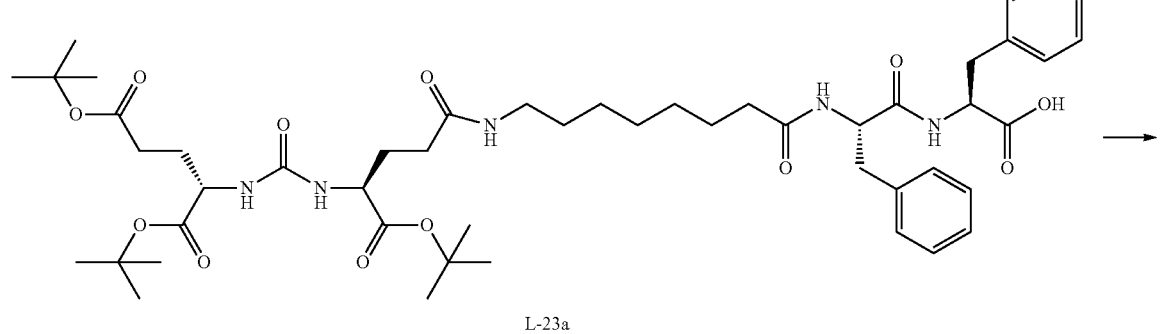

L-23a

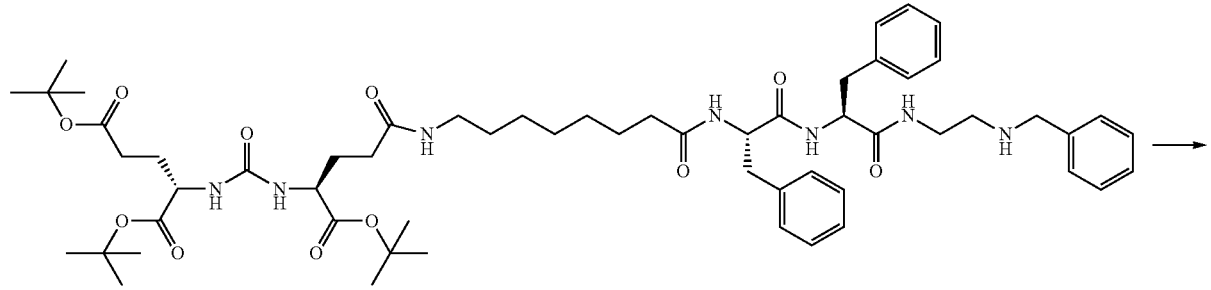

L-23b

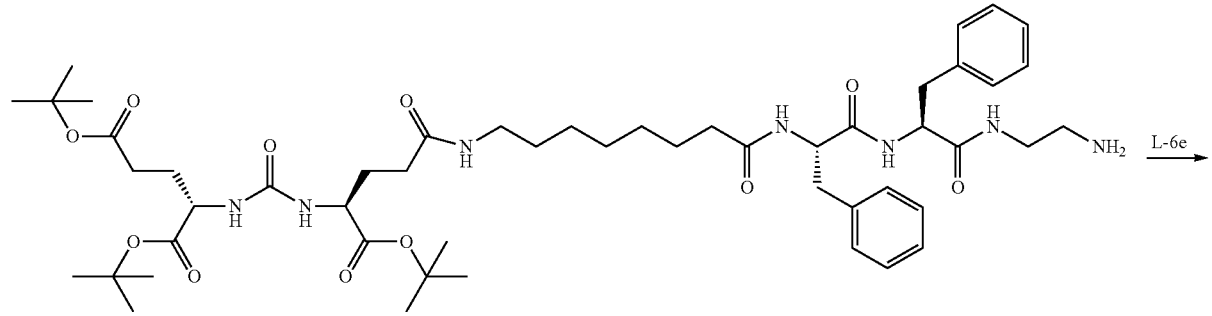

L-23c

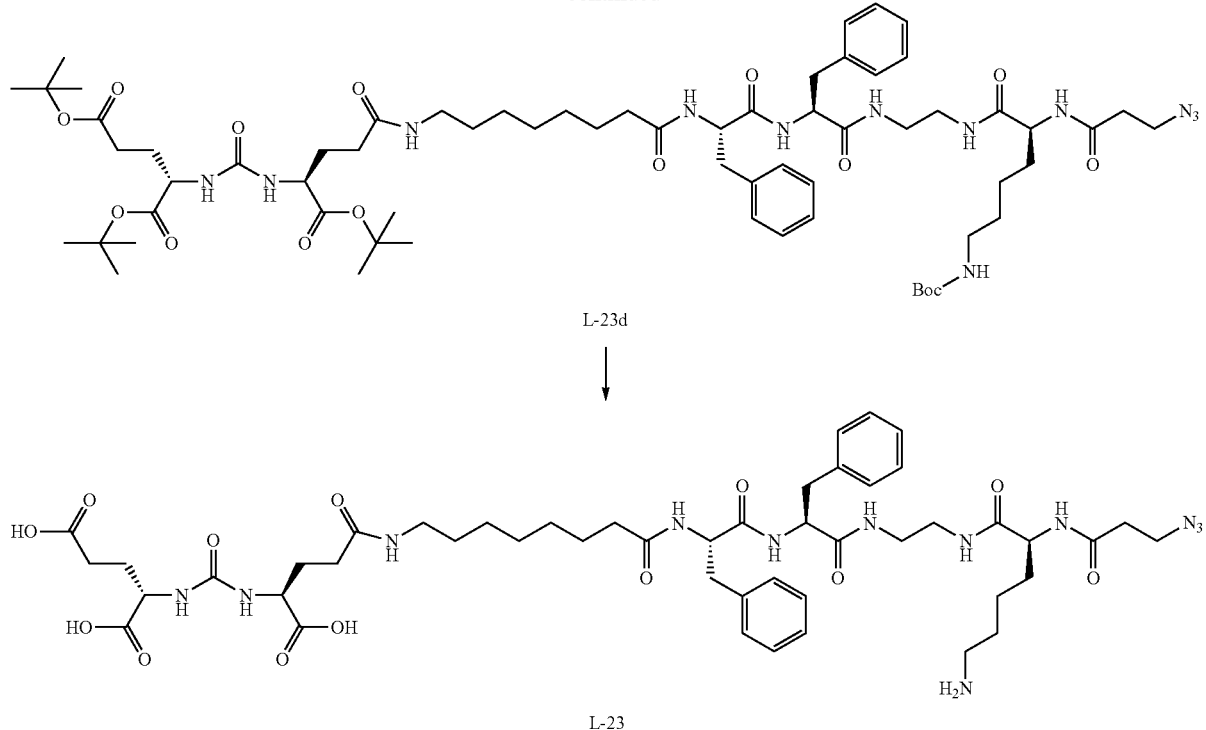

L-23d

L-23

Preparation of Compound L-23a

Compound L-23a was obtained by a similar method described in WO2009/026177 and *J. Med. Chem.* 2015, 58, 3094-3103.

Preparation of Compound L-23b

A solution of compound L-23a (90 mg, 0.097 mM) and N-Benzylethylenediamine (17.5 mg, 0.116 mM) in DMF (3 mL) at 0° C. under a nitrogen atmosphere were added HBTU (48 mg, 0.126 mM) and DIPEA (52 μL, 0.29 mM), and then the mixture was stirred for 2 hours at room temperature. After the reaction was completed, the mixture was separated and purified with Prep-HPLC to obtain compound L-23b (35 mg, 30%). EI-MS m/z: 1079 (M$^+$Na), 1057 (M$^+$), 529 (M$^+$/2).

Preparation of Compound L-23c

To a solution of compound L-23b (30 mg, 0.028 mM) in ethanol (10 mL) was added 10% Pd/C (20 mg), and stirred for 3 hours under hydrogen atmosphere. After the reaction was completed, the reaction mixture was filtered by celite, and concentrated under reduced pressure to obtain compound L-23c (27 mg, 99%). EI-MS m/z: 989 (M$^+$Na)+, 967 (M+), 484 (M$^+$/2).

Preparation of Compound L-23d

A solution of compound L-23c (25 mg, 0.025 mM) and compound L-6e (17.7 mg, 0.050 mM) in DMF (2 mL) at 0° C. under a nitrogen atmosphere were added HBTU (14.7 mg, 0.037 mM) and DIPEA (13.8 μL, 0.075 mM) and stirred for 3 hours at room temperature. After the reaction was completed, the mixture was separated and purified with Prep-HPLC and the solution was lyophilized to obtain compound L-23d (18 mg, 54%). EI-MS m/z: 1292 (M$^+$), 646 (M$^+$/2).

Preparation of Compound L-23

To a solution of compound L-23d (8 mg, 0.006 mM) in DCM (2 mL) at 0° C. was added TFA (1 mL) was added dropwise and stirred for 2 hours at room temperature. After the reaction was completed, the mixture was concentrated under reduced pressure to obtain compound L-23(7 mg, 99%). EI-MS m/z: 1024 (M$^+$).

[Preparation Example 21] Preparation of Linker L-24

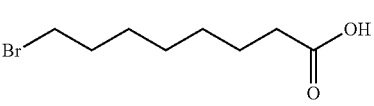

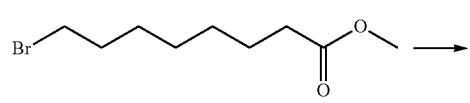

L-24a

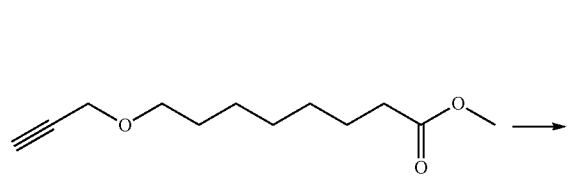

L-24b

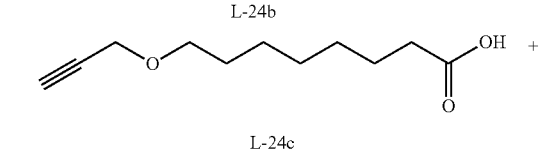

L-24c

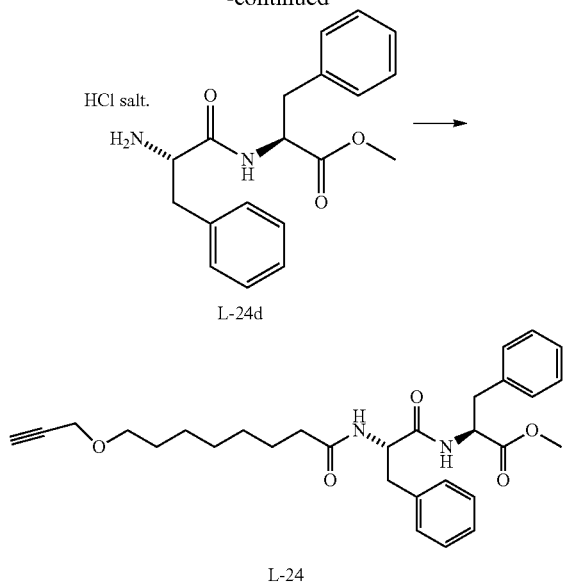

Preparation of Compound L-24a

To a solution of 8-bromooctanoic acid (1 g, 4.48 mM) in anhydrous methanol (20 mL) at 0° C. under a nitrogen atmosphere was slowly added thionyl chloride (3 mL) and stirred for 12 hours at room temperature. After the reaction was completed, the mixture was concentrated under reduced pressure and dried to obtain compound L-24a (1.06 g, 99%).

$^1$H NMR (400 MHz, CDCl$_3$) δ 3.66 (s, 3H), 3.40 (t, J=7.2 Hz, 2H), 2.30 (t, J=7.2 Hz, 2H), 1.84 (q, J=7.2 Hz, 2H), 1.61 (m, 2H), 1.43 (m, 2H), 1.36-1.31 (m, 4H).

Preparation of Compound L-24c

To a solution of propargyl alcohol (147 mg, 2.52 mM) in DMF (5 mL) was added dropwise NaH (60% dispersion in mineral oil, 70 mg) at 0° C. under a nitrogen atmosphere. After stirring at 0° C. rred for 10 minutes, compound L-24a (300 mg, 1.26 mM) dissolved in DMF (1 mL) was added dropwise. The mixture was stirred for 2 hours at 50° C. The mixture was cooled to 0° C. The mixture was extracted with EA (50 mL) and 2 M-HCl aqueous solution (50 mL), the the organic layer was dried over anhydrous MgSO$_4$, filtered and concentrated under reduced pressure. The obtained compound L-24b was dissolved in Methanol (5 mL) and 6N NaOH aqueous solution (2 mL) was added thereto. After the mixture was stirred for 4 hours at room temperature, the reaction mixture was extracted with EA (100 mL) and 2 M-HCl aqueous solution (100 mL). Then, the organic layer was dried over anhydrous Na$_2$SO$_4$, filtered and concentrated under reduced pressure. The residue was purified by column chromatography to obtain compound L-24c (150 mg, 60%).

$^1$H NMR (400 MHz, CDCl$_3$) δ 4.13 (s, 2H), 3.50 (t, J=6.4 Hz, 2H), 2.41 (s, 1H), 2.35 (t, J=7.2 Hz, 2H), 1.65-1.56 (m, 4H), 1.40-1.30 (m, 6H).

Preparation of Compound L-24d

To a solution of L-phenylalanine (3 g, 18.16 mM) in H$_2$O (15 mL) and 1,4-dioxane (15 mL) was added NaHCO$_3$ (2.28 g, 27.24 mM) and BOC anhydride (4.75 g, 21.79 mmol) at 0° C. and stirred for 16 hours at room temperature. After the reaction was completed, the reaction solution was concentrated under reduced pressure to reduce the volume by half. The mixture was extracted with diethylether (200 mL) and H$_2$O (100 mL) and then the water layer was acidified by 2 M-HCl aqueous solution (200 mL). The mixture was extracted with EA (200 mL) and the organic layer was dried over anhydrous Na$_2$SO$_4$, filtered and concentrated under reduced pressure to obtain BOC-L-phenylalanine (4 g, 83%). A solution of the obtained BOC-L-Phe-OH (460 mg, 1.73 mM) and H-Phe-OMe.HCl (411 mg, 1.90 mM) in DMF (5 mL) were added HBTU (790 mg, 2.07 mM) and DIPEA (617 μL, 3.46 mM) in turn, and stirred for 3 hours at room temperature. After the reaction was completed, the mixture was extracted with EA (100 mL), distilled water (100 mL), and brine (100 mL) and the organic layer was dried over anhydrous Na$_2$SO$_4$, filtered and concentrated under reduced pressure. The residue was purified by column chromatography to obtain compound BOC-L-Phe-Phe-OMe (680 mg, 92%). To a solution of BOC-L-Phe-Phe-OMe (300 mg, 0.70 mM) in DCM (8 mL) was added dropwise 4 M-HCl in Dioxane (1.5 mL) at 0° C., and stirred for 2 hours at room temperature. After the reaction was completed, the mixture was concentrated under reduced pressure, and washed with n-Hexane (100 mL) and dried under high vacuum to obtain compound L-24d (255 mg, 99%).

$^1$H NMR (400 MHz, CD3OD) δ 7.37-7.27 (m, 7H), 7.23-7.21 (m, 3H), 4.92 (m, 1H), 4.72 (m, 1H), 4.04 (m, 1H), 3.65 (s, 3H), 3.34-3.17 (m, 2H), 3.04-2.94 (m, 2H); EI-MS m/z: 327 (M$^+$), 654 (2M$^+$).

Preparation of Compound L-24

A solution of compound L-24d (140 mg, 0.385 mM) and compound L-24c (70 mg, 0.35 mM) in DMF (3 mL) at 0° C. under a nitrogen atmosphere were added HBTU (160 mg, 0.42 mM) and DIPEA (188 μL, 1.05 mM) in turn, and stirred for one hour at room temperature. After the reaction was completed, the mixture was extracted with EA (100 mL) and brine (100 mL). Then, the organic layer was dried over anhydrous Na$_2$SO$_4$, filtered and concentrated under reduced pressure. The residue was purified by column chromatography to obtain compound L-24 (156 mg, 87%).

$^1$H NMR (400 MHz, CDCl$_3$) δ 7.30-7.18 (m, 8H), 7.00-6.97 (m, 2H), 6.17 (d, J=7.6 Hz, 1H), 5.93 (d, J=8.0 Hz, 1H), 4.73 (m, 1H), 4.61 (m, 1H), 4.15-4.09 (m, 2H), 3.68 (s, 3H), 3.49 (t, J=6.8 Hz, 2H), 3.10-2.94 (m, 4H), 2.41 (t, J=2.4 Hz, 1H), 2.11 (m, 2H), 1.59-1.49 (m, 4H), 1.36-1.23 (m, 6H); EI-MS m/z: 507 (M$^+$).

[Preparation Example 22] Preparation of Ligand-Linker L-25

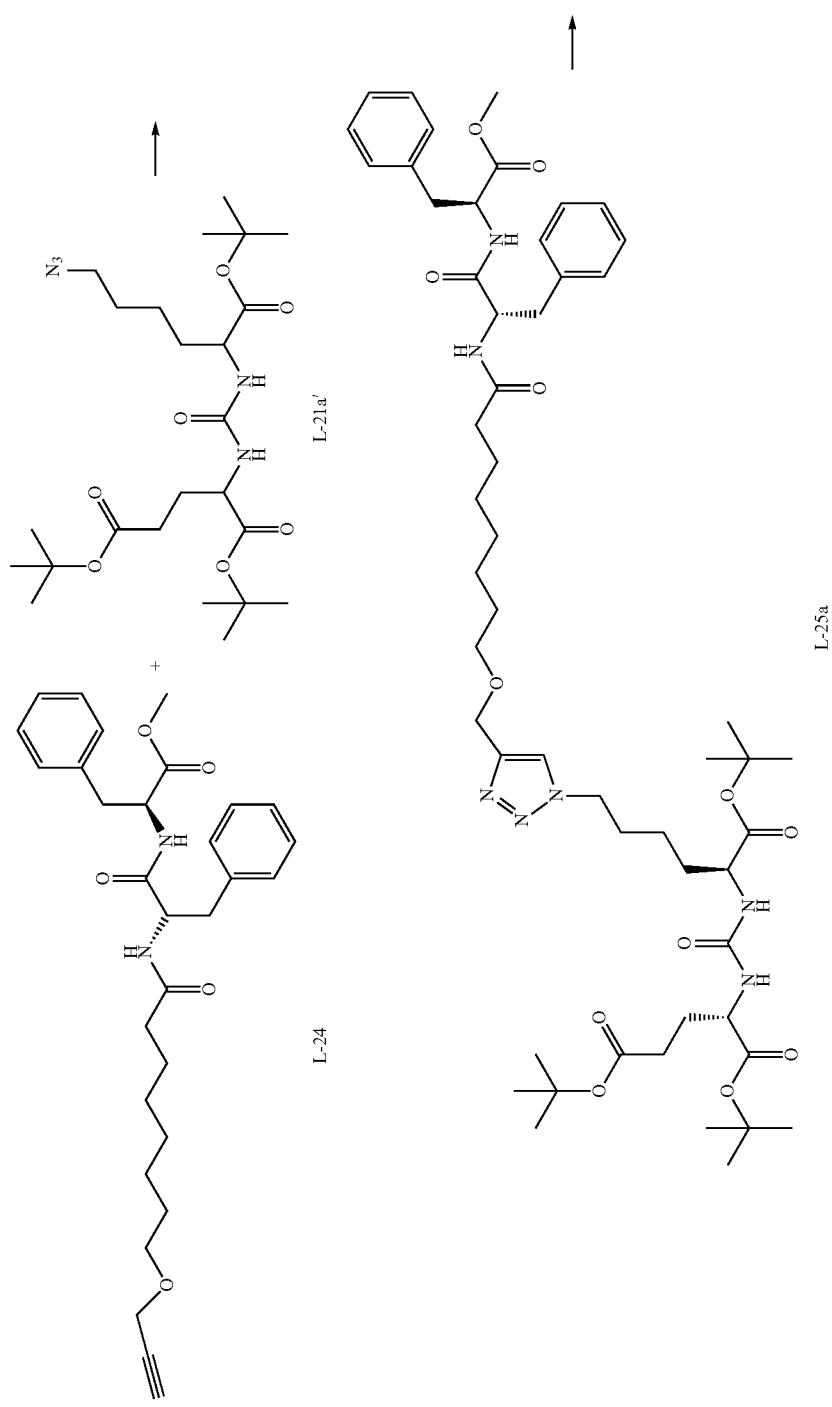

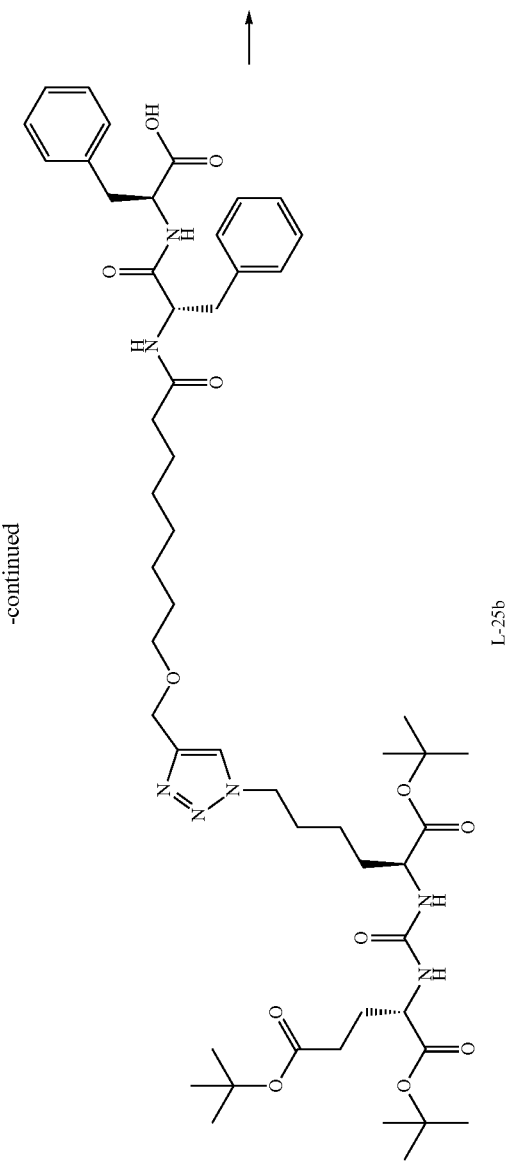

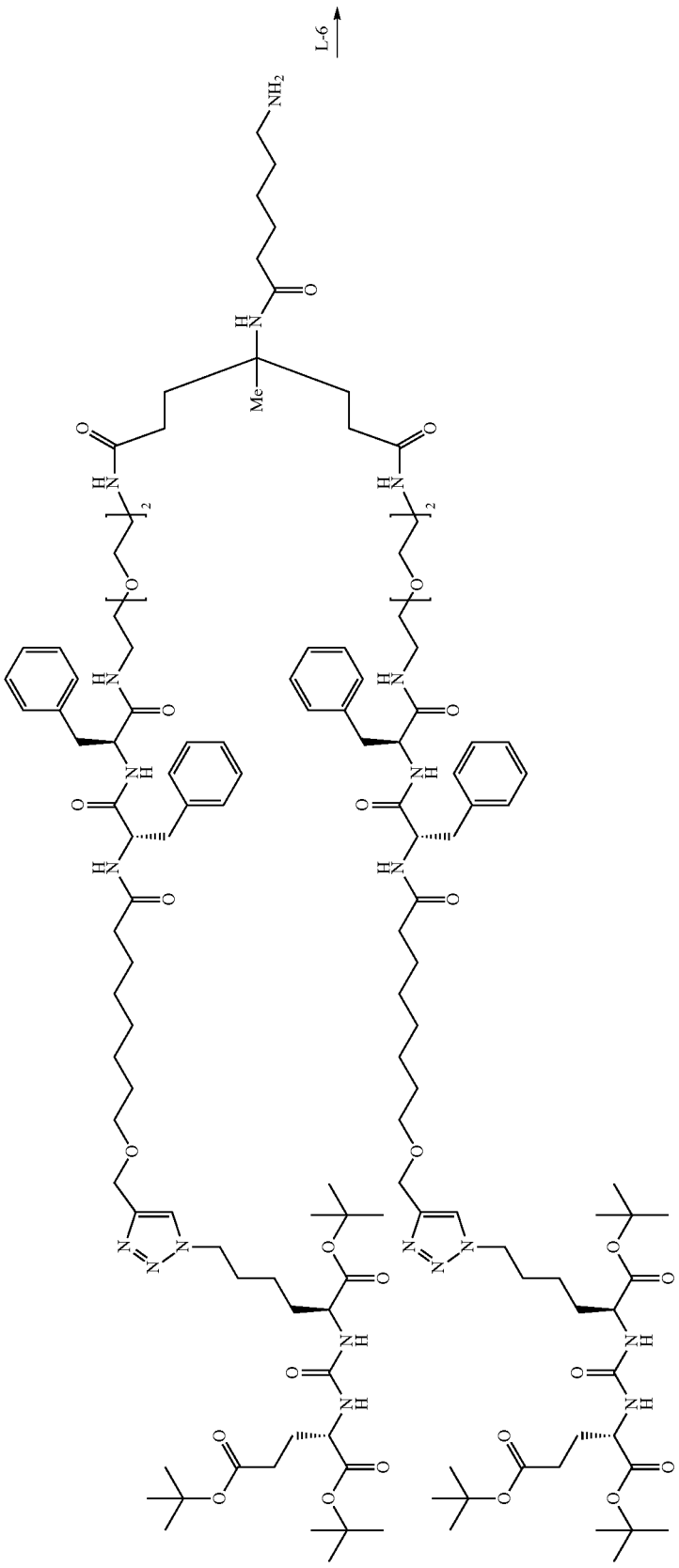

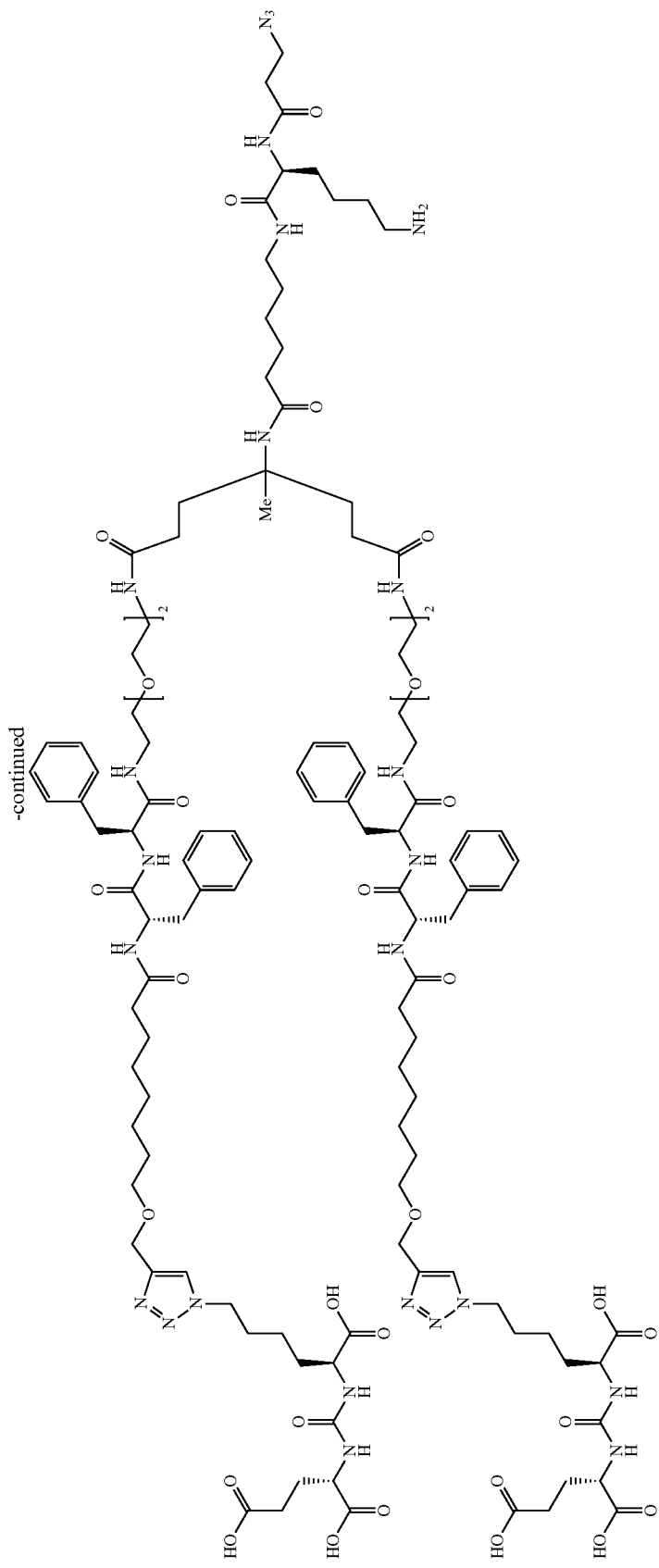
-continued
L-25

Preparation of Compound L-25a

A solution of compound L-24 (150 mg, 0.23 mM) and compound L-21a' (152 mg, 0.23 mM) in ethanol (5 mL) and DMSO (1 mL) were added 1 M-sodium ascorbate (50 μL) and 0.1 M-CuSO$_4$ (500 μL) in turn, and stirred for 1 hour at room temperature. After the reaction was completed, the mixture was extracted with EA (100 mL) and brine (100 mL). The organic layer was dried over anhydrous MgSO$_4$, filtered and concentrated under reduced pressure. The residue was purified by column chromatography to obtain compound L-25a (227 mg, 75%).

$^1$H NMR (400 MHz, CDCl$_3$) δ 7.54 (s, 1H), 7.29-7.16 (m, 8H), 7.03-6.99 (m, 2H), 6.44 (d, J=7.6 Hz, 1H), 6.23 (d, J=7.6 Hz, 1H), 5.47 (d, J=8.2 Hz, 1H), 5.38 (d, J=8.0 Hz, 1H), 4.79 (m, 1H), 4.67 (m, 1H), 4.61 (s, 2H), 4.37-4.22 (m, 4H), 3.67 (s, 3H), 3.49 (t, J=6.8 Hz, 2H), 3.10-2.96 (m, 4H), 2.37-2.26 (m, 2H), 2.13-2.04 (m, 3H), 1.92-1.72 (m, 3H), 1.65-1.48 (m, 6H), 1.45 (s, 9H), 1.42 (s, 18H), 1.31-1.22 (m, 6H); EI-MS m/z: 1021 (M$^+$).

Preparation of Compound L-25b

To a solution of compound L-25a (50 mg, 0.049 mM) in Methanol (3 mL) was slowly added the aqueous solution of NaOH (20 mg) dissolved in H$_2$O (1 mL) at 0° C., and stirred for one hour at room temperature. After the reaction was completed, the mixture was extracted with EA (50 mL) and 2 M-HCl aqueous solution (50 mL). Then, the organic layer was dried over anhydrous MgSO$_4$, filtered and concentrated under reduced pressure to obtain compound L-25b (49 mg, 99%). EI-MS m/z: 1007 (M$^+$).

Preparation of Compound L-25c

Compound L-25c was prepared by a similar method to the preparation method of the compounds L-8a, L-8b and L-8c, and compound L-18a and L-18b using the compound L-25b. Yield 19%; EI-MS m/z: 1270 (M$^+$/2).

Preparation of Compound L-25

Compound L-25 was prepared by a similar method to the preparation method of the compounds L-18c and L-18, using the compound L-25c. EI-MS m/z: 1215.3 (M$^+$/2)

[Preparation Example 23] Preparation of Ligand-Linker L-26

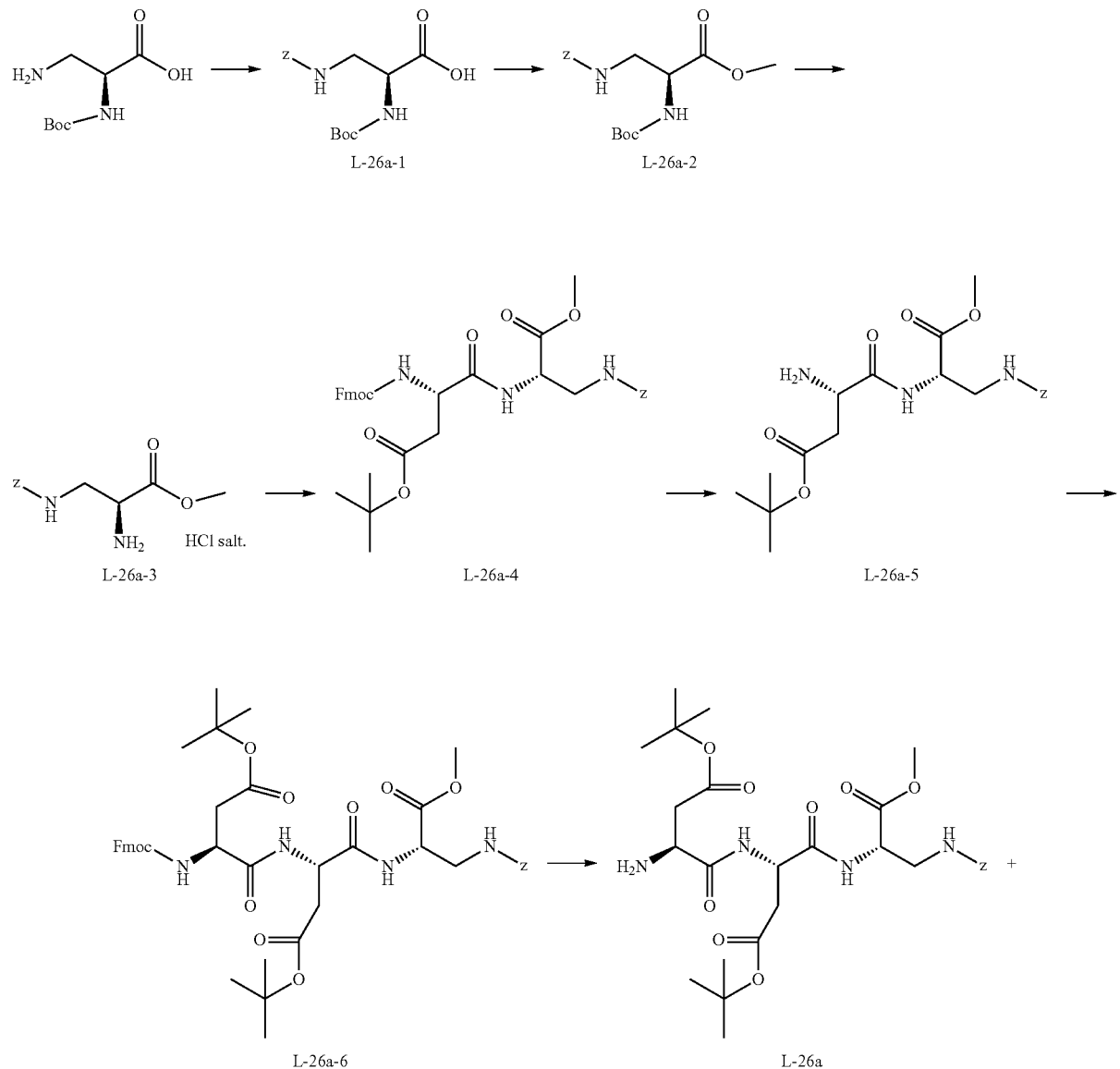

-continued
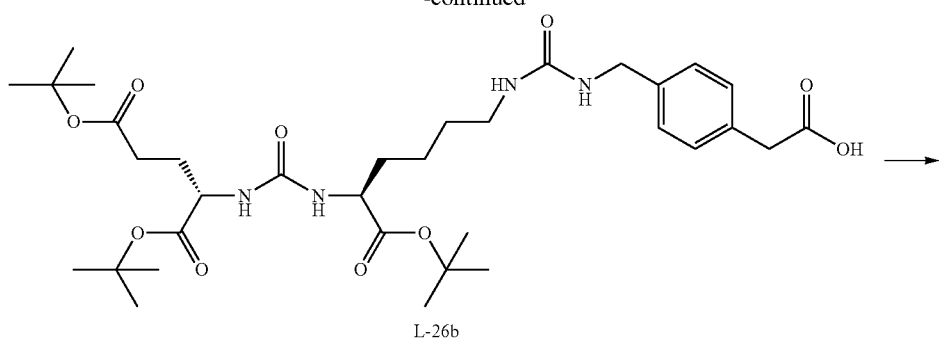
L-26b
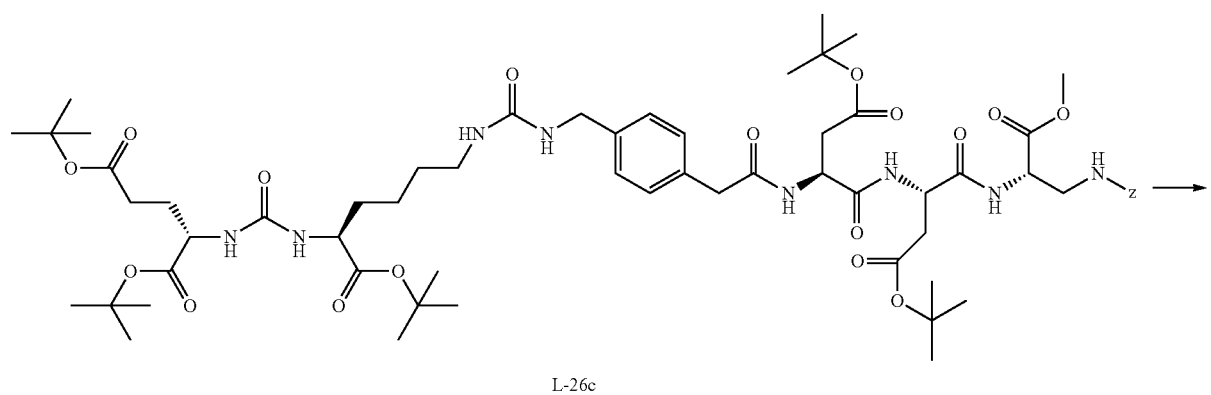
L-26c
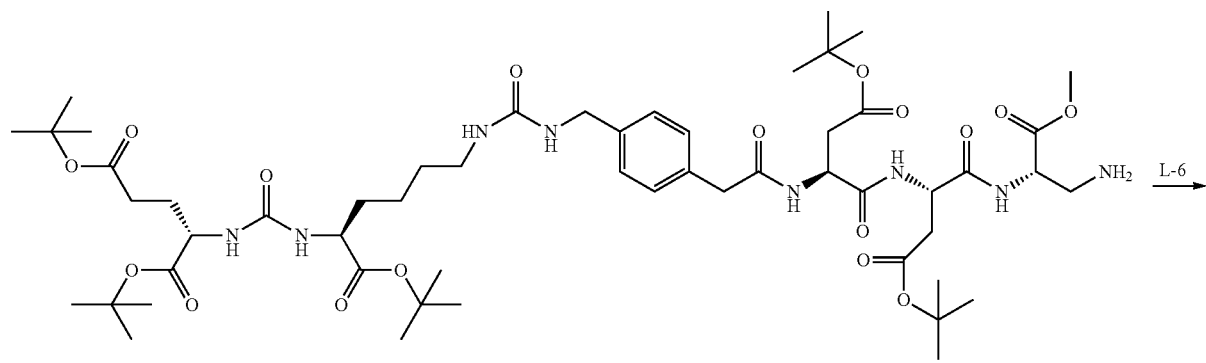
L-26d
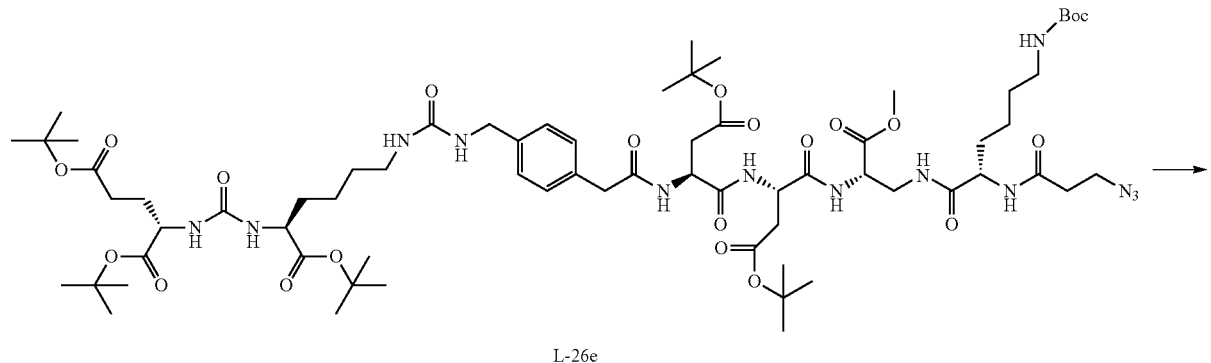
L-26e

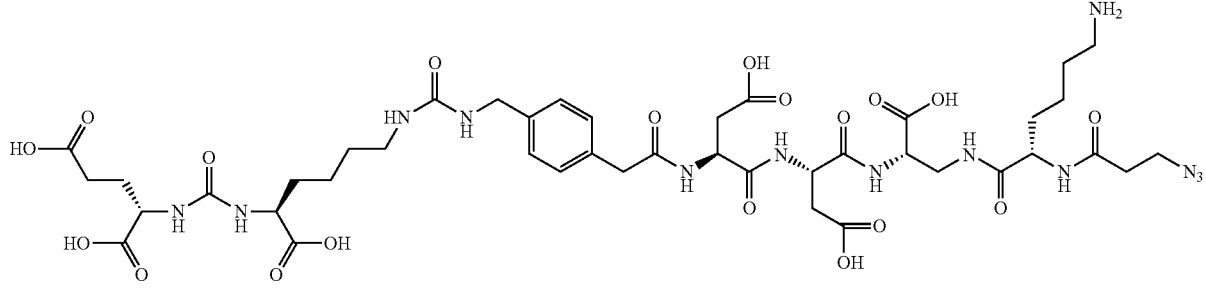

L-26

Preparation of Compound L-26-a-1

N-Boc-Dap-OH (1 g, 4.89 mM) was dissolved in 1,4-dioxane (15 mL), aqueous solution of $Na_2CO_3$ (1.14 g, 10.76 mM) dissolved in $H_2O$ (10 mL) and benzyl chloroformate (770 mg, 5.38 mM) were in turn added at 0° C. After stirring for 2 hours at room temperature, the mixture was extracted with EA (100 mL) and 2 M-HCl (100 mL). Then, the organic layer was dried over anhydrous $MgSO_4$, filtered and concentrated under reduced pressure. The residue was purified by column chromatography to obtain compound L-26a (1.25 g, 75%).

$^1$H NMR (400 MHz, $CDCl_3$) δ 7.34 (m, 5H), 5.79 (brs, 1H), 5.41 (brs, 1H), 5.10 (m, 2H), 4.31 (m, 1H), 3.70-3.57 (m, 2H), 1.44 (s, 9H).

Preparation of Compound L-26a-2

Compound L-26a (1.1 g, 3.25 mM) was dissolved in DMF (15 mL) at 0° C. under a nitrogen atmosphere, $K_2CO_3$ (494 mg, 3.57 mM) was added, and then the mixture was stirred for 15 minutes. Iodomethane (810 μL, 13.0 mM) was added thereto, and the mixture was additionally stirred for 2 hours. After the reaction was completed, the mixture was neutralized with 2 M-HCl aqueous solution (300 mL) and extracted with EA (300 mL). The organic layer was dried over anhydrous $MgSO_4$, filtered and concentrated under reduced pressure. The residue was purified by column chromatography to obtain compound L-26a-2 (1.04 g, 91%).

$^1$H NMR (400 MHz, $CDCl_3$) δ 7.36-7.28 (m, 5H), 5.38 (m, 1H), 5.16-5.04 (m, 3H), 4.35 (m, 1H), 3.73 (s, 3H), 3.58 (m, 2H), 1.42 (s, 9H).

Preparation of Compound L-26a-3

Compound L-26a-3 was synthesized via a similar manner to the preparation method of the compound L-6b (86%). EI-MS m/z: 253 ($M^+$).

Preparation of Compound L-26a-4

Compound L-26a-4 was synthesized via a similar synthetic route to the preparation method of the compound L-8b using Fmoc-Asp (OtBu)—OH (705 mg, 1.705 mM) and compound L-26a-3 (450 mg, 1.55 mM). Yield 99%.

$^1$H NMR (400 MHz, $CDCl_3$) δ 7.76 (m, 2H), 7.59 (m, 2H), 7.40 (m, 2H), 7.36-7.26 (m, 7H), 5.86 (d, J=7.6 Hz, 1H), 5.38 (m, 1H), 5.06 (m, 2H), 4.60-4.53 (m, 2H), 4.50-4.38 (m, 2H), 4.28 (m, 1H), 3.75 (s, 3H), 3.68 (m, 2H), 3.01 (m, 1H), 2.64 (m, 1H), 1.42 (s, 9H); EI-MS m/z: 646 ($M^+$).

Preparation of Compound L-26a-5

To a solution of compound L-26a-4 (1 g, 1.54 mM) in THF (25 mL) was added dropwise piperidine (3 mL) at 0° C. and stirred for 30 minutes. After the reaction was completed, the mixture was concentrated under reduced pressure, and washed with n-Hexane (100 mL) three times and dried under high vacuum to obtain compound L-26a-5 (510 mg, 78%).

Preparation of Compound L-26a-6

The similar method to the preparation method of the compound L-26a-4 was used to obtain compound L-26a-6 (40%).

Preparation of Compound L-26a

Compound L-26a was synthesized via a similar manner to the preparation method of the compound L-26a-5 (99%).

Preparation of Compound L-26c

A solution of compound L-26b (30 mg, 0.044 mM), prepared by a similar method as described in WO2014078484, and compound L-26a (45 mg, 0.074 mM) in DMF (3 mL) were added HBTU (18.4 mg, 0.048 mM) and DIPEA (23.6 μL, 0.132 mM) at 0° C. under a nitrogen atmosphere, and stirred for one hour at room temperature. After the reaction was completed, the reaction mixture was extracted with EA (50 mL) and brine (100 mL). The organic layer was dried over anhydrous MgSO4, filtered and concentrated under reduced pressure. The residue was purified by column chromatography to obtain compound L-26c (50 mg, 90%). EI-MS m/z: 1256 ($M^+$).

Preparation of Compound L-26d

Compound L-26d was synthesized via a similar manner to the preparation method of the compound L-5 (90%). EI-MS m/z: 1122 ($M^+$).

Preparation of Compound L-26e

Compound L-26e was synthesized via a similar manner to the preparation method of the compound L-8d (21%). EI-MS m/z: 1447 ($M^+$), 724 ($M^+/2$).

Preparation of Compound L-26

To a solution of compound L-26e (11 mg, 0.0076 mM) in Methanol (1 mL) was added NaOH aqueous solution (20 mg in 1 mL $H_2O$, 0.2 mL) at 0° C. and stirred for one hour. After the reaction was completed, the mixture was adjusted to have acidic pH with 2 M-HCl aqueous solution (50 mL), and extracted with EA (50 mL). The organic layer was dried over anhydrous $MgSO_4$, filtered concentrated under reduced pressure. The residue was dissolved in DCM (2 mL), TFA (1 mL) was added thereto, and then the mixture was stirred for 1 hour at room temperature. The reaction mixture was concentrated under reduced pressure to obtain compound L-26 (8 mg, 99%). EI-MS m/z: 1052 ($M^+$).

[Preparation Example 24] Preparation of Linker L-27

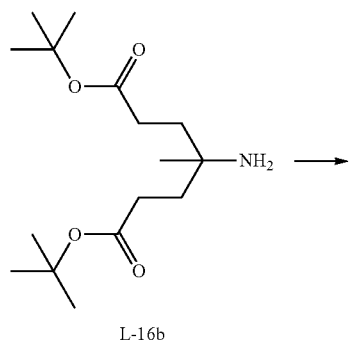

L-16b

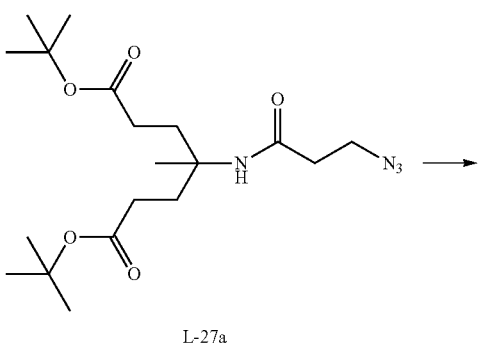

L-27a

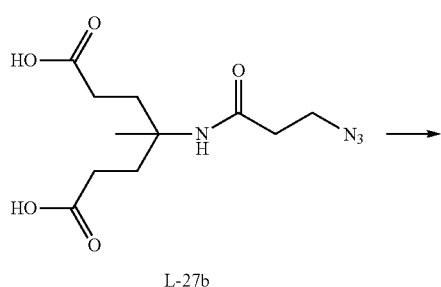

L-27b

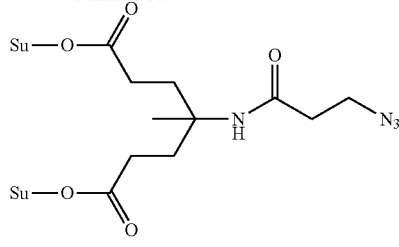

L-27

Preparation of Compound L-27a

The similar method to the preparation method of the compound L-16c was used to prepare compound L-27a (50%)

$^1$H NMR (400 MHz, CDCl$_3$) δ 6.06 (brs, 1H), 3.58 (t, J=6.4 Hz, 2H), 2.33 (t, J=6.4 Hz, 2H), 2.27 (t, J=7.6 Hz, 4H), 2.05 (m, 2H), 1.89 (m, 2H), 1.44 (s, 18H), 1.31 (s, 3H).

Preparation of Compound L-27b

The similar method to the preparation method of the compound L-16d was used to prepare compound L-27b (99%)

$^1$H NMR (400 MHz, CD$_3$OD) δ 3.58 (t, J=6.4 Hz, 2H), 2.41 (m, 2H), 2.35-2.21 (m, 6H), 1.85 (m, 2H), 1.21 (s, 3H).

Preparation of Compound L-27

Compound L-27 was synthesized via a similar manner to the preparation method of the compound L-16 (99%)

$^1$H NMR (400 MHz, CDCl$_3$) δ 5.67 (s, 1H), 3.57 (t, J=6.4 Hz, 2H), 2.90-2.81 (m, 8H), 2.68-2.55 (m, 4H), 2.33 (t, J=6.4 Hz, 2H), 1.99-1.88 (m, 4H), 1.30 (s, 1H)

[Preparation Example 25] Preparation of Ligand-Linker L-28

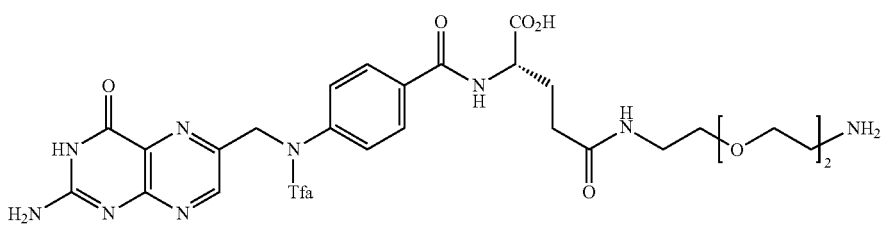

L-28a

↓ L-27

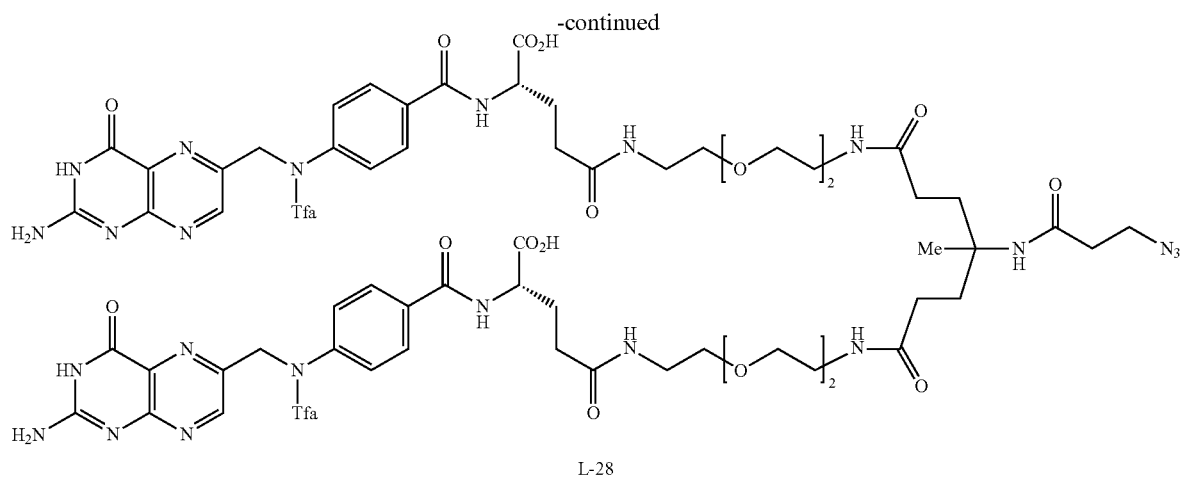

L-28

Compound L-28 was prepared from compound L-28a and compound L-27 by a similar method as described in Preparation Example 16. Yield 80%; EI-MS m/z: 1586 (M⁺).

¹H NMR (400 MHz, CD3OD) δ 8.83 (s, 2H), 7.95 (d, J=8.0 Hz, 2H), 7.68 (d, J=8.0 Hz, 2H), 5.23 (s, 4H), 4.57 (m, 2H), 3.58-3.46 (m, 20H), 3.43-3.33 (m, 4H), 2.44-2.26 (m, 9H), 2.23-2.07 (m, 3H), 1.84 (m, 2H).

[Preparation Example 26] Preparation of Linker L-29

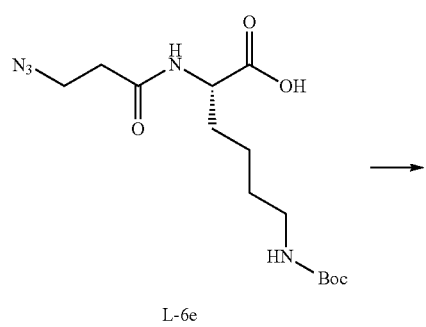

L-6e

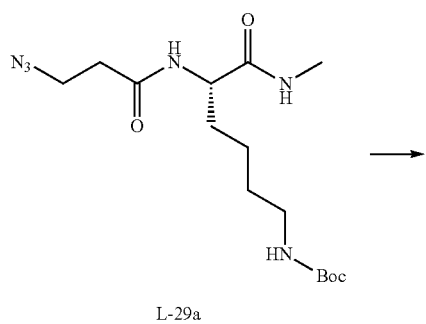

L-29a

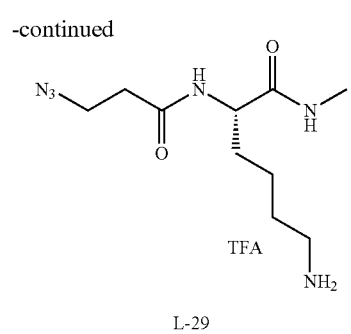

L-29

Preparation of Compound L-29

Compound L-6e (98 mg, 0.29 mmol) was dissolved in DMF (2 mL) at room temperature under a nitrogen atmosphere, methylamine (171 µL, 0.34 mmol, CAS No. 74-89-5), PyBOP (215.1 mg, 0.43 mmol), DIPEA (147.1 µL, 0.86 mmol) were added, and then the mixture was stirred for 5 hours at room temperature. After the reaction was completed, the mixture was extracted with EA (20 mL) and distilled water (20 mL). The organic layer was dried over anhydrous Na₂SO₄, filtered and concentrated under reduced pressure. The residue was purified by column chromatography to obtain compound L-29a (101.7 mg, 99%).

¹H NMR (400 MHz, CDCl₃) δ 6.45 (brs, 1H), 6.23 (brs, 1H), 4.64 (brs, 1H), 4.38 (q, J=7.6, 5.6 Hz, 1H), 3.63 (t, J=6.4 Hz, 2H), 3.16-3.04 (m, 2H), 2.82 (d, J=4.8 Hz, 3H), 2.47 (t, J=6.4 Hz, 2H), 1.92-1.80 (m, 1H), 1.56-1.46 (m, 2H), 1.44 (s, 9H), 1.40-1.32 (m, 2H); EI-MS m/z: 357 (M⁺).

Preparation of Compound L-29

To a solution of compound L-29a (101.7 mg, 0.29 mmol) in DCM (50 mL) at 0° C. under a nitrogen atmosphere was added TFA (1 mL), and the mixture was stirred for 2 hours at room temperature. After the reaction was completed, the mixture was concentrated under reduced pressure four times by using toluene (20 mL) as a co-solvent, thereby removing TFA. Compound L-29 was used directly in the next step without further purification (68.3 mg, 64%). EI-MS m/z: 257 (M⁺).

[Preparation Example 27] Preparation of Linker L-30

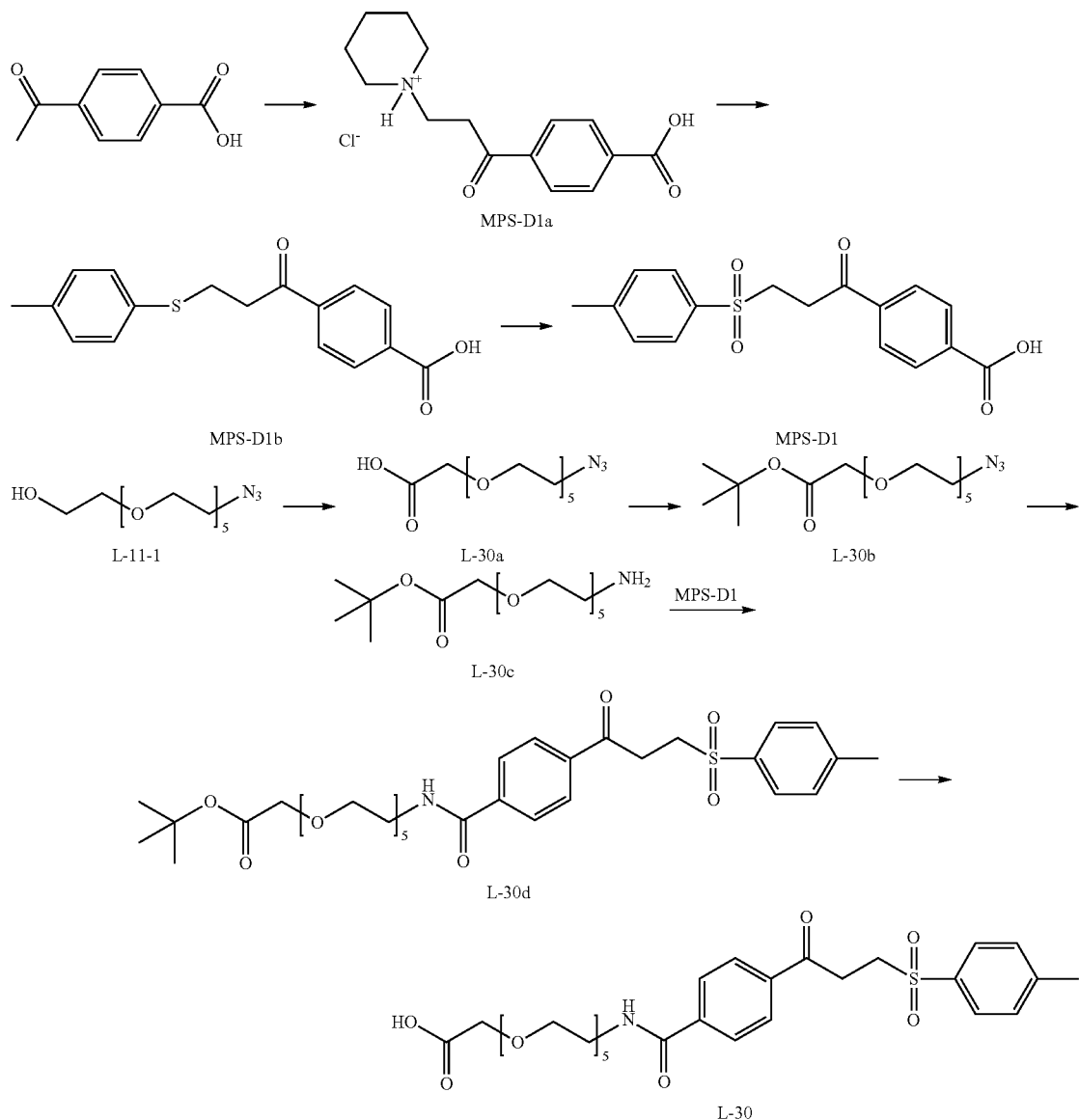

Preparation of compound MPS-D1a 4-acetylbenzoic acid (9 g, 54.82 mmol) was dissolved in EtOH (50 mL) at room temperature under a nitrogen atmosphere. Piperidine hydrochloric acid salt (6.66 g, 54.82 mmol) and paraformaldehyde (4.95 g, 164.5 mmol) were added thereto, followed by concentrated hydrochloric acid (0.6 mL). The mixture was stirred for 16 hours at 100° C. After the reaction was completed, the mixture was cooled to room temperature and acetone (90 mL) was added dropwise, the mixture was stirred for 1 hour at 0° C. The solid was filtered and washed with ether (30 mL×2) to obtain compound MPS-D1a (6.11 g, 38%).

$^1$H NMR (400 MHz, DMSO-$d_6$) δ 8.08 (s, 4H), 5.73 (s, 1H), 3.65 (t, J=7.2 Hz, 2H), 3.35 (t, J=7.2 Hz, 2H), 3.31 (m, 6H), 1.74 (s, 4H).

Preparation of Compound MPS-D1b

MPS-D1a (6.11 g, 20.52 mmol) was dissolved in EtOH (40 mL) and MeOH (26 mL) at room temperature under a nitrogen atmosphere. 4-Methoxybenzenethiol (2.55 g, 20.52 mmol) and piperidine (0.3 mL, 3.08 mmol) were added thereto, and the mixture was stirred for 16 hours at 100° C. After the reaction was completed, the mixture was cooled to 0° C. and stirred for one hour at 0° C., and the solid was filtered and washed with ether (30 mL×2) to obtain compound MPS-D1b (5.56 g, 90%).

$^1$H NMR (400 MHz, CDCl$_3$) δ 8.04-7.99 (m, 4H), 7.27 (d, J=8.4 Hz, 2H), 7.15 (d, J=7.6 Hz, 2H), 3.39-3.36 (m, 2H), 3.25-3.21 (m, 2H), 2.27 (s, 3H).

Preparation of Compound MPS-D1

MPS-D1b (5.56 g, 18.51 mmol) was dissolved in MeOH (90 mL) and distilled water (90 mL) at room temperature under a nitrogen atmosphere, the mixture was cooled to 0° C., and oxone (25.03 g, 40.72 mmol) was added thereto, the mixture was stirred at room temperature for 14 hours. After the reaction was completed, distilled water (100 mL) was added for the dissolution, and then the mixture was extracted with chloroform (150 mL×3) and the organic layer was washed with brine (200 mL). The organic layer was dried over anhydrous Na$_2$SO$_4$, filtered and concentrated under reduced pressure to obtain compound MPS-D1 (5.29 g, 86%).

$^1$H NMR (400 MHz, CDCl$_3$) δ 8.04-7.99 (m, 4H), 7.81 (d, J=8.4 Hz, 2H), 7.46 (d, J=8.4 Hz, 2H), 3.63 (t, J=7.2 Hz, 2H), 3.41 (t, J=7.2 Hz, 2H), 2.44 (s, 3H). EI-MS m/z: 333 (M$^+$).

Preparation of Compound L-30a

Compound L-11-1 (2 g, 6.51 mmol) was dissolved in acetone (56 mL) under a nitrogen atmosphere and then Jones reagent solution (5 mL) was added dropwise at −5° C. After the addition was completed, the mixture was stirred for 2 hours at room temperature. After the reaction was completed, the mixture was filtered by celite, filtered and concentrated under reduced pressure. The reaction mixture was extracted with DCM (20 mL×2) and water (5 mL), and then organic layer was dried over anhydrous Na$_2$SO$_4$, filtered and concentrated under reduced pressure. The residue was purified by column chromatography to obtain compound L-30a (1.85 g, 89%).

$^1$H NMR (400 MHz, CDCl$_3$) δ 4.15 (s, 2H), 3.76-3.67 (m, 18H), 3.40 (t, J=4.8 Hz, 2H).

Preparation of Compound L-30b

A solution of compound L-30a (500 mg, 1.56 mmol) in DCM (10 mL) under a nitrogen atmosphere were added t-BuOH (305 μL, 3.11 mmol), DIC (292.5 μL, 1.87 mmol) and DMPA (19 mg, 0.16 mmol) and stirred for 4 hours at room temperature. After the reaction was completed, the mixture was extracted with DCM (30 mL×2) and water (5 mL). The organic layer was dried over anhydrous Na$_2$SO$_4$, filtered and concentrated under reduced pressure. The residue was purified by column chromatography to obtain compound L-30b (278.5 mg, 47%).

$^1$H NMR (400 MHz, CDCl$_3$) δ 4.01 (s, 2H), 3.70-3.66 (m, 18H), 3.38 (t, J=4.8 Hz, 2H), 1.47 (s, 9H).

Preparation of Compound L-30c

To a solution of compound L-30b (278 mg, 0.74 mmol) in EtOH (5 mL) wad added Pd/C (236 mg, 0.11 mmol) and 4 M-HCl (in 1,4-Dioxane) solution (2 drops). After stirring at room temperature for 1 hour under hydrogen gas, the mixture was filtered through celite and washed with EtOH. The filtrate was concentrated to obtain compound L-30c (255.3 mg, 89.2%).

$^1$H NMR (400 MHz, DMSO) δ 8.32 (s, 1H), 3.98 (s, 2H), 3.55-3.40 (m, 18H), 3.86 (t, J=5.6 Hz, 2H), 2.70-2.64 (m, 2H), 1.42 (s, 9H).

Preparation of Compound L-30d

The similar method to the preparation method of the compound L-8b was used to obtain compound-30d (71%).

$^1$H NMR (400 MHz, CDCl$_3$) δ 7.95 (s, 4H), 7.82 (d, J=8.0 Hz, 2H), 7.38 (d, J=8.0 Hz, 2H), 7.33-7.30 (m, 1H), 3.98 (s, 2H), 3.68-3.63 (m, 18H), 3.55-3.53 (m, 2H), 3.49-3.47 (m, 2H), 2.95 (s, 1H), 2.88 (s, 1H), 2.46 (s, 3H) 1.46 (s, 9H). EI-MS m/z: 666 (M$^+$).

Preparation of Compound L-30

To a solution of compound L-30d (120 mg, 0.18 mmol) in DCM (8 mL) under a nitrogen atmosphere at 0° C. was added TFA (4 mL) and the mixture was warm to room temperature. After stirring for 2 hours, the mixture was concentrated under reduced pressure four times by using toluene as co-solvent to remove TFA. After the reaction mixture was dissolved in DMF, NSH (31 mg, 0.27 mmol) and EDCI (52 mg, 0.27 mmol) were added thereto. The reaction mixture was stirred overnight at room temperature and concentrated under reduced pressure and used directly in the next step without further purification (127 mg, crude). EI-MS m/z: 707 (M$^+$).

[Preparation Example 28] Preparation of Linker L-31

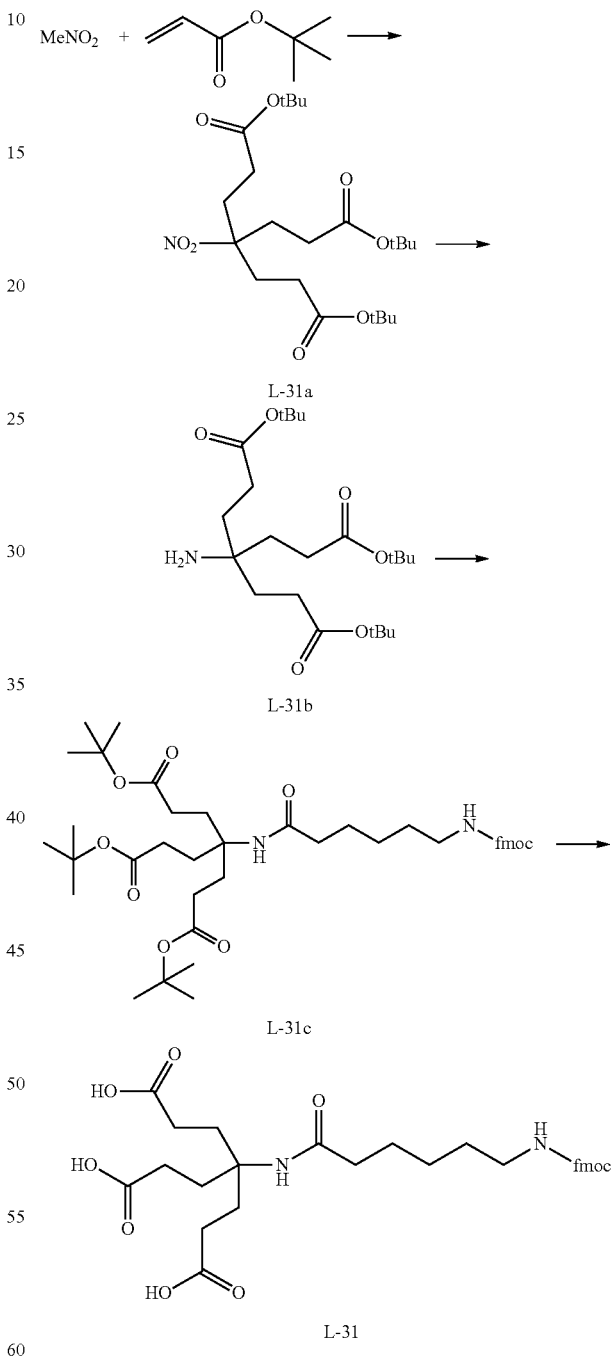

Preparation of Compound L-31a

A solution of nitroethane (6.1 g, 100 mmol) in DME (1,2-dimethoxyethane) (20 mL) was added tetramethylammonium hydroxide pentahydrate (540 mg). t-Butyl acrylate (45.4 mL, 310 mmol) was added dropwise for minutes at 70° C. Tetramethyl ammonium hydroxide pentahydrate (540 mg) was further added, and then the mixture was stirred for 30 minutes. The reaction was cooled to room temperature, and tetramethylammonium hydroxide pentahydrate (540 mg) was further added thereto. After the reaction was completed, the mixture was concentrated under reduced pressure, and extracted with EA (200 mL) and 0.1 N HCl solution (50 mL). The organic layer was dried over anhydrous $Na_2SO_4$, filtered and concentrated under reduced pressure. The residue was recrystallized from EtOH to obtain compound L-31a (30.3 g, 68%).

Preparation of Compound L-31b

A solution of compound L-31a (1.5 g, 3.37 mmol) in ethanol (20 mL) was added Raney Ni. Hydrogen gas was bubbled through the reaction mixture for 5 hours at room temperature. After the reaction was completed, the mixture was filtered through celite to remove Raney Ni, and concentrated under reduced pressure to obtain compound L-31b (1.3 g, 93%).

$^1$H NMR (400 MHz, $CDCl_3$) δ 2.25 (t, J=8.0 Hz, 5H), 2.24-2.18 (m, 1H), 1.61 (t, J=9.2 Hz, 5H), 1.45 (s, 27H).

Preparation of Compound L-31c

A solution of compound L-31b (988 mg, 2.38 mmol) in DMF (10 mL) at room temperature under a nitrogen atmosphere were added 6-(Fmoc-amino)hexanoic acid (840 mg, 2.38 mmol), PyBOP (1.48 g, 2.85 mmol) and DIPEA (0.6 mL, 3.57 mmol), and stirred overnight at room temperature. After the reaction was completed, the mixture was extracted with EA (20 mL) and distilled water (20 mL). The organic layer was dried over anhydrous $Na_2SO_4$, filtered and concentrated under reduced pressure. The residue was purified by column chromatography to obtain compound L-31c (951.9 mg, 54%).

$^1$H NMR (400 MHz, $CDCl_3$) δ 7.76 (d, J=8.0 Hz, 2H), 7.60 (d, J=7.6 Hz, 2H), 7.40 (t, J=7.2 Hz, 2H), 7.31 (t, J=7.6 Hz, 2H), 5.90 (s, 1H), 5.02-4.92 (m, 1H), 4.39 (d, J=6.4 Hz, 2H), 4.22 (t, J=6.8 Hz, 1H), 3.20 (q, J=7.2, 6.8, 1H), 2.22 (t, J=7.6 Hz, 6H), 2.12 (t, J=7.6 Hz, 2H), 1.97 (t, J=8.0 Hz, 6H), 1.64-1.59 (m, 2H), 1.55-1.48 (m, 2H), 1.43 (s, 27H), 1.38-1.32 (m, 2H); EI-MS m/z: 751 ($M^+$).

Preparation of Compound L-31

To a solution of compound L-31c (951.9 mg, 1.27 mmol) in DCM (10 mL) at 0° C. under a nitrogen atmosphere was added TFA (4 mL). After stirring for 6 hours at room temperature, the mixture was concentrated under reduced pressure four times by using toluene (20 mL) as co-solvent to remove the excess TFA. Compound L-31 was used directly in the next step without further purification (720 mg, crude. quant).

$^1$H NMR (400 MHz, DMSO-$d_6$) δ 7.88 (d, J=7.6 Hz, 2H), 7.68 (d, J=7.6 Hz, 2H), 7.41 (t, J=7.2 Hz, 2H), 7.33 (t, J=7.2 Hz, 2H), 7.25 (t, J=5.2 Hz, 1H), 7.13 (s, 1H), 4.28 (d, J=6.8 Hz, 2H), 4.20 (t, J=6.4 Hz, 1H), 2.95 (q, J=8.8 6.8, 1H), 2.11 (t, J=6.8 Hz, 6H), 2.04 (t, J=7.2 Hz, 2H), 1.87-1.77 (m, 6H), 1.50-1.42 (m, 2H), 1.42-1.34 (m, 2H), 1.26-1.15 (m, 2H); EI-MS m/z: 583 ($M^+$).

[Preparation Example 29] Preparation of Ligand-Linker L-32

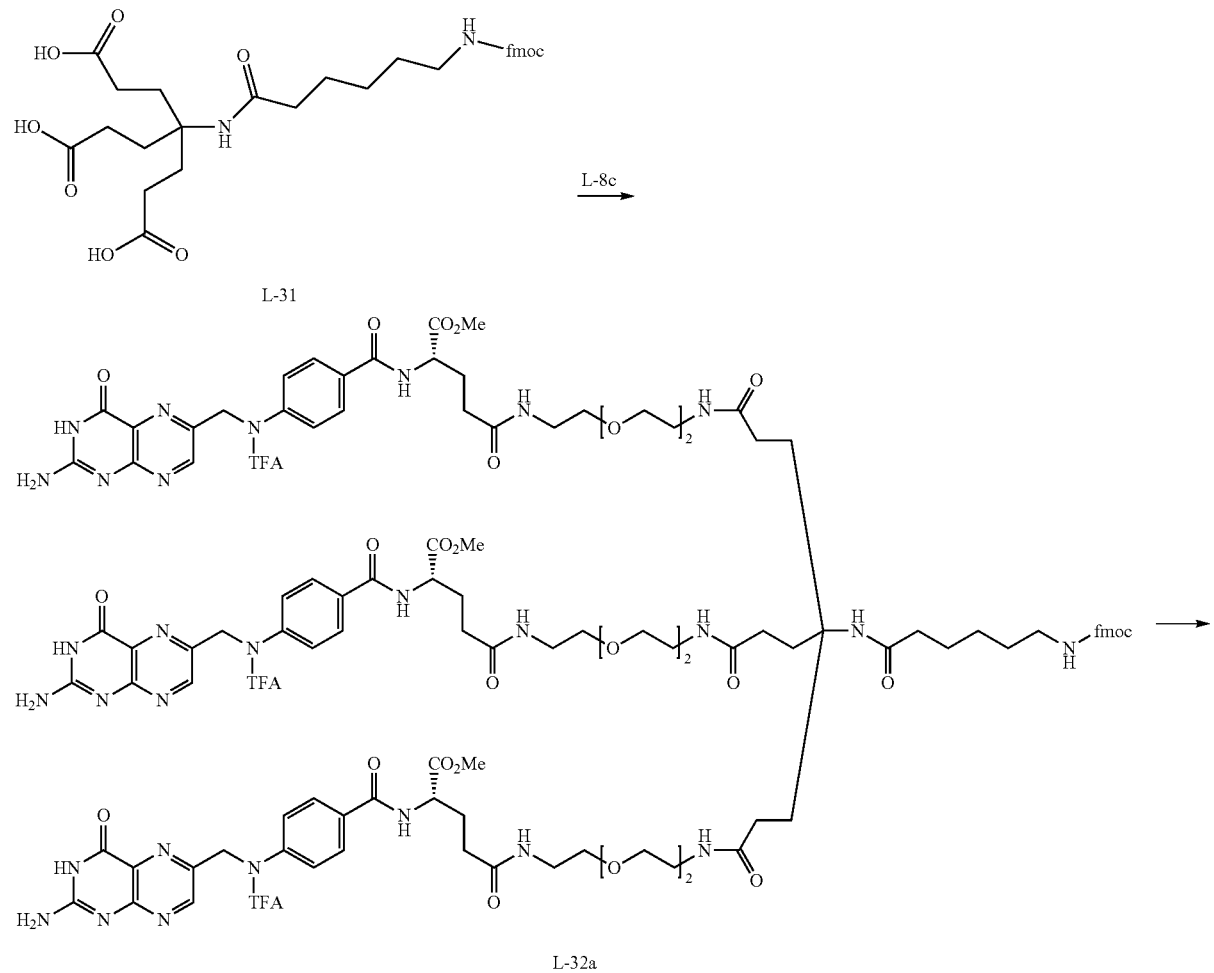

111 112
-continued
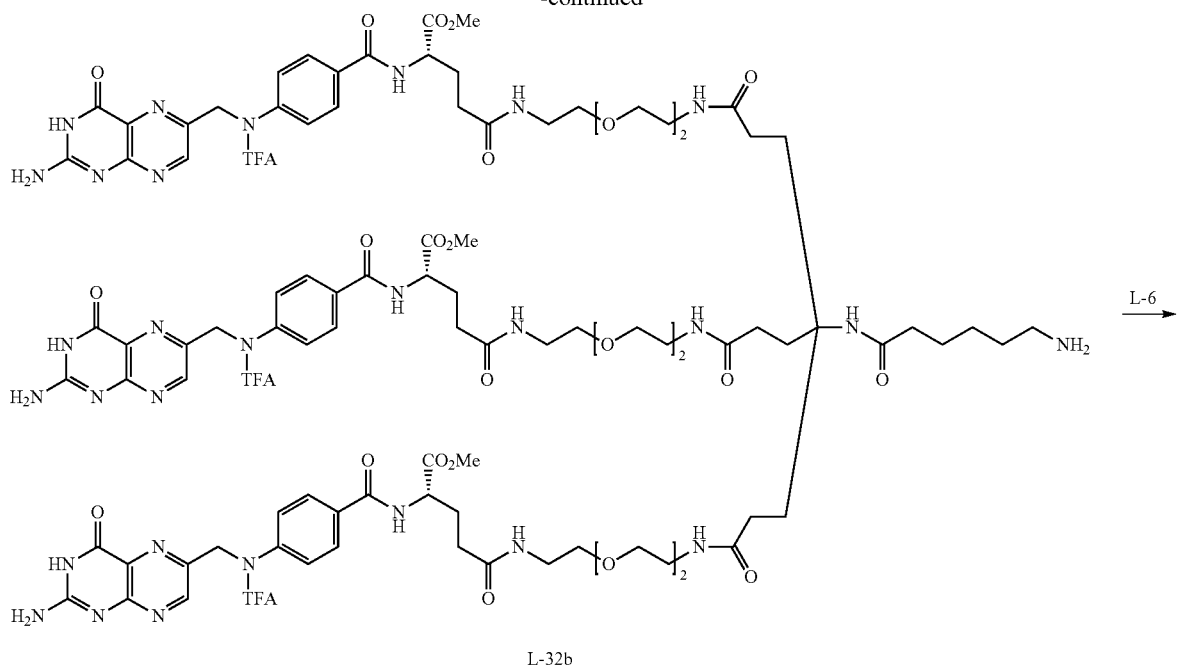
L-32b
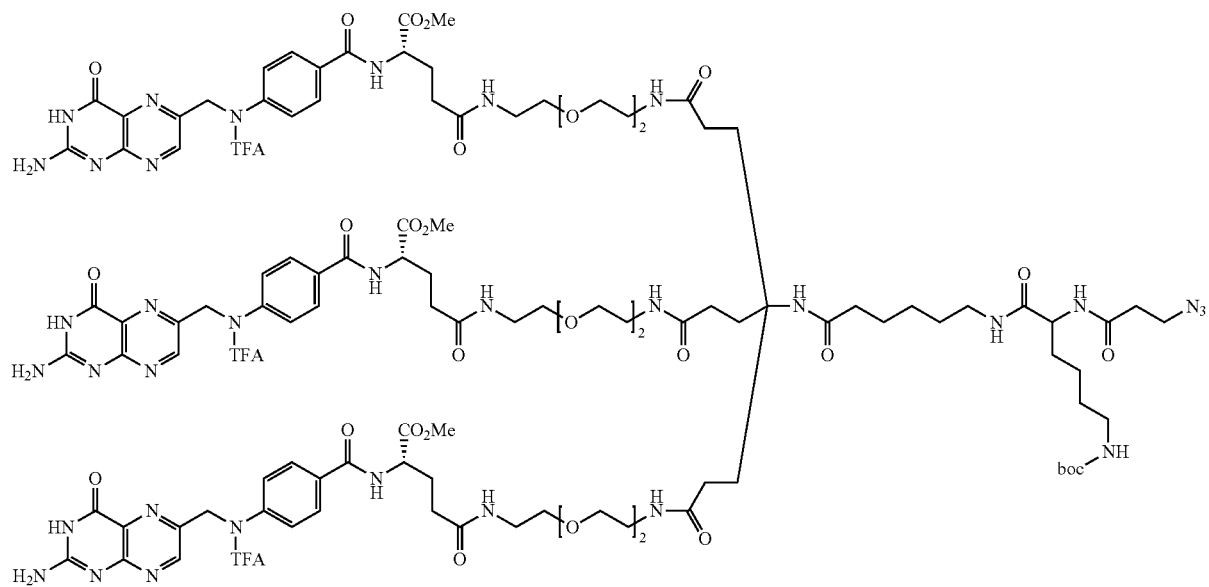
L-32c

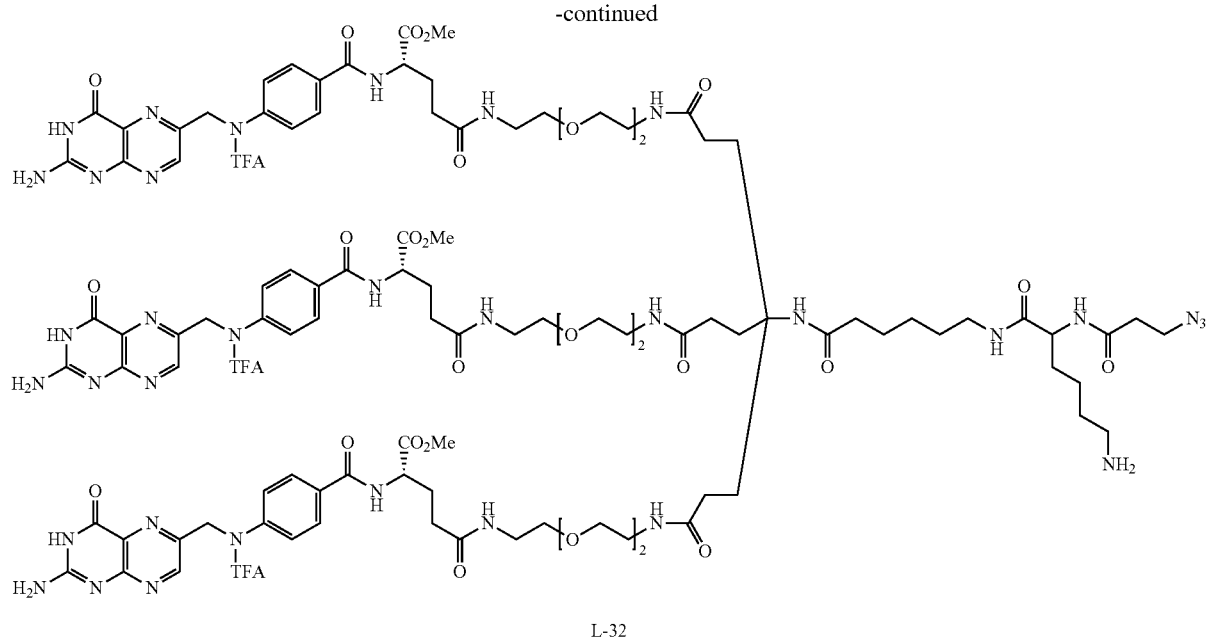

L-32

Preparation of Compound L-32a

To a solution of compound L-31 (300 mg, 0.52 mmol) in DMF (5 mL) at room temperature under a nitrogen atmosphere were added EDCI (345.5 mg, 1.80 mmol) and N-hydroxysuccinimide (207.4 mg, 1.802 mmol). After stirring overnight, compound L-8c (1.41 g, 1.55 mmol) and DIPEA (879 µL, 5.15 mmol) were added thereto. After stirring for 6 hours at room temperature, the resultant residue was diluted with MeOH and the precipitate was filtered. The solid was washed with MeoH and ether and dried under high to obtain compound L-32a (1.3 g, crude.). EI-MS m/z: 1288 (M$^+$/2).

Preparation of Compound L-32b

To a solution of compound L-32a (500 mg, 0.19 mmol) was dissolved in DMF (2 mL) under a nitrogen atmosphere was added dropwise piperidine (29 µL, 0.29 mmol), and the mixture was stirred for 2 hours. After the reaction was completed, the resultant residue was diluted with methanol (5 mL) and EA (15 mL) and the precipitate was filtered. The solid was washed with EA and ether and dried under high pressure to obtain brown solid compound L-32b (337 mg, 74%). EI-MS m/z: 1176 (M$^+$/2).

Preparation of Compound L-32c

To a solution of compound L-32b (150 mg, 0.064 mmol) in DMF (2 mL) at room temperature under a nitrogen atmosphere were added compound L-6 (31 mg, 0.07 mmol) and DIPEA (17 µL, 0.096 mmol), and the mixture was stirred for 3 hours at room temperature. After the reaction was completed, the resultant residue was diluted with EA (10 mL). The brown solid compound was washed with EA and ether to obtain compound L-32c (220.6 mg, crude). EI-MS m/z: 1339 (M$^+$/2).

Preparation of Compound L-32

To a solution of compound L-32c (70 mg, 0.023 mmol) in DCM (2 mL) at room temperature under a nitrogen atmosphere was added TFA (0.2 mL), and the mixture was stirred for 2 hours at room temperature. After the reaction was completed, the resulting mixture was concentrated under reduced pressure and the residue was purified by prep-HPLC to obtain compound L-32 (17.8 mg, 23%). EI-MS m/z: 1289 (M$^+$/2).

[Preparation Example 30] Preparation of Linker L-33

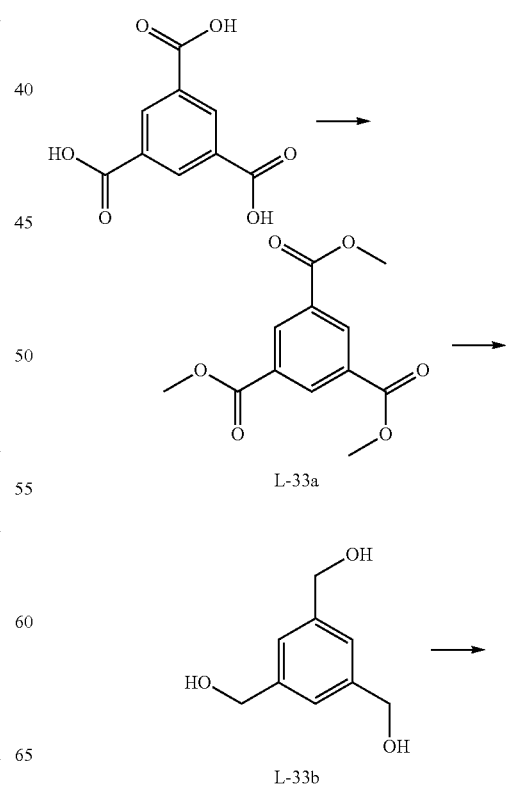

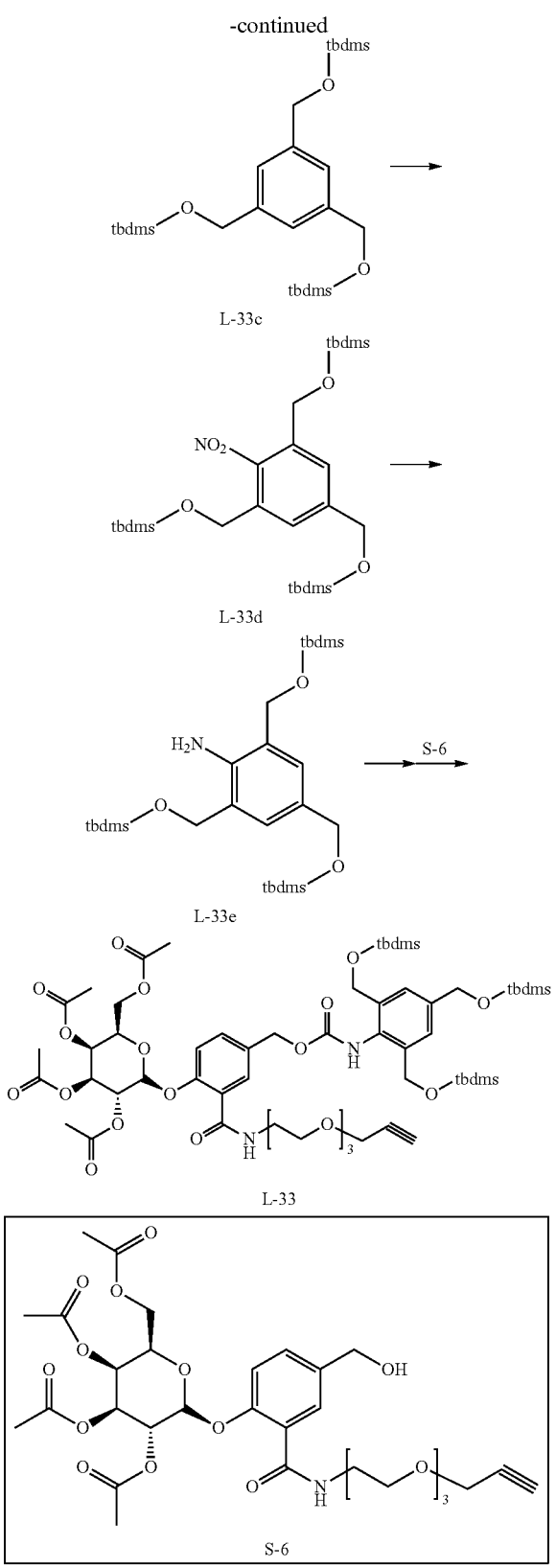

Preparation of Compound L-33a

A solution of trimesic acid (5.0 g, 23.73 mmol) in methanol (200 mL) at room temperature under a nitrogen atmosphere was treated with $H_2SO_4$ (1.5 mL) and stirred at 60° C. for 19 hours. After the reaction was completed, the mixture was concentrated under reduced pressure, and extracted with EA (500 mL) and $NaHCO_3$ aqueous solution (300 mL). Then, the organic layer was dried over anhydrous $Na_2SO_4$, filtered and concentrated under reduced pressure. The residue was purified by column chromatography to obtain compound L-33a (5.88 g, 98%).

$^1$H NMR (400 MHz, $CDCl_3$) δ 8.80 (s, 3H), 3.96 (s, 9H).

Preparation of Compound L-33b

To a solution of compound L-33a (2.0 g, 7.93 mmol) in THF (40 mL) at 0° C. under a nitrogen atmosphere was added LAH (1.2 g, 31.72 mmol) dropwise. The mixture was stirred at 60° C. for 5 hours. After the reaction was completed, the reaction was quenched with water (1.6 mL) and 15% NaOH aqueous solution (0.8 mL), and EA (500 mL) was added thereto. The mixture was filtered through celite and the filtrate was concentrated under reduced pressure. The residue was purified by column chromatography to obtain compound L-33b (1.1 g, 83%).

$^1$H NMR (400 MHz, CD3OD) δ 7.26 (s, 3H), 4.61 (s, 6H).

Preparation of Compound L-33c

To a solution of compound-33b (1.1 g, 6.54 mmol) in DMF (25 mL) at 0° C. under a nitrogen atmosphere were added TBDMS-Cl (4.9 g, 32.7 mmol) and imidazole (2.2 g, 32.7 mmol), and the mixture was stirred for 3 hours at room temperature. After the reaction was completed, the reaction mixture was extracted with EA (500 mL) and distilled water (200 mL), and the organic layer was dried over anhydrous $Na_2SO_4$, filtered and concentrated under reduced pressure. The residue was purified by column chromatography to obtain compound L-33c (3.02 g, 90%).

$^1$H NMR (400 MHz, $CDCl_3$) δ 7.16 (s, 3H), 4.73 (s, 6H), 0.94 (s, 27H), 0.10 (s, 18H).

Preparation of Compound L-33d

To a solution of compound L-33c (0.5 g, 0.98 mmol) in $Ac_2O$ (4 mL) at 0° C. under a nitrogen atmosphere was added 61% Nitric acid (0.2 mL), and the mixture was stirred for one hour. After the reaction was completed, the reaction mixture was extracted with EA (500 mL) and $NaHCO_3$ aqueous solution (300 mL), and then the organic layer was dried over anhydrous $Na_2SO_4$, filtered and concentrated under reduced pressure. The residue was purified by column chromatography to obtain compound L-33d (370 mg, 68%).

$^1$H NMR (400 MHz, $CDCl_3$) δ 7.51 (s, 2H), 4.77 (s, 6H), 0.94 (s, 27H), 0.94 (s, 18H).

Preparation of Compound L-33e

To a solution of compound L-33d (370 mg, 0.67 mmol) in methanol (5 mL) at room temperature was added 5% Pd/C (43 mg, 0.02 mmol), and then the mixture was stirred for 30 minutes under hydrogen atmosphere. After the reaction was completed, the mixture was filtered through celite and the filtrate was concentrated under reduced pressure to obtain compound L-33e (283 mg, 81%).

$^1$H NMR (400 MHz, $CDCl_3$) δ 6.94 (s, 2), 4.73 (s, 6H), 0.89 (s, 27H), 0.05 (s, 18H).

Preparation of Compound L-33

To a solution of compound L-33e (0.6 g, 1.14 mmol) in DCM (20 mL) at room temperature under a nitrogen atmosphere were added triphosgene (406 mg, 1.37 mmol) and TEA (0.8 mL, 5.47 mmol) and the mixture was stirred for 1 hour. Compound S-6 (759 mg, 1.14 mmol) obtained in Example 1 and TEA (0.24 mL, 1.17 mmol) were added thereto. After stirring for 15 hours, the reaction mixture was extracted with DCM (100 mL) and water (100 mL), and the organic layer was dried over anhydrous $Na_2SO_4$, filtered and concentrated under reduced pressure. The residue was purified by column chromatography to obtain compound L-33 (914 mg, 66%).

$^1$H NMR (400 MHz, $CDCl_3$) δ 8.10 (s, 1H), 7.52-7.46 (m, 2H), 7.38-7.32 (m, 1H), 7.29 (s, 2H), 7.08-7.02 (m, 1H), 5.56-5.46 (m, 2H), 5.22-5.08 (m, 4H), 4.71-4.62 (m, 6H), 4.26-4.08 (m, 5H), 3.82-3.74 (m, 1H), 3.72-3.62 (m, 10H), 3.58-3.48 (m, 1H), 2.44-2.40 (m, 1H), 2.23 (s, 3H), 2.06 (s, 6H), 2.03 (s, 3H), 0.93-0.90 (m, 27H), 0.09-0.06 (s, 18H); EI-MS m/z: 1242 (M$^+$+Na).
[Preparation Example 31] Preparation of Linker L-34
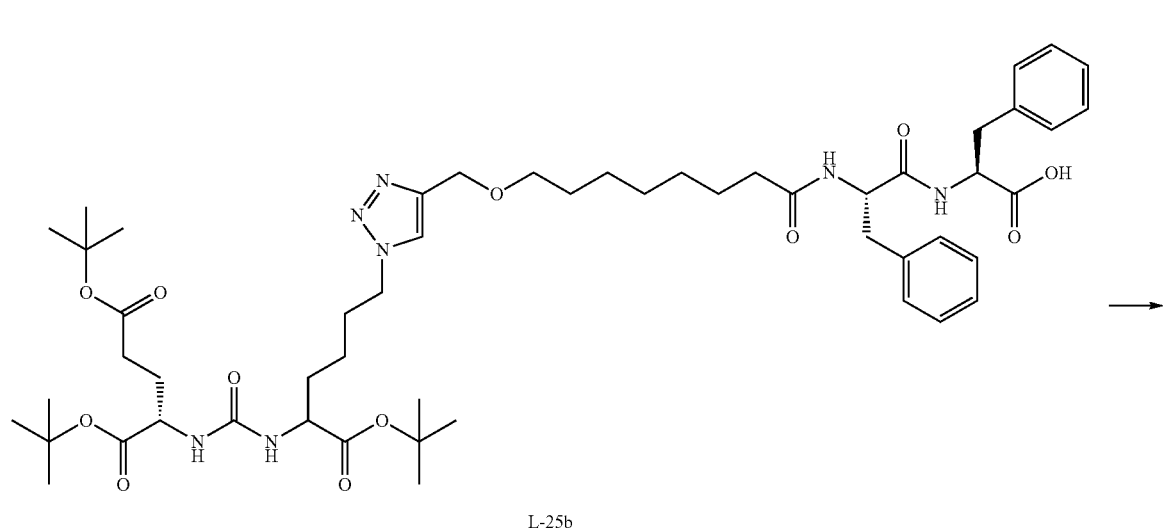
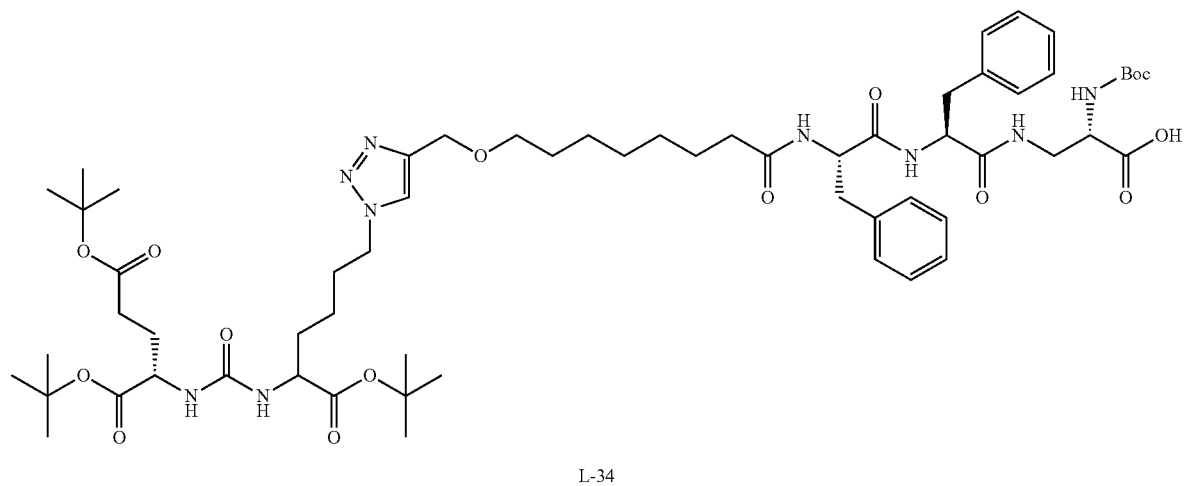
Compound L-34 was obtained by using compound L-25b with a similar method to the preparation method of the compound L-8b. Yield 27%; EI-MS m/z: 1193 (M$^+$).
[Preparation Example 32] Preparation of Ligand-Linker L-35
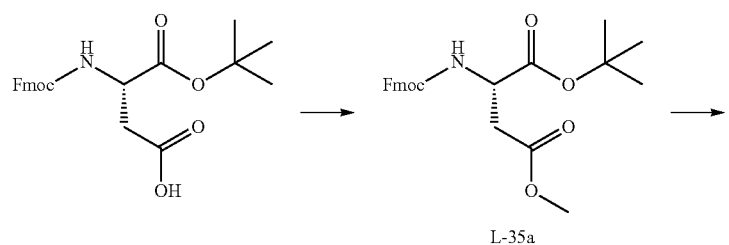

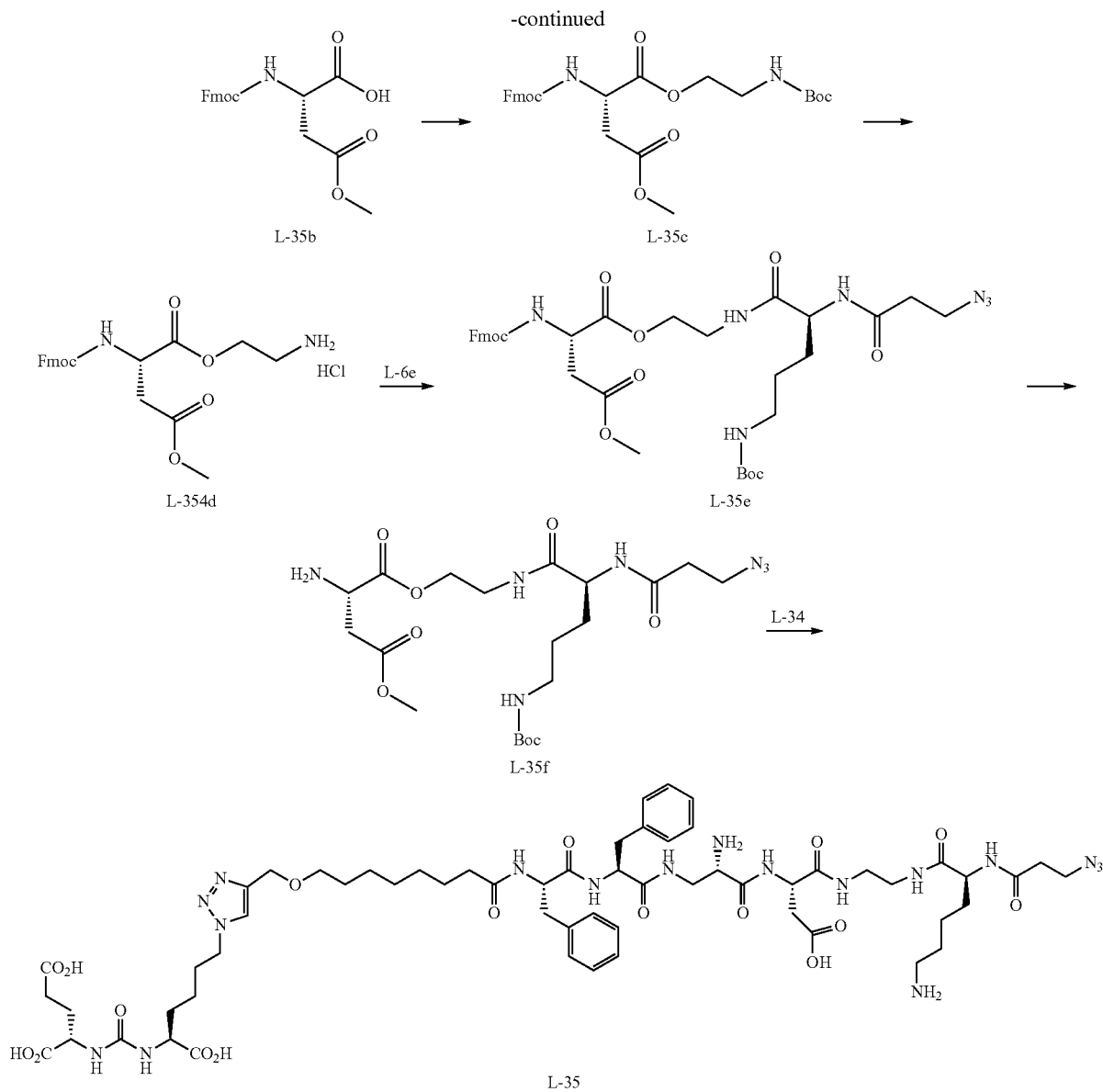

Preparation of Compound L-35a

Fmoc-Asp-(OtBu) (1 g, 2.43 mM) was dissolved in MeOH (2 mL) and DCM (10 mL) at 0° C. under a nitrogen atmosphere, DIC (490 μL, 3.16 mM) and DMAP (59 mg, 0.48 mM) were in turn added. The mixture was stirred for 12 hours at room temperature. After the reaction was completed, the resulting mixture was concentrated under reduced pressure and was purified by column chromatography to obtain compound L-35a (1.0 g, 97%).

$^1$H NMR (400 MHz, CDCl$_3$) δ 7.75 (d, J=8.0 Hz, 2H), 7.61 (d, J=7.2 Hz, 2H), 7.42 (t, J=7.6 Hz, 2H), 7.33 (t, J=7.2 Hz, 2H), 5.76 (d, J=8.4 Hz, 1H), 4.54 (m, 1H), 4.40 (m, 2H), 4.25 (m, 1H), 3.71 (s, 3H), 2.97, (m, 2H), 1.45 (s, 9H)

Preparation of Compound L-35b

To a solution of compound L-35a (590 mg, 1.38 mM) in DCM (6 mL) at 0° C. under a nitrogen atmosphere was added TFA (3 mL). After stirring for 4.5 hours at room temperature, the resulting mixture was concentrated under reduced pressure to obtain compound L-35b (510 mg, 99%).

$^1$H NMR (400 MHz, CDCl$_3$) δ 7.78 (d, J=8.0 Hz, 2H), 7.61 (d, J=7.2 Hz, 2H), 7.43 (t, J=7.6 Hz, 2H), 7.32 (t, J=7.2 Hz, 2H), 5.86 (d, J=8.4 Hz, 1H), 4.69 (m, 1H), 4.43 (m, 2H), 4.25 (m, 1H), 3.74 (s, 3H), 3.07, (m, 2H).

Preparation of Compound L-35c

A solution of compound L-35b (510 mg, 1.38 mM) and N-Boc-ethylenediamine (265 mg, 1.66 mM) in DMF (10 mL) at 0° C. under a nitrogen atmosphere were treated with HBTU (789 mg, 2.08 mM) and DIPEA (483 μL, 2.77 mM) in turn, and the mixture was stirred for 4 hours at room temperature. After the reaction was completed, the mixture was extracted with EA (50 mL) and brine (50 mL). The organic layer was dried over anhydrous Na$_2$SO$_4$, filtered and concentrated under reduced pressure. The residue was purified by column chromatography to obtain compound L-35c (430 mg, 61%).

$^1$H NMR (400 MHz, CDCl$_3$) δ 7.78 (d, J=8.0 Hz, 2H), 7.61 (d, J=7.2 Hz, 2H), 7.43 (t, J=7.6 Hz, 2H), 7.33 (t, J=7.2 Hz, 2H), 6.87 (m, 1H), 5.87 (d, J=6.0 Hz, 1H), 4.89 (m, 1H), 4.53 (m, 3H), 4.24 (m, 1H), 3.71 (s, 3H), 3.38-3.25 (m, 4H), 3.07 (m, 1H), 2.70 (m, 1H), 1.42 (2, 9H); EI-MS m/z: 512 (M⁺).

Preparation of Compound L-35d

To a solution of compound L-35c (280 mg, 0.54 mM) in CH₂Cl₂ (10 mL) at 0° C. under a nitrogen atmosphere was added 4N HCl in 1,4-dioxane (2.0 mL), and the mixture was stirred for 3 hours at room temperature. After the reaction was completed, the resulting mixture was concentrated under reduced pressure to obtain compound L-35d (245 mg, 99%). EI-MS m/z: 448 (M⁺).

Preparation of Compound L-35e

A solution of compound L-35d (245 mg, 0.54 mM) and compound L-6e (225 mg, 0.65 mM) in DMF (5 mL) at 0° C. under a nitrogen atmosphere were treated with HBTU (250 mg, 0.65 mM) and DIPEA (293 µL, 1.62 mM) in turn, and the mixture was stirred for 30 minutes at room temperature. After the reaction was completed, the mixture was extracted with EA (20 mL) and brine (20 mL). The organic layer was dried over anhydrous Na₂SO₄, filtered and concentrated under reduced pressure. The residue was purified by column chromatography to obtain compound L-35e (270 mg, 67%).

¹H NMR (400 MHz, CDCl₃) δ 7.78 (d, J=7.2 Hz, 2H), 7.61 (m, 2H), 7.43 (t, J=7.2 Hz, 2H), 7.34 (t, J=7.2 Hz, 2H), 6.92 (m, 1H), 6.85 (m, 1H), 6.50 (m, 1H), 6.15 (m, 1H), 4.74 (m, 1H), 4.53 (m, 3H), 4.32 (m, 1H), 4.24 (m, 1H), 3.72 (s, 3H), 3.54-3.40 (m, 5H), 3.25 (m, 1H), 3.09 (m, 3H), 2.78 (m, 1H), 2.40 (m, 2H), 1.42 (2, 9H); EI-MS m/z: 737 (M⁺).

Preparation of Compound L-35f

To a solution of compound L-35e (50 mg, 0.067 mM) in THF (4 mL) at room temperature under a nitrogen atmosphere was added piperidine (0.2 mL), and the mixture was stirred for 30 minutes at room temperature. After the reaction is completed, the mixture was diluted with EA (20 mL) and concentrated under reduced pressure. The resulting residue was washed with hexane (20 mL) two times and dried under reduced pressure. The residue was purified by prep-HPLC and lyophilized to obtain compound L-35f. Yield 18 mg, 53%; EI-MS m/z: 515 (M⁺).

Preparation of Compound L-35

A solution of compound L-35f (6 mg, 0.005 mM) and compound L-34 (3.9 mg, 0.0075 mM) in DMF (1 mL) at 0° C. under a nitrogen atmosphere was treated with HBTU (2.5 mg, 0.0065 mM) and DIPEA (2.7 µL, 0.015 mM), and the mixture was stirred for one hour at room temperature. After the reaction is completed, the reaction mixture was extracted with EA (20 mL) and brine (10 mL). The organic layer was dried over anhydrous Na₂SO₄, filtered and concentrated under reduced pressure. Then, the residue was dissolved in THF (1 mL) and distilled water (0.3 mL) at 0° C., 2 N NaOH aqueous solution (1 mL) was added thereto, and the mixture was stirred for 20 minutes at 0° C. The reaction mixture was extracted with EA (10 mL) and 2N HCl aqueous solution (5 mL). The organic layer was dried over anhydrous Na₂SO₄, filtered and concentrated under reduced pressure, and immediately after the mixture was dissolved in DCM (3 mL), TFA (1 mL) was added and the mixture was stirred at 0° C. for 30 minutes. After the reaction was completed, the compound was concentrated under reduced pressure. The residue was purified by prep-HPLC and lyophilized to obtain compound L-35 (5 mg, 75%). EI-MS m/z: 1307 (M⁺).

[Preparation Example 33] Preparation of Ligand-Linker L-36

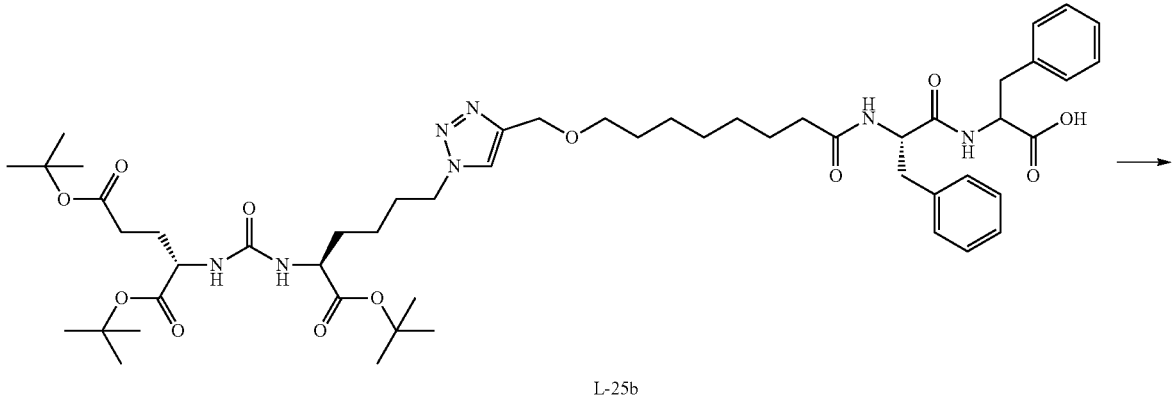

L-25b

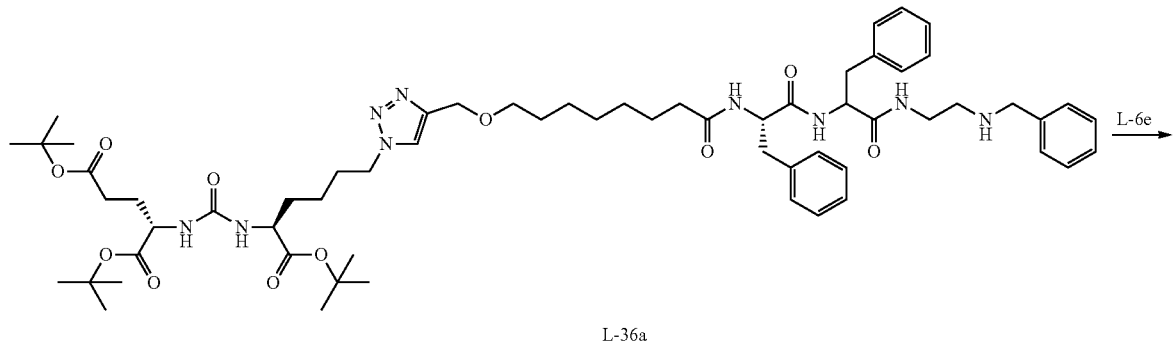

L-36a

-continued

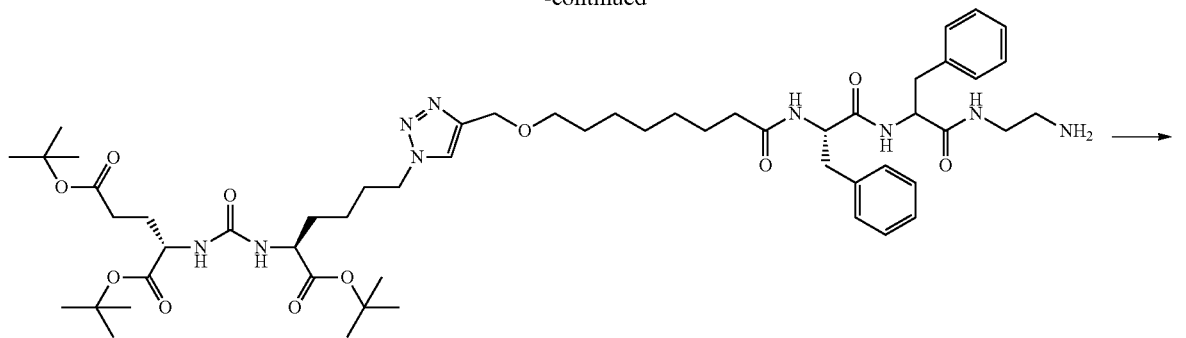

L-36b

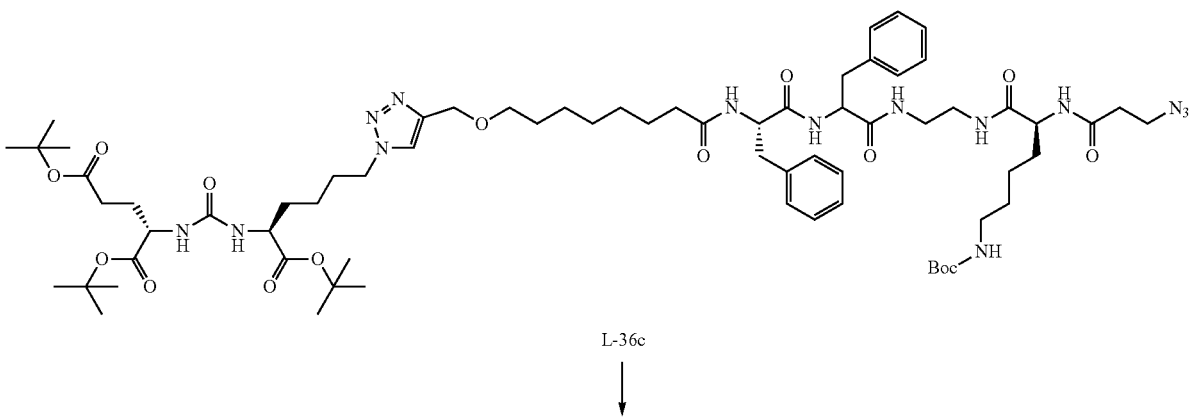

L-36c

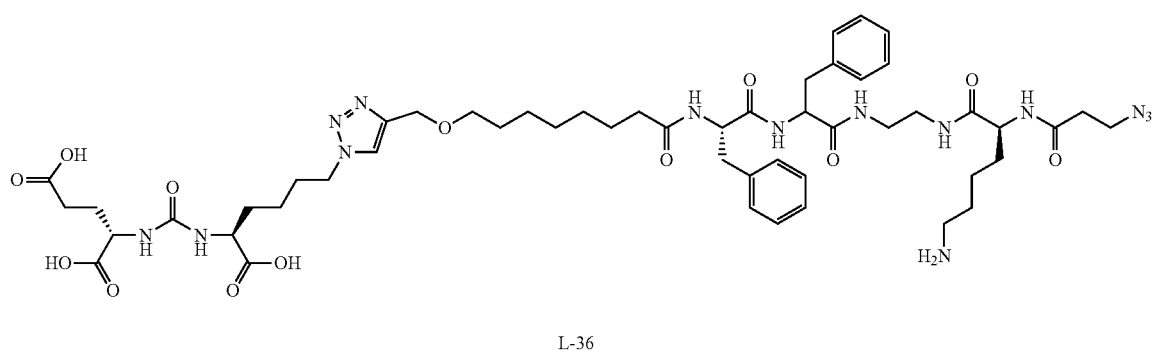 [SMILES: [N-]=[N+]=NCCC(=O)N[C@@H](CCCCN)C(=O)NCCNC(=O)C(Cc1ccccc1)NC(=O)[C@H](Cc1ccccc1)NC(=O)CCCCCCCOCc1cn(CCCC[C@H](NC(=O)N[C@@H](CCC(=O)O)C(=O)O)C(=O)O)nn1]

L-36

Preparation of Compound L-36a

Compound L-25 (Preparation Example 22) was used to obtain compound L-36a with a similar method to the preparation method of the compound L-23b of Preparation Example 20. Yield 70%; EI-MS m/z: 1139 (M⁺).

Preparation of Compound L-36b

Compound L-36a was used to obtain compound L-36b with a similar method to the preparation method of compound L-23c of Preparation Example 20. Yield 75%; EI-MS m/z: 1049 (M⁺).

Preparation of Compound L-36c

Compound L-36b was used to obtain compound L-36b with a similar method to the preparation of the compound L-23d of Preparation Example 20. Yield 49%; EI-MS m/z: 688 (M⁺/2).

Preparation of Compound L-36

Compound L-36c was used to obtain compound L-36 with a similar method to the preparation method of the compound L-23 of Preparation Example 20. Yield 99%; EI-MS m/z: 1106 (M⁺).

[Example 1] Synthesis of BGal-SIG-Toxin (S-9)

-continued

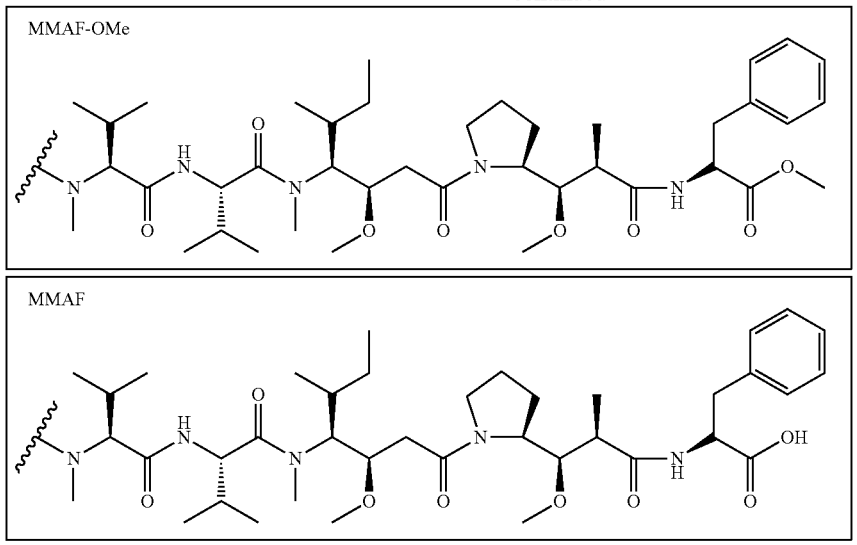

Preparation of Compound S-1

β-D-galactose pentaacetate (Alfa, CAS 4163-60-4, 5.0 g, 12.81 mmol) was dissolved in 33% HBr in AcOH (20 mL) at 0° C. under a nitrogen atmosphere. The reaction mixture was stirred for 4 hours at room temperature. After the reaction is completed, the mixture was concentrated under reduced pressure and then EA (1000 mL) and sodium bicarbonate aqueous solution (1000 mL) were added thereto. The organic layer was dried over anhydrous $Na_2SO_4$, filtered and concentrated under reduced pressure. The residue was purified by column chromatography to obtain compound S-1 (5.2 g, 99%).

$^1$H NMR (400 MHz, $CDCl_3$) δ 6.70 (d, J=4.0 Hz, 1H), 5.52 (d, J=2.4 Hz, 1H), 5.41 (dd, J=7.6, 2.8 Hz, 1H), 5.05 (dd, J=6.4, 4.0 Hz, 1H), 4.49 (t, J=6.4 Hz, 1H), 4.22-4.09 (m, 2H), 2.16-2.01 (m, 12H).

Preparation of Compound S-2

5-formylsalicylic acid (8.3 g, 49.96 mmol) was dissolved in THF (100 mL) at room temperature under a nitrogen atmosphere followed by DIPA (17.4 mL, 99.92 mmol) and then allyl bromide (21.62 mL, 249.8 mmol). The mixture was reflux for 15 hours. After the reaction was completed, the mixture was extracted with distilled water (100 mL) and EA (100 mL), and the organic layer was dried over anhydrous $Na_2SO_4$, filtered and concentrated under reduced pressure. The residue was purified by column chromatography to obtain compound S-2(9.4 g, 91.2%).

$^1$H NMR (400 MHz, $CDCl_3$) δ 11.37 (s, 1H), 9.90 (s, 1H), 8.42 (d, J=1.2 Hz, 1H), 8.02 (dd, J=8.4, 1.2 Hz, 1H), 7.12 (d, J=8.4 Hz, 1H), 6.11-6.01 (m, 1H), 5.49-5.36 (m, 2H), 4.90 (d, J=6.0 Hz, 2H)

Preparation of Compound S-3

A molecular sieve (5.0 g) was put into a round-bottom flask and was dried with heat under reduced pressure. Compound S-1 (5.0 g, 12.12 mmol) and compound S-2 (2.5 g, 12.12 mmol) and molecular sieve (5.0 g) were stirred in acetonitrile (100 mL) under a nitrogen atmosphere. $Ag_2O$ (8.43 g, 36.37 mmol) was added to the mixture and the mixture was stirred at room temperature for 1.5 hours. After the reaction was completed, the mixture was extracted with distilled water (100 mL) and EA (100 mL), and the organic layer was dried over anhydrous $Na_2SO_4$, filtered and concentrated under reduced pressure. The residue was purified by column chromatography to obtain compound S-3 (3.77 g, 58%).

$^1$H NMR (400 MHz, $CDCl_3$) δ 10.02 (s, 1H), 8.28 (d, J=1.6 Hz, 1H), 8.00 (dd, J=6.8, 1.6 Hz, 1H), 7.29 (d, J=8.8 Hz, 1H), 6.09-5.98 (m, 1H), 5.62-5.57 (m, 1H), 5.49 (d, J=3.2 Hz, 1H), 5.40 (d, J=17.2 Hz, 1H), 5.32-5.28 (m, 1H), 5.18 (d, J=8.0 Hz, 1H), 5.12 (dd, J=7.2, 3.2 Hz, 1H), 4.82 (d, J=6.0 Hz, 2H), 4.28-4.10 (m, 4H), 2.20 (s, 3H), 2.08 (s, 6H), 2.02 (s, 3H)

Preparation of Compound S-4

Compound S-3 (3.70 g, 6.90 mmol) was dissolved in isopropyl alcohol (20 mL) and chloroform (100 mL) at room temperature under a nitrogen atmosphere, and then silica gel (29 g) was added thereto. $NaBH_4$ (653 mg, 17.24 mmol) was added to the mixture at 0° C., and then the mixture was stirred for 1.5 hours. After the reaction was completed, the mixture was extracted with distilled water (200 mL) and DCM (200 mL), and the organic layer was dried over anhydrous sodium sulfate, filtered and concentrated under reduced pressure. The residue was purified by column chromatography to obtain compound S-4 (3.51 g, 95%).

$^1$H NMR (400 MHz, $CDCl_3$) δ 7.75 (s, 1H), 7.46 (d, J=8.0 Hz, 1H), 7.18 (d, J=8.8 Hz, 1H), 6.08-5.97 (m, 1H), 5.58-5.52 (m, 1H), 5.46 (d, J=3.2 Hz, 1H), 5.39 (d, J=17.2 Hz, 1H), 5.28 (d, J=10.4 Hz, 1H), 5.10 (dd, J=6.8, 3.6 Hz, 1H), 5.06 (d, J=8.0 Hz, 1H), 4.78 (d, J=5.2 Hz, 1H), 4.68 (d, J=6.0 Hz, 2H), 4.27-4.04 (m, 3H), 2.19 (S, 3H), 2.08 (S, 3H), 2.07 (S, 3H), 2.02 (S, 3H), 1.72 (t, J=6.0 Hz, 1H).

Preparation of Compound S-5

Compound S-4 (3.5 g, 6.50 mmol) was dissolved in DCM (70 mL) under a nitrogen atmosphere, $Pd(PPh_3)_4$(376 mg, 0.33 mmol), triphenylphosphine (426 mg, 1.62 mmol), and pyrolidine (555 mg, 7.80 mmol) were added thereto. The mixture was stirred for 30 minutes at room temperature. After the reaction is completed, the mixture was diluted with distilled water (100 mL) and adjusted to have pH 3 with 2N—HCl aqueous solution. The mixture was diluted with DCM (100 mL). The organic layer was dried over anhydrous $Na_2SO_4$, filtered and concentrated under reduced pressure to obtain compound S-5 (3.2 g, crude).

$^1$H NMR (400 MHz, $CDCl_3$) δ 8.09 (s, 1H), 7.60 (d, J=7.6 Hz, 1H), 7.18 (d, J=8.4 Hz, 1H) 5.61-5.55 (m, 1H), 5.49 (s,

1H), 5.24 (d, J=7.6 Hz, 1H), 5.16 (d, J=10.4 Hz, 1H), 4.72 (s, 2H), 4.26-4.10 (m, 3H), 2.21 (s, 3H), 2.11 (s, 3H), 2.07 (s, 3H), 2.03 (s, 3H).

Preparation of Compound S-6

A solution of compound S-5 (1.1 g, 2.21 mmol) and compound L-1 (455 mg, 2.43 mmol) in DMF (15 mL) at room temperature under a nitrogen atmosphere were treated with PyBOP (1.5 g, 2.87 mmol) and DIPEA (0.57 mL, 3.31 mmol). After stirring for 2 hours at room temperature, the mixture was extracted with distilled water (20 mL) and EA (20 mL), and the organic layer was dried over anhydrous $Na_2SO_4$, filtered and concentrated under reduced pressure. The residue was purified by column chromatography to obtain compound S-6(1.24 g, 84%).

$^1$H NMR (400 MHz, $CDCl_3$) δ 8.03 (d, J=1.6 HZ, 1H), 7.46 (d, J=8.4 Hz, 1H), 7.35 (t, J=4.8 Hz, 1H), 7.06 (d, J=8.4 Hz, 1H), 5.56-5.48 (m, 2H), 5.17-5.12 (m, 2H), 4.69 (s, 2H), 4.27-4.10 (m, 5H), 3.82-3.48 (m, 12H), 2.42 (s, 1H), 2.23 (s, 3H), 2.07 (s, 3H), 2.06 (s, 3H), 2.03 (s, 3H); EI-MS m/z: 668 ($M^+$).

Preparation of BGal-SIG Linker Compound S-7

To a solution of compound S-6 (2.36 g, 3.61 mmol) in DMF (30 mL) under a nitrogen atmosphere was added Bis(4-nitrophenyl)carbonate (1.21 g, 3.97 mmol) and followed by addition of DIPEA (943 μL, 5.42 mmol). The mixture was stirred for 3 hours at room temperature. After the reaction was completed, the mixture was extracted with brine (30 mL) and EA (30 mL). The organic layer was dried over anhydrous $Na_2SO_4$, filtered and concentrated under reduced pressure. The residue was purified by column chromatography to obtain BGal-SIG linker compound S-7 (2.57 g, 87%).

$^1$H NMR (400 MHz, $CDCl_3$) δ 8.29-8.26 (d, J=8.8 Hz, 2H), 8.15 (s, 1H), 7.53-7.51 (dd, J=8.8 Hz, 1H), 7.39-7.37 (d, J=8.8 Hz, 2H), 7.08-7.06 (d, J=8.8 Hz, 1H) 5.41-5.27 (m, 6H), 4.23-4.19 (m, 3H), 4.21-4.18 (m, 3H), 3.77-3.52 (m, 15H), 2.43 (s, 1H), 2.06 (s, 9H); EI-MS m/z: 833 ($M^+$).

Preparation of Compound S-8

Compound S-7 (200 mg, 0.24 mmol) was dissolved in DMF (3 mL) at room temperature under a nitrogen atmosphere. MMAF-OMe (Preparation Example 7, 179 mg, 0.24 mmol) and HOBT (7.4 mg, 0.05 mmol) were added followed by the addition of pyridine (1.0 mL) and diisopropyl ethylamine (42 μL, 0.24 mmol). The mixture was stirred for 19 hours at room temperature. After the reaction was completed, the mixture was extracted with EA (100 mL), distilled water (300 mL), brine (100 mL) and 1N hydrochloric acid aqueous solution (20 mL). The organic layer was dried over anhydrous $Na_2SO_4$, filtered and concentrated under reduced pressure. The residue was purified by column chromatography to obtain compound S-8 (247 mg, 72%).

EI-MS m/z: 1440 ($M^+$).

Preparation of BGal-SIG-Toxin Compound S-9

To a solution of compound S-8 (100 mg, 0.07 mmol) in methanol (1.8 mL) was added LiOH (22 mg, 0.52 mmol) dissolved in water (1.8 mL) at −20° C. under a nitrogen atmosphere. The mixture was stirred at −5° C. for 4 hours. After the reaction was completed, the resulting residue was diluted with 2N hydrochloric acid aqueous solution (3 mL) and purified by prep-HPLC to obtain BGal-SIG-Toxin compound S-9 (78 mg, 89%). EI-MS m/z: 1258 ($M^+$).

[Example 2] Preparation of Ligand-Drug Conjugates (1) and (2)

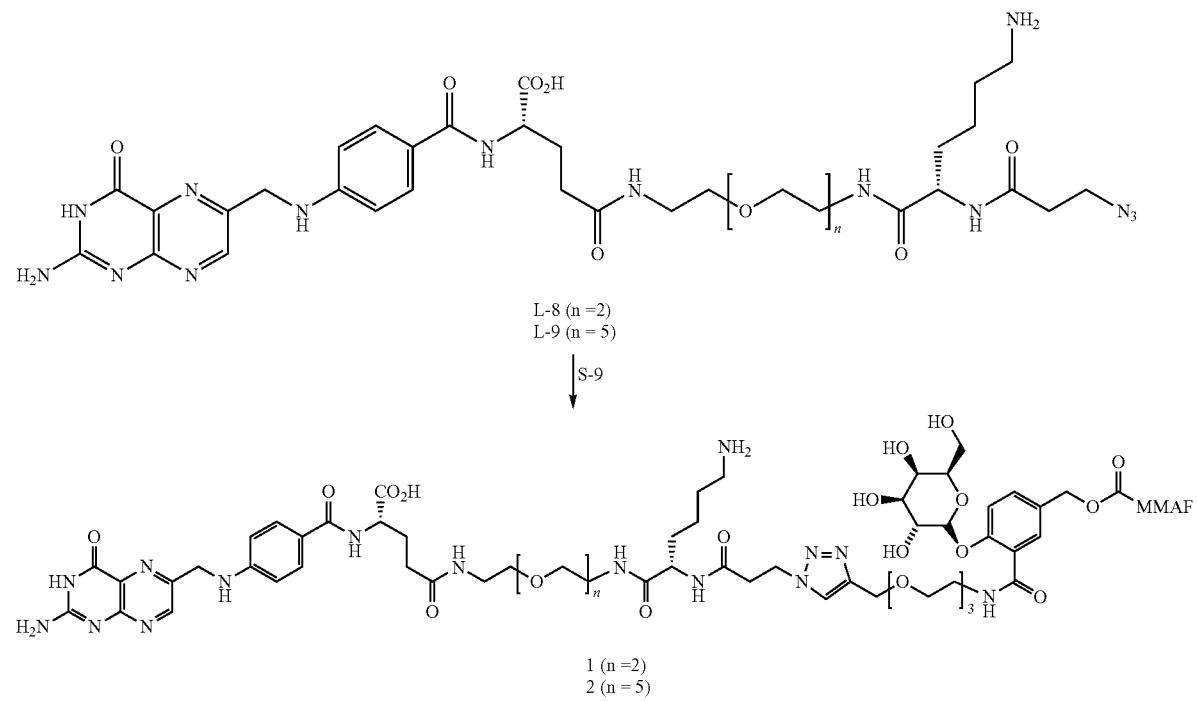

Preparation of Ligand-Drug Conjugate (1)

A solution of compound L-8 (20 mg, 0.02 mmol) prepared by Preparation Example 8 and compound S-9 (22.08 mg, 0.02 mmol) prepared by Example 1 in ethanol (2 mL) and distilled water (0.5 mL) at room temperature under nitrogen atmosphere were treated with 1M Sodium ascorbate (35 μL, 0.04 mmol) and 0.1 M $CuSO_4$ (70 μL, 0.01 mmol) and stirred for 2.5 hours. After the reaction was completed, the mixture was purified by prep-HPLC to obtain ligand-drug conjugate (1) (32.2 mg, 77%). EI-MS m/z: 2055 (M$^+$).

Preparation of Ligand-Drug Conjugate (2)

Compound L-9 (Preparation Example 8) and compound S-9 (Example 1) were used to prepare ligand-drug conjugate (2) with a similar method to the preparation method of ligand-drug conjugate 1. EI-MS m/z: 2187 (M$^+$).

[Example 3] Preparation of Ligand-Drug Conjugate (3)

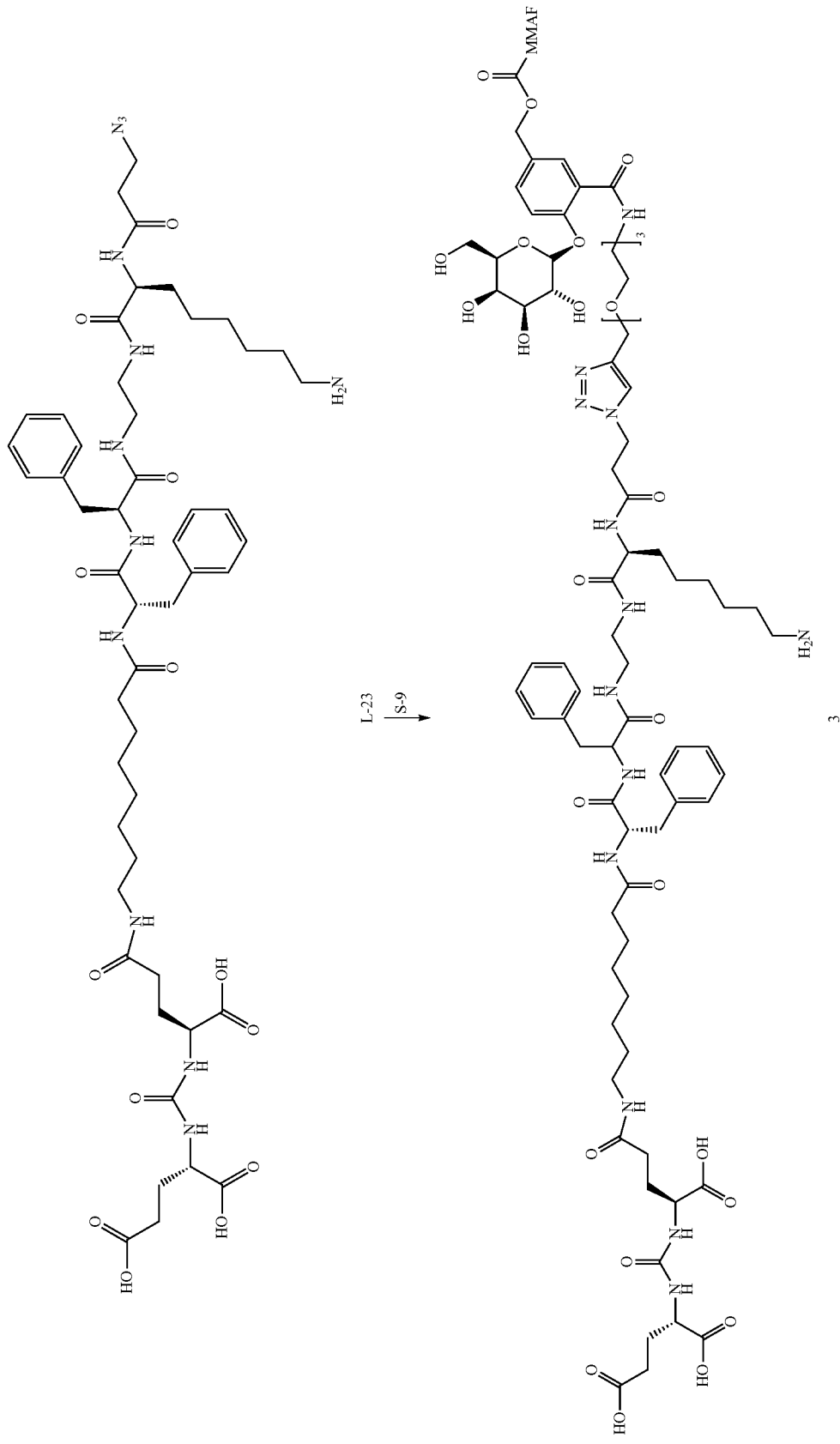

Compound L-23 (Preparation Example 20) and compound S-9 (Example 1) were used to prepare ligand-drug conjugate (3) with a similar method to the preparation method of ligand-drug conjugate (1). Yield 29.7%; EI-MS m/z: 1141 ($M^+/2$)

[Example 4] Preparation of Ligand-Drug Conjugate (4)

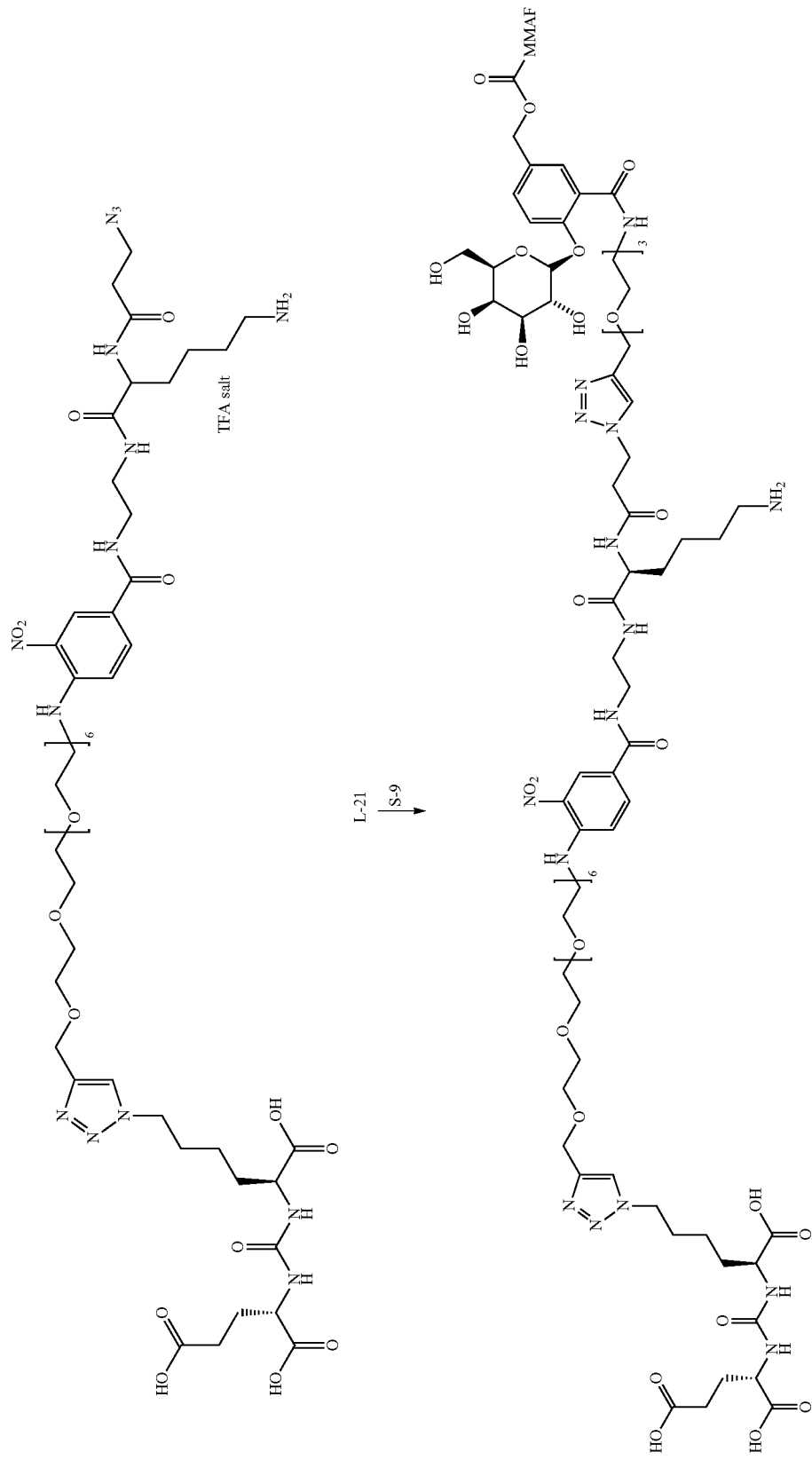

Compound L-21 (Preparation Example 18) and compound S-9 (Example 1) were used to prepare ligand-drug conjugate (4) with a similar method to the preparation method of ligand-drug conjugate (1). EI-MS m/z: 2487 (M$^+$), 1244 (M$^+$/2), 830 (M$^+$/3)

[Example 5] Preparation of Ligand-Drug Conjugate (5)

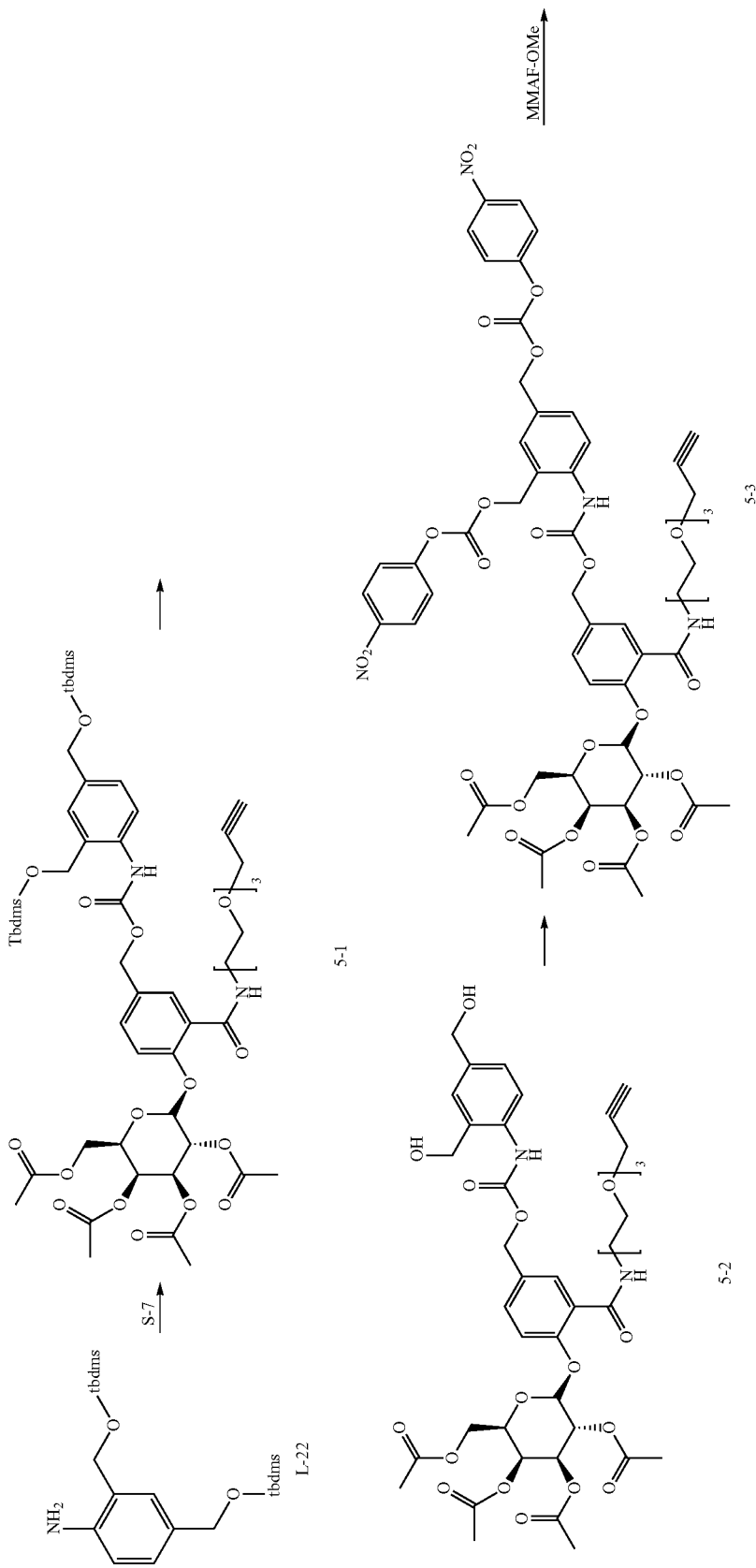

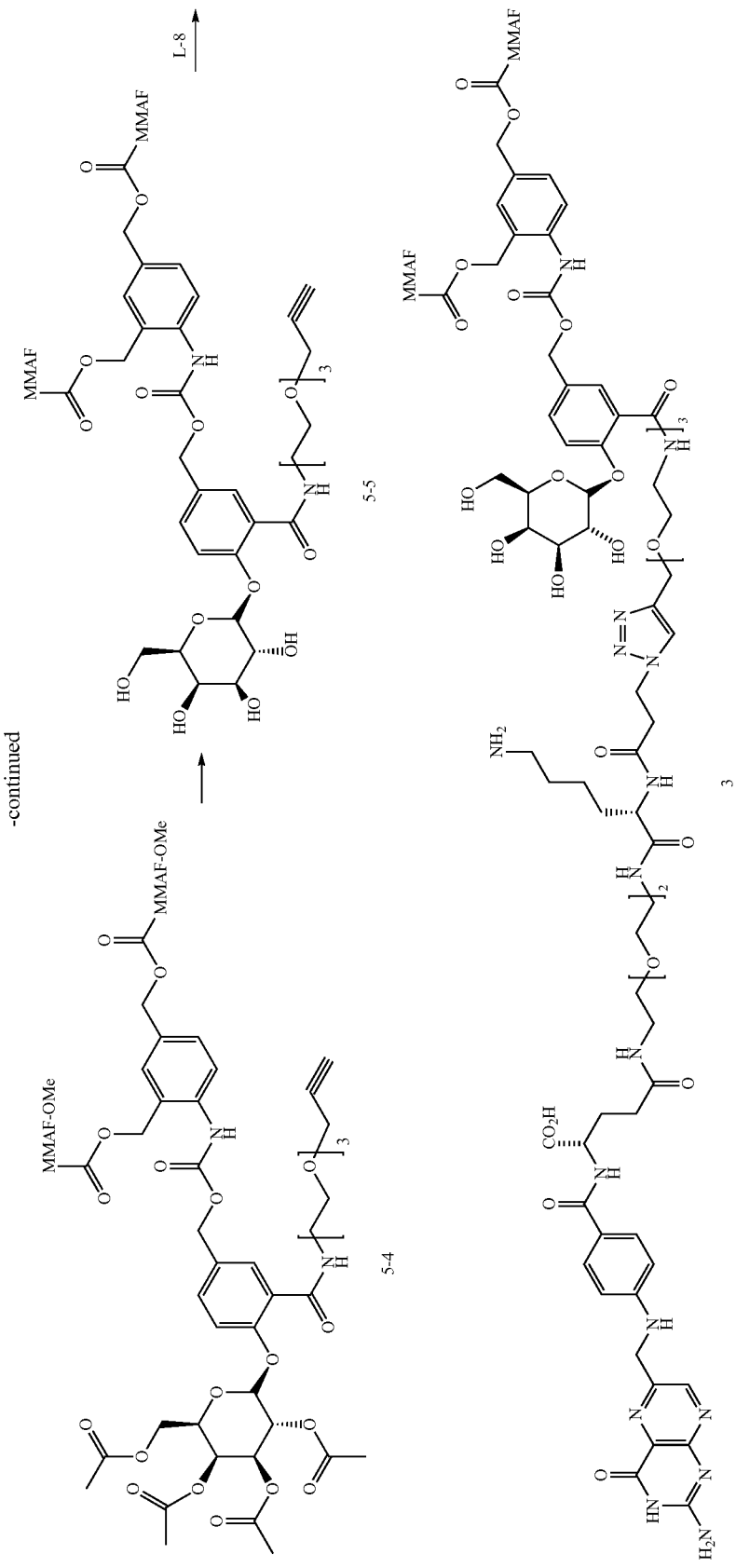

Preparation of Compound 5-1

A solution of compound S-7 (260 mg, 0.31 mmol) and compound L-22 (122 mg, 0.32 mmol) in DMF (2 mL) at room temperature under a nitrogen atmosphere were treated with HOBt (24 mg, 0.16 mmol), Pyridine (2 mL) and DIPEA (108 μL, 0.62 mmol). The mixture was stirred for 28 hours at 40° C. After the reaction was completed, the mixture was extracted with EA (250 mL), distilled water (50 mL) and 2N HCl aqueous solution (50 mL). The organic layer was dried over anhydrous $Na_2SO_4$, filtered and concentrated under reduced pressure. The residue was purified by column chromatography to obtain compound 5-1 (208 mg, 62%).

$^1$H NMR (400 MHz, $CDCl_3$) δ 8.35 (s, 1H), 8.10 (s, 1H), 7.95 (s, 1H), 7.52-7.46 (m, 1H), 7.38-7.18 (m, 3H), 7.08-7.02 (m, 1H), 5.58-5.48 (m, 2H), 5.20-5.11 (m, 4H), 4.71 (s, 2H), 4.66 (S, 2H), 4.24-4.08 (m, 5H), 3.82-3.74 (m, 1H), 3.72-3.62 (m, 10H), 3.58-3.48 (m, 1H), 2.44-2.40 (m, 1H), 2.23 (s, 3H), 2.06 (s, 6H), 2.03 (s, 3H), 0.92 (s, 9H), 0.88 (s, 9H), 0.08 (s, 6H), 0.07 (s, 6H); EI-MS m/z: 1076 (M$^+$).

Preparation of Compound 5-2

A solution of compound 5-1 (205 mg, 0.19 mmol) in DCM (3 mL) was treated with TFA (0.8 mL) at 0° C. under a nitrogen atmosphere. The mixture was stirred for 1.5 hours. After the reaction is completed, the reaction mixture was extracted with DCM (50 mL) and $NaHCO_3$ aqueous solution (150 mL). TEA (20 mL) was added to the organic layer, and the mixture was stirred for 30 minutes. The reaction solution was extracted with distilled water (100 mL), and the organic layer was dried over anhydrous $Na_2SO_4$, filtered and concentrated under reduced pressure to obtain compound 5-2 (122 mg, 75%).

$^1$H NMR (400 MHz, $CDCl_3$) δ 8.11 (s, 1H), 8.01 (s, 1H), 7.90 (s, 1H), 7.48 (d, J=8.8 Hz, 1H), 7.38-7.33 (m, 1H), 7.31 (d, J=8.4 Hz, 1H), 7.20 (s, 1H), 7.06 (d, J=8.4 Hz, 1H), 5.55-5.49 (m, 2H), 5.20-5.12 (m, 4H), 4.71 (d, J=4.8 Hz, 2H), 4.64 (d, J=8.8 Hz, 2H), 4.26-4.10 (m, 5H), 3.81-3.74 (m, 1H), 3.72-3.62 (m, 10H), 3.58-3.48 (m, 1H), 2.42-2.41 (m, 1H), 2.33 (s, 1H), 2.22 (s, 3H), 2.07 (s, 3H), 2.06 (s, 3H), 2.03 (s, 3H), 1.74 (s, 1H); EI-MS m/z: 847 (M$^+$).

Preparation of Compound 5-3

To a solution of compound 5-2 (70 mg, 0.08 mmol) in DMF (1 mL) at room temperature under a nitrogen atmosphere were added Bis(PNP) (63 mg, 0.21 mmol) and DIPEA (36 μL, 0.21 mmol). The mixture was stirred for 2 hours at room temperature. After the reaction was completed, the mixture was extracted with EA (100 mL) and distilled water (100 mL). The organic layer was dried over anhydrous $Na_2SO_4$, filtered and concentrated under reduced pressure. The residue was purified by column chromatography to obtain compound 5-3 (72 mg, 74%).

$^1$H NMR (400 MHz, $CDCl_3$) δ 8.29-8.25 (m, 4H), 8.17 (s, 1H), 7.96-7.91 (m, 1H), 7.52-7.48 (m, 4H), 7.47-7.35 (m, 5H), 7.06 (d, J=8.0 Hz, 1H), 5.54-5.49 (m, 2H), 5.31 (s, 2H), 5.27 (s, 2H), 5.20-5.16 (m, 4H), 4.28-4.10 (m, 5H), 3.81-3.74 (m, 1H), 3.72-3.62 (m, 10H), 3.58-3.48 (m, 1H), 2.43-2.41 (m, 1H), 2.23 (s, 3H), 2.06 (s, 6H), 2.03 (s, 3H); EI-MS m/z: 1178 (M$^+$).

Preparation of Compound 5-4

A solution of compound 5-3 (60 mg, 0.05 mmol) and MMAF (76 mg, 0.10 mmol) in DMF (1.5 mL) at room temperature under a nitrogen atmosphere were treated with $HOBt.H_2O$ (8 mg, 0.05 mmol), pyridine (0.5 mL) and DIPEA (35 μL, 0.20 mmol). The mixture was stirred for 14 hours. After the reaction was completed, the mixture was extracted with EA (250 mL), distilled water (50 mL) and 2N HCl aqueous solution (50 mL). The organic layer was dried over anhydrous $Na_2SO_4$, filtered and concentrated under reduced pressure. The residue was purified by column chromatography to obtain compound 5-4 (68.7 mg, 56%). EI-MS m/z: 2391 (M$^+$).

Preparation of Compound 5-5

To a solution of compound 5-4 (50 mg, 0.02 mmol) in methanol (2 mL) and distilled water (1 mL) at −5° C. was added $LiOH—H_2O$ (18 mg, 0.42 mmol), and the mixture was stirred for 5 hours at 0° C. After the reaction is completed, the mixture was adjusted to have pH 2 to 3 with 2N HCl aqueous solution, purified by prep-HPLC to obtain compound 5-5 (32 mg, 70%). EI-MS m/z: 2195 (M$^r$)

Preparation of Ligand-Drug Conjugate (5)

Compound L-8 (Preparation Example 8) and compound 5-5 were used to prepare ligand-drug conjugate (5) with a similar method to the preparation method of ligand-drug conjugate (1). EI-MS m/z: 2992 (M$^+$).

[Example 6] Preparation of Ligand-Drug Conjugate (6)

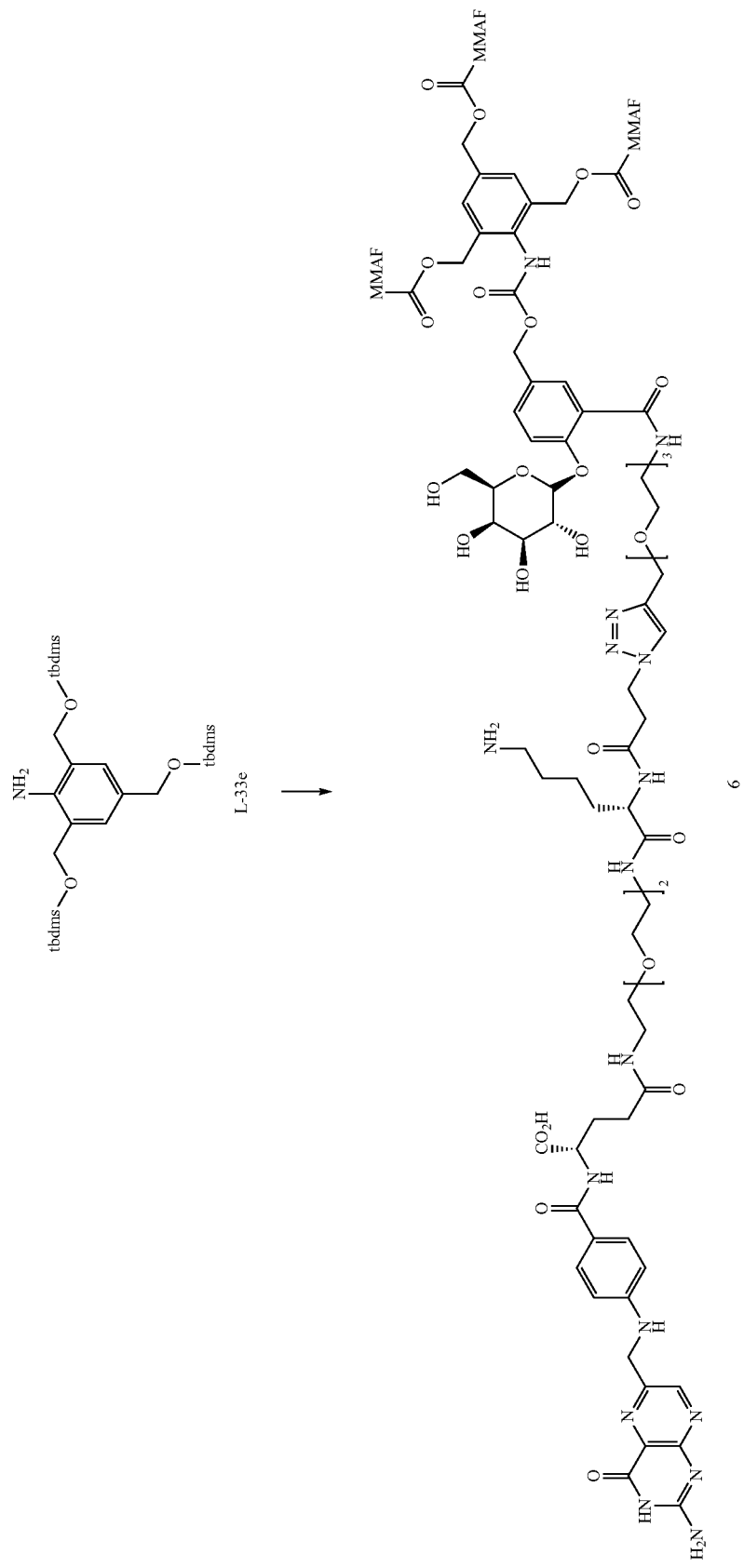

Compound L-33e (Preparation Example 30) was used to prepare ligand-drug conjugate (6) with a similar method to the preparation method of ligand-drug conjugate (5).

[Example 7] Preparation of Ligand-Drug Conjugates (7), (8) and (9)

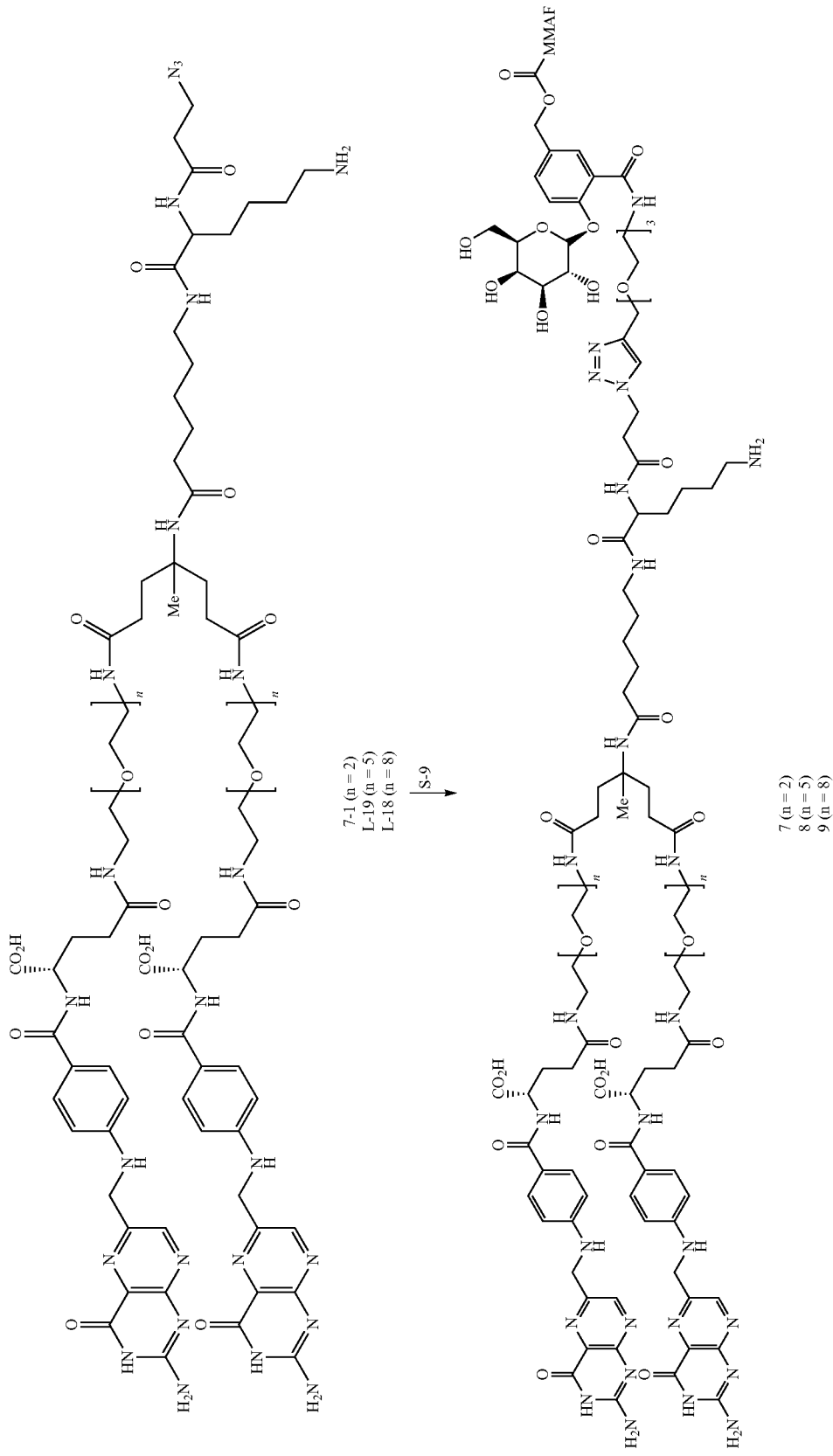

Preparation of Ligand-Drug Conjugate (7)

Compound 7-1 and compound S-9 (Example 1) were used to prepare ligand-drug conjugate (7) with a similar method to the preparation method of ligand-drug conjugate (1). Yield 14%; EI-MS m/z: 1446 (M$^+$/2)

Preparation of Ligand-Drug Conjugate (8)

Compound L-19 (Preparation Example 16) and compound S-9 (Example 1) were used to prepare ligand-drug conjugate (8) with a similar method to the preparation method of ligand-drug conjugate (1). Yield 17.4%; EI-MS m/z: 1578 (M$^+$).

Preparation of Ligand-Drug Conjugate (9)

Compound L-18 (Preparation Example 16) and compound S-9 (Example 1) were used to prepare ligand-drug conjugate (9) in a similar method to the preparation method of ligand-drug conjugate (1). Yield 24%; EI-MS m/z: 1710 (M$^+$).

[Example 8] Preparation of Ligand-Drug Conjugates (10) and (11)

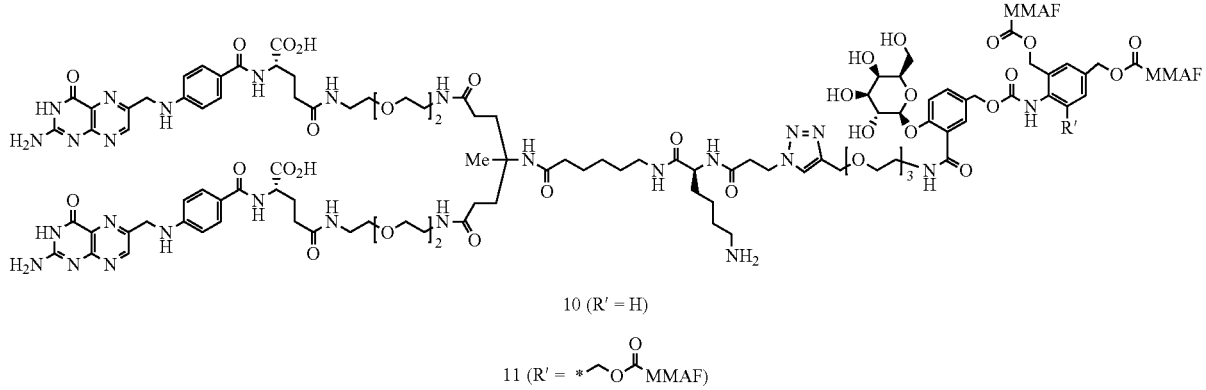

10 (R' = H)

11 (R' = *~O-C(=O)-MMAF)

Compound 7-1 was used to prepare ligand-drug conjugate (10) with a similar method to the preparation method of ligand-drug conjugate (5). Yield 26%; EI-MS m/z: 1277 (M$^+$/3).

Preparation of Compound (11)

Compound 7-1 was used to prepare ligand-drug conjugate (11) in a similar method to the preparation method of ligand-drug conjugate (6). Yield 52%; EI-MS m/z: 1540 (M$^+$/3)

[Example 9] Preparation of Ligand-Drug Conjugate (12)

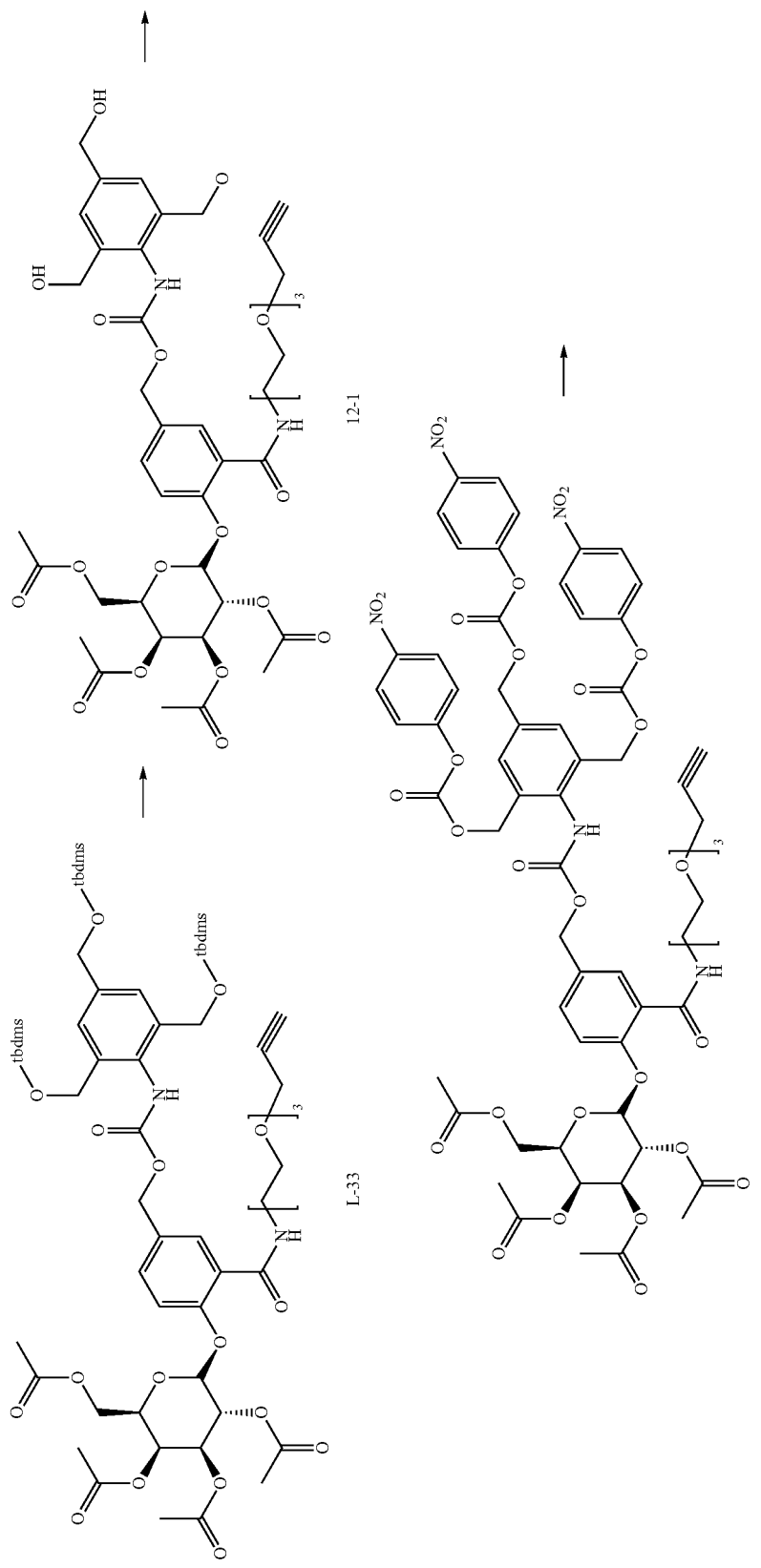

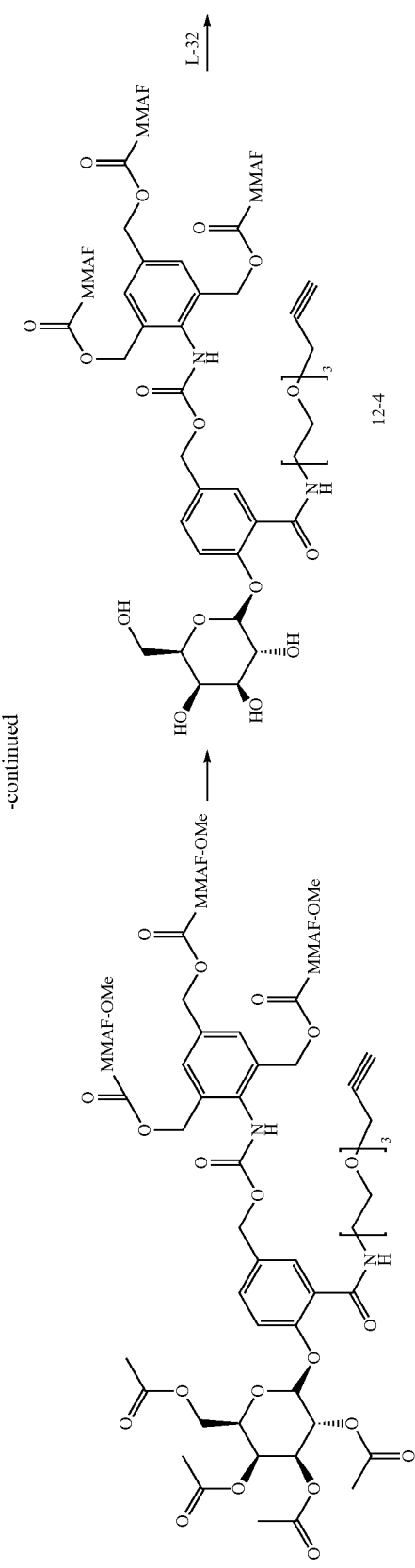
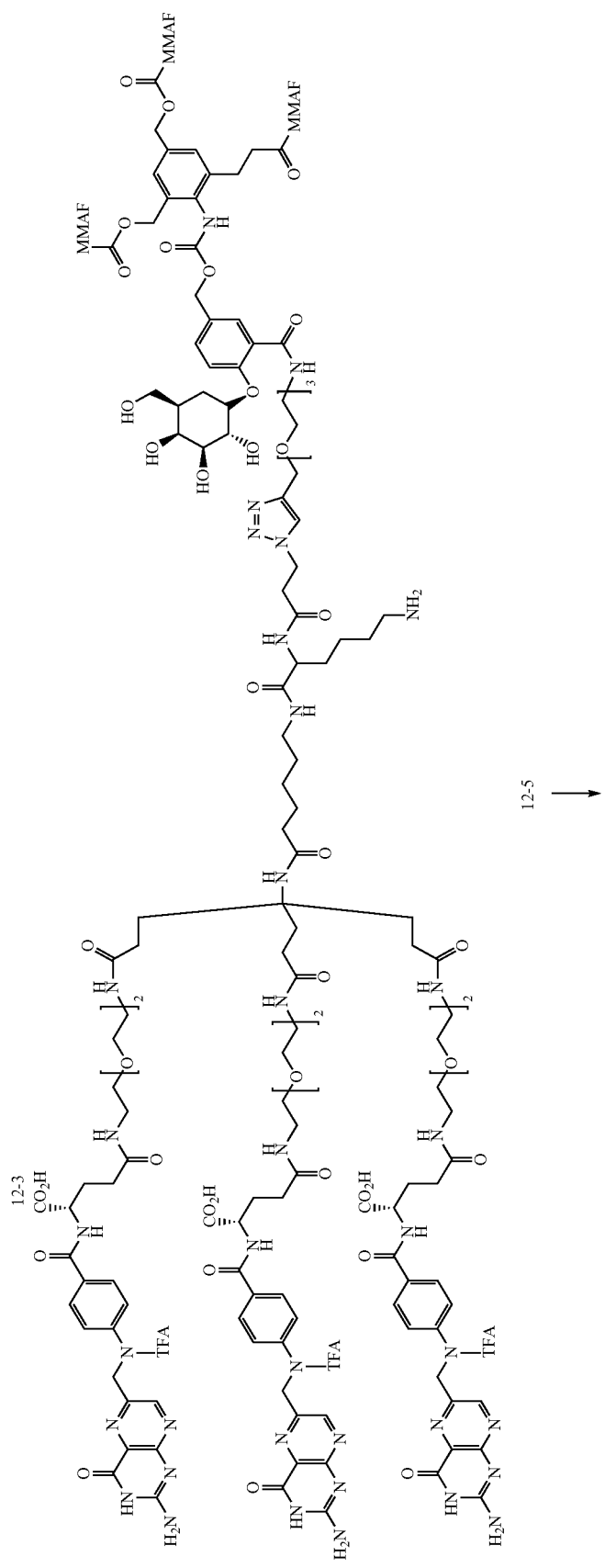

-continued
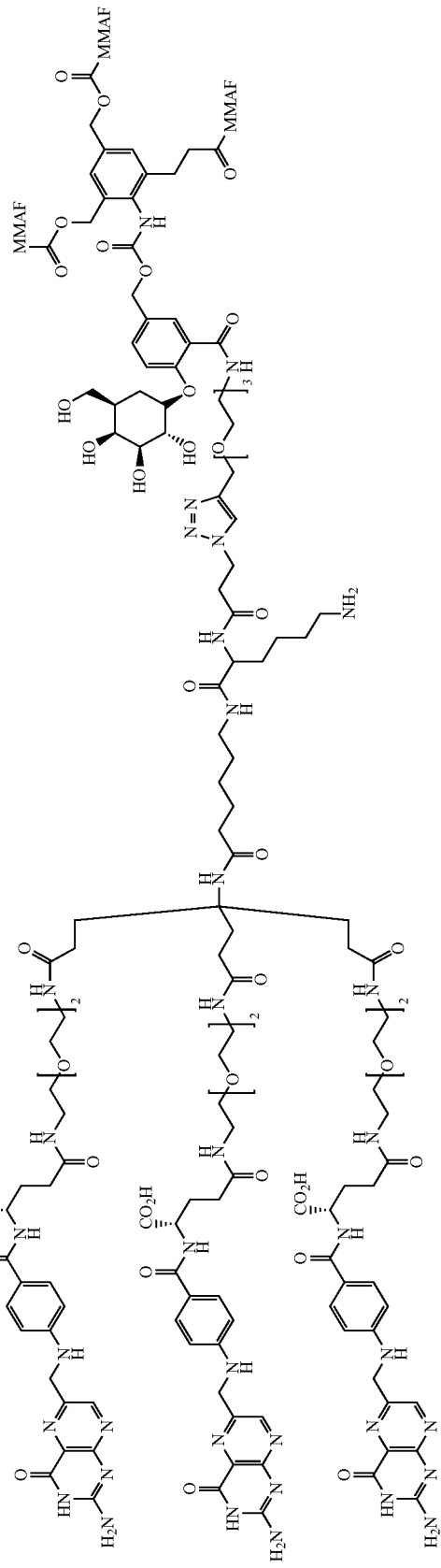

Preparation of Compound 12-1

Compound L-33 (Preparation Example 30) was used to obtain compound 12-1 with a similar method to the preparation method of the compound 5-2 of Example 5. Yield 82%.

$^1$H NMR (400 MHz, CDCl$_3$) δ 8.12 (s, 1H), 7.69 (s, 1H), 7.52-7.46 (m, 1H), 7.44-7.36 (m, 1H), 7.31 (s, 2H), 7.06-7.02 (m, 1H), 5.56-5.46 (m, 2H), 5.26-5.10 (m, 4H), 4.67-4.48 (m, 6H), 4.26-4.08 (m, 5H), 3.84-3.50 (m, 12H), 2.48-2.44 (m, 1H), 2.22 (s, 3H), 2.07 (s, 3H), 2.06 (s, 3H), 2.03 (s, 3H); EI-MS m/z: 877 (M$^+$).

Preparation of Compound 12-2

Compound 12-1 was used to obtain compound 12-2 with a similar method to the preparation method of the compound 5-3 of example 5. Yield 81%.

$^1$H NMR (400 MHz, CDCl$_3$) δ 8.29-8.24 (m, 6H), 8.17 (s, 1H), 7.66 (s, 2H), 7.48-7.32 (m, 9H), 7.06-7.02 (m, 1H), 5.56-5.46 (m, 2H), 5.36-5.34 (m, 6H), 5.20-5.10 (m, 4H), 4.26-4.08 (m, 5H), 3.82-3.50 (m, 12H), 2.46-2.40 (m, 1H), 2.23 (s, 3H), 2.06 (s, 6H), 2.03 (s, 3H); EI-MS m/z: 1373 (M$^+$).

Preparation of Compound 12-3

Compound 12-2 was used to obtain compound 12-3 in a similar method to the preparation method of the compound 5-4 of example 5. Yield 56%; EI-MS m/z: 1065 (M$^+$/3).

Preparation of Compound 12-4

Compound 12-3 was used to obtain compound 12-4 in a similar method to the preparation method of the compound 5-5 of example 5. Yield 61%; EI-MS m/z: 995 (M$^+$/3).

Preparation of Compound 12-5

A solution of compound L-32 (Preparation Example 29) (7.0 mg, 0.0023 mmol) and compound 12-4 (6.9 mg, 0.0023 mmol) in ethanol (2.0 mL) and distilled water (0.5 mL) at room temperature under a nitrogen atmosphere were treated with 1M sodium ascorbate (23 μL, 0.023 mmol) and 0.1M CuSO$_4$ (46 μL, 0.0046 mmol). The the mixture was stirred for 6 hours at room temperature. After the reaction was completed, the mixture was purified by prep-HPLC to obtain conjugate 12-5 (5.6 mg, 40%). EI-MS m/z: 1854 (M$^+$/3).

Preparation of Ligand-Drug Conjugate (12)

To a solution of compound 12-5 (5.6 mg, 0.0009 mmol) ed in MeOH (1.5 mL) and distilled water (0.5 mL) at 0° C. under a nitrogen atmosphere was added LiOH (2.8 mg, 0.065 mmol), and the mixture was stirred for 15 hours at 0° C. After the reaction was completed, the mixture was adjusted to have pH 2 to 3 with 2N HCl aqueous solution, purified by prep-HPLC to obtain ligand-drug conjugate (12) (2.0 mg, 41%). EI-MS m/z: 1744 (M/3+1)

[Example 10] Preparation of Ligand-Fluorescent Substance (FA-Cy5)

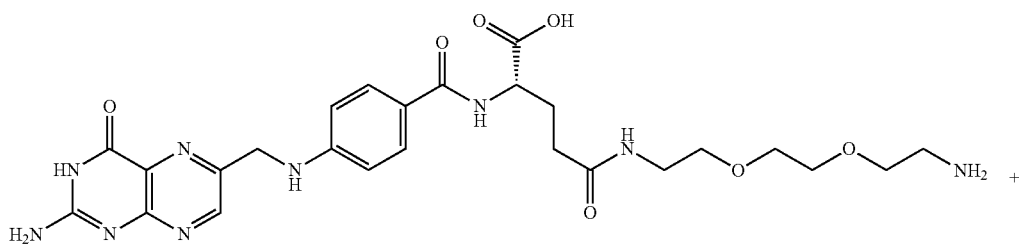

L-10a

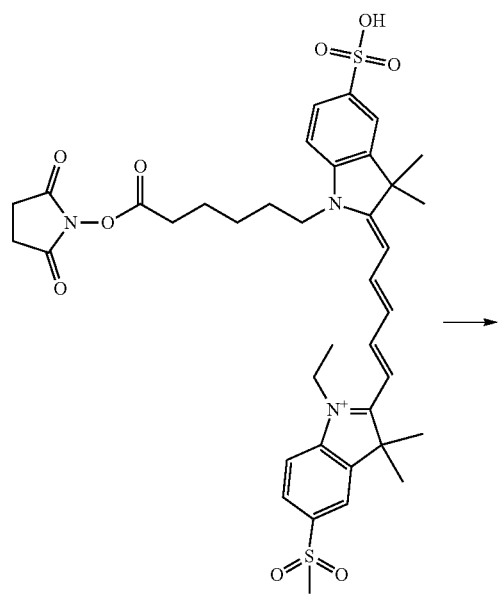

Cy5 NHS ester

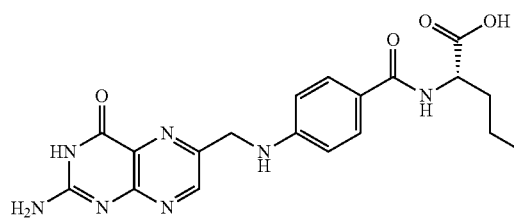
FA-Cy5
FA-Cy5 was synthesized via a similar synthetic route as described in Anal. Biochem. 2013, 432, 59-62, and Cy5 NHS ester was purchased from Lab Service Korea, and was used.
[Example 11] Preparation of Ligand-Drug Conjugate (13)

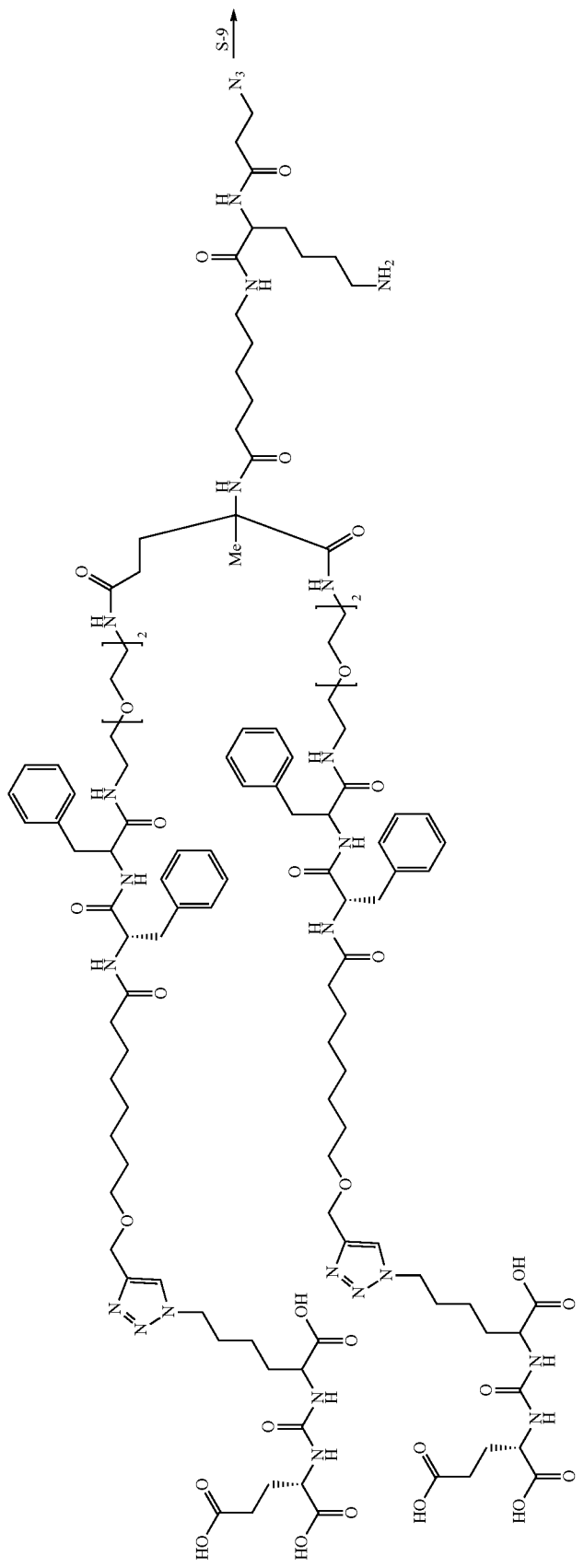
L-25

-continued
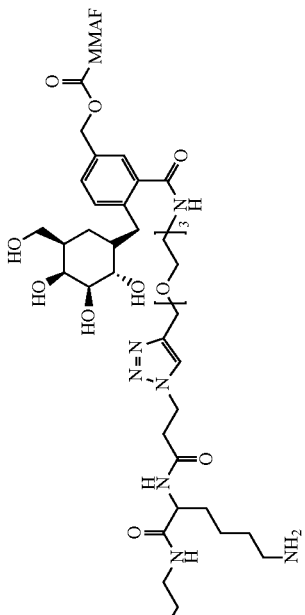
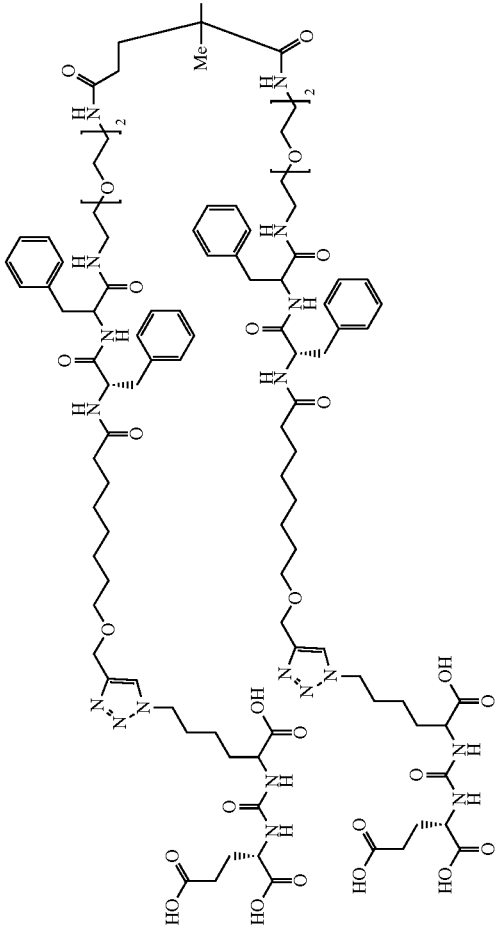

Compound L-25 (Preparation Example 22) and compound S-9 (Example 1) were used to prepare ligand-drug conjugate (13) with a similar method to the preparation method of ligand-drug conjugate (1). Yield 23%; EI-MS m/z: 922 (M$^+$/3), 1229 (M$^+$/2)

[Example 12] Preparation of Ligand-Drug Conjugate (14)

Compound-36 (Preparation Example 33) and compound S-9 (Example 1) were used to prepare ligand-drug conjugate (14) with a similar method to the preparation method of ligand-drug conjugate (1). Yield 23%; EI-MS m/z: 788 (M$^+$/3), 1182 (M$^+$/2)

[Example 13] Preparation of Ligand-Drug Conjugate (15)

Compound L-35 (Preparation Example 32) and compound S-9 (Example 1) were used to prepare ligand-drug conjugate (15) with a similar method to the preparation method of ligand-drug conjugate (1). Yield 23%; EI-MS m/z: 855 (M$^+$/3), 1282 (M$^+$/2)

[Example 14] Preparation of Ligand-Drug Conjugate (16)

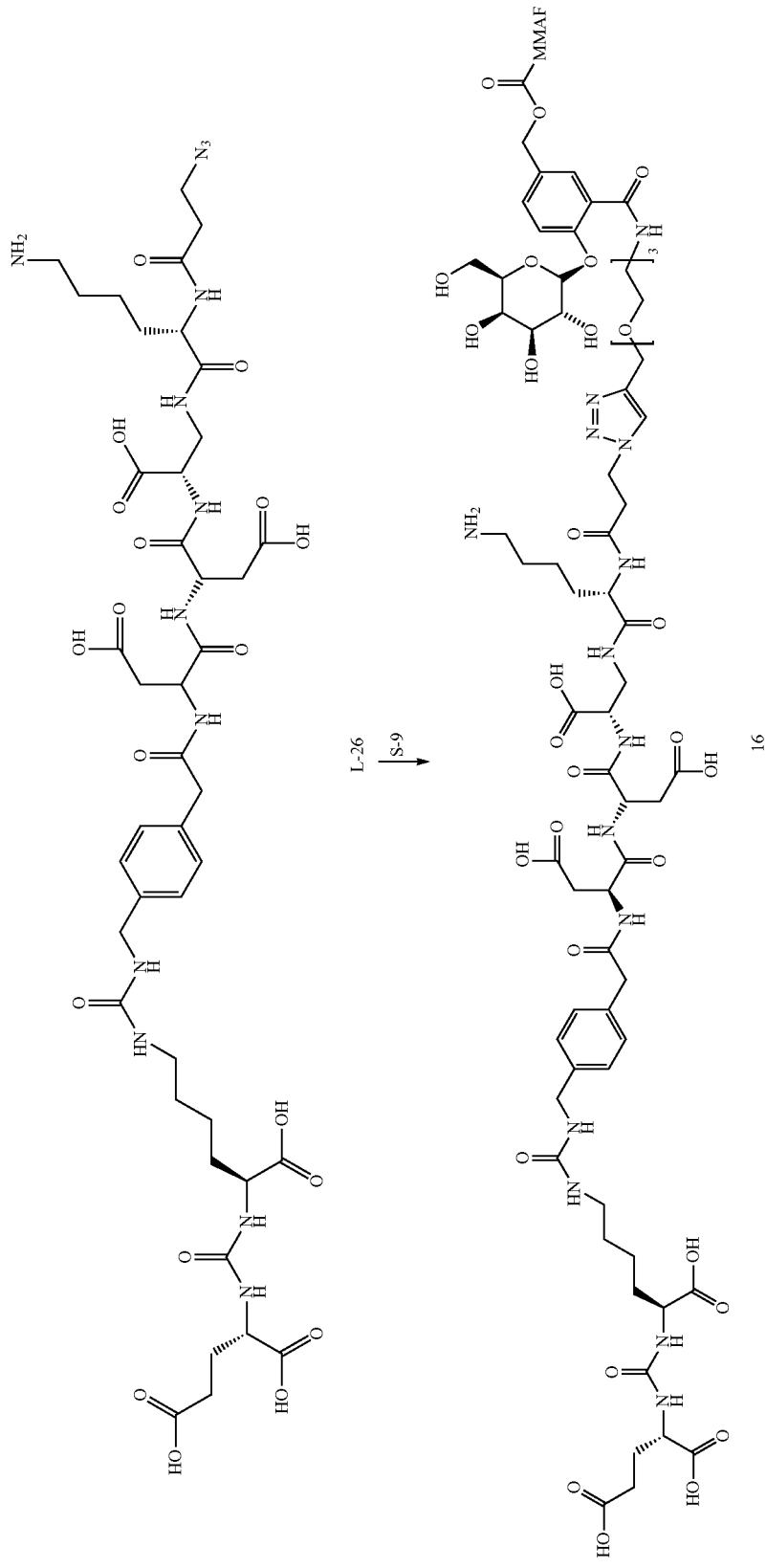

Compound L-35 (Preparation Example 32) and compound S-9 (Example 1) were used to prepare ligand-drug conjugate (15) with a similar method to the preparation method of ligand-drug conjugate (1). Yield 23%; EI-MS m/z: 1156 (M+/2), 771 (M+/3)
[Example 15] Preparation of Compound (17) for Constructing the Conjugate
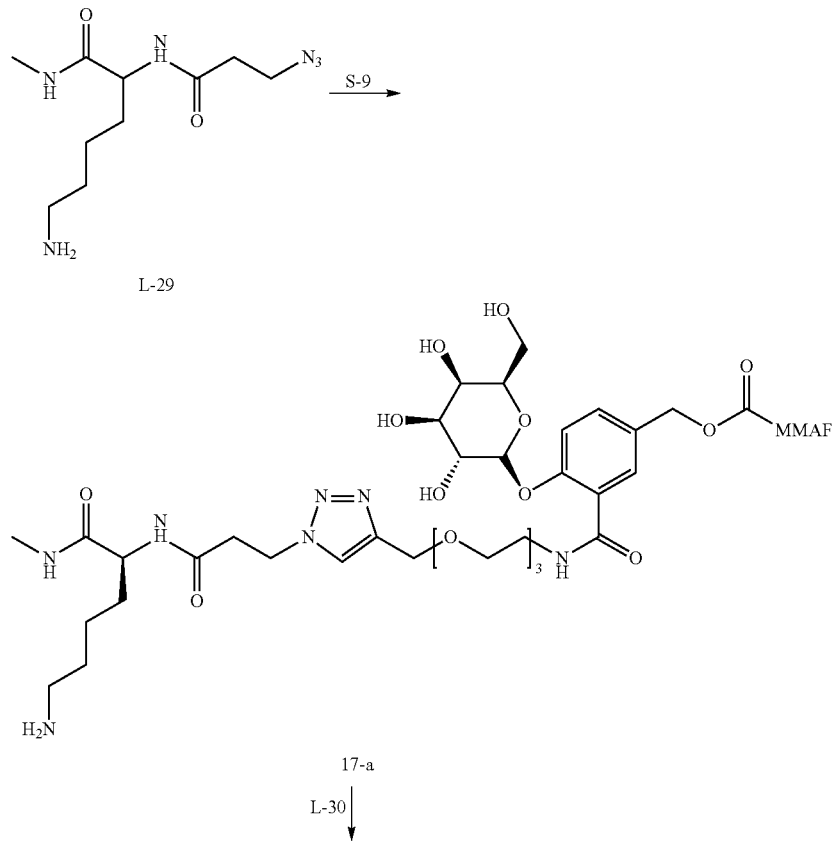
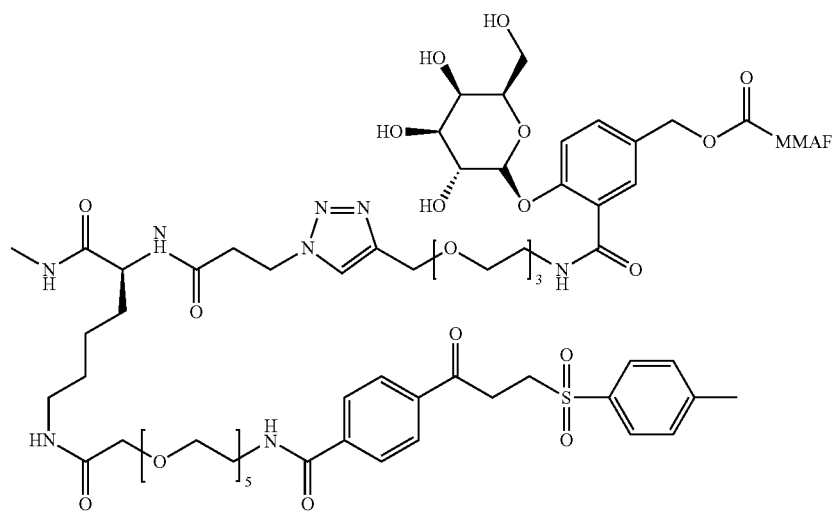

Preparation of Compound 17-a

A solution of compound L-29 (Preparation Example 26) (9.0 mg, 0.024 mmol) and compound S-9 (Example 1) (20 mg, 0.016 mmol) in ethanol (2 mL) and distilled water (0.5 mL) at room temperature under a nitrogen atmosphere were treated with 1M sodium ascorbate (32 μL, 0.032 mmol) and 0.1M CuSO$_4$ (64 μL, 0.0064 mmol), the mixture was stirred for 1 hour. After the reaction was completed, the reaction mixture was purified by prep-HPLC to obtain compound 17-a (14.3 mg, 55%). EI-MS m/z: 1514 (M$^+$).

Preparation of Compound 17

A solution of compound 17-a (13.4 mg, 0.008 mmol) and compound L-30 (Preparation Example 27) (5.8 mg, 0.008 mmol) in DMF (1 mL) under a nitrogen atmosphere was added DIPEA (4.3 μL, 0.02 mmol), and the mixture was stirred for 1 hour at room temperature. After the reaction was completed, the mixture was purified by prep-PHLC to obtain compound (17) (7.2 mg, 42%). EI-MS m/z: 2106 (M$^+$).

[Example 16] Preparation of Compound (18) for Constructing the Conjugate

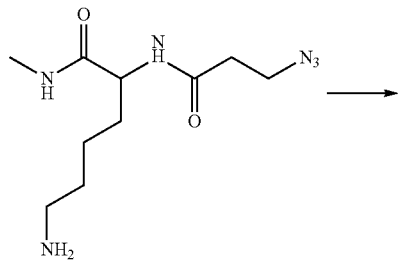

L-29

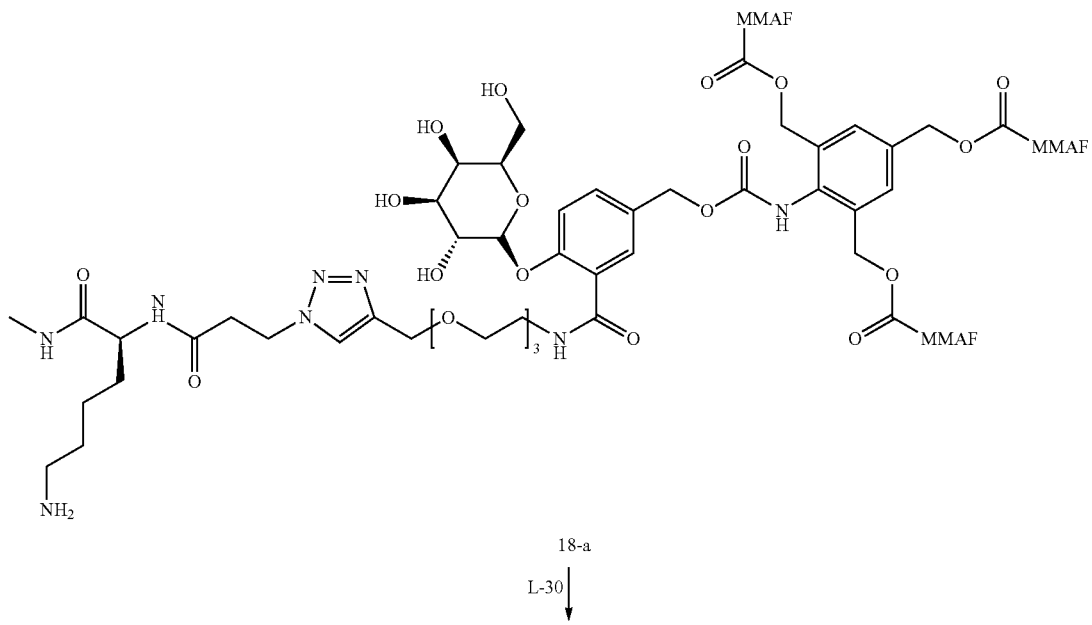

18-a

L-30

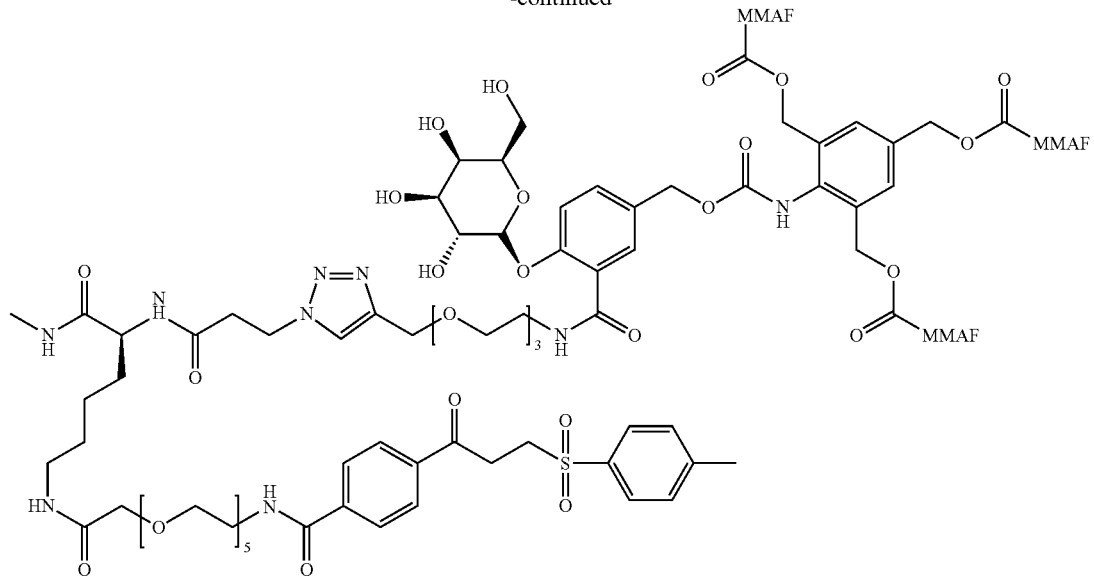

18

Preparation of Compound 18-a

Compound L-29 (Preparation Example 26) and compound 12-4 (Example 9) were used to obtain compound 18-a with a similar method to the preparation method of the compound 17-a. Yield 71%; EI-MS m/z: 1080 (M$^+$/3).

Preparation of Compound 18

Compound 18-a and compound L-30 (Preparation Example 27) were used to obtain compound (18) with a similar method to the preparation method of the compound (17). Yield 33%; EI-MS m/z: 1277 (M$^+$/3)

[Comparative Example 1] Preparation of BG-MMAF (A-6, A-7)

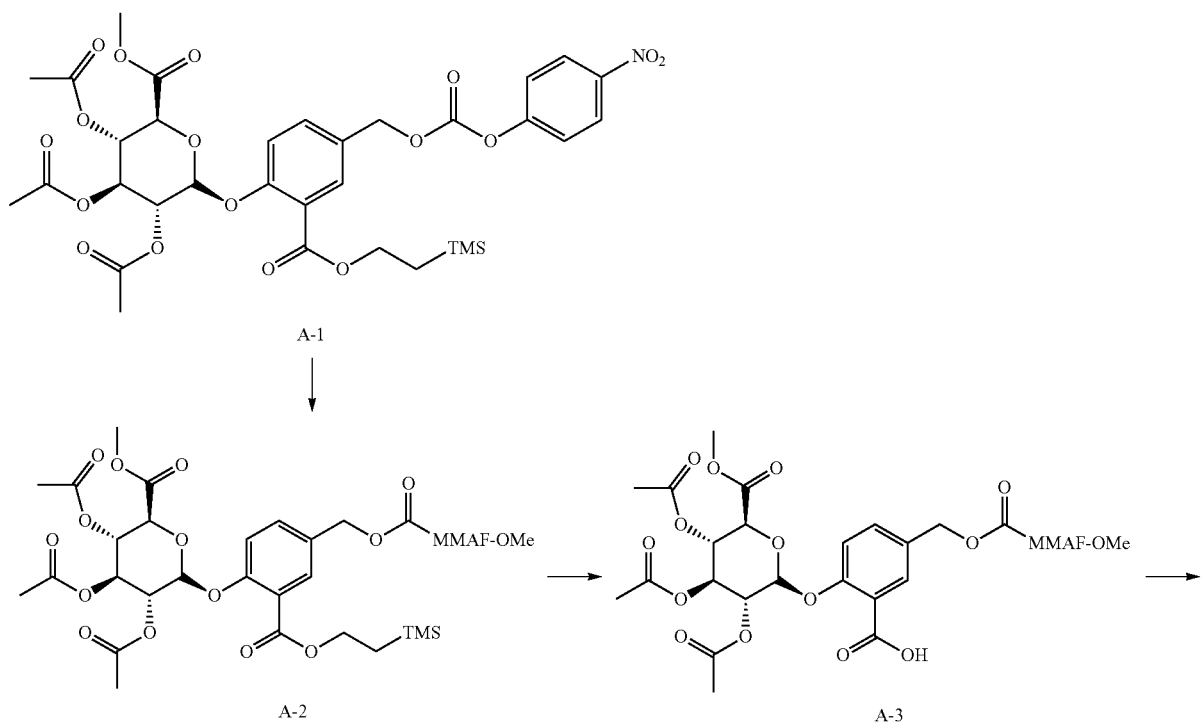

-continued

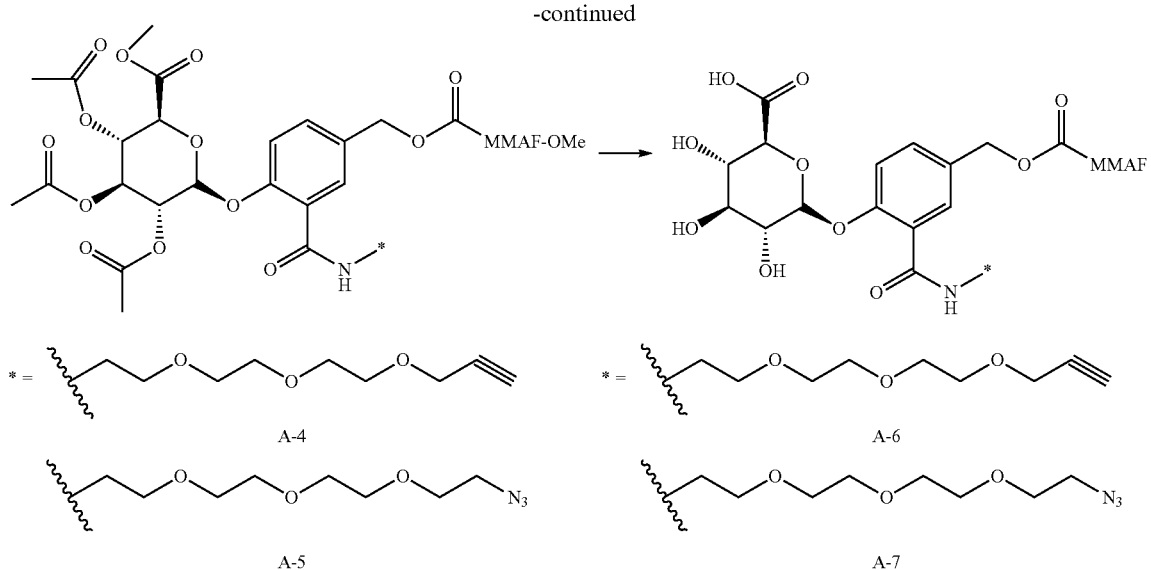

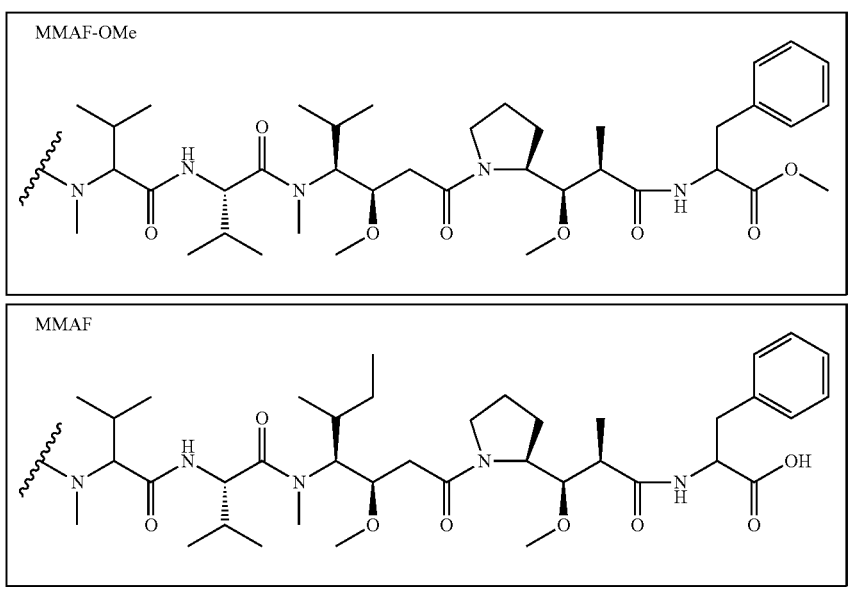

Preparation of Compounds A-1, A-2 and A-3

Each substance was obtained by preparing it with a similar method to that described in Examples 2 and 3 of Korean Patent Laid-Open Publication No. 10-2015-0137015.

Preparation of Compound A-4

A solution of compound A-3 (360 mg, 0.29 mmol) and L-1 (64 mg, 0.34 mmol, Preparation Example 1) in DMF (5 mL) at 0° C. under a nitrogen atmosphere were treated with DIPEA (75 μL, 0.43 mmol) and PyBOP (224 mg, 0.43 mmol). The mixture was stirred for 2 hours at room temperature. After the reaction was completed, the mixture was extracted with EA (100 mL), distilled water (50 mL), and brine (50 mL). The organic layer was dried over anhydrous $Na_2SO_4$, filtered and concentrated under to obtain compound A-4 (410 mg, crude). EI-MS m/z: 1426 ($M^+$).

Preparation of Compound A-5

With a method similar to that for preparing compound A-4, compound A-3 (100 mg, 0.08 mmol) and 2-{2-[2-(2-azidoethoxy)ethoxy]ethoxy}ethanamine (64 mg, 0.34 mmol) were used to obtain compound A-5 (86 mg, 75%). EI-MS m/z: 1457 ($M^+$).

Preparation of Compound A-6

To a solution of compound A-4 (410 mg, 0.29 mmol) was dissolved in methanol (7 mL) at −20° C. under a nitrogen atmosphere was added dropwise LiOH (91 mg, 2.16 mmol) dissolved in water (7 mL), and the mixture was stirred for 4 hours at −5° C. After the reaction was completed, 2 N HCl aqueous solution (7 mL) was added thereto. The resulting mixture was purified by prep-HPLC to obtain compound A-9 (230 mg, 63%, 2 steps). EI-MS m/z: 1272 ($M^+$).

Preparation of Compound A-7

With a similar method to that for preparing compound A-6, compound A-5 (1.0 g, 0.69 mmol) was used to obtain compound A-7 (801 mg, 89%). EI-MS m/z: 1303 ($M^+$).

[Comparative Example 2] Preparation of Ligand-Drug Conjugate (Beta Glucuronide Linker) (B)

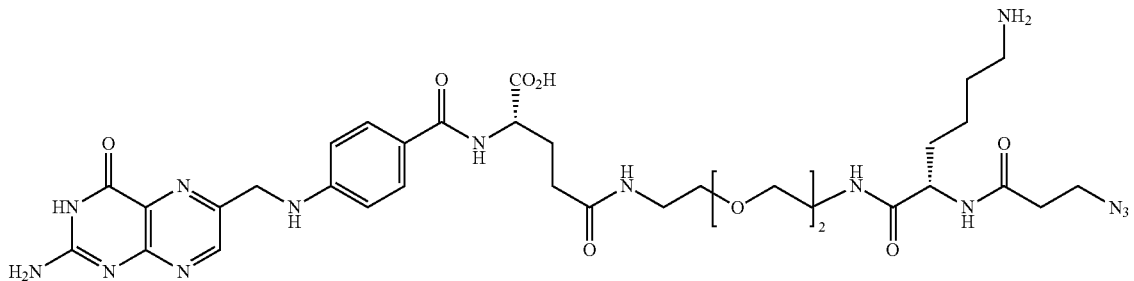

A solution of compound L-10 (Preparation Example 9) (12 mg) and compound A-7 (Comparative Example 1) (11 mg, 0.01 mmol) in ethanol (2 mL) and distilled water (0.5 mL) at room temperature under a nitrogen atmosphere were treated with 1M sodium ascorbate (64 μL, 0.06 mmol) and 0.1 M CuSO$_4$ (128 μL, 0.01 mmol), and then the mixture was stirred for 17 hours at room temperature. After the reaction was completed, the mixture was purified by prep-HPLC were conducted to obtain ligand-drug conjugate B (10 mg, 3 steps, 42%). EI-MS m/z: 2263 (M$^+$).

[Comparative Example 3] Preparation of Ligand-Drug Conjugate (Beta Glucuronide Linker) (C)

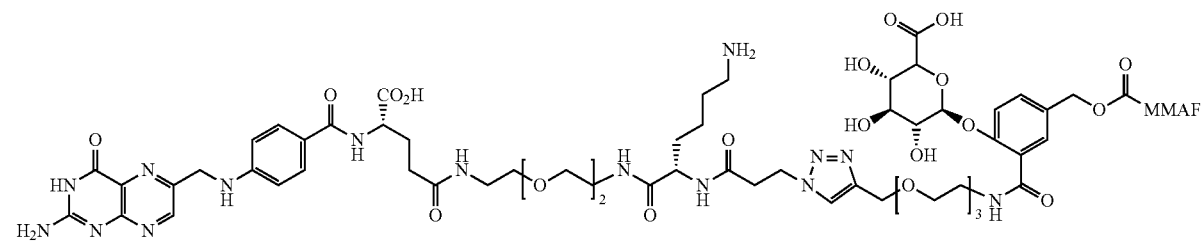

L-8

A-6 ↓

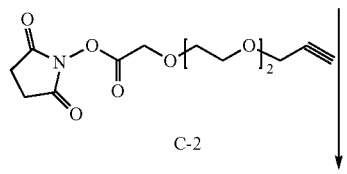

C-1

C-2

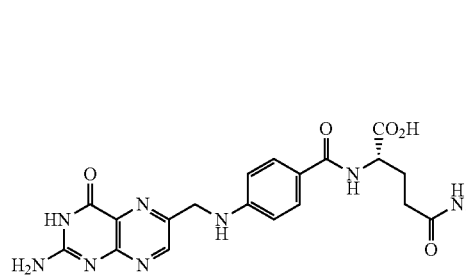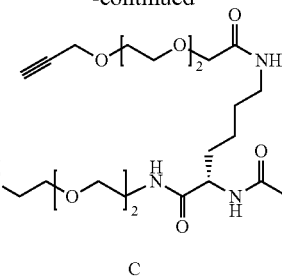

C

Preparation of Compound C-1

Compound L-8 (Preparation Example 8) and compound A-6 (Comparative Example 1) were used to obtain compound C with a similar method to the preparation method of Comparative Example 2. EI-MS m/z: 2069 (M+).

Preparation of Compound C

Compound L-4 (Preparation Example 4) (0.78 mg, 0.004 mmol) was dissolved DMF (1 mL) at room temperature under a nitrogen atmosphere. N-Hydroxy-succinimide (0.53 mg, 0.005 mmol) and EDCI.HCl (0.88 mg, 0.005 mmol) were added, and then the mixture was stirred for 4 hours. After the reaction was completed, LC/MS was used to identify compound C-2. Compound C-1 (8.4 mg, 0.003 mmol) and triethylamine (5 μL, 0.04 mmol) were added to the reaction solution, and the mixture was stirred for 3 hours and purified with prep-HPLC to obtain ligand-drug conjugate C (6.6 mg). EI-MS m/z: 2253 (M+).

[Comparison Example 4] Preparation of Ligand-Drug Conjugate (Beta Glucuronide Linker) (D)

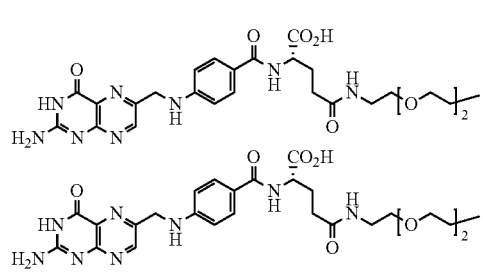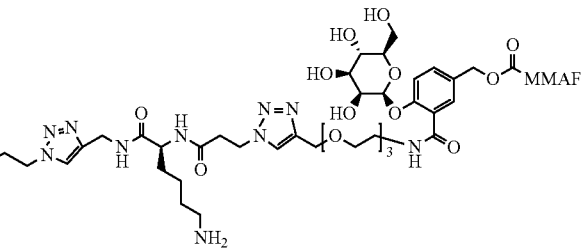

D

Compound L-10a (Preparation Example 9), compound L-27 (Preparation Example 24), compound L-7 (Preparation Example 6) and compound S-1 (Example 1) were used to obtain ligand-drug conjugate D with a similar method as described in Example 7. EI-MS m/z: 1487 (M+/2), 991 (M+/3)

[Test Example 1] Enzymatic Cleavage Assay Evaluation of Linker-Drug (Compounds S-9 and A-6)

In order to identify the reactivity of compound S-9 of Example 1 to β-galactosidase, the difference of the reactivity to β-glucuronidase between compound S-9 of Example 1 and compound A-6 of Comparative Example 1 was compared.

After compound S-9 of Example 1 and compound A-6 of Comparative Example 1 were respectively dissolved in DMSO at the concentration of 10 mM, the resulting solution was diluted with PBS (phosphate buffered saline) buffer solution to make 500 μM of solution.

An enzyme reaction solution for compound S-9 of Example 1 was prepared by adding 1 mg/mL enzyme solution (60 μL) to the mixed solution comprising PBS buffer solution (2640 μL) and 500 μM compound S-9 solution (300 μL), then the reaction was initiated in the incubator set as 37° C.

An enzyme reaction solution for compound A-6 of Comparative Example 1 was prepared by adding 1 mg/mL enzyme solution (60 μL) to the mixed solution comprising PBS buffer solution (2640 μL) and 500 μM compound A-6 solution (300 μL), then the reaction was initiated in the incubator set as 37° C.

Beta-galactosidase enzyme from *Escherichia coli* (Sigma G4155) was used for the reaction mixture comprising compound S-9 and beta-glucuronidase enzyme from *Escherichia coli* (Sigma G7396) was used for the reaction mixture comprising compound A-6 in the comparison test.

Figure 3:
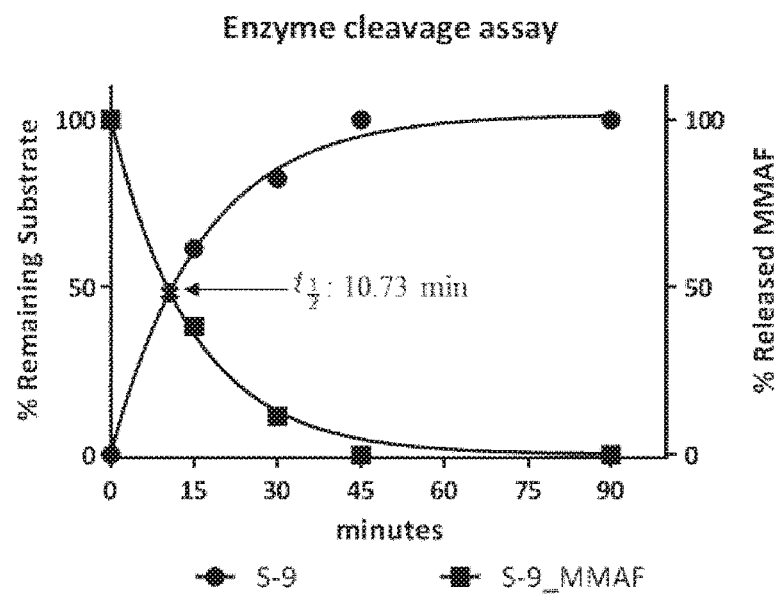
FIG. 3-results of an enzymatic cleavage assay in Test Example 1
Figure 3:
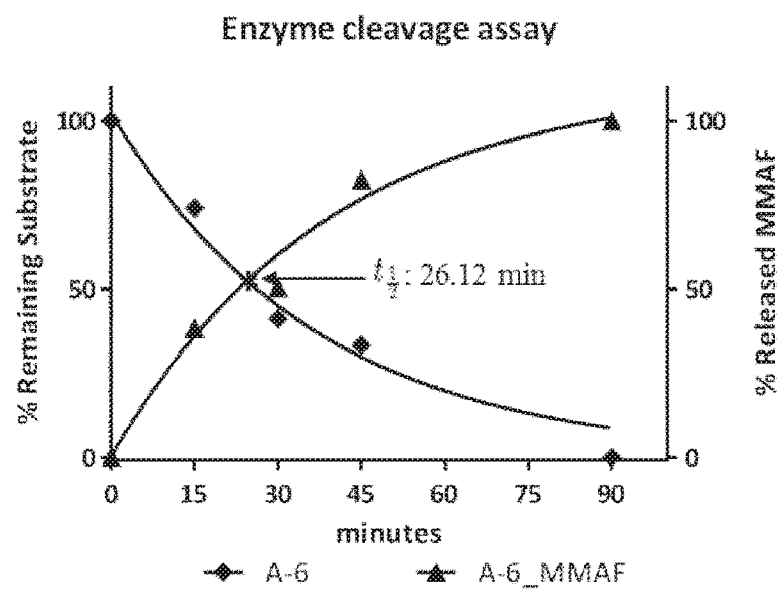

The enzyme reaction solutions were taken in an aliquot 0 minute (prior to the reaction), 15 minutes, 30 minutes, 45 minutes, 90 minutes after the reaction in each of 500 μL, and both MMAF by an enzyme reaction and remaining compound S-9 and compound A-6 were quantitatively analyzed using HPLC. Test results above were shown in FIG. 3, and the hydrolysis half-life by enzyme of compound S-9 and comparative compound A-6 was confirmed to be respectively 10.7 minutes (compound S-9) and 26.0 minutes (compound A-6).

Also, it could be confirmed that MMAF was rapidly released via a 1,6-elimination reaction followed by enzymatic hydrolysis of beta-galactosidase or beta-glucuronidase on both of two compounds.

In particular, it was confirmed that the reactivity for the enzyme reaction in the experimental results using beta-galactosidase was two times or more faster than those using beta-glucuronidase.

From these results, it could be noted that the compound comprising the self-immolative linker bound to β-galactoside has good drug-releasing effect, compared with the compound bound to existing glucuronide.

[Test Example 2] Stability Evaluation of Linker-Drug (Compound S-9 and A-6) in Human and Mouse Plasma Experiments as described below were conducted to see stability of compound S-9 of Example 1 and compound A-6 of Comparative Example 1 in human and mouse plasma.

After compound S-9 (Example 1) and compound A-6 (Comparative Example 1) were dissolved in DMSO at the concentration of 10 mM, mouse plasma (Innovative research, product No. IGMS-N) and human plasma (Innovative research, product No. IPLA-N) were mixed to make final concentration of 100 μM (final 1% DMSO). Each of compound S-9 (Example 1) and compound A-6 (Comparative Example 1) was incubated in a mixed solution of plasma at 37° C., with shaking. Prior to the reaction and on 1, 2, 5, 7, and 9 days after the reaction, the sample was taken in an aliquot in 50 μL, and 200 μL of acetonitrile comprising internal standard substance (5 ng/mL disopyramide) for the precipitation of plasma protein to stop the reaction was added and mixed, and then a centrifugation (4° C., 20 minutes, 4000 rpm) was conducted. Each supernatant after centrifugation was collected and analyzed with LC-MS/MS.

Figure 4:
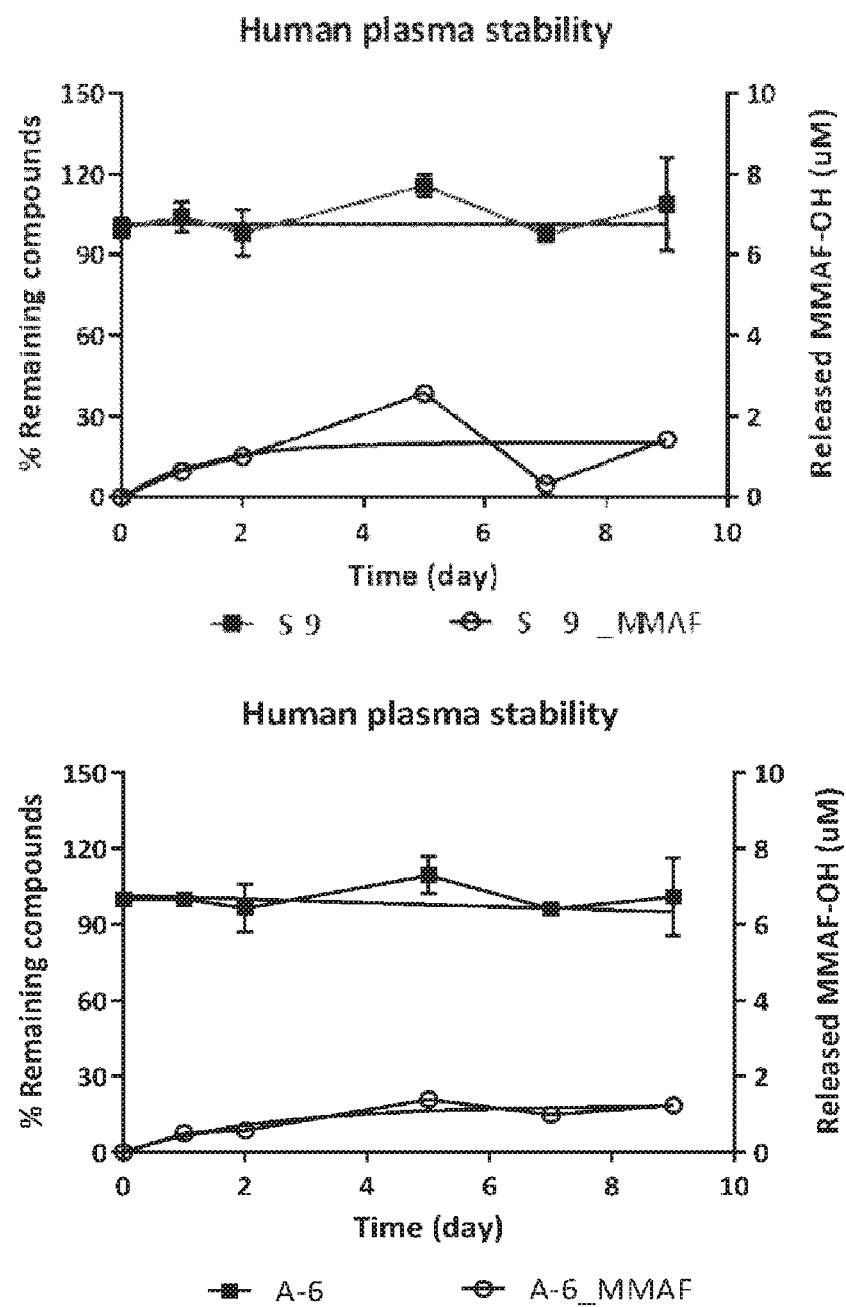
FIG. 4-results for a stability evaluation of the human plasma in Test Example 2
Figure 5:
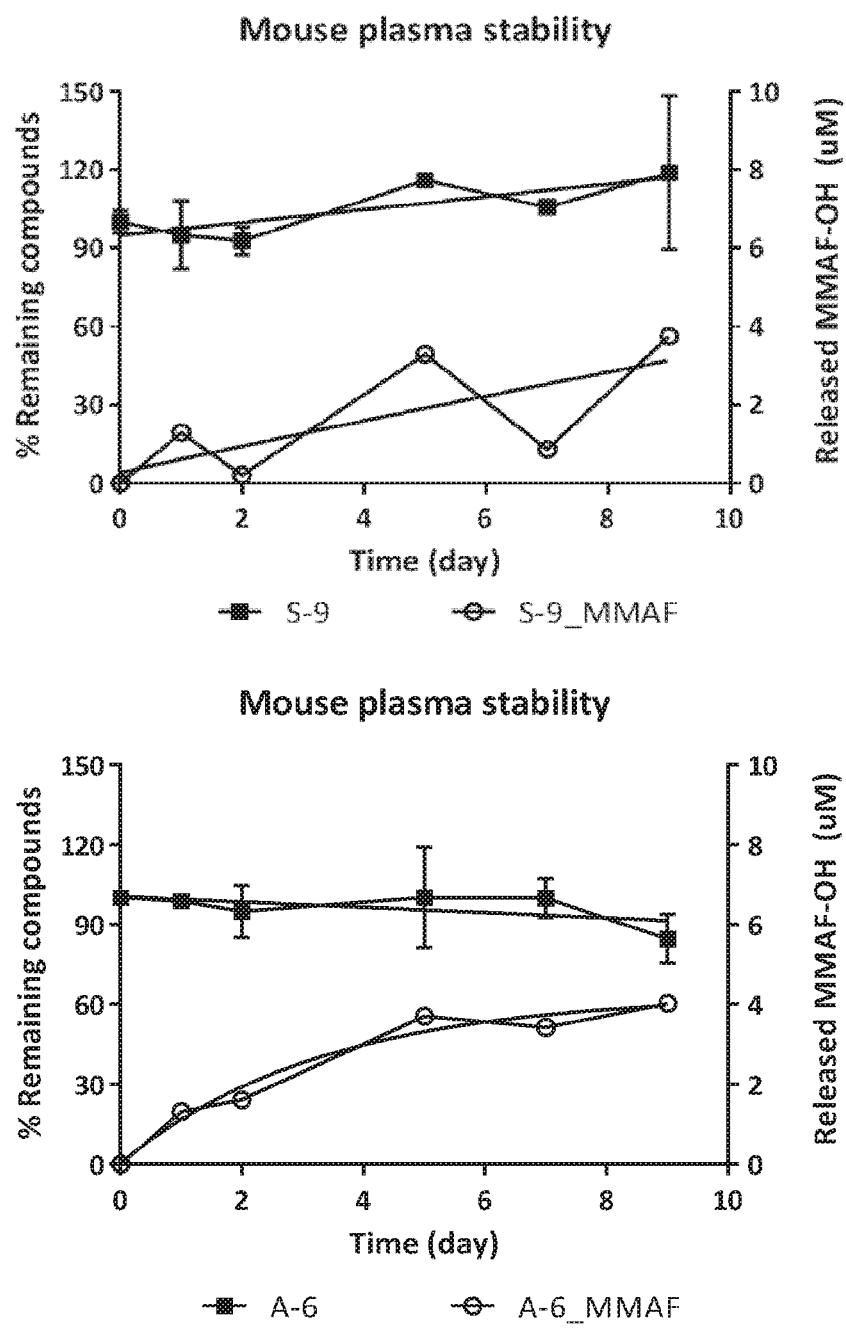
FIG. 5-results for a stability evaluation of the mouse plasma in Text Example 2

The results measuring an amount of compound S-9 and compound A-6, and released drug MMAF remaining in the sample using LC-MS/MS were shown in FIGS. 4 and 5. From these results, compound S-9 galactoside linker remained by ninth day in mouse and human plasma, and could be noted as being very stable as same as comparative compound A-6.

[Test Example 3] Binding Affinity of the Ligand-Drug to Receptor

Experiments by using a method similar to the method disclosed in Analytical Biochemistry (2013), 432, 59-62 were conducted to measure binding affinity of ligand-drug conjugate 1 (Example 2) having beta-galactoside linker and ligand-drug conjugate B (Comparative Example 2) having beta-glucuronide linker to folate receptor.

Figure 6:
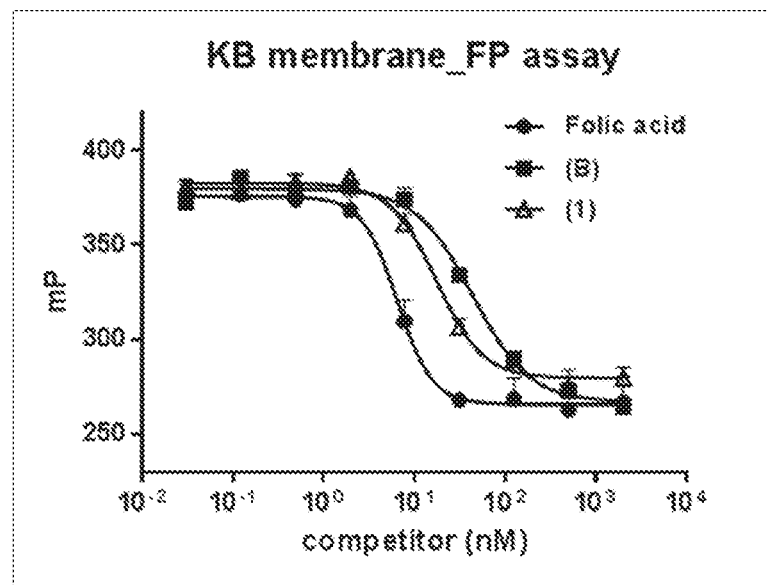
FIG. 6-results for a binding affinity of ligand-drug conjugates to receptors in Test Example 3

Soluble plasma membrane from KB human cancer cells were isolated using plasma membrane protein extraction kit (ab65400) (Abcam company). 0.5 μg plasma membrane protein per well was added to 96-well plate, and folic acid was treated for competition with a concentration of 0.0305-2000 nM (four-fold serial dilution) of ligand-drug conjugate (B) prepared in Comparative Example 2 above and ligand-drug conjugate (1) prepared in Example 2 above. After the preincubation for 15 minutes, FA-Cy5 tracer prepared in Preparation Example 10 was treated with a concentration of 1 nM, and after the reaction for 2 hours at 37° C., synergy2 microplate reader (BioTek company) (ex/em=635/688 nm) was used to measure polarized light. The test results were shown in FIG. 6 and Table 1, and ligand-drug conjugate (1) showed 2.5-fold better binding affinity than (B), in terms of binding affinity ($IC_{50}$). Therefore, in the case of compound (1) to which galactoside linker is introduced, it could be confirmed that it has better binding affinity for folic acid receptor, compared with compound (B) to which glucuronide linker is introduced.

TABLE 1

Binding affinity of ligand-drug conjugate to folic acid receptor

| | Compound | $IC_{50}$ (nM) KB cell |
|---|---|---|
| | Folic acid | 6.46 |
| Ligand-drug conjugate | (B) (Comparative Example 2) | 43.81 |
| | (1) (Example 2) | 17.55 |

[Test Example 4] In Vitro Cytotoxicity Evaluation of Ligand-Drug Conjugates

Figure 7:
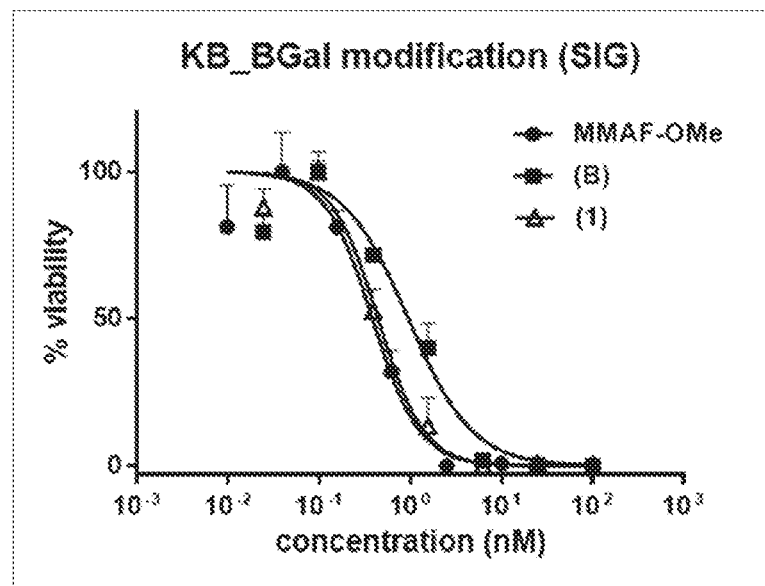
FIG. 7-in vitro cytotoxicity evaluation of ligand-drug conjugates in Test Example 4

KB cancer cell line was seeded 30,000 cells per well of a 96-well plate, and after the culture for 24 hours, the drug MMAF-OMe was treated with a concentration of 0.0097~10 nM (4-fold serial dilution), ligand-drug conjugate (B) prepared in Comparative Example 2 and ligand-drug conjugate (1) prepared in Example 2 were treated with a concentration of 0.0244-100 nM (4-fold serial dilution). The number of live cell after 72 hours was quantified by using 3-(4,5-dimethylthiazol-2-yl)-2,5-diphenyltetrazolium bromide (MTT) dye as chromogenic reagent. And then formazan reduced by oxidoreductase present in live cells were dissolved in DMSO, and quantified. The test results were shown in FIG. 7 and Table 2, ligand-drug conjugate (1) showed about twofold better cytotoxicity than conjugate (B). Therefore, in the case of compound (1) to which galactoside linker is introduced, it could be confirmed that it has better efficacy compared with compound (B) to which glucuronide linker is introduced.

TABLE 2

Cell cytotoxicity of ligand-drug conjugate

| | Compound | $IC_{50}$ (nM) KB cell |
|---|---|---|
| drug | MMAF-OMe | 0.38 ± 0.17 |
| Ligand-drug conjugate | (B) (Comparative Example 2) | 0.95 ± 0.16 |
| | (1) (Example 2) | 0.44 ± 0.12 |

[Test Example 5] Preparation of Protein-Drug Conjugates

Figure 9:
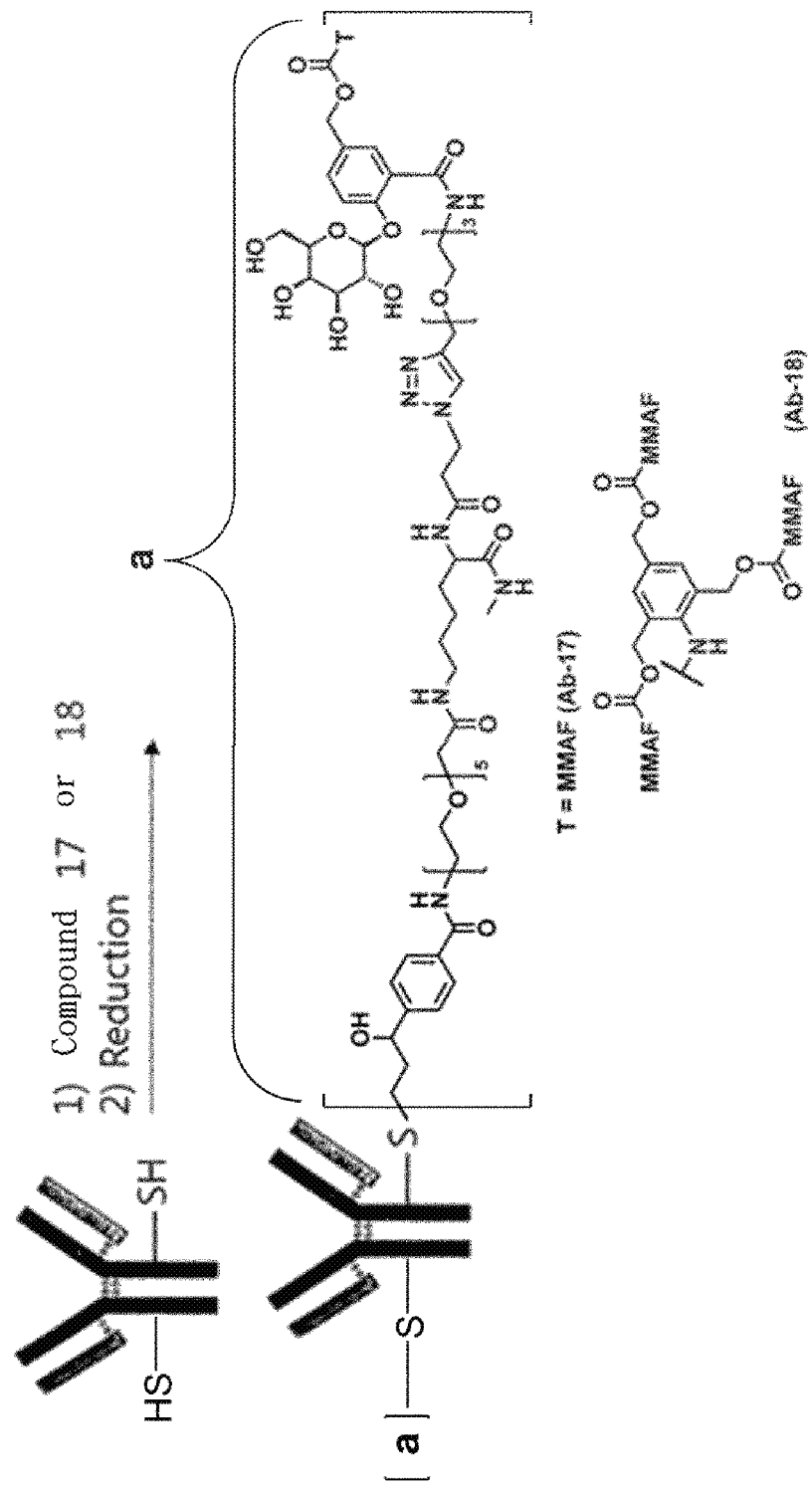
FIG. 9-structures of thiomab drug conjugate (TDC) Ab-17 and Ab-18 which are prepared in Test Example 5

Compound 17 obtained in Example 15 and compound 18 obtained in Example 16 were subjected to a specific conjugation reaction to Herceptin substituted with thiol group at a particular position (for example, heavy chain 121 of the antibody) to prepare Ab-17 and Ab-18 as thiomab drug conjugate (TDC), with reference to a method etc., as disclosed in Nature Biotechnology, 2008, 26, 925-932, Bioconjugate Chem., 2013, 24, 1256-1263, Bioconjugate Chem., 2016, 27, 1324-1331, Bioconjugate Chem. 2014, 25, 460-469. And the results were shown in FIG. 9.

Herceptin used in this test (https://www.drugbank.ca/drugs/DB00072, purchasing site: ybiologics) was prepared by purifying the antibody secreted into the culture with transient transfection of DNA into HEK293 cell, wherein alanine present at position 121 of heavy chain of the antibody was engineered with cysteine.

To prepare Ab-17 and Ab-18, TCEP (Tris(2-Carboxyethyl)Phosphine) as reducing agent was added with 10-50 equivalents per one equivalent of the purified antibody, and reacted for one hour at 37° C. to conduct a reduction of thiol group of introduced cysteine, and then, PD-10 desalting column (GE healthcare, 17-0851-01) was used to eliminate the remaining TCEP, and oxidative reaction proceeded slowly for three days at 4° C. and disulfide bond reduced in part by the treatment of TCEP was restored to a native state. Compound 17 obtained in Example 15 and compound 18 obtained in Example 16 were added with 2 to 10 equivalents and were reacted for 3 hours at room temperature, then 100 equivalents of $NaBH_4$ corresponding to the compound was added and reacted for one hour at room temperature to increase stability of drugs by reducing a ketone group in the compound. Antibody-drug conjugate was prepared by eliminating remaining compound 17, compound 18 or $NaBH_4$ etc., using PD-10 after the reaction. At this time, drug-antibody ratio (DAR) was measured by using HPLC chromatography analysis.

[Test Example 6] In Vitro Cytotoxicity Evaluation of Ligand-Drug Conjugates

SKBR-3 cancer cell line was seeding to a 96-well plate in 2,000 to 8,000 per well and was cultured for 24 hours. Ab-17 and Ab-18 obtained in Test Example 6 were treated with a serial dilution in 1/4 from 50 nM to 0.0008 nM, and control drug T-DM1 (Roche CAS No. 1018448-65-1) was treated with a serial dilution in 1/4 from 50 nM to 0.0008 nM. Live cells after 96 hours were quantified by dissolving MTT dye in a buffer solution to be 5 mg/mL and then adding it in 1/10 to each well of the plate. Formazan formed by a reduction of MTT dye with mitochondria oxidoreductase in the cell was dissolved in DMSO, and a quantification was conducted by measuring an absorbance at 550 nm, and the results were shown in Table 3 below.

TABLE 3 cell cytotoxicity of antibody-drug conjugate

| Antibody-drug conjugate | DAR | SKBR-3 $IC_{50}$ (nM) |
|---|---|---|
| Ab-17 | 3.5 | 0.005 |
| Ab-18 | 1.41 | 0.009 |
| TDM-1 | 4.18 | 0.021 |

[Test Example 7] Enzymatic Cleavage Assay Evaluation of Ligand-Drug Conjugates (1) and (B)

In order to identify the reactivity of ligand-drug conjugate (1) of Example 2 to β-galactosidase, the difference of the reactivity to R-glucuronidase between it and ligand-drug conjugate (B) of Comparative Example 2 as a comparative material was compared.

Ligand-drug conjugate (1) of Example 2 and ligand-drug conjugate (B) of Comparative Example 2 were respectively dissolved in DMSO to a concentration of 9 mM, and then each of them was mixed with PBS buffer solution to prepare 500 μM of solution.

An enzyme reaction solution for ligand-drug conjugate (1) of Example 2 was prepared by adding 1 mg/mL enzyme solution (10 μL) to the mixed solution comprising PBS buffer solution (440 μL) and 500 μM ligand-drug conjugate (1) solution (50 μL) of Example 2, then the reaction was initiated in 37° C. of the incubator.

An enzyme reaction solution for ligand-drug conjugate (B) of Comparative Example 2 was prepared by adding 1 mg/mL enzyme solution (10 μL) to the mixed solution comprising PBS buffer solution (440 μL) and 500 μM ligand-drug conjugate (B) solution (50 μL) of Comparative Example 2, then the reaction was initiated in 37° C. of the incubator.

Beta-galactosidase enzyme (Sigma G4155) in E. coli was used for the reaction mixture comprising ligand-drug conjugate (1) of Example 2 and beta-glucuronidase enzyme (Sigma G7396) in E. coli was used for the reaction mixture comprising ligand-drug conjugate (B) of Comparative Example 2 for the comparison experiment.

Figure 8:
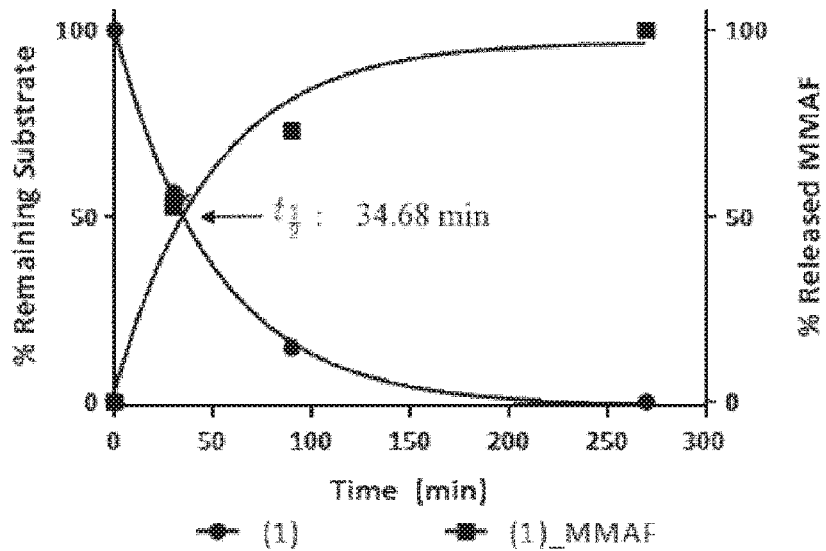
FIG. 8-enzymatic cleavage assay evaluation of ligand-drug conjugates in Test Example 7
Figure 8:
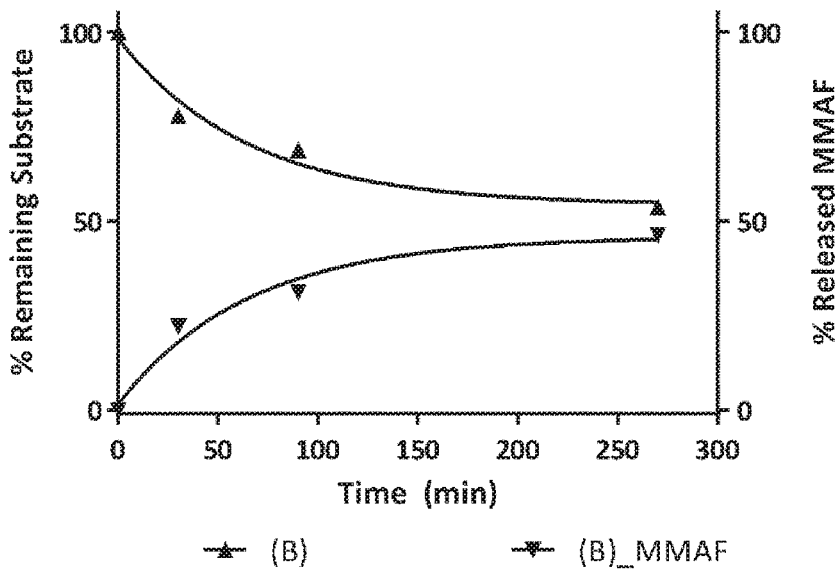

The enzyme reaction solutions were taken in aliquot 0 minute prior to the reaction, 30 minutes, 90 minutes and 270 minutes after the reaction in each of 500 μL, and MMAF freed by an enzyme reaction with remaining ligand-drug conjugate (1) or ligand-drug conjugate (B) was quantitatively analyzed with a method of HPLC. Test results above were shown in FIG. 8, and hydrolysis half-life by enzyme of ligand-drug conjugate (1) and comparative ligand-drug conjugate (B) was respectively measured to be 34.68 minutes (ligand-drug conjugate (1)) and not less than 270 minutes (ligand-drug conjugate (B)). That is, in the case of compound (1) to which galactoside linker is introduced, it could be confirmed that it has more rapid hydrolysis rate 6 times or more, relative to comparison compound (B) to which glucuronide linker is introduced.

In addition, it could be confirmed that MMAF was rapidly released via a 1,6-elimination reaction by enzymatic hydrolysis of beta-galactosidase on ligand-drug conjugate (1).

From these results, it could be noted that the compound comprising the self-immolative linker bound to R-galactoside has good drugs-releasing effect, compared with the compound bound to existing glucuronide.

INDUSTRIAL APPLICABILITY

The β-galactoside-introduced self-immolative linker according to the present invention is simpler than an existing known linker in terms of a method for preparation thereof, and since it does not induce side-reaction, it is expediently purified and separated. In addition, the linker has a better affinity for water and thus improves physical properties of a conjugate prepared by the same.

In addition, a compound comprising the R-galactoside-introduced self-immolative linker according to the present invention comprises a protein (for example, an oligopeptide, a polypeptide, an antibody, etc) or a ligand having a binding specificity for the desired target, an active agent having specific function or activity (for example, a drug, a toxin, a ligand, a probe for a detection) and a self-immolative linker comprised of a glycosidic bond which may render the active agent to be selectively released in the target cell and thus has an advantage designed to selectively release the active agent by using β-galactosidase which is an enzyme over-expressed in the target cell. In particular, it may be used in drugs to which β-galactoside is difficult to be applied, and thus may be well utilized in a development of an anti-cancer agent for the target treatment.

The invention claimed is:

1. A compound comprising a β-galactoside-introduced self-immolative linker represented by Chemical Formula 1 below:

[Chemical Formula 1]

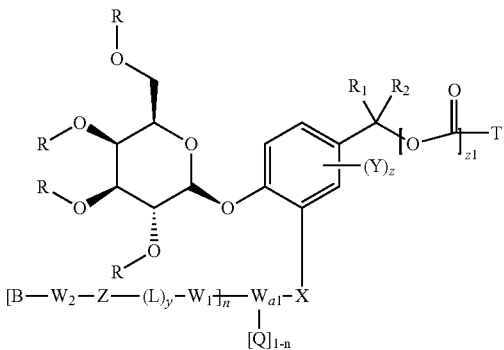

in Chemical Formula 1,
R is hydrogen or a hydroxy protection group;
X is —C(=O)—, —NH—, —O—, or —S—;
T is an active agent;
Q is B'—U1-$(CH_2CH_2X_3)_{p4}$—$(CH_2)_{p3}$—$Wa_4$-$Q_2$-$W_{a3}$—$W_1$-;
n is an integer of 0 or 1;
Y is hydrogen, halo$C_1$-$C_8$alkyl, halogen, cyano or nitro;
z is an integer of 1 to 3, and Y may be the same or different from each other, if z is an integer of not less than 2;
z1 is an integer of 0 or 1;
$W_1$ is ⊢$W_{a2}$—$(CH_2)_{a1}$—$W_{b1}$-$Q_1$⊣;
$W_2$ is ⊢$W_{a4}$-$Q_2$-$W_{a3}$⊣;
$W_{a1}$ and $W_{a2}$ are each independently —NH—, —C(=O)—, or —CH$_2$—;
$W_{a3}$ and $W_{a4}$ are each independently —NH—, —C(=O)—, —CH$_2$—, —C(=O)NH—, —NHC(=O)—, or triazolylene;
$W_{b1}$ is an amide bond or triazolylene;
L is an amino acid, peptide, or amide bond as a linker connecting $W_{a2}$ and Z;
Z is a single bond, —$W_{a5}$—$(CH_2)_{a2}$—$W_{b2}$—$(CH_2)_{a3}$—$W_{a6}$—, or —$W_{a7}$—$(CH_2)_{a4}$—CR'R"—X"—;
R' is $C_1$-$C_8$alkyl or B—$W_{a8}$-$Q_3$-$W_{c1}$—$(CH_2)_{a5}$—;
R" is B—$W_{a8}$-$Q_3$-$W_{c1}$—$(CH_2)_{a5}$—;
$Q_1$ and $Q_3$ are each independently —$(CH_2)_{a6}$—$(X_1CH_2CH_2)_{b1}$—$(CH_2)_{a7}$—;
$X_1$ and $X_3$ are each independently —O—, —S—, —NH—, or —CH$_2$—;
X" is —NHC(=O)—$(CH_2)_{a8}$—$W_{a9}$— or —C(=O)NH—$(CH_2)_{a8}$—$W_{a9}$—;
$W_{a5}$, $W_{a6}$, $W_{a7}$, $W_{a8}$, and $W_{a9}$ are each independently —NH—, —C(=O)—, or —CH$_2$—;
$W_{b2}$ is an amide bond or triazolylene;
$W_{c1}$ is —NHC(=O)— or —C(=O)NH—;
$Q_2$ is a saturated or unsaturated alkylene, which is linear or branched with a carbon number of 1 to 50, satisfying any one of (i) to (iii) below;
(i) at least one —CH$_2$— in the alkylene is substituted with one or more heteroatoms selected from —NH—, —C(=O), —O—, and —S—,
(ii) at least one arylene or heteroarylene is included in the alkylene,
(iii) the alkylene is further substituted with one or more selected from the group consisting of $C_1$-$C_{20}$alkyl, $C_6$-$C_{20}$aryl$C_1$-$C_8$alkyl, —$(CH_2)_{s1}$COOR$_3$, —$(CH_2)_{s1}$COR$_3$, —$(CH_2)_{s2}$CONR$_4$R$_5$, and —$(CH_2)_{s2}$NR$_4$R$_5$;
arylene or heteroarylene of (ii) above may be further substituted with nitro;
$R_3$, $R_4$, and $R_5$ are each independently hydrogen or $C_1$-$C_{15}$ alkyl;
$X_2$ is —O—, —S—, —NH—, or —CH$_2$—;
U1 is bound to B' in the position of asterisk (*) with a linking group selected from the following structures:

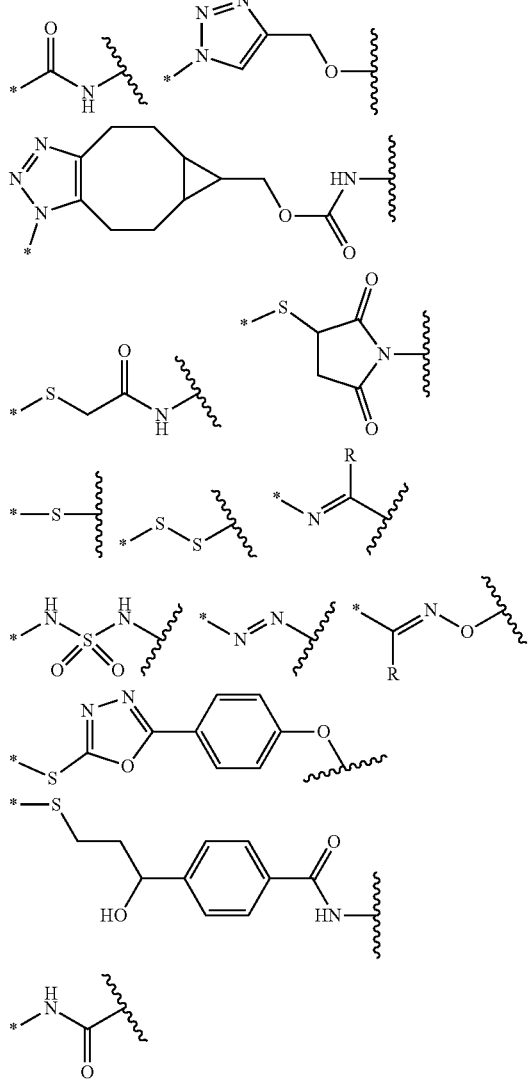

R is C1-C10 alkyl, C6-20 aryl or C2-C20 heteroaryl;
B and B' are each independently a ligand or a protein having properties selectively targeting a particular organ with a drug, a tissue or a cell, that is, properties binding to a receptor;
a1, a2, a3, a4, a5, a6, a8, b1, p1, p2, p3 and p4 are each independently an integer of 1 to 10;
a7, y, s1, s2 and s4 are each independently an integer of 0 to 10; and
$R_1$ and $R_2$ are each independently hydrogen, $C_1$-$C_8$alkyl or $C_3$-$C_8$cycloalkyl.

2. The compound of claim 1, wherein L comprises one or more units represented by the following Chemical Formula A or B.

[Chemical Formula A]

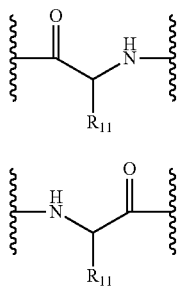

[Chemical Formula B]

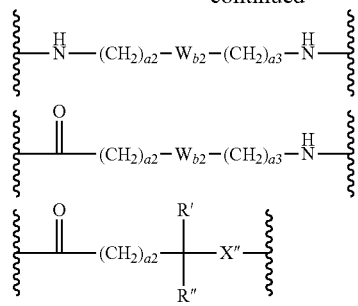

in Chemical Formulas A and B, $R_{11}$ is hydrogen, $C_1$-$C_8$alkyl, —$(CH_2)_{s3}COOR_{13}$, —$(CH_2)_{s3}COR_{13}$, —$(CH_2)_{s3}CONR_{14}R_{15}$ or —$(CH_2)_{s4}NR_{14}R_{15}$;

$R_{13}$, $R_{14}$, and $R_{15}$ are each independently hydrogen or $C_1$-$C_{15}$ alkyl;

s3 and s4 are each independently an integer of 1 to 10;

$X_3$ is —O—, —S—, —NH—, or —$CH_2$—; and p3 and p4 are each independently an integer of 1 to 10.

3. The compound of claim 1, wherein X is —C(=O)—, $W_{a1}$ is —NH—.

4. The compound of claim 1, wherein Z is a single bond or is selected from the following structures:

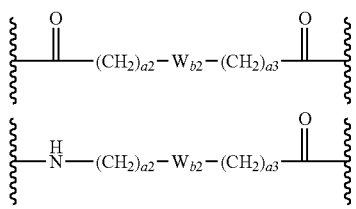

in the structures, $W_{b2}$ is —C(=O)NH—, —NHC(=O)—,

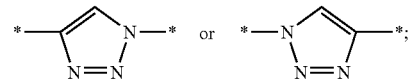

R' is $C_1$-$C_8$alkyl or B—NH—$(CH_2)_{a6}$—$(X_1CH_2CH_2)_{b1}$—NH—C(=O)—$(CH_2)_{a5}$—;

R" is B—NH—$(CH_2)_{a6}$—$(X_1CH_2CH_2)_{b1}$—NH—C(=O)—$(CH_2)_{a5}$—;

X" is —NHC(=O)—$(CH_2)_{a8}$—NH— or —C(=O)NH—$(CH_2)_{a8}$—NH—;

a2, a3, a4, a5, a6, a8 and b1 are each independently an integer of 1 to 10;

$X_1$ is —O—, —S—, —NH—, or —$CH_2$—; and

B is the same as defined in claim 1.

5. The compound of claim 1, wherein $Q_2$ is selected from the following Chemical Formula C to Chemical Formula I:

[Chemical Formula C]

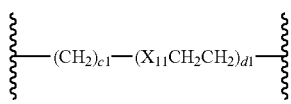

[Chemical Formula D]

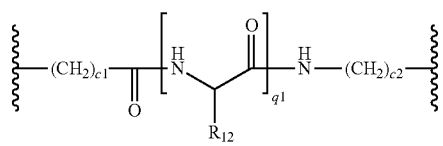

[Chemical Formula E]

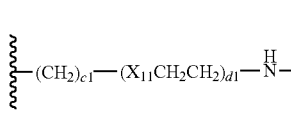

[Chemical Formula F]

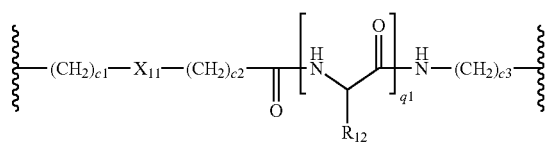

[Chemical Formula G]

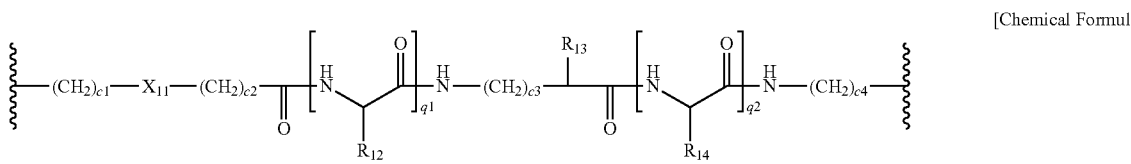

[Chemical Formula H]    [Chemical Formula I]

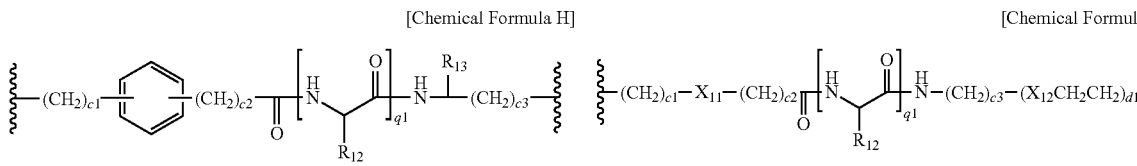

in Chemical Formulas C to I, $X_{11}$ and $X_{12}$ are each independently —O—, —S—, —NH—, or —CH$_2$—

$R_{12}$ to $R_{14}$ are each independently hydrogen, $C_1$-$C_{20}$alkyl, $C_6$-$C_{20}$aryl$C_1$-$C_8$alkyl, —(CH$_2$)$_{s1}$COOR$_3$, —(CH$_2$)$_{s1}$COR$_3$, —(CH$_2$)$_{s2}$CONR$_4$R$_5$ or —(CH$_2$)$_{s2}$NR$_4$R$_5$;

$R_3$, $R_4$, and $R_5$ are each independently hydrogen or $C_1$-$C_{15}$ alkyl;

$X_2$ is —O—, —S—, —NH—, or —CH$_2$—;

$R^a$ is hydrogen or nitro;

c1, c2, c3, c4, and d1 are each independently an integer of 1 to 10;

q1 and q2 are each independently an integer of 0 to 5;

s1 and s2 are each independently an integer of 0 to 5; and p1 and p2 are each independently an integer of 1 to 10.

6. The compound of claim 1, wherein the active agents are a drug, a toxin, an affinity ligand, a probe for a detection or a combination thereof.

7. The compound of claim 6, wherein the drugs are cytokine, an immuno-regulatory compound, an anti-cancer agent, an anti-virus agent, an anti-bacteria agent, an anti-fungi agent, a helminthic or a combination thereof.

8. The compound of claim 1, wherein the ligand is selected from the group consisting of peptides, tumor cell-specific peptides, tumor cell-specific aptamers, tumor cell-specific carbohydrates, tumor cell-specific monoclonal or polyclonal antibodies and antibody fragments.

9. The compound of claim 1, wherein the proteins are an oligopeptide, a polypeptide, an antibody, a fragment of antigenic polypeptide or a Repebody.

10. The compound of claim 9, wherein the antibody is selected from the group consisting of an intact polyclonal antibody, an intact monoclonal antibody, an antibody fragment, a single chain Fv (scFv) mutant, a multispecific antibody, a bispecific antibody, a chimeric antibody, humanized antibody, a human antibody, a fusion protein comprising an antigenic determinant portion of an antibody, and other modified immunoglobulin molecule comprising an antigen recognition site.

11. The compound of claim 10, wherein the antibody is selected from the group consisting of Muromonab-CD3 Abciximab, Rituximab, Daclizumab, Palivizumab, Infliximab, Trastuzumab (herceptin), Etanercept, Basiliximab, Gemtuzumabozogamicin, Alemtuzumab, Ibritumomab tiuxetan, Adalimumab, Alefacept, Omalizumab, Efalizumab, Tositumomob-I$^{131}$, Cetuximab, Bevacizumab, Natalizumab, Ranibizumab, Panitumumab, Eculizumab, Rilonacept, Certolizumab pegol, Romiplostim, AMG-531, CNTO-148, CNTO-1275, ABT-874, LEA-29Y, Belimumab, TACI-Ig, Second generation anti-CD20, ACZ-885, Tocilizumab, Atlizumab, Mepolizumab, Pertuzumab, Humax CD20, Tremelimumab (CP-675 206), Ticilimumab, MDX-010, IDEC-114, Inotuzumabozogamycin, HuMax EGFR, Aflibercept, VEGF Trap-Eye, HuMax-CD4, Ala-Ala, ChA-glyCD3, TRX4, Catumaxomab, IGN101, MT-201, Pregov-omab, CH-14.18, WX-G250, AMG-162, AAB-001, Motavizumab, MEDI-524, efumgumab, Aurograb®, Raxibacumab, Third generation anti-CD20, LY2469298, and Veltuzumab.

12. The compound of claim 1, wherein the compound is selected from the following structures:

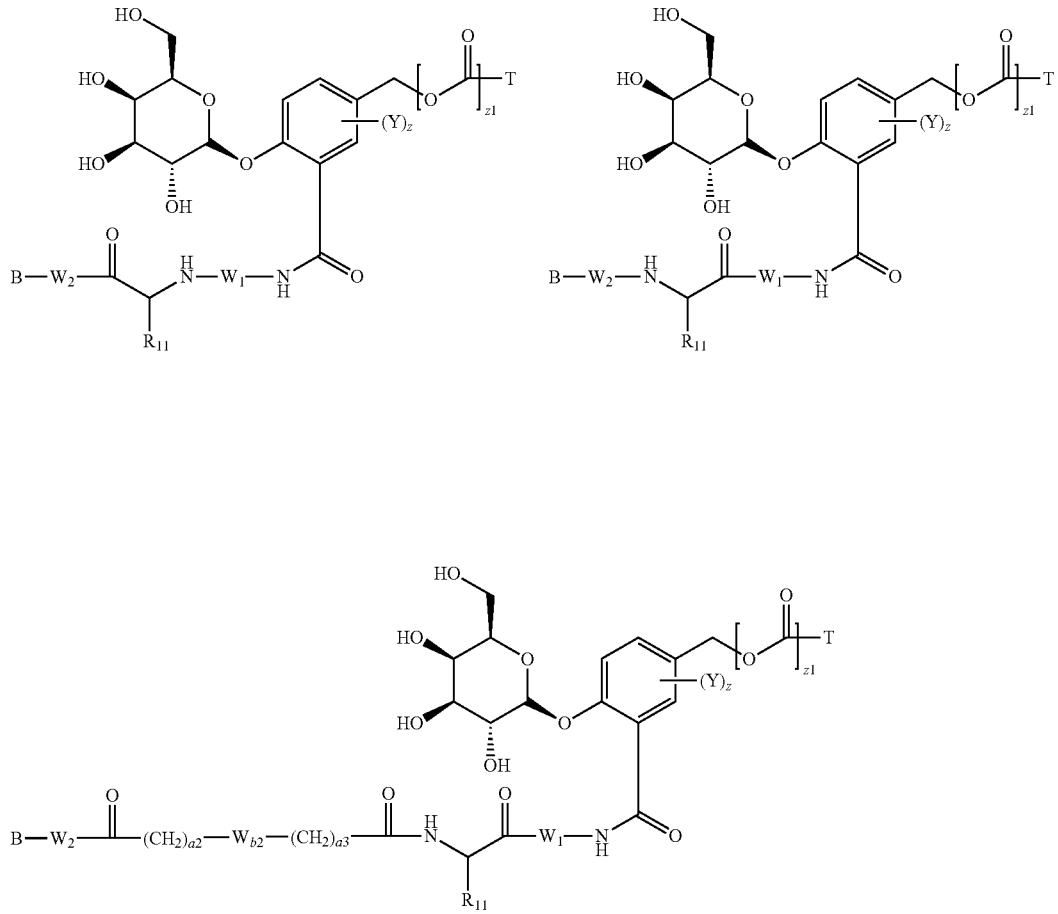

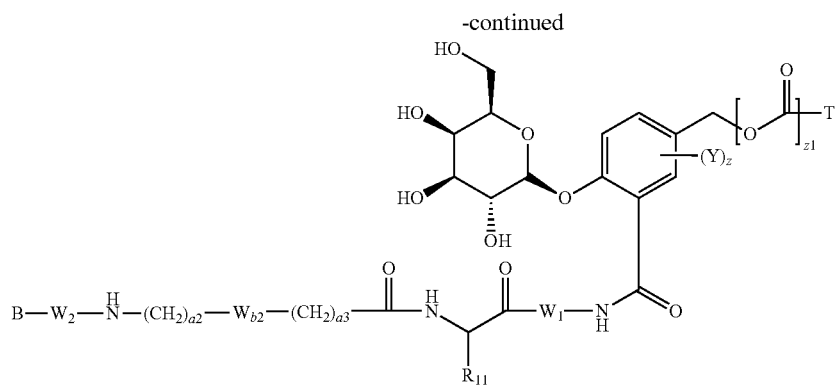
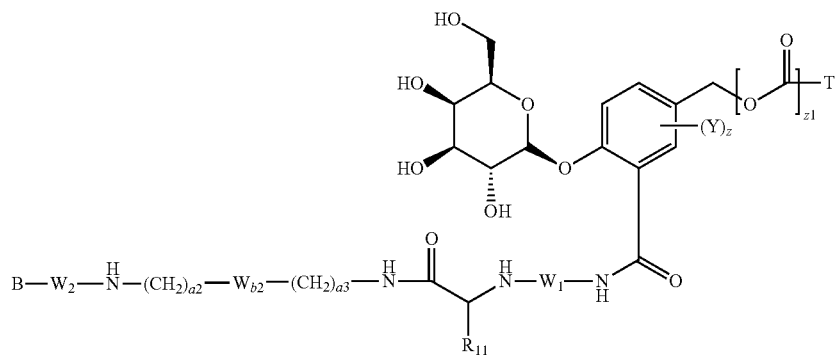
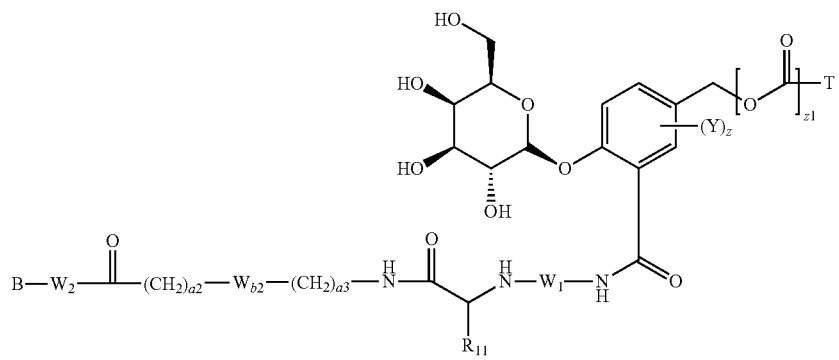
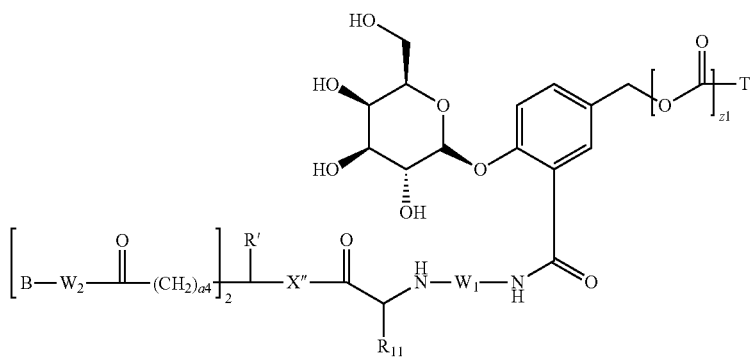

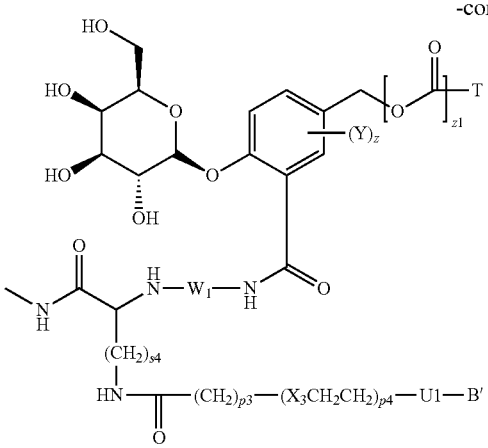
in the structures,
Y is hydrogen, haloC$_1$-C$_8$alkyl, halogen, cyano or nitro;
z is an integer of 1 to 3, and Y may be the same or different from each other, if z is an integer of not less than 2;
z1 is an integer of 0 or 1;
W$_1$ is selected from the following structures:
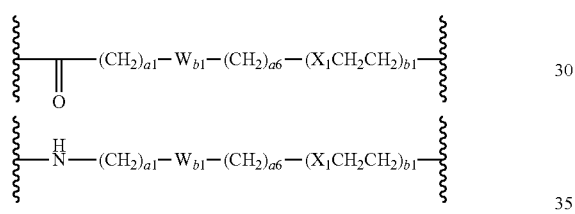
W$_2$ is selected from the following structures:
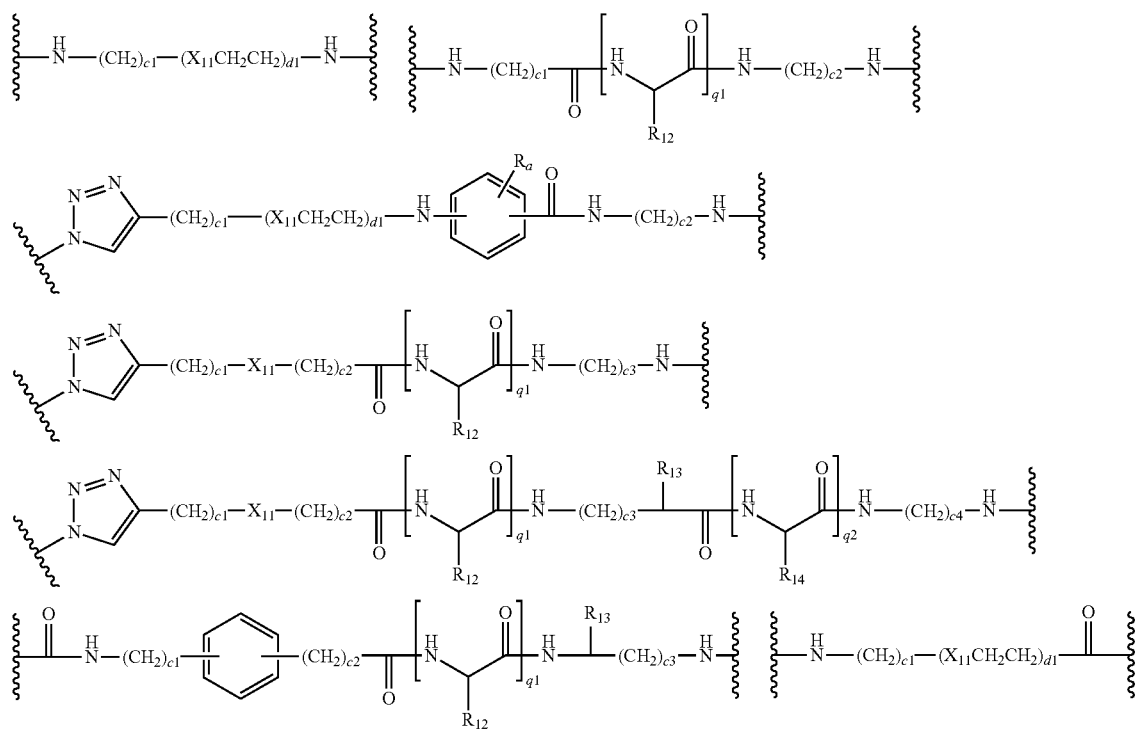

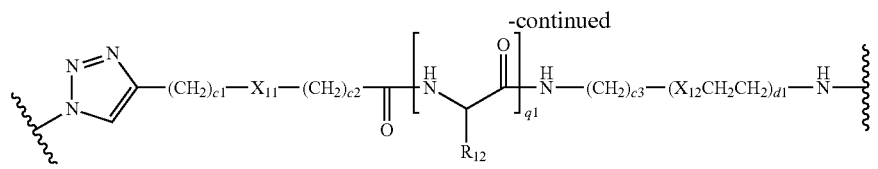

-continued $X_1$, $X_{11}$ and $X_{12}$ are each independently —O—, —S—, —NH—, or —CH$_2$—;

$W_{b1}$ and $W_{b2}$ are each independently —C(=O)NH—, —NHC(=O)—,

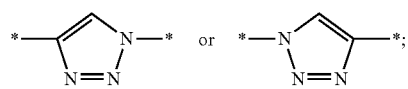

$R_{11}$ is hydrogen, C$_1$-C$_8$alkyl, —(CH$_2$)$_{s3}$COOR$_{13}$, —(CH$_2$)$_{s3}$COR$_{13}$, —(CH$_2$)$_{s3}$CONR$_{14}$R$_{15}$ or —(CH$_2$)$_{s4}$NR$_{14}$R$_{15}$, R$_{13}$, R$_{14}$, and R$_{15}$ are each independently hydrogen or C$_1$-C$_{15}$ alkyl;

$X_3$ is —O—, —S—, —NH—, or —CH$_2$—;

$R_{12}$ to $R_{14}$ are each independently hydrogen, C$_1$-C$_{20}$alkyl, C$_6$-C$_{20}$arylC$_1$-C$_8$alkyl, —(CH$_2$)$_{s1}$COOR$_3$, —(CH$_2$)$_{s1}$OR$_3$, —(CH$_2$)$_{s2}$CONR$_4$R$_5$ or —(CH$_2$)$_{s2}$NR$_4$R$_5$;

$R_3$, $R_4$, and $R_5$ are each independently hydrogen or C$_1$-C$_{15}$ alkyl;

$X_2$ is —O—, —S—, —NH—, or —CH$_2$—;

$R^a$ is hydrogen or nitro;

R' is C$_1$-C$_8$alkyl or B—NH—(CH$_2$)$_{a6}$—(X$_1$CH$_2$CH$_2$)$_b$—NH—C(=O)—(CH$_2$)$_{a5}$—;

X" is —NHC(=O)—(CH$_2$)$_{a8}$—NH— or —C(=O)NH—(CH$_2$)$_{a8}$—NH—;

a1, a2, a3, a4, a5, a6, a8, b1, c1, c2, c3, c4, d1, p1, p2, p3, and p4 are each independently an integer of 1 to 10;

q1 and q2 are each independently an integer of 0 to 5;

s1, s2, s3, and s4 are each independently an integer of 0 to 5;

B'—U1— is

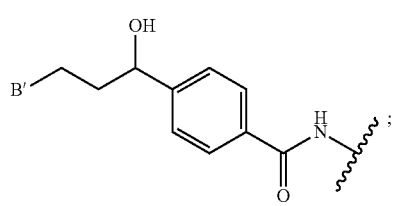

B' is an antibody;

B is a ligand selected from the following structures:

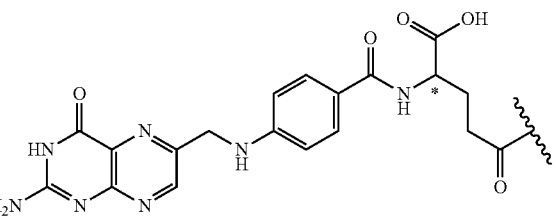

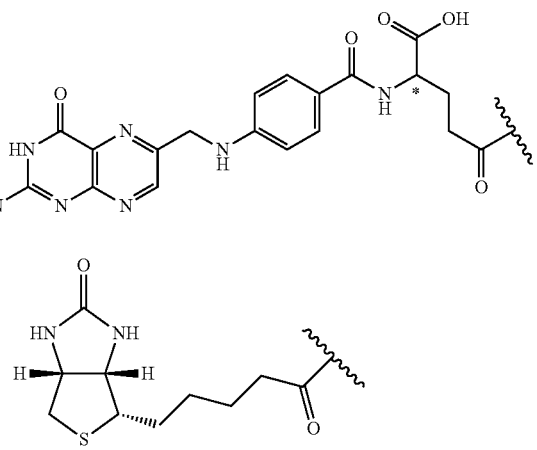

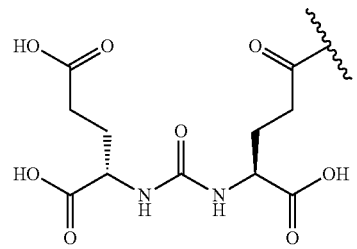

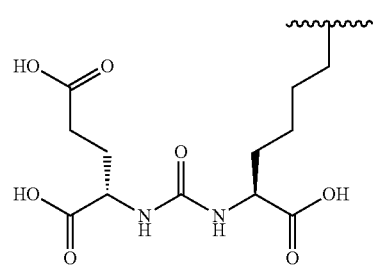

T is a drug selected from the following structures:

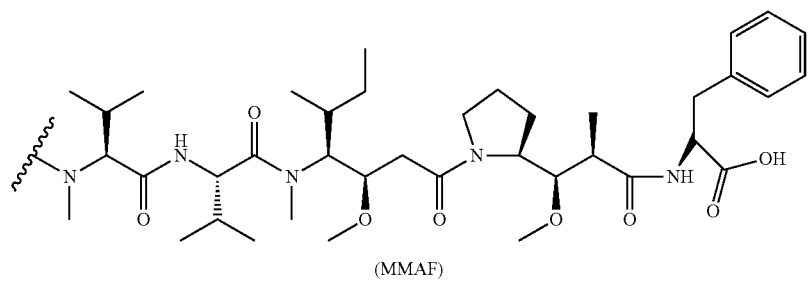

(MMAF)

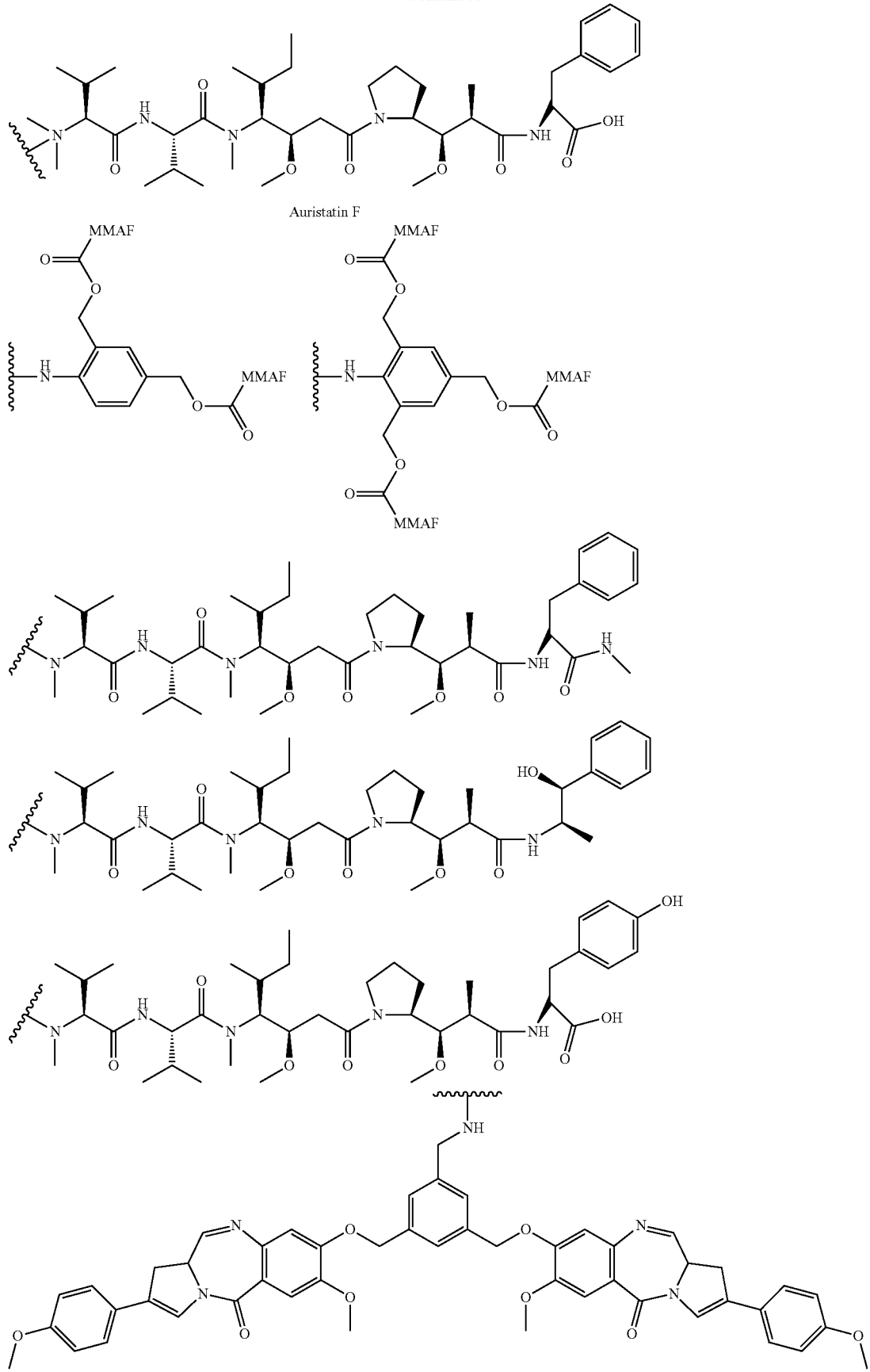

-continued
203  204
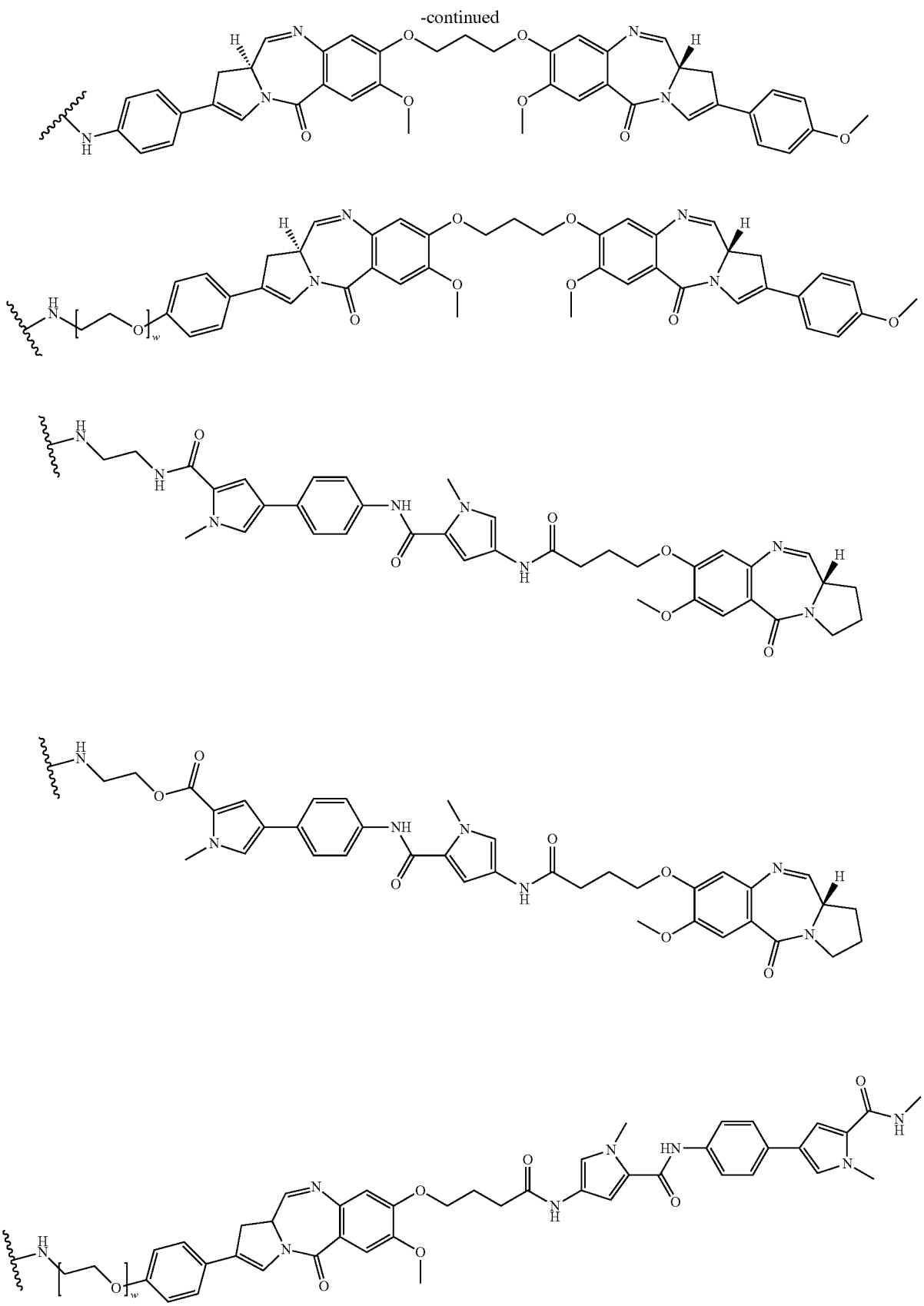
w is an integer of 1 to 10.

13. A compound represented by Chemical Formula 2 below:

[Chemical Formula 2]

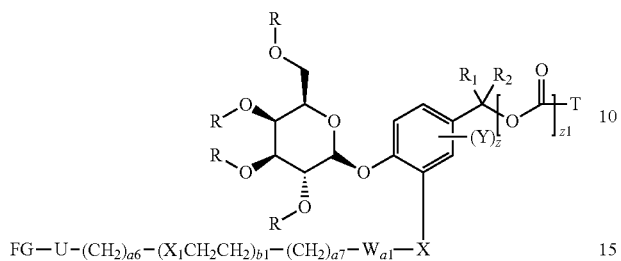

FG—U—(CH$_2$)$_{a6}$—(X$_1$CH$_2$CH$_2$)$_{b1}$—(CH$_2$)$_{a7}$—W$_{a1}$—X in Chemical Formula 2, R is hydrogen or a hydroxy protecting group;
X is —C(=O)—, —NH—, —O—, —CH$_2$— or —S—;
W$_{a1}$ is —NH—, —CH$_2$— or —C(=O)—;
T is an active agent;
Y is hydrogen, haloC$_1$-C$_8$alkyl, halogen, cyano or nitro;
U is a single bond or

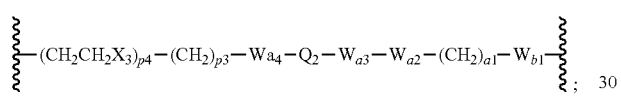

W$_{a2}$ is —NH—, —C(=O)—, or —CH$_2$—;
W$_{a3}$ and W$_{a4}$ are each independently —NH—, —C(=O)—, —CH$_2$—, —C(=O)NH—, —NHC(=O)—, or triazolylene;
Q$_2$ is

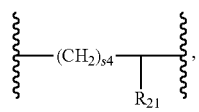

R$_{21}$ is C$_1$-C$_{20}$alkyl, C$_6$-C$_{20}$arylC$_1$-C$_8$alkyl, —(CH$_2$)$_{s1}$COOR$_3$, —(CH$_2$)$_{s1}$COR$_3$, —(CH$_2$)$_{s2}$CONR$_4$R$_5$ or —(CH$_2$)$_{s2}$NR$_4$R$_5$;
R$_3$, R$_4$, and R$_5$ are each independently hydrogen or C$_1$-C$_{15}$ alkyl;
s1 and s2 are each independently an integer of 0 to 10;
W$_{b1}$ is —C(=O)NH—, —NHC(=O)—,

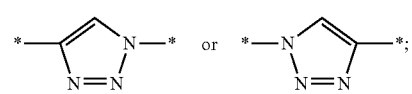

a1 is each independently an integer of 1 to 10;
s4 is an integer of 0 to 10;
p3 and p4 are each independently an integer of 1 to 10;
FG is —NH$_2$, —C≡CH, C$_4$-C$_{10}$cycloalkynyl, —N$_3$, —COOH, —SO$_3$H, —OH, —NHOH, —NHNH$_2$, —SH, haloacetamide (—NHC(O)CH$_2$-hal, wherein hal is halogen), maleimide

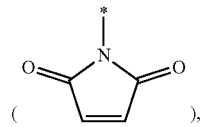

halogen, tosylate (TsO$^-$), aldehyde (—COH), ketone (—COR, wherein R is C1-C10alkyl, C6-C20aryl, C2-C20 heteroaryl), diene,

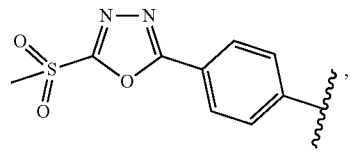

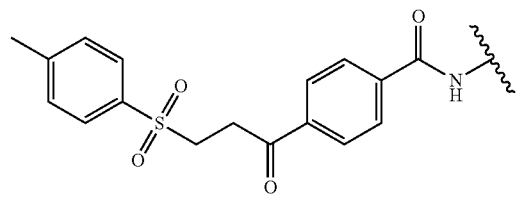

or —OP(=O) (OH)$_2$;

X$_1$ and X$_3$ are each independently —O—, —S—, —NH—, or —CH$_2$—;
a6 and b1 are each independently an integer of 1 to 10;
a7 is an integer of 0 to 10;
z is an integer of 1 to 3, and Y may be the same or different from each other, if z is an integer of not less than 2;
z1 is an integer of 0 or 1; and
R$_1$ and R$_2$ are each independently hydrogen, C$_1$-C$_8$alkyl or C$_3$-C$_8$cycloalkyl.

14. The compound of claim 13, wherein the compound is represented by Chemical Formula 3 below.

[Chemical Formula 3]

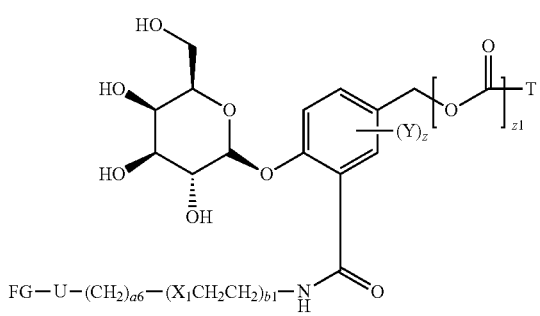

in Chemical Formula 3,
Y is hydrogen, haloC$_1$-C$_8$alkyl, halogen, cyano or nitro;
z is an integer of 1 to 3, and Y may be the same or different from each other, if z is an integer of not less than 2;
z1 is an integer of 0 or 1;

U is a single bond or

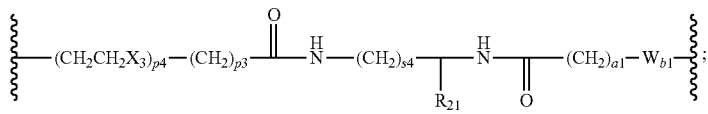

$R_{21}$ is $C_1$-$C_{20}$alkyl, $C_6$-$C_{20}$aryl$C_1$-$C_8$alkyl, —(CH$_2$)$_{s1}$COOR$_3$, —(CH$_2$)$_{s1}$COR$_3$, —(CH$_2$)$_{s2}$CONR$_4$R$_5$ or —(CH$_2$)$_{s2}$NR$_4$R$_5$;

$R_3$, $R_4$, and $R_5$ are each independently hydrogen or $C_1$-$C_{15}$ alkyl;

s1 and s2 are each independently an integer of 0 to 10;

$W_{b1}$ is —C(=O)NH—, —NHC(=O)—,

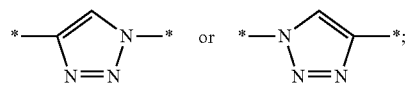

a1 is each independently an integer of 1 to 10;
s4 is an integer of 0 to 10;
p3 and p4 are each independently an integer of 1 to 10;
FG is —NH$_2$, —C≡CH, $C_4$-$C_{10}$cycloalkynyl, —N$_3$, —COOH, —SO$_3$H, —OH, —NHOH, —NHNH$_2$, —SH, haloacetamide (—NHC(O)CH$_2$-hal, wherein hal is halogen), maleimide

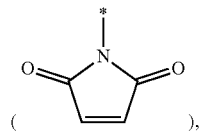

halogen, tosylate (TsO⁻), aldehyde (~COH), ketone (~COR, wherein R is C1-C10alkyl, C6-C20aryl, C2-C20 heteroaryl), diene,

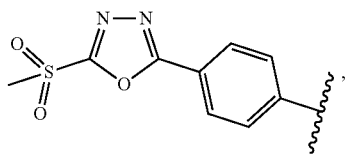

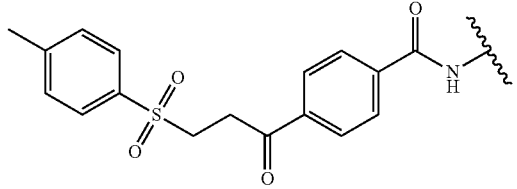

or —OP(=O)(OH)$_2$;

$X_1$ and $X_3$ are each independently —O—, —S—, —NH—, or —CH$_2$—;

a6 and b1 are each independently an integer of 1 to 10;

T is a drug selected from the following structures: and

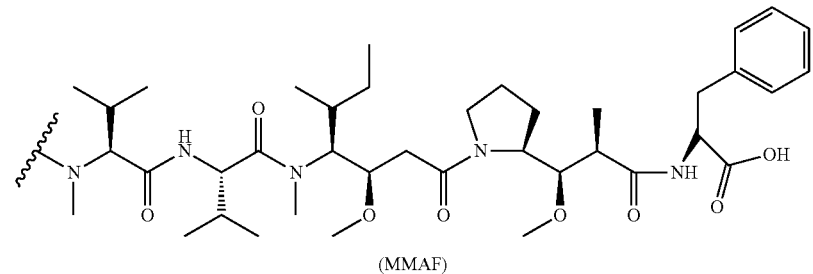

(MMAF)

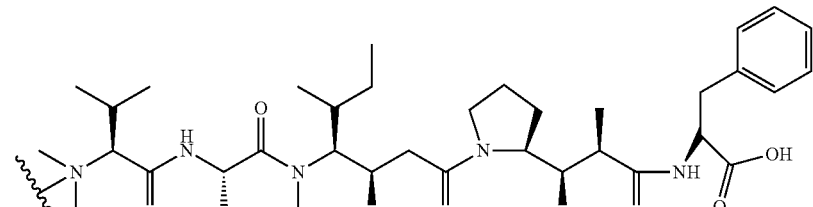

Auristatin F

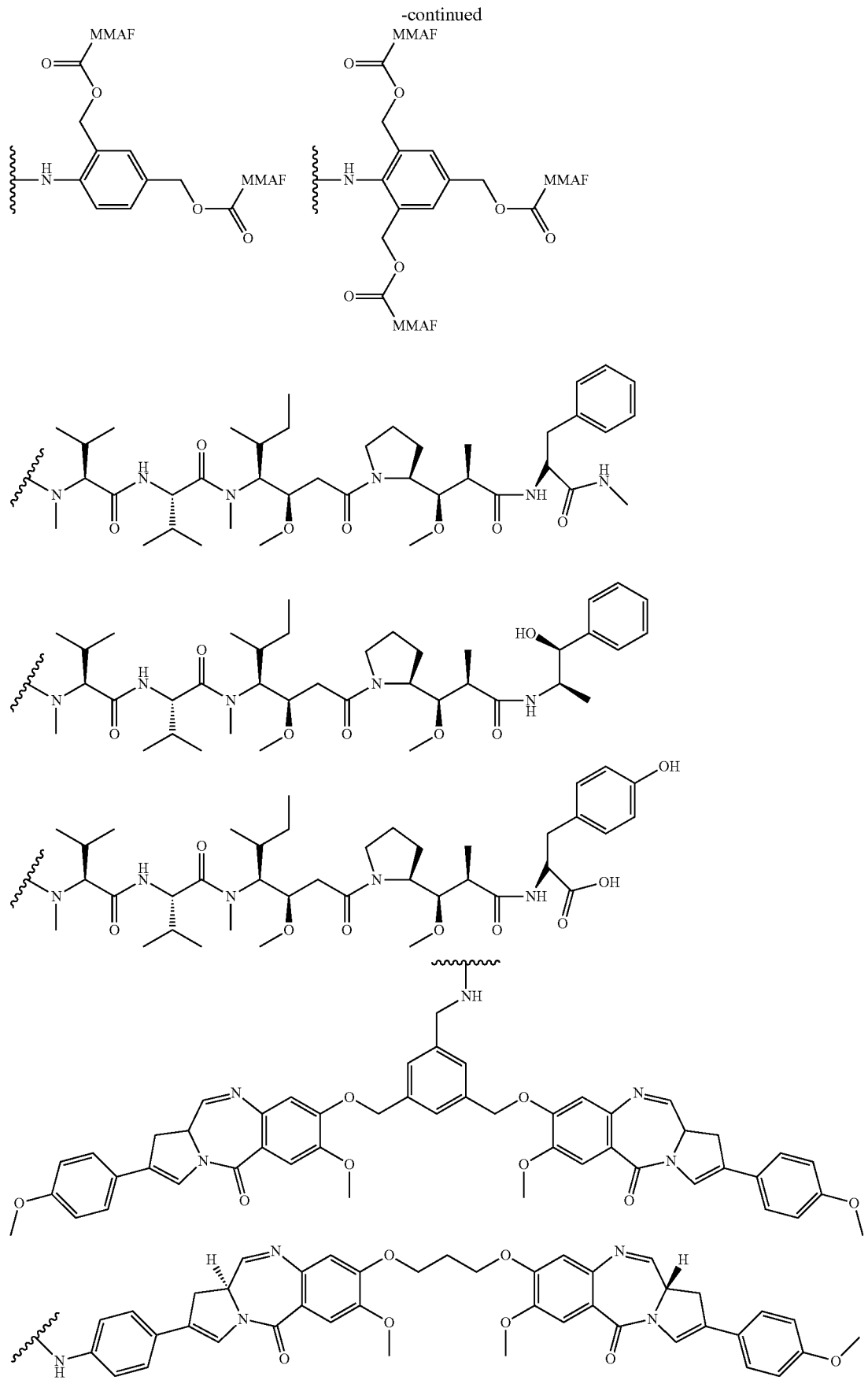

211     -continued     212
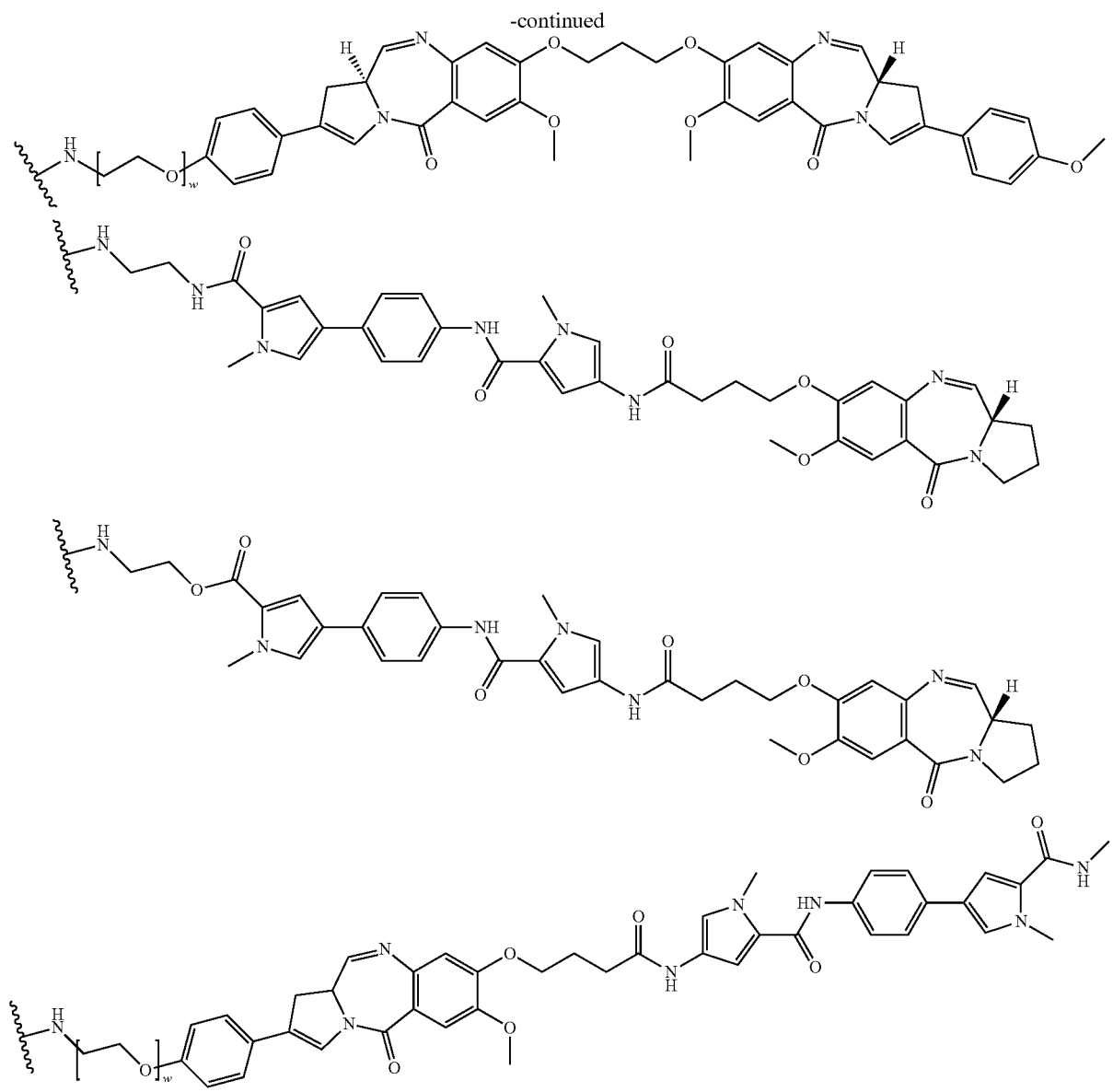
w is an integer of 1 to 10.
* * * * *